US012716079B2

(12) United States Patent
Pomraning et al.

(10) Patent No.: US 12,716,079 B2
(45) Date of Patent: Aug. 25, 2026

(54) PROCESS CONTROL FOR 3-HYDROXYPROPIONIC ACID PRODUCTION BY ENGINEERED STRAINS OF ASPERGILLUS NIGER

(71) Applicant: Battelle Memorial Institute, Richland, WA (US)

(72) Inventors: Kyle R. Pomraning, Walden, CO (US); Ziyu Dai, Richland, WA (US); Jon K. Magnuson, Richland, WA (US); Beth A Hofstad, Richland, WA (US); Jeffrey J. Czajka, Richland, WA (US); Joonhoon Kim, Kirkland, WA (US); Shuang Deng, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 398 days.

(21) Appl. No.: 18/365,091

(22) Filed: Aug. 3, 2023

(65) Prior Publication Data

US 2024/0052382 A1 Feb. 15, 2024

Related U.S. Application Data

(60) Provisional application No. 63/394,663, filed on Aug. 3, 2022.

(51) Int. Cl.

| | |
|---|---|
| ***C12P 7/42*** | (2006.01) |
| ***C12N 9/04*** | (2006.01) |
| ***C12N 9/10*** | (2006.01) |
| ***C12N 9/88*** | (2006.01) |

(52) U.S. Cl.

CPC .............. *C12P 7/42* (2013.01); *C12N 9/0006* (2013.01); *C12N 9/1096* (2013.01); *C12N 9/88* (2013.01); *C12Y 101/01059* (2013.01); *C12Y 206/01018* (2013.01); *C12Y 401/01011* (2013.01)

(58) Field of Classification Search

CPC ........... C12P 7/42; C12N 9/1096; C12N 9/88; C12N 9/0006

See application file for complete search history.

(56) References Cited

U.S. PATENT DOCUMENTS 10,947,548 B2 * 3/2021 Deng .................. C12N 9/1096

FOREIGN PATENT DOCUMENTS

WO WO/2008/027742 A1 3/2008

OTHER PUBLICATIONS

Borodina et al., "Establishing a synthetic pathway for high-level production of 3-hydroxypropionic acid in *Saccharomyces cerevisiae* via beta-alanine," *Metab Eng.* 27:57-64, 2015.

Dai et al., "Identification of Genes Associated with Morphology in *Aspergillus niger* by Using Suppression Subtractive Hybridization," *Environ Microbiol.* 70(4):2474-85, 2004.

Guyot et al. "Extremely rapid acclimation of *Escherichia coli* to high temperature over a few generations of a fed-batch culture during slow warming." *MicrobiologyOpen* 3(1): 52-63, 2014.

Ji et al., "Metabolic Engineering of Yeast for the Production of 3-Hydroxypropionic Acid," *Front Microbiol.* 9:2185, 2018.

Jiang et al., "Biosynthetic pathways for 3-hydroxypropionic acid production," *Appl Microbiol Biotechnol.* 82(6):995-1003, 2009.

Kildegaard et al., "Production of 3-hydroxypropionic acid from glucose and xylose by metabolically engineered *Saccharomyces cerevisiae*," *Metab Eng Commun.* 2:132-6, 2015.

Kildegaard et al., "Engineering and systems-level analysis of *Saccharomyces cerevisiae* for production of 3-hydroxypropionic acid via malonyl-CoA reductase-dependent pathway," *Microb Cell Fact.* 15(1):1-13, 2016.

Kumar et al., "Recent advances in biological production of 3-hydroxypropionic acid," *Biotechnol Adv.* 31(6):945-61, 2013.

Li et al. "High Production of 3-Hydroxypropionic Acid in Klebsiella pneumoniae by Systematic Optimization of Glycerol Metabolism," *Scientific Reports* 6:26932, 10 pages, 2016.

Matsakas et al., "Biological Production of 3-Hydroxypropionic Acid: An Update on the Current Status," *Ferment*, 4(1):13, 2018.

Pomraning et al., "Integration of Proteomics and Metabolomics Into the Design, Build, Test, Learn Cycle to Improve 3-Hydroxypropionic Acid Production in Aspergillus pseudoterreus," *Front Bioeng Biotechnol* 9:603832, 2021.

Suyama et al., "Production of 3-hydroxypropionic acid via the malonyl-CoA pathway using recombinant fission yeast strains," *J Biosci Bioeng.* 124(4):392-9, 2017.

Takayama et al., "Enhancing 3-hydroxypropionic acid production in combination with sugar supply engineering by cell surface-display and metabolic engineering of Schizosaccharomyces pombe," *Microb Cell Factories.* 17(1):1-11, 2018.

Talarico et al. "Utilization of Glycerol as a Hydrogen Acceptor by Lactobacillus reuteri: Purification of 1,3-Propanediol:NAD+ Oxidoreductase," *Applied and Environmental Microbiology* 56(4): 943-948, 1990.

Wang et al. "Enhanced production of β-alanine through co-expressing two different subtypes of L-aspartate-α-decarboxylase," *Journal of Industrial Microbiology & Biotechnology* 47:465-474, 2020.

* cited by examiner

*Primary Examiner* — Tekchand Saidha

(74) *Attorney, Agent, or Firm* — Klarquist Sparkman, LLP

(57) ABSTRACT

Provided herein are recombinant *Aspergillus niger* capable of producing 3-hydroxypropionic acid (3-HP). Also provided are methods of producing 3-hydroxypropionic acid (3-HP) and related kits.

19 Claims, 47 Drawing Sheets

Specification includes a Sequence Listing.

FIG. 2A
FIG. 2B
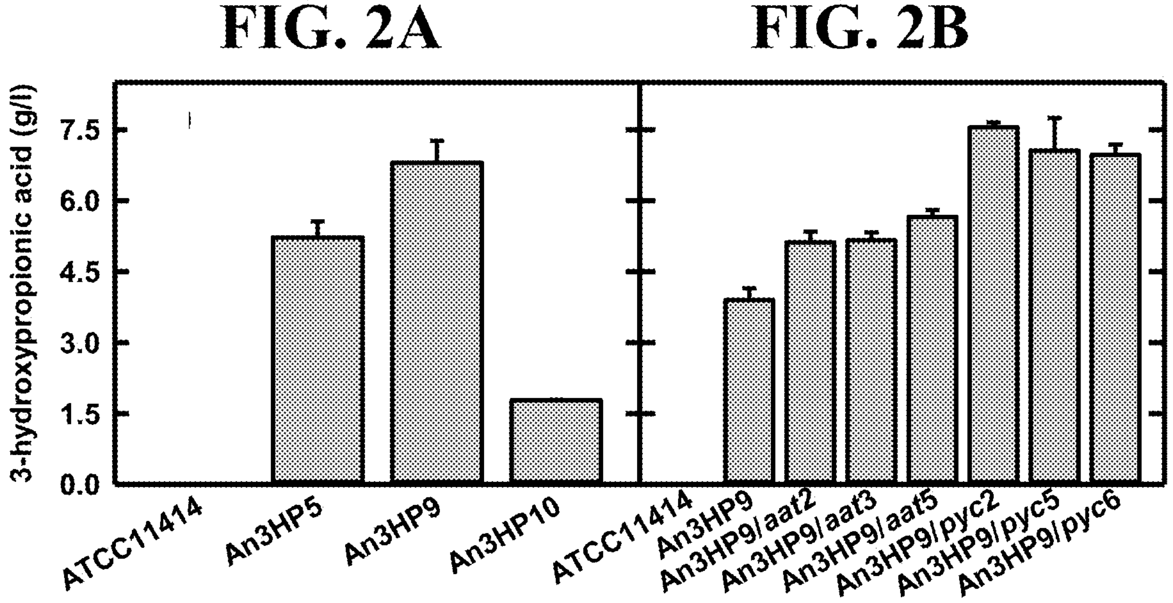
FIG. 2C
FIG. 2D
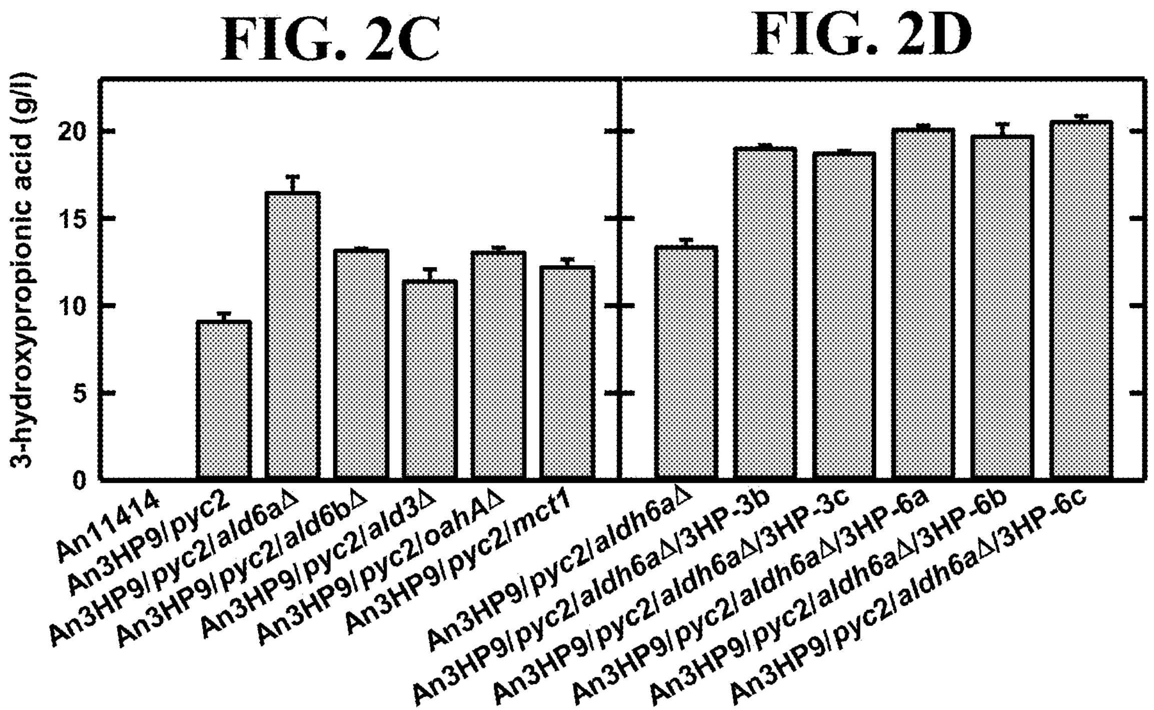

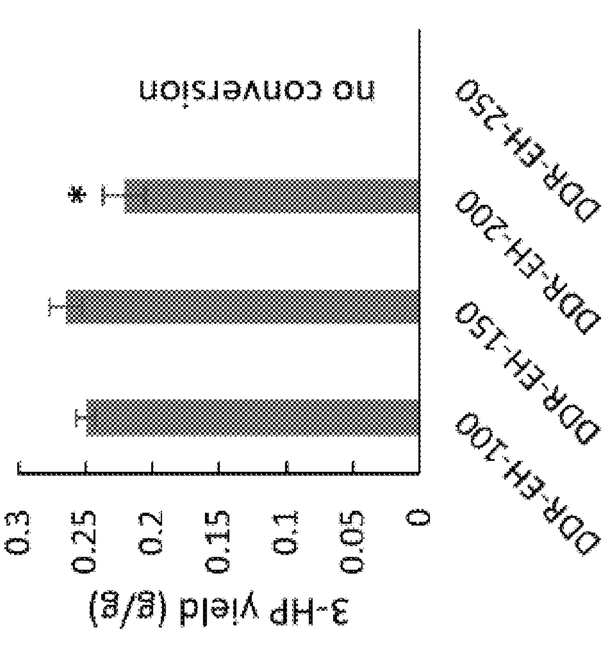
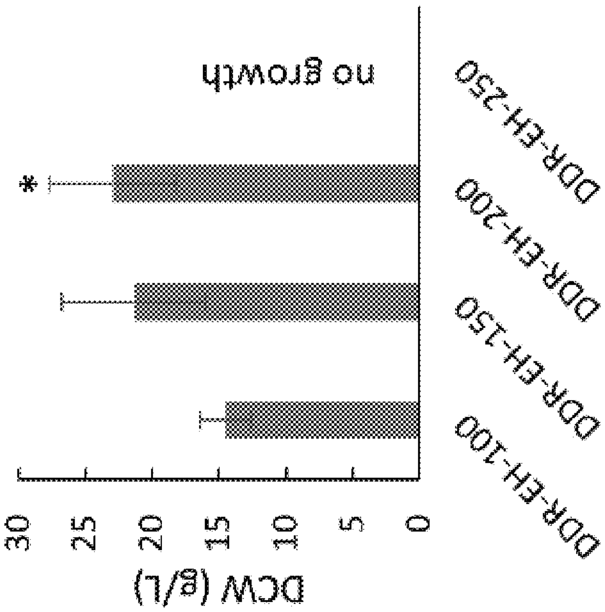
FIG. 5A

FIG. 5C
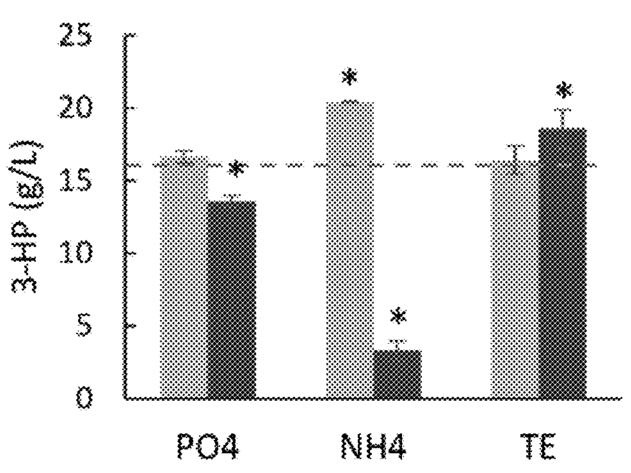
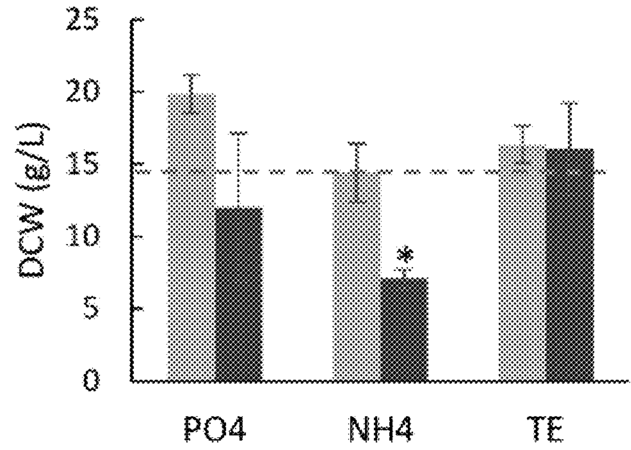
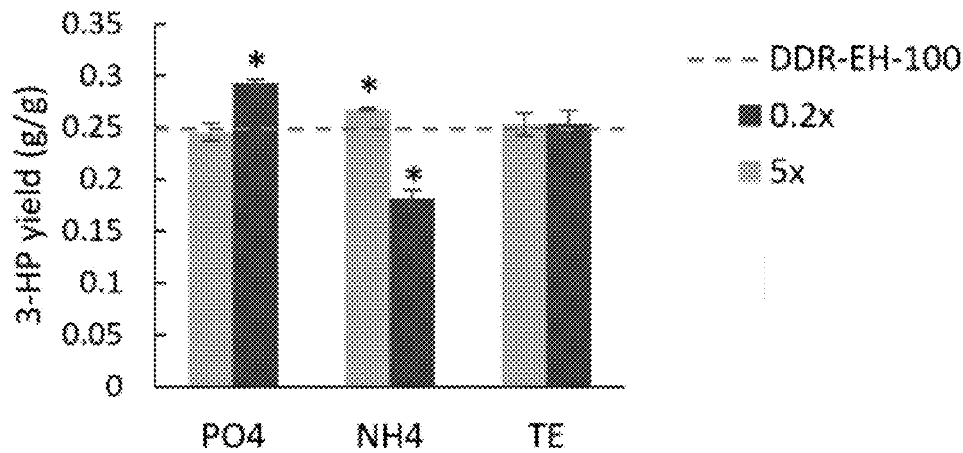

FIG. 8A

| Strain name | Relevant genotype | Reference |
|---|---|---|
| | **Parent strain:** *Aspergillus pseudoterreus* ATCC32359 (AP) | |
| AP*cad1*Δ | *cad1::hph* | Pomraning et al., 2021 |
| Ap3HP2 | *cad*::**3HP**[*gpdA*p-*panD-elf3*t-*bapat-eno1*p, *gpdA*p-*hpdh-trpC*t, *ptrA*, (1 copy)*] | Pomraning et al., 2021 |
| Ap3HP6 | *cad*::**3HP**[*gpdA*p-*panD-elf3*t-*bapat-eno1*p, *gpdA*p-*hpdh-trpC*t, *ptrA*, (2 copies)] | Pomraning et al., 2021 |
| Ap3HP6/HP7 or 16 | *cad*::**3HP**[*gpdA*p-*panD-elf3*t-*bapat-eno1*p, *gpdA*p-*hpdh-trpC*t, *ptrA*, (2 copies)]/**3HP**[*gpdA*p-*panD-elf3*t-*bapat-eno1*p, *gpdA*p-*hpdh-trpC*t, *hph*, (unknown copies)] | This work |
| Ap3HP6/HP-*aat* series | *cad*::**3HP**[*gpdA*p-*panD-elf3*t-*bapat-eno1*p, *gpdA*p-*hpdh-trpC*t, *ptrA*, (2 copies)]//**3HP-*aat*** [*gpdA*p-*panD-elf3*t-*bapat*:*eno1*p, *gpdA*p-*hpdh-trpC*t, *hph*, *tef1*p:*aat*:*pgk1*t, (unknown copies)] | This work |

| Strain name | Relevant genotype | Reference |
|---|---|---|
| | **Parent strain:** *Aspergillus niger* ATCC 11414 (An) | |
| An3HP5 | **3HP**[*gpdA*p-*panD-elf3*t-*bapat-eno1*p, *gpdA*p-*hpdh-trpC*t, *ptrA*, (unknown copies)] | This work |
| An3HP9 | **3HP**[*gpdA*p-*panD-elf3*t-*bapat-eno1*p, *gpdA*p-*hpdh-trpC*t, *ptrA*, (12 copies)**] | This work |
| An3HP10 | **3HP**[*gpdA*p-*panD-elf3*t-*bapat-eno1*p, *gpdA*p-*hpdh-trpC*t, *ptrA* (unknown copies)] | This work |
| An3HP9/*aat2, 3, or 5* | **3HP**[*gpdA*p-*panD-elf3*t-*bapat-eno*p, *gpdA*p-*hpdh-trpC*t, *ptrA*, (12 copies)]/***aat***[*ble*, *tef1*p-*aat-pgk1*t) (An3HP9/*aat2*: 5 copies)] | This work |
| An3HP9/*pyc*2, 5, or 6 | **3HP**[*gpdA*p-*panD-elf3*t-*bapat-eno*p, *gpdA*p-*hpdh-trpC*t, *ptrA*, (12 copies)]/***pyc***[*ble*, *mbf1*p-*pyc-pgk1*t (An3HP9/*pyc*2: 8 copies)] | This work |

*copy number estimated by Southern blotting analysis; **copy numbers estimated by whole genomic DNA sequencing.

FIG. 8B

| Strain name | Relevant genotype | Reference |
|---|---|---|
| | **Parent strain:** *Aspergillus niger* ATCC 11414 (An) | |
| An3HP9/*pyc2*/*oahA*Δ | **3HP**[*gpdA*p-*panD-elf3*t-*bapat-eno*p, *gpdA*p-*hpdh-trpC*t, *ptrA*, (12 copies)]/***pyc***[*ble*, *mbf1*p-*pyc-pgk1*t (An3HP9/*pyc*2: 8 copies)]/***oahA*Δ**(*oahA*::*hph*) | This work |
| An3HP9/*pyc2*/*ald6a*Δ | **3HP**[*gpdA*p-*panD-elf3*t-*bapat-eno*p, *gpdA*p-*hpdh-trpC*t, *ptrA*, (12 copies)]/***pyc***[*ble*, *mbf1*p-*pyc-pgk1*t (An3HP9/*pyc*2: 8 copies)]/***ald6a*Δ**(*ald6a*::*hph*) | This work |
| An3HP9/*pyc2*/*ald6b*Δ | **3HP**(*gpdA*p-*panD-elf3*t-*bapat-eno*p, *gpdA*p-*hpdh-trpC*t, *ptrA*, (12 copies)]/***pyc***[/*ble*, *mbf1*p-*pyc-pgk1*t (An3HP9/*pyc*2: 8 copies)]// ***ald6b*Δ**(*ald6b*::*hph*) | This work |
| An3HP9/*pyc2*/*ald3*Δ | **3HP**(*gpdA*p-*panD-elf3*t-*bapat-eno*p, *gpdA*p-*hpdh-trpC*t, *ptrA*, (12 copies)]/***pyc***[/*ble*, *mbf1*p-*pyc-pgk1*t (An3HP9/*pyc*2: 8 copies)]/***ald3*Δ**(*ald3*::*hph*) | This work |
| An3HP9/*pyc2*/*uga2*Δ | **3HP**[*gpdA*p-*panD-elf3*t-*bapat-eno*p, *gpdA*p-*hpdh-trpC*t, *ptrA*, (12 copies)]/***pyc***[*ble*, *mbf1*p-*pyc-pgk1*t (An3HP9/*pyc*2: 8 copies)]//**uga2Δ**(*uga2*::*hph*) | This work |
| An3HP9/*pyc2*/*mct1* | 3HP[*gpdA*p-*panD-elf3*t-*bapat-eno*p, *gpdA*p-*hpdh-trpC*t, *ptrA*, (12 copies)]*pyc*[/*ble*, *mbf1*p-*pyc-pgk1*t (An3HP9/*pyc*2: 8 copies)]/*mct1*(*pmbfA*p-*mct1-msft*, *nat1*) | This work |
| An3HP9/*pyc2*/*ald6a*Δ/3HP-6 | 3HP(*gpdA*p-*panD-elf3*t-*bapat-eno*p, *gpdA*p-*hpdh-trpC*t, *ptrA*, (12 copies)]/*pyc*[*ble*, *mbf1*p-*pyc-pgk1*t (An3HP9/*pyc*2: 8 copies)]/*ald6*Δ(*ald6a*::*hph*)/3HP[*ubi4*p-*panD-elf3*t-*bapat-ubiSp*, *mbfA*p-*hpdh-trpC*t, loxP-*nptII* (15copies)] | This work |

FIG. 9

| | Copy number estimate | | | | | |
|---|---|---|---|---|---|---|
| **Strain** | Tc*pmD* | Bc*hapat* | Ec*hpdh* | *aat1* | *pyc2* | *ald6a* |
| **ATCC 11414** | 0 | 0 | 0 | 1 | 1 | 1 |
| **An3HP9/*aat1*** | 12 | 13 | 11 | 5 | 1 | 1 |
| **An3HP9/*pyc2/ald6a*Δ/3HP-6** | 26 | 29 | 25 | 1 | 8 | 0 |

FIG. 10

| Host | Carbon source | Titer (g/L) | Rate (g/Lh) | Yield (g/g) | $NH_4$ (g/L) | $PO_4$ (g/L) | Additives | pH |
|---|---|---|---|---|---|---|---|---|
| *E. coli* | glucose (pure) | 40.6 | 0.56 | 0.19 | 3.0 | 9.8 | vitamins, IPTG | 7.0, $NH_3$ |
| *S. pombe* | glucose (pure) | 11.2 | 0.12 | 0.12 | 5.0 | 2.2 | vitamins | 5.0, $NH_3$ |
| *S. cerevisiae* | glucose (pure) | 13.7 | 0.17 | 0.17 | 15.0 | 6.0 | vitamins | 5.0, NaOH |
| *S. cerevisiae* | glucose (pure) | 9.2 | 0.13 | 0.09 | 15.0 | 6.0 | vitamins | 3.5, NaOH |
| *S. cerevisiae* | glucose (pure) | 9.8 | 0.09 | 0.13 | 15.0 | 6.0 | vitamins | 5.0, NaOH |
| *S. cerevisiae* | xylose (pure) | 7.4 | 0.06 | 0.29 | 15.0 | 3.0 | vitamins | 5.0, NaOH |
| *C. glutamicum* | glucose/xylose (pure) | 54.8 | 0.76 | 0.49 | 24.0 | 2.5 | vitamins, IPTG, corn steep liquor | 7.2, $NH_3$ |
| *E. coli* | glucose/xylose (pure) | 37.6 | 0.63 | 0.17 | 4.0 | 13.5 | vitamins, IPTG, yeast extract | 6.8, $NH_3$ |
| *E. coli* | glucose/xylose (pure) | 53.7 | 0.63 | 0.13 | 4.0 | 13.5 | vitamins, IPTG, yeast extract | 6.8, $NH_3$ |
| *E. coli* | glucose/xylose (pure) | 29.7 | 0.54 | 0.36 | 4.0 | 13.5 | vitamins, IPTG, yeast extract | 6.8, $NH_3$ |
| *A. niger* | glucose/xylose (hydrolysate) | 36.0 | 0.21 | 0.48 | 2.4 | 0.1 | - | ~2.0, no control |

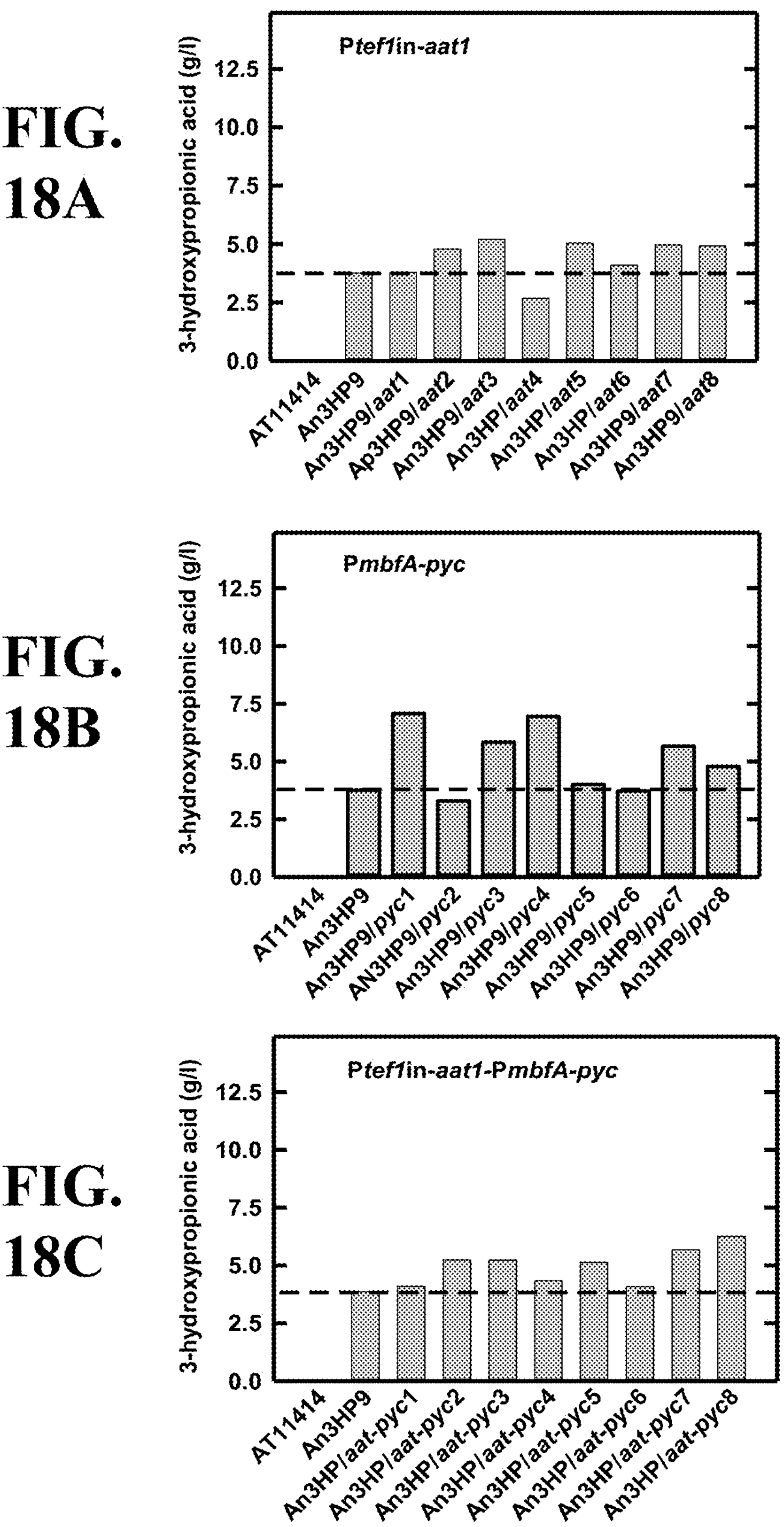
FIG. 18A
Ptef1in-aat1
3-hydroxypropionic acid (g/l)
0.0
2.5
5.0
7.5
10.0
12.5
AT11414
An3HP9
An3HP9/aat1
Ap3HP9/aat2
An3HP9/aat3
An3HP/aat4
An3HP/aat5
An3HP/aat6
An3HP9/aat7
An3HP9/aat8
FIG. 18B
PmbfA-pyc
3-hydroxypropionic acid (g/l)
0.0
2.5
5.0
7.5
10.0
12.5
AT11414
An3HP9
An3HP9/pyc1
AN3HP9/pyc2
An3HP9/pyc3
An3HP9/pyc4
An3HP9/pyc5
An3HP9/pyc6
An3HP9/pyc7
An3HP9/pyc8
FIG. 18C
Ptef1in-aat1-PmbfA-pyc
3-hydroxypropionic acid (g/l)
0.0
2.5
5.0
7.5
10.0
12.5
AT11414
An3HP9
An3HP/aat-pyc1
An3HP/aat-pyc2
An3HP/aat-pyc3
An3HP/aat-pyc4
An3HP/aat-pyc5
An3HP/aat-pyc6
An3HP/aat-pyc7
An3HP/aat-pyc8

Control parameters in 0.5 L bioreactors
pH control (aerobic, 2 VVM)
Aeration rate (pH 2, NaOH)
Glucose conv. (g/L)
3-HP (g/L)
Citric acid (g/L)
Day
uncontrolled
pH 2 (KOH)
pH 3 (KOH)
pH 4 (KOH)
pH 5 (KOH)
pH 6 (KOH)
pH 3 (NaOH)
pH 3 (NH3)
0.1 vvm
0.2 vvm
0.4 vvm
0.7 vvm
1.1 vvm

FIG. 23A
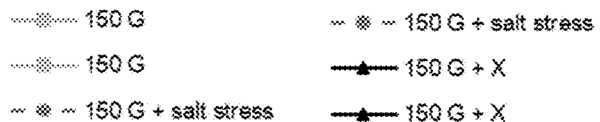
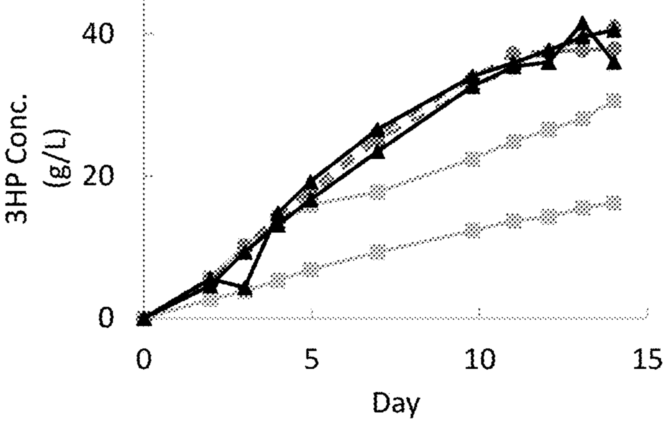
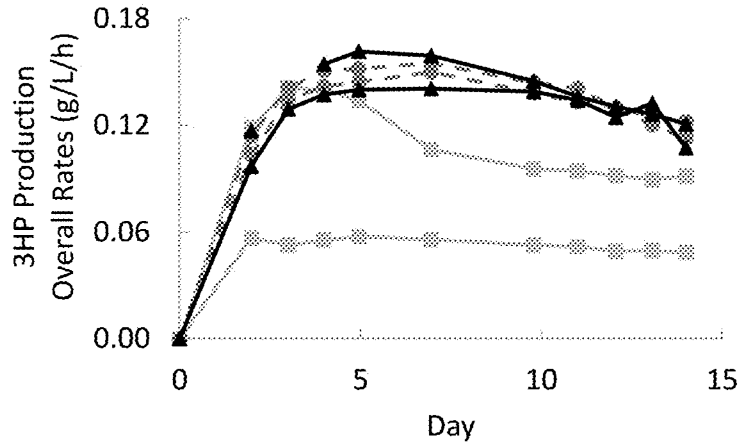
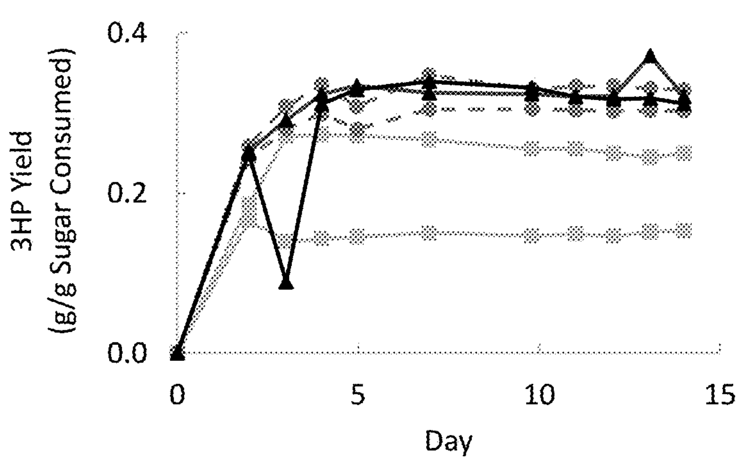

FIG. 23C
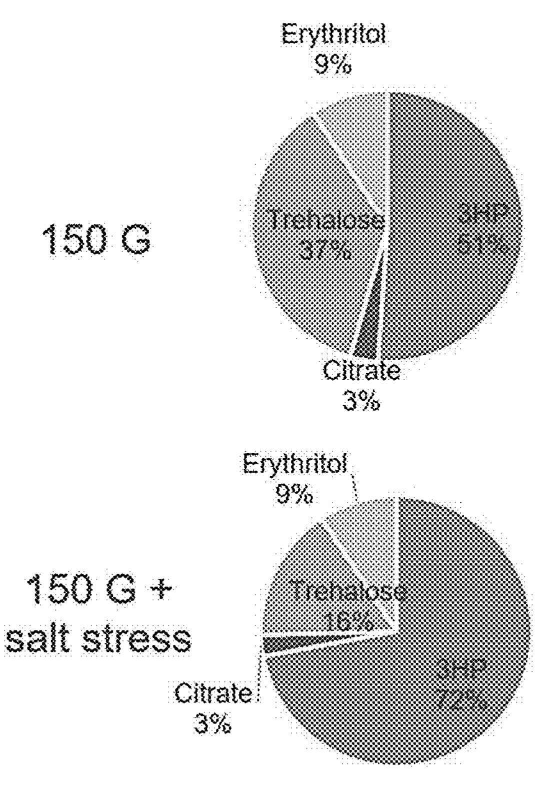
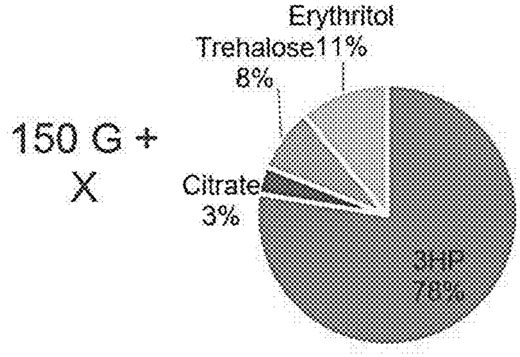

Multiple bioreactor (0.5 L) runs (n=20)

3HP Titer (g/L)
35.0
30.0
25.0
20.0
15.0
10.0
5.0
0.0
150 g/L glucose
150 g/L xylose
100 g/L glucose, 50 g/L xylose
150 g/L glucose, 0.8% NaCl
150 g/L glucose, 1.4% NaCl
150 g/L glucose, 2.0% NaCl
150 g/L glucose, 0.8% Sorbitol
150 g/L glucose, 1.4% Sorbitol
150 g/L glucose, 2.0% Sorbitol
150 g/L glucose, pH stress (5 M NaOH addition to pH ~2.5)
150 g/L glucose, 2.0 % Lactic acid
150 g/L glucose, 2P
150 g/L glucose, 1 g/L YE
150 g/L glucose, 2P 1 g/L YE Titer (g/L)
0
10
20
30
40
Glucose
Glucose + Xylose
Glucose + 2 g/L P
Glucose + 1 g/L Yeast Extract
Glucose + 2 g/L P, 1 g/L YE Rate (g/L/h)
0.00
0.05
0.10
0.15
0.20
Glucose
Glucose + Xylose
Glucose + 2 g/L P
Glucose + 1 g/L Yeast Extract
Glucose + 2 g/L P, 1 g/L YE Yield (g/g)
0.0
0.1
0.2
0.3
0.4
0.5
Glucose
Glucose + Xylose
Glucose + 2 g/L P
Glucose + 1 g/L Yeast Extract
Glucose + 2 g/L P, 1 g/L YE

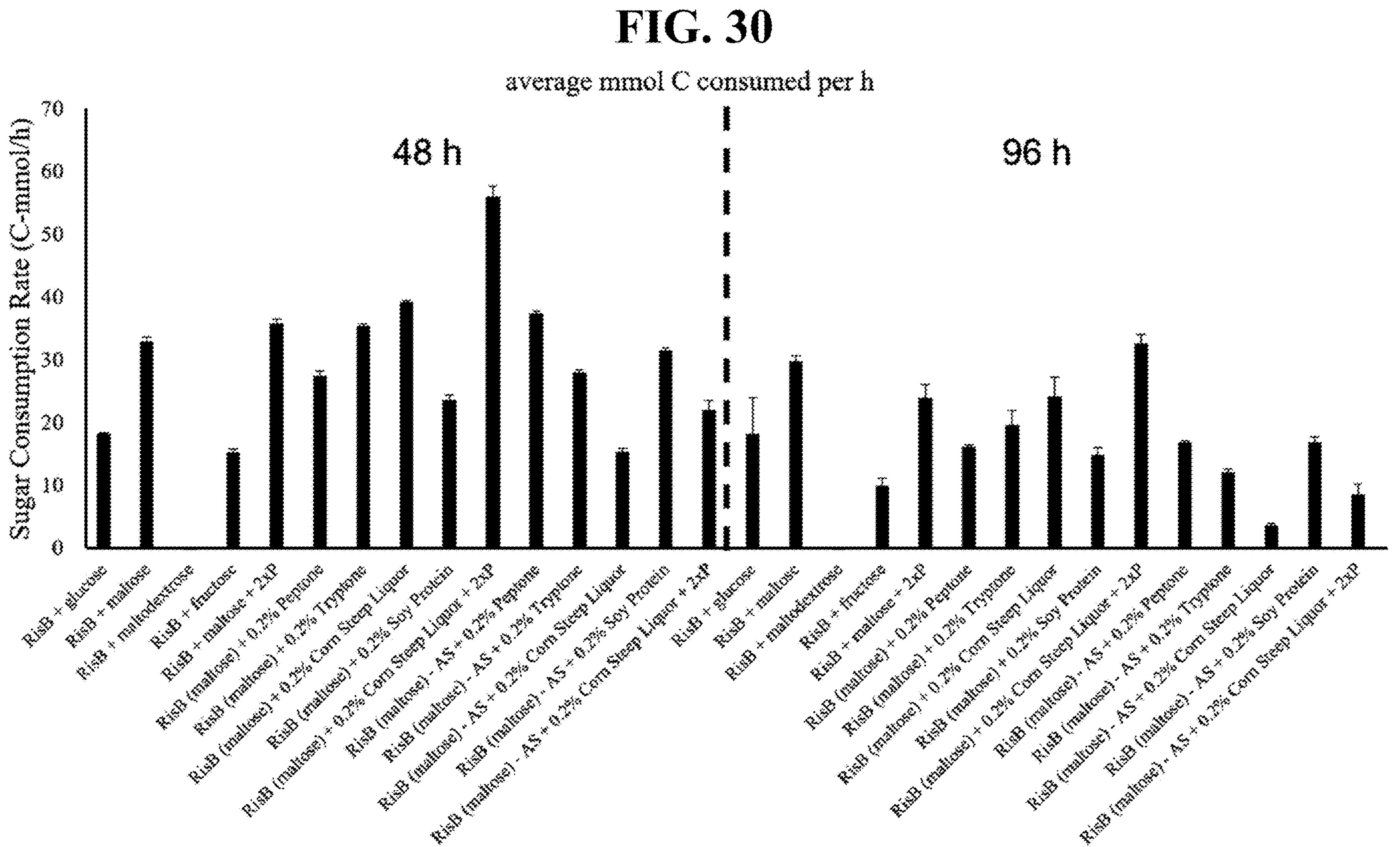
FIG. 30
average mmol C consumed per h
48 h
96 h
Sugar Consumption Rate (C-mmol/h)
0
10
20
30
40
50
60
70
RisB + glucose
RisB + maltose
RisB + maltodextrose
RisB + fructose
RisB + maltose + 2xP
RisB (maltose) + 0.2% Peptone
RisB (maltose) + 0.2% Tryptone
RisB (maltose) + 0.2% Corn Steep Liquor
RisB (maltose) + 0.2% Soy Protein
RisB (maltose) + 0.2% Corn Steep Liquor + 2xP
RisB (maltose) - AS + 0.2% Peptone
RisB (maltose) - AS + 0.2% Tryptone
RisB (maltose) - AS + 0.2% Corn Steep Liquor
RisB (maltose) - AS + 0.2% Soy Protein
RisB (maltose) - AS + 0.2% Corn Steep Liquor + 2xP
RisB + glucose
RisB + maltose
RisB + maltodextrose
RisB + fructose
RisB + maltose + 2xP
RisB (maltose) + 0.2% Peptone
RisB (maltose) + 0.2% Tryptone
RisB (maltose) + 0.2% Corn Steep Liquor
RisB (maltose) + 0.2% Soy Protein
RisB (maltose) + 0.2% Corn Steep Liquor + 2xP
RisB (maltose) - AS + 0.2% Peptone
RisB (maltose) - AS + 0.2% Tryptone
RisB (maltose) - AS + 0.2% Corn Steep Liquor
RisB (maltose) - AS + 0.2% Soy Protein
RisB (maltose) - AS + 0.2% Corn Steep Liquor + 2xP CSL = corn steep liquor
TE = trace elements CSL = corn steep liquor
TE = trace elements

SEQUENCE LISTING

```
Sequence total quantity: 143
SEQ ID NO: 1            moltype = AA  length = 540
FEATURE                 Location/Qualifiers
source                  1..540
                        mol_type = protein
                        organism = Tribolium castaneum
SEQUENCE: 1
MPATGEDQDL VQDLIEEPAT FSDAVLSSDE ELFHQKCPKP APIYSPVSKP VSFESLPNRR  60
LHEEFLRSSV DVLLQEAVFE GTNRKNRVLQ WREPEELRRL MDFGVRSAPS THEELLEVLK  120
KVVTYSVKTG HPYFVNQLFS AVDPYGLVAQ WATDALNPSV YTYEVSPVFV LMEEVVLREM  180
RAIVGFEGGK GDGIFCPGGS IANGYAISCA RYRFMPDIKK KGLHSLPRLV LFTSEDAHYS  240
IKKLASFQGI GTDNVYLIRT DARGRMDVSH LVEEIERSLR EGAAPFMVSA TAGTTVIGAF  300
DPIEKIADVC QKYKLWLHVD AAWGGGALVS AKHRHLLKGI ERADSVTWNP HKLLTAPQQC  360
STLLLRHEGV LAEAHSTNAA YLFQKDKFYD TKYDTGDKHI QCGRRADVLK FWFMWKAKGT  420
SGLEKHVDKV FENARFFTDC IKNREGFEMV IAEPEYTNIC FWYVPKSLRG RKDEADYKDK  480
LHKVAPRIKE RMMKEGSMMV TYQAQKGHPN FFRIVFQNSG LDKADMVHLV EEIERLGSDL  540

SEQ ID NO: 2            moltype = AA  length = 451
FEATURE                 Location/Qualifiers
source                  1..451
                        mol_type = protein
                        organism = Bacillus cereus
SEQUENCE: 2
MELMIVQVTE QTQSLKKTDE KYLWHAMRGA APSPTNLIIT KAEGAWVTDI DGNRYLDGMS  60
GLWCVNVGYG RKELARAAFE QLEEMPYFPL TQSHVPAIKL AEKLNEWLDD EYVIFFSNSG  120
SEANETAFKI ARQYHQQKGD HGRYKFISRY RAYHGNSMGA LAATGQAQRK YKYEPLGQGF  180
LHVAPPDTYR NPEDVHTLAS AEEIDRVMTW ELSQTVAGVI MEPIITGGGI LMPPDGYMEK  240
VKEICEKHGA LLICDEVICG FGRTGKPFGF MNYGVKPDII TMAKGITSAY LPLSATAVRR  300
EVYEAFVGSD DYDRFRHVNT FGGNPAACAL ALKNLEIMEN EKLIERSKEL GERLLYELED  360
VKEHPNVGDV RGKGLLLGIE LVEDKQTKEP ASIEKMNKVI NACKEKGLII GKNGDTVAGY  420
NNILQLAPPL SITEEDFTFI VKTMKECLAQ L                                451

SEQ ID NO: 3            moltype = AA  length = 248
```

-continued

```
FEATURE                Location/Qualifiers
source                 1..248
                       mol_type = protein
                       organism = Escherichia coli
SEQUENCE: 3
MIVLVTGATA GFGECITRRF IQQGHKVIAT GRRQERLQEL KDELGDNLYI AQLDVRNRAA  60
IEEMLASLPA EWCNIDILVN NAGLALGMEP AHKASVEDWE TMIDTNNKGL VYMTRAVLPG  120
MVERNHGHII NIGSTAGSWP YAGGNVYGAT KAFVRQFSLN LRTDLHGTAV RVTDIEPGLV  180
GGTEFSNVRF KGDDGKAEKT YQNTVALTPE DVSEAVWWVS TLPAHVNINT LEMMPVTQSY  240
AGLNVHRQ                                                          248

SEQ ID NO: 4           moltype = DNA  length = 11528
FEATURE                Location/Qualifiers
source                 1..11528
                       mol_type = other DNA
                       organism = synthetic construct
SEQUENCE: 4
ggttgtagca gcgtaaacac atggatagtt aaataatcgg atgtacaccc actgttggaa  60
atgacggggg cctacaacac gagattatct gatccaattt ctgttcgttg gcattctatc  120
attcgcagcg aaaattgtcc tattaaattg accatgacca aacaatctgc ggacagcaac  180
gcaaagtcag gagttacgtc cgaaatatgt cattgggcat ccaacctggc cactgacgac  240
atcccttcgg acgtattaga aagagcaaaa taccttattc tcgacggtat tgcatgtgcc  300
tgggttggtg caagagtgcc ttggtcagag aagtatgttc aggcaacgat gagctttgag  360
ccgccggggg cctgcagggt gattggatat ggacaggtaa attttattca ctctagacgg  420
tccacaaagt atactgacga tccttcgtat agaaactggg gcctgttgca gcagccatga  480
ccaattccgc tttcatacag gctacggagc ttgacgacta ccacagcgaa gcccccctac  540
actctgcaag cattgtcctt cctgcggtct ttgcagcaag tgaggtctta gccgagcagg  600
gcaaaacaat ttccggtata gatgttattc tagccgccat tgtggggttt gaatctggcc  660
cacggatcgg caaagcaatc tacggatcgg acctcttgaa caacggctgg cattgtggag  720
ctgtgtatgg cgctccagcc ggtgcgctgg ccacaggaaa gctcctcggt ctaactccag  780
actccatgga agatgctctc ggaattgcgt gcacgcaagc ctgtggttta atgtcggcgc  840
aatacggagg catggtaaag cgtgtgcaac acggattcgc agcgcgtaat ggtcttcttg  900
ggggactgtt ggcccatggt gggtacgagg caatgaaagg tgtcctggag agatcttacg  960
gcggtttcct caagatgttc accaaggcta ctatgaaaga ccgcgatggg ccgatagtag  1020
tagttacttc cattacatca tctcatccgc ccggttcctc gcctccgcgg cagtctacgg  1080
gtaggatcgt agcaaaaacc cgggggatag acccgtcgtc ccgagctgga gttccgtata  1140
acctaggtag aaggtatcaa ttgaacccga acaactggca aaacattctc gagatcgtag  1200
gagtgagtac ccggcgtgat ggagggggag cacgctcatt ggtccgtacg gcagctgccg  1260
agggggagca ggagatccaa atatcgtgag tctcctgctt tgcccggtgt atgaaaccgg  1320
aaaggactgc tggggaactg gggagcggcg caagccggga atcccagctg acaattgacc  1380
catcctcatg ccgtggcaga gcttgaggta gcttttgccc cgtctgtctc cccggtgtgc  1440
gcattcgact gggcgcggca tctgtgcctc ctccaggagc ggaggaccca gtagtaagta  1500
ggcctgacct ggtcgttgcg tcagtccaga ggttccctcc cctacccttt ttctacttcc  1560
cctcccccgc cgctcaactt ttctttccct tttactttct ctctctcttc ctcttcatcc  1620
atcctctctt catcacttcc ctcttccctt catccaattc atcttccaag tgagtcttcc  1680
tccccatctg tccctccatc tttcccatca tcatctccct tcccagctcc tcccctcctc  1740
tcgtctcctc acgaagcttg actaaccatt accccgccac atagacacat ctaaacaatg  1800
cccgccaccg gcgaggacca ggacctggtg caggacctga tcgaggaacc cgccaccttc  1860
tccgacgccg tcctgtcctc cgacgaggaa ctgttccacc agaagtgccc caagccggct  1920
ccgatctaca gccccgtcag caagcccgtc agcttcgagt ccctgccgaa ccgccgcctg  1980
cacgaagagt tcctccgctc ctccgtcgac gtcctgctgc aagaggccgt gttcgagggc  2040
accaaccgca agaaccgcgt cctgcagtgg cgcgagcccg aagaactgcg ccgcctgatg  2100
gacttcggcg tccgcagcgc cccgtccacg catgaggaac tgctcgaggt cctgaagaag  2160
gtcgtcacct actccgtcaa gaccggccat ccgtacttcg tcaaccagct gttctccgcc  2220
gtcgatccct acggcctggt cgcccagtgg gccaccgacg cgctgaaccc ctccgtctac  2280
acctacgagg tcagccccgt gttcgtcctg atggaagagg tcgtcctgcg cgagatgcgc  2340
gccatcgtcg gcttcgaagg cggcaaaggc gacggcatct tctgccctgg cggctcgatc  2400
gccaacggct acgccatcag ctgcgcccgc taccgcttca tgcccgacat caagaagaag  2460
ggcctgcact ccctgccgcg cctggtcctg ttcacctccg aggacgccca ctactcgatc  2520
aagaagctgg cctcgttcca aggcatcggc accgacaacg tctacctgat ccgcaccgac  2580
gctcgcggtc gcatggacgt cagccacctg gtcgaagaga tcgagcgctc cctccgcgag  2640
ggcgctgccc cgttcatggt cagcgccacc gccggcacca ccgtcatcgg cgccttcgat  2700
cccatcgaga agatcgccga cgtctgccag aagtacaagc tctggctgca cgtcgacgcc  2760
gcctggggcg gaggcgctct ggtgtccgct aagcaccgcc atctgctgaa gggcatcgag  2820
cgcgccgact ccgtcacctg gaatccccac aagctgctga ccgctccgca gcagtgcagc  2880
accctgctgc tgcgccacga gggcgtcctg gccgaggcgc actccaccaa cgccgcctac  2940
ctgttccaga aggacaagtt ctacgacacc aagtacgaca ccggcgacaa gcacatccag  3000
tgcggccgtc gcgccgacgt gctgaagttc tggttcatgt ggaaggccaa gggcacctcc  3060
ggcctcgaga agcacgtgga caaggtgttc gagaacgccc gcttcttcac cgactgcatc  3120
aagaaccgtg agggcttcga gatggtgatc gccgagcctg agtacaccaa catctgtttc  3180
tggtacgtcc ccaagagcct gcgcggacgc aaggacgagg ccgactacaa ggacaagctg  3240
cacaaggtcg cccctcgcat caaagaacgc atgatgaagg aaggctccat gatggtcacc  3300
taccaggcgc agaagggcca tccgaatttc ttccgcatcg tctttcagaa ctccggcctg  3360
gacaaggccg acatggtcca tctggtcgag gaaatcgaac gcctgggctc cgacctctga  3420
tgggttggat gacgatgact tcatgtgatt ttgttattta gaatatttta tatttccttt  3480
tcttcttctc accaccgatc cccttaacac tcttgcttca tttgcttcag atttctcggt  3540
ttcttctttt ttcttctccc cagttatcca ctatatcttt gctagaccgg cctgcgccct  3600
ggcatgcatc ataaaatcat gtccgttggt catcatctgt tttgtatatc cgtcatataa  3660
agtattcttt tattccctcc cccctcggtc gtctttcgct gtcccgcttc ctacctccgg  3720
```

-continued

```
tttatagagc atggttcatc tcttccgtac atttccgttg gtactagcat ttatgtcttc  3780
agctagtata gaagctgccg cagttgttcg cttactacct gcctaagtcc ttaacttttt  3840
aaagtgttta acctatacgt agtgttaaac gagtactggg aggtggtgag gtagaaaatg  3900
ttctgcacgg gcagtgggta tttggtagtg tgtaaggcgg ttatttatca ggctgacgct  3960
aaagacttct atgggagcag tatgggatcg cggctcatag aagtacacaa aatctaagag  4020
tcgtttgata attaattgat tcccggcagg gtcttcttgg gattgagaga actggttact  4080
ttgatttgag atattgtaaa gcttaaggct cttaacacgt acgagcgaaa cagcaggggg  4140
gaaatcggga aaaggggcgt ggggtgaata aaaaagttga aataagacac tgtatcttgc  4200
tgggggtgaa taaagagaga ataaaagaga ggtaaattcc actcagcccc ttttcttcgc  4260
tctccaaaca tcaaactccg ccggccgacc cacaggatcc cgaacaagtg gaagatatgt  4320
gccggtccag acccttcgca cagctaaaag cagaccttca taagcgtttc cgggtagtat  4380
tcgcacacct gaactggcac gtcggggaca caactgtttt tgatacacaa gaacacacac  4440
cacccatcta ggactcagag ctgggccaga cattccttca tagtcttgac gatgaaggtg  4500
aagtcctctt cggtgatgga cagcggaggg gcgagctgca ggatgttgtt gtagccggcc  4560
acggtgtcgc cgttcttgcc gatgatcaga cccttctctt tgcaggcgtt gatgaccttg  4620
ttcatctttt cgatggaggc gggctctttg gtctgcttat cctcgacgag ttcgataccc  4680
agcaggaggc ccttgccgcg gacgtccccg acgttggggt gctctttgac gtcctccaac  4740
tcgtacagca ggcgctcgcc cagttctttg gaccgctcga tgagcttctc gttttccatg  4800
atctcgaggt tcttcagggc cagcgcgcag gcggcagggt tgccgccgaa ggtgttgaca  4860
tggcggaagc ggtcgtagtc gtcggagccg acgaaggcct cgtagacctc gcggcggacc  4920
gcggtggcag acagcggcag gtaggccgag gtgataccct tggccatggt gataatgtcg  4980
ggcttgacgc cgtagttcat gaagccgaag ggcttgccgg tgcgaccgaa gccgcagatg  5040
acctcgtcgc agatcagcag ggcgccgtgc ttttcgcaga tctctttgac cttttccatg  5100
tagccgtccg gcggcatcag gatgccacca ccggtgatga tgggttccat gatgacgccg  5160
gcgacggtct gggacagctc ccaggtcatg acgcggtcga tttcttcggc ggaggccagg  5220
gtgtgcacgt cctcggggtt gcgataggtg tccggagggg ccacgtgcag gaagccctga  5280
ccgaggggct cgtacttgta cttgcgctgg gcctgaccgg tcgcggccag ggcacccatg  5340
gagttgccgt ggtaggcgcg gtagcgagag atgaacttgt agcggccgtg gtcacccttc  5400
tgctggtggt actggcgggc gatcttgaag gcggtttcgt tggcctccga gccggagttg  5460
gagaagaaga tgacgtactc gtcgtccagc cactcgttca gcttctcggc cagcttgatg  5520
gcggggacgt gcgactgcgt cagcgggaag tacggcatct cttccagctg ctcgaaggca  5580
gcgcgagcca gctctttgcg gccgtagccg acgttgacgc accacaggcc ggacatgccg  5640
tccaggtagc ggttgccgtc gatgtcggtg acccacgcgc cttcggcctt ggtgatgatc  5700
aggttggtcg gactcggagc ggcaccgcgc atggcgtgcc acaggtactt ctcgtcggtt  5760
ttcttcaggc tctgggtctg ctcggtgacc tggacgatca tcagttccat gttgatggac  5820
tggaggggga tgagttatgg atcagtgaaa ctgggagaaa acaaagatgg caaagggaga  5880
acatggccca gatataggaa aaaacggagg aggcaaaaat gtaagcgctc cggacttgct  5940
gtttcggtgt gcactagcag cagcgggggg gaaggtggtg agtgttcacc gaggacccaa  6000
aaagaatgag cggatggcgg atgagtgacg gagaagggaa ggacgggggg ggaattagag  6060
gtggagaggt ccgatccatc aaatagacca ggctcggcac agccaagttt cccaaatgat  6120
caactaatca atgggacttg gtgctaaatc cggagatgcc agatcattga tagacagaca  6180
ggatggagtg atggcatata gacaggagga tggatggatg gatagatgga ggggtcaagc  6240
acaacatggt gggatgatgg cggggtcatg actagcagct aagaggaaga agaggaggat  6300
gaaatggaca gagaaagatg ggaggggtga taaaatgagt atatgggaca agtcatactt  6360
acaggacctt gaagatggtg gttgtactat ctaagaaagg ctttttttga gagtactctt  6420
aacacaagag gaggagggag gagggggaag tagtagataa ataataaaca cgaccacaga  6480
cttgctacag gctacttctt gtaagctcga gtttctgtac agtgaccggt gactctttct  6540
ggcatgcgga gagacggacg gacgcagaga gaagggctga gtaataagcc actggccaga  6600
cagctctggc ggctctgagg tgcagtggat gattattaat ccgggaccgg ccgcccctcc  6660
gccccgaagt ggaaaggctg gtgtgcccct cgttgaccaa gaatctattg catcatcgga  6720
gaatatggag cttcatcgaa tcaccggcag taagcgaagg agaatgtgaa gccaggggtg  6780
tatagccgtc ggcgaaatag catgccatta acctaggtac agaagtccaa ttgcttccga  6840
tctggtaaaa gattcacgag atagtacctt ctccgaagta ggtagagcga gtacccggcg  6900
cgtaagctcc ctaattggcc catccggcat ctgtagggcg tccaaatatc gtgcctctcc  6960
tgctttgccc ggtgtatgaa accggaaagg ccgctcagga gctggccagc ggcgcagacc  7020
gggaacacaa gctggcagtc gacccatccg gtgctctgca ctcgacctgc tgaggtccct  7080
cagtccctgg taggcagctt tgccccgtct gtccgcccgg tgtgtcggcg gggttgacaa  7140
ggtcgttgcg tcagtccaac atttgttgcc atattttcct gctctcccca ccagctgctc  7200
ttttcttttc tctttctttt cccatcttca gtatattcat cttcccatcc aagaaccttt  7260
atttccccta agtaagtact ttgctacatc catactccat ccttcccatc ccttattcct  7320
ttgaaccttt cagttcgagc tttcccactt catcgcagct tgactaacag ctaccccgct  7380
tgagcagaca tcaccatgat cgtgctggtc acgggcgcga ccgccggttt cggcgagtgc  7440
atcacccgcc gcttcatcca gcagggccac aaggtgatcg ctaccggacg ccgccaagag  7500
cgcctccaag agctgaagga tgagctgggc gacaacctgt acattgccca gctggacgtg  7560
cgcaaccggg ctgccatcga agaaatgctc gcctcgctgc ccgccgagtg gtgcaacatc  7620
gacatcctgg tcaacaacgc cggtctggcc ctcggcatgg aaccggcgca caaggccagc  7680
gtcgaggact gggaaaccat gatcgacacc aacaacaagg gactcgtcta catgacccgc  7740
gctgtgctgc ccggcatggt cgagcgcaac cacggccaca tcatcaacat cggctccacc  7800
gctggcagct ggccctacgc tggcggcaac gtctatggcg cgaccaaggc gttcgtccgc  7860
cagttctccc tgaacctgcg caccgacctg cacggcaccg ccgtccgcgt gaccgacatt  7920
gagcccggtc tggtcggcgg caccgagttc agcaacgtcc gcttcaaggg cgacgacggc  7980
aaggccgaga aaacctacca gaacaccgtc gctctgaccc ctgaggatgt cagcgaggcc  8040
gtctggtggg tcagcactct gcccgcgcac gtcaacatca acaccctcga gatgatgccc  8100
gtcacgcagt cctacgccgg cctgaacgtc caccgccaat aggaccgatg gctgtgtaga  8160
agtactcgcc gatagtggaa accgacgccc cagcactcgt ccgagggcaa aggaatagag  8220
tagatgccga ccgggatcca cttaacgtta ctgaaatcat caaacagctt gacgaatctg  8280
gatataagat cgttggtgtc gatgtcagct ccggagttga gacaaatggt gttcaggatc  8340
tcgataagat acgttcattt gtccaagcag caaagagtgc cttctagtga tttaatagct  8400
ccatgtcaac aagaataaaa cgcgtttcgg gtttacctct tccagataca gctcatctgc  8460
```

-continued

```
aatgcattaa tgcattggac ctcgcaaccc tagtacgccc ttcaggctcc ggcgaagcag  8520
aagaatagct tagcagagtc tattttcatt ttcgggagac gagatcaagc agatcaacgg  8580
tcgtcaagag acctacgaga ctgaggaatc cgctctctga cagacgggca attgattacg  8640
ggatcccatt ggtaacgaaa tgtaaaagct aggagatcgt ccgccgatgt caggatgatt  8700
tcacttgttt cttgtccggc tcaccggtca aagctaaaga ggagcaaaag gaacggatag  8760
aatcgggtgc cgctgatcta tacggtatag tgcccttatc acgttgactc aacccatgct  8820
atttaactca acccctcctt ctgaacccca ccatcttctt ccttttcctc tcatcccaca  8880
caattctcta tctcagattt gaattccaaa agtcctcgga cgaaactgaa caagtcttcc  8940
tcccttcgat aaacctttgg tgattggaat aactgaccat cttctatagt tcccaaacca  9000
accgacaatg taaatacact cctcgattag ccctctagag ggcatacgat ggaagtcatg  9060
gaatactttt ggctggactc tcacaatgat caaggtatct taggtaacgt ctttggcgtg  9120
ggccggtgtt cgttcccagt catcgatgca ttcacatgcc ctccctaagc tgggccctag  9180
actctaggat cctagtctag aaggacatgg catcgatgga ctgggttcgt tctgagatta  9240
tacggctaaa acttgatctg gataatacca gcgaaaaggg tcatgccttc tctcgttctt  9300
cctgttgatg gaatggctaa cagatgatag tcattgcaac ttgaaacatg tctcctccag  9360
ctgccatcta cgaacccact gtggccgcta ccggcctcaa gggtaaggtc gtggtttctg  9420
agaccgtccc cgttgaggga gcttctcaga ccaagctgtt ggaccatttc ggtggcaagt  9480
gggacgagtt caagttcgcc cctatccgcg aaagccaggt ctctcgtgcc atgaccagac  9540
gttactttga ggacctggac aagtacgctg aaagtgacgt tgtcattgtt ggtgctggtt  9600
cctgcggtct gagcactgcg tacgtcttgg ccaaggctcg tccggacctg aagattgcta  9660
tcgtcgaggc cagcgtctct cctggtcagt agtccatgat ggattgcctt gcactcagct  9720
ttccggaact aacgtgcaat aggtggcggt gcctggttgg gtggccaact cttttctgct  9780
atggtcatgc gccgtcccgc ggaagtcttc ctgaacgagc tgggtgttcc ttacgaagag  9840
gacgcaaacc ccaactacgt tgtcgtcaag cacgcctccc tgtttacctc gacactcatg  9900
tcgaaggttc tctccttccc caatgtcaag ctcttcaatg ctaccgctgt tgaggacttg  9960
atcacccgtc cgaccgagaa cggcaacccc cagattgctg gtgttgtcgt caactggacg  10020
ctggtcaccc ttcaccacga tgatcactcc tgcatggacc ccaacactat caacgctcct  10080
gtcatcatca gtaccactgg tcacgatggg ccattcggcg ccttctgtgc gaagcgcttg  10140
gtgtccatgg gcagcgtcga caagctaggt ggcatgcgtg gtctcgacat gagctcggcc  10200
gaggatgcca tcgtcaagaa cacccgcgag gttactaagg gcttgataat cggcggtatg  10260
gagctgtctg aaattgatgg ctttaaccgc atgggcccta ccttcggtgc catggttctc  10320
agtggtgtca aggctgccga ggaggcattg aaggtgttcg acgagcgtca gcgcgagtgt  10380
gctgagtaaa tgactcacta cccgaatggg ttcagtgcat gaaccggatt tgtcttacgg  10440
tctttgacga taggggaatg atgattatgt gatagttctg agatttgaat gaactcgtta  10500
gctcgtaatc cacatgcata tgtaaatggc tgtgtcccgt atgtaacggt ggggcattct  10560
agaataatta tgtgtaacaa gaaagacagt ataatacaaa caaagatgca agagcggctc  10620
ctcagcaaca ttcgccatgt tcatgtacag ctttcaacgg cctcgaacag tcactgtgga  10680
tggataccag aggagagacc catcagttca atcgcagggc agatgagtgt cgcatacatt  10740
ctcgccgtcc agctggtcga ccagcaatgt cttttgtccc agttttctga gtttgatgac  10800
aacctggaga ggccagaagt ttgggatctg gccaggaagg ttacttcatc tcaaagcgaa  10860
gagtttgatc aagacggcaa ctgtctcagt gcgggtcgcg tgaggattga gttcaacgat  10920
ggttcttcta ttacggaaag tgtcgagaag cctcttggtg tcaaagagcc catgccaaac  10980
gaacggattc tccacaaata ccgaaccctt gctggtagcg tgacggacga atcccgggtg  11040
aaagagattg aggatcttgt cctcggcctg gacaggctca ccgacattag cccattgctg  11100
gagctgctga attgccccgt gaaatcgcca ctggtataaa tgggaagcga tatggaaaca  11160
tttcatgtca cgggcacaaa ttctaggtca tatcgtacct ggatggtgaa accaccagcg  11220
gtttagcaga tagaagatag actccttctg ctctgcgttg cgtcttgaat ttagttcgtt  11280
cactggctta agaacttaga atgcaataca gtctctctta tttcttatta aaatcacgta  11340
ttcccacatt cggcgactgg aggatacgaa agcagtgttg gtggtgctcc ccgtaatgga  11400
tatgattttg ctgactggac tattctatga ccattccctc caacggagat cctttctcga  11460
cactttagat gttgacgctg tctggaggaa ctacttttgc gctgcaaaga ctatgagcag  11520
tggagctg                                                           11528
```

```
SEQ ID NO: 5            moltype = AA  length = 1192
FEATURE                 Location/Qualifiers
source                  1..1192
                        mol_type = protein
                        organism = Aspergillus niger
SEQUENCE: 5
MAAPRQPEEA VDDTEFIDDH HDQHRDSVHT RLRANSAIMQ FQKILVANRG EIPIRIFRTA  60
HELSLQTVAV YSHEDRLSMH RQKADEAYMI GKRGQYTPVG AYLAIDEIVK IALEHGVHLI  120
HPGYGFLSEN AEFARKVEQS GMVFVGPTPQ TIESLGDKVS ARQLAIRCDV PVVPGTPGPV  180
ERYEEVKAFT DTYGFPIIIK AAFGGGGRGM RVVRDQAELR DSFERATSEA RSAFGNGTVF  240
VERFLDRPKH IEVQLLGDNH GNVVHLFERD CSVQRRHQKV VEIAPAKDLP ADVRDRILAD  300
AVKLAKSVNY RNAGTAEFLV DQQNRYYFIE INPRIQVEHT ITEEITGIDI VAAQIQIAAG  360
ATLEQLGLTQ DRISTRGFAI QCRITTEDPS KGFSPDTGKI EVYRSAGGNG VRLDGGNGFA  420
GAIITPHYDS MLVKCTCRGS TYEIARRKVV RALVEFRIRG VKTNIPFLTS LLSHPVFVDG  480
TCWTTFIDDT PELFALVGSQ NRAQKLLAYL GDVAVNGSSI KGQIGEPKLK GDIIKPVLHD  540
AAGKPLDVSV PATKGWKQIL DSEGPEAFAR AVRANKGCLI MDTTWRDAHQ SLLATRVRTI  600
DLLNIAHETS HALANAYSLE CWGGATFDVA MRFLYEDPWD RLRKLRKAVP NIPFQMLLRG  660
ANGVAYSSLP DNAIYHFCKQ AKKCGVDIFR VFDALNDVDQ LEVGIKAVHA AEGVVEATIC  720
YSGDMLNPSK KYNLPYYLDL VDKVVQFKPH VLGIKDMAGV LKPQAARLLI GSIRERYPDL  780
PIHVHTHDSA GTGVASMIAC AQAGADAVDA ATDSLSGMTS QPSIGAILAS LEGTEHDPGL  840
NSAQVRALDT YWAQLRLLYS PFEAGLTGPD PEVYEHEIPG GQLTNLIFQA SQLGLGQQWA  900
ETKKAYESAN DLLGDVVKVT PTSKVVGDLA QFMVSNKLTA EDVIARAGEL DFPGSVLEFL  960
EGLMGQPYGG FPEPLRSRAL RDRRKLDKRP GLYLEPLDLA KIKSQIRENY GAATEYDVAS  1020
YAMYPKVFED YKKFVAKFGD LSVLPTRYFL AKPEIGEEFH VELEKGKVLI LKLLAIGPLS  1080
EQTGQREVFY EVNGEVRQVS VDDKKASVEN TARPKAELGD SSQVGAPMSG VVVEIRVHDG  1140
LEVKKGDPIA VLSAMKMEMV ISAPHSGKVS SLLVKEGDSV DGQDLVCKIV KA          1192
```

```
SEQ ID NO: 6            moltype = DNA  length = 1955
FEATURE                 Location/Qualifiers
source                  1..1955
                        mol_type = genomic DNA
                        organism = Aspergillus niger
SEQUENCE: 6
atggccgccc gtcggtctat tgtccgttcc atccccgctc tccgcgccgc ctctccccgc  60
acggccgtgg ccacctccag atctgtagct gcagcttcgg cctcgaggcg cctttctact  120
gttataatgc cctcttcttc ttcgacaact tcttctgcaa catctaagct ctcctcatcc  180
tcacctgcca ccatgtcagc aacacgtcga ctccacgcta ctgcccagca gttcaccccc  240
gcaactacct ccgcggctac taccgccacc gagtacccga cggaccatag ccccatcgcc  300
aaccccatcg acaccgccaa tttcctggac aaccaatttg tggcttctaa ggctaccacc  360
tggatcgatc tgcacgatcc tgctaccaac aacctcgtta ctcgggtgcc gcaaagcacc  420
gatgaggaac tccgtgccgc cgtcgagtcg gccgagaagg ccttcccagc ctggcgcgca  480
accagcgtta ttgccaagca gcagatcatg ttcaagttcg tgagcttgat tcgtgccaac  540
tgggaccgac ttgctgcatc catcactctc gagcagggca agacctttgc cgatgccaag  600
ggcgatgttc tccgcggtct tcaagttgcc gaaacagcat gtggtattac cacccagcta  660
acgggcgagg tgctcgaagt ggccaaggat atggagacta ggagctacag agagcccttg  720
ggtgtggttg ctgccatttg tcctttcagt aagtgattct gcatccgtcc tgcaagctag  780
gtgacattgt ccgacgctaa ccgcaccccc tcgccttctc ggcagacttc cccgcaatga  840
ttcccctgtg gtgcatcccc atcgctaccg tgacgggcaa ctgtctcatc ctcaagccat  900
ctgagcggga ccccggagct gcaatgatcc tggccgagct ggcccgggaa gcaggcttcc  960
cccccggtgt catcaacatt gtccacggct ccgccaagac agtcgatttc atcctcgacg  1020
aacccgccat caaggccatc agcttcgtcg gcagcaaccg cgccggagag tacatctaca  1080
cccgcggctc tgccaacggc aagcgtgtcc aggccaatct gggcgccaag aaccatgccg  1140
ccgtagtccc agactgcaac aagaaccaga ccctgaacgc cctcgtcgga gcggccttcg  1200
gtgctgccgg ccaacgctgc atggccctca gtacggtcgt catggtcggc gagactcagg  1260
actggctccc cgagatggcc gaacgggcca aggccctgaa cgtcaacgga ggcttcgaag  1320
aaggcgctga cctcggcccc gtcatcagcc ccgaaagcaa gaagcgcatc gaagacctga  1380
tcgccagcgc cgaagaagag ggtgcgacca tcctcctcga cggcagaggc tacaagccag  1440
agaagtaccc caacggcaac tttgtaagct tccacccaac ccccttcccc gtctcctatc  1500
cagctacatc ttctctctaa ccagcaccaa aaccacaggt tggccccacc atcatcacca  1560
acgtaacccc cgaaatgaaa tgctacaagg aagaaatctt cggccccgtc ctcgtctgct  1620
tgtccgtgcc cacactagac gacgccattg agctcatcaa caagaacgag tacggaaacg  1680
gagctgccat cttcactcgc tccggttcca cggcctctcg cttccagaag gacatcgagg  1740
ccggccaggt cggtgttaac gtgcccattc ctgtgccgtt gcccatgttc tctttcaccg  1800
gtaacaagaa gagtattgcc ggcggtggcg ctaatacttt ctatggtaag cccgggttgc  1860
aattttacac gcagcagaag acggtgacta gtttgtggag gagtgaggat gctgttagca  1920
ctaaggctca tacggttatg ccgactcatt cgtga                              1955

SEQ ID NO: 7            moltype = DNA  length = 1713
FEATURE                 Location/Qualifiers
source                  1..1713
                        mol_type = genomic DNA
                        organism = Aspergillus niger
SEQUENCE: 7
atgtcaagat cgcagaattg gacgaatgct ttggatccgg tatttggttt gatcaacctc  60
agattattgc gattagtgct aaagtgaagg acaggtttca caacgtctac tttgcagggt  120
cccggggagt acgcttcagg aagtaaagcg ggctgttgat gctgctgaag atgcccagcc  180
tggatgggct gctctggggt tccaggtgag gcgtgaacat ctgttgcggc tggtggatgt  240
attgagacag atgtctcctg agattgtaag ctgccgggac agctgacagg caaaggagtg  300
gaactgacga tcgtaggtga cctgcctgtc tcgagaagtt ggaaagacat tagccgatgc  360
agacgcggag gttttccgtg gtctggactg catacatgcc gcatgttcga tcgggcctga  420
aatggctggc atgtttttag gaggcgatgc aacattgctg caaactttct acgagccagt  480
tgtgagtcta gatgccggtt aactacagat atgctactaa cagaccgtgg cagggcgtct  540
gtgtctcaat cactccattt agctttccct tcatgattcc cctgtggtcg cttccgtacg  600
cgcttatcac tggcaacacc gtcatcctga aaccatccga gaaaacacca actacgtctt  660
cgttattagc gcaggcattc atcaagactg gcttccctcc cggggtcttc aatgtgctcc  720
acggcggccc atccacagtg cagatgcttg tgacccagcc gacggttcaa gcggtgagtt  780
tcgttgggtc cgagtcagca gctaggcagg tgcatgacct ggcaagggcc gcagggaagc  840
gaatacaagc cgagtgtggt ggtaagaatc atggggttgt cttggaggat gctaatatgt  900
cctcgacgct ttttgcgatc gctggaagtg cctttggggc cgccggtcag cgttgtatgg  960
ccttgagcgt agcggtgttt gtaggtgcga cgagagactg gatacctagg ctggtggagc  1020
tggcacagtc gatggtagta ggatgtggtg gtgatcagga atctaagatt gggccgttga  1080
ttgacaaaac agccaaagac aaagtcagcg agatgatcca gcgagcagtt gaggagagag  1140
caaccgttct tttggacggt cgagatattg aggtccccgg ctatccggat ggcaacttca  1200
tgggcccaac tattctcggg gatgtgcaga cttacatgga atgctatcag gcggaaatat  1260
ttgggcctgt gctcatctgc atggaggtgg acactcttga ggaagcgatc gatctgataa  1320
gccaaaataa gtgtcagtct cccacaaccc gggcttgaag gggatggatt gctgacctga  1380
tcgcagatgg taacggatgc tctattttca ccaccagcgg caagcatgca aatacgttcc  1440
aacgctgtgt caatgttggt cagattggtg tcaacatccc gttgatcggt atggcggtcc  1500
ccatttccgt agcgcaacca acccctgaca gtacaacagc gccgtatgga accgcggtcc  1560
gaacgagcaa caaagattct ttcctgggtg gtgagtgccc agacatctcc ggtggaagga  1620
aagctgacct ctgcagatcg acattcccct gggaagacat attggccatt tttcacaaca  1680
actaaaacgg tctcatctcg atgggatcag tga                                1713

SEQ ID NO: 8            moltype = DNA  length = 1758
FEATURE                 Location/Qualifiers
```

-continued

```
source                  1..1758
                        mol_type = genomic DNA
                        organism = Aspergillus niger
SEQUENCE: 8
atgcccttct cctccttccc cgctcccttt cgctgtcttt ccttctcctc tctgcggctg  60
cgtggtgtgt cattctcccg tctgccagtt gttcctttct cccctcatcg tcatcacttc  120
catagctcgt ccatcacaat gagcgatctg tccgtgcagc tgacagcccc gaatgggcgc  180
acatacgccc agccggttgg tttgttcatc aacaatgaat ttgtcgcttc caagtccggc  240
gagaagttcg ccaccatcaa cccttcgtac gtgacctccc aatcctagta tctttcttgg  300
atctgctgct gaccagtgct agaaatgaag cggaaatcac ctcggtctat gctgcgggtg  360
aagaagacgt ggatattgct gtgaaggctg cccggaaagc cctcaaccac ccgtcatgga  420
agttgttgcc tccgactgaa cggggcaccc tgatgttgaa gctggccgac ttgatcgagc  480
agcacaagga gacgcttgcc accattgaaa cgtgggacaa tggtagggag cctcgcattg  540
tcctcaaagg cgatcaccat gtactgattc tctccaggca agccatactc agtttcgctg  600
aacgatgacc tgggagaggt tgttggctgc ctccggtact atgctggata cgccgacaag  660
gtccatggtc agactattag caccaccccg gccaagtttg cctatactct tcgtcagcca  720
attggtgtcg tgggtcagat tatcccctgg aacttccctc tcgcgatggc tgcctggaag  780
ttgggtcctg ccttggcctg cggaaacacc gtggttctga aaccggctga gcagactccg  840
ctcagtgttc tctatcttgc caatctcatc aaggaagccg gtttcccgcc aggtgttgtc  900
aacatcctga acggctttgg acgcgtagct ggaagtgcgc tcgtgaccca ccccggggtg  960
gacaaggttg ccttcacagg ttcgacgttg actggccgcg aaattatgaa gttggctgca  1020
ggcaccctga agaacattac gctcgagaca ggtggcaaat ctcctctggt cgtcttcagt  1080
gatgccgata tcgaccaggc cgctaagtgg gcgcatgcgg gtatcatgta caaccaagga  1140
caggtttgca ccgccacctc tcgtatcctg gtgcacgagt ccgtctatga caagttcgtg  1200
gcgctcttca aggaagccgt ggccaacacc agcaaggtgg gcgatccctt tgccgacgac  1260
accttccagg gtccccaggt caccaaggcc caatacgacc gcgtgctctc ctatatcgaa  1320
gctggaaagt ccgaaggagc gaccctggtg gccggtggcg agccgttcaa gaacgtcggc  1380
gacggcaagg gtttctttat cgcgcccacc atcttcacca acgtcaagga taacatgcgg  1440
atctaccggg aggaggtttt cggaccattt gtcgtgattt ccagcttctc agaggaggat  1500
gaggctgtga gacgggccaa cgatacgacc tatggactgg gcgctgccct gttcaccaag  1560
gacattgagc gtgcacaccg ggttgcgtcg gagatcgaag cgggcatggt ctggatcaac  1620
agcagcaacg acagcgatat ccgtgtgcct ttcgggggtg tgaagcagag cggaattggg  1680
cgcgaacttg gcgaggccgg tctggaggcc tactcacaga tcaaagcggt ccatgtcaac  1740
ttgggaacga agctgtag                                                1758

SEQ ID NO: 9            moltype = DNA  length = 1232
FEATURE                 Location/Qualifiers
source                  1..1232
                        mol_type = genomic DNA
                        organism = Aspergillus niger
SEQUENCE: 9
atgaaagttg atacccccga ttctgcttcc accatcagca tgaccaacac tatcaccatc  60
accgtagagc aggacggtat ctatgagatc aacggtgccc gtcaagagcc cgtggtcaac  120
ctgaacatgg tcaccggtgc gagcaaactg cgcaagcagc ttcgcgagac caatgagttg  180
ctcgtgtgtc ctggtgtgta cgacggtctg tccgcccgta ttgccatcaa cctgggcttc  240
aagggcatgt acatggtatg ttggattcct cacactacct ttccccacag tcaacacttc  300
tccgcttccg cgatggagaa aaaagatcat actaacggaa gggtcagacc ggcgccggta  360
ctaccgcgtc tagactgggc atggccgatc tgggtctagc ccacatctac gacatgaaga  420
ccaacgcgga gatgatcgca aacctggacc cctacggtcc tcccctgatc gcagacatgg  480
acactggcta cggaggtgag aatcccccat ctccactgtc tgccaagaca taatgatcta  540
cccgcgccaa aaagcaaaac ggcaatatag acccagttcc ccactaacac aaaaaaaaaa  600
caaaaatagg ccccctgatg gtcgcccgtt ccgttcaaca atacatccaa gccggagtcg  660
cgggattcca catcgaagat cagatccaaa acaagcgatg cggacacctg gcaggcaagc  720
gcgtcgtcac catggacgaa tacttgactc gcatccgcgc cgccaagctc accaaggacc  780
gcctccgcag cgacatcgtg ctgattgccc gcaccgacgc cctccagcag cacggctacg  840
acgagtgcat tcgccgcctt aaggccgccc gcgatcttgg cgccgatgtt ggtctcctcg  900
agggcttcac cagtaaggag atggcgaggc ggtgtgtcca ggaccttgcg ccttggccgc  960
ttcttctcaa catggtggag aacggtgctg ggccggttat ttccgtcgat gaggctaggg  1020
aaatgggctt ccgcattatg atcttctcgt tcgcttgcat tactcctgcc tatatgggga  1080
ttacggctgc tctggagagg ctcaagaagg atggtgtggt tgggttgccc gaggggatgg  1140
ggccgaagaa gctgtttgag gtttgcggat tgatggactc ggtgagggtt gataccgagg  1200
ctggtggaga tgggtttgct aatggtgttt aa                                1232

SEQ ID NO: 10           moltype = DNA  length = 50
FEATURE                 Location/Qualifiers
source                  1..50
                        mol_type = other DNA
                        organism = synthetic construct
SEQUENCE: 10
ccctcgaggt cgacggtatc gatagatatc ggttgtagca gcgtaaacac             50

SEQ ID NO: 11           moltype = DNA  length = 33
FEATURE                 Location/Qualifiers
source                  1..33
                        mol_type = other DNA
                        organism = synthetic construct
SEQUENCE: 11
tctttcatag tagccttggt gaacatcttg agg                               33
```

```
SEQ ID NO: 12          moltype = DNA  length = 34
FEATURE                Location/Qualifiers
source                 1..34
                       mol_type = other DNA
                       organism = synthetic construct
SEQUENCE: 12
atgttcacca aggctactat gaaagaccgc gatg                              34

SEQ ID NO: 13          moltype = DNA  length = 36
FEATURE                Location/Qualifiers
source                 1..36
                       mol_type = other DNA
                       organism = synthetic construct
SEQUENCE: 13
cgccggtggc gggcattgtt tagatgtgtc tatgtg                            36

SEQ ID NO: 14          moltype = DNA  length = 33
FEATURE                Location/Qualifiers
source                 1..33
                       mol_type = other DNA
                       organism = synthetic construct
SEQUENCE: 14
catctaaaca atgcccgcca ccggcgagga cca                               33

SEQ ID NO: 15          moltype = DNA  length = 35
FEATURE                Location/Qualifiers
source                 1..35
                       mol_type = other DNA
                       organism = synthetic construct
SEQUENCE: 15
atccaaccca tcagaggtcg gagcccaggc gttcg                             35

SEQ ID NO: 16          moltype = DNA  length = 33
FEATURE                Location/Qualifiers
source                 1..33
                       mol_type = other DNA
                       organism = synthetic construct
SEQUENCE: 16
gggctccgac ctctgatggg ttggatgacg atg                               33

SEQ ID NO: 17          moltype = DNA  length = 33
FEATURE                Location/Qualifiers
source                 1..33
                       mol_type = other DNA
                       organism = synthetic construct
SEQUENCE: 17
tctggcccag ctctgagtcc tagatgggtg gtg                               33

SEQ ID NO: 18          moltype = DNA  length = 35
FEATURE                Location/Qualifiers
source                 1..35
                       mol_type = other DNA
                       organism = synthetic construct
SEQUENCE: 18
catctaggac tcagagctgg gccagacatt ccttc                             35

SEQ ID NO: 19          moltype = DNA  length = 36
FEATURE                Location/Qualifiers
source                 1..36
                       mol_type = other DNA
                       organism = synthetic construct
SEQUENCE: 19
gtccatcaac atggaactga tgatcgtcca ggtcac                            36

SEQ ID NO: 20          moltype = DNA  length = 33
FEATURE                Location/Qualifiers
source                 1..33
                       mol_type = other DNA
                       organism = synthetic construct
SEQUENCE: 20
cgatcatcag ttccatgttg atggactgga ggg                               33

SEQ ID NO: 21          moltype = DNA  length = 102
FEATURE                Location/Qualifiers
source                 1..102
                       mol_type = other DNA
                       organism = synthetic construct
SEQUENCE: 21
gaactagtgg atcccccggg ctgcgttaac tcgagcttac aagaagtagc cggctacttc  60
```

-continued

```
ttgtaagctc gagttaacgc agcccggggg atccactagt tc                    102

SEQ ID NO: 22           moltype = DNA  length = 99
FEATURE                 Location/Qualifiers
source                  1..99
                        mol_type = other DNA
                        organism = synthetic construct
SEQUENCE: 22
tgaccagcac gatcatggtg atgtctgctc aagcttgagc agacatcacc atgatcgtgc  60
tggtcacttg agcagacatc accatgatcg tgctggtca                         99

SEQ ID NO: 23           moltype = DNA  length = 33
FEATURE                 Location/Qualifiers
source                  1..33
                        mol_type = other DNA
                        organism = synthetic construct
SEQUENCE: 23
agacatcacc atgatcgtgc tggtcacggg cgc                               33

SEQ ID NO: 24           moltype = DNA  length = 66
FEATURE                 Location/Qualifiers
source                  1..66
                        mol_type = other DNA
                        organism = synthetic construct
SEQUENCE: 24
gccatcggtc ctattggcgg tggacgttca ggcgcctgaa cgtccaccgc caataggacc  60
gatggc                                                             66

SEQ ID NO: 25           moltype = DNA  length = 33
FEATURE                 Location/Qualifiers
source                  1..33
                        mol_type = other DNA
                        organism = synthetic construct
SEQUENCE: 25
cgtccaccgc caataggacc gatggctgtg tag                               33

SEQ ID NO: 26           moltype = DNA  length = 66
FEATURE                 Location/Qualifiers
source                  1..66
                        mol_type = other DNA
                        organism = synthetic construct
SEQUENCE: 26
cccgtctgtc agagagcgga ttcctcagtc tcgcgagact gaggaatccg ctctctgaca  60
gacggg                                                             66

SEQ ID NO: 27           moltype = DNA  length = 37
FEATURE                 Location/Qualifiers
source                  1..37
                        mol_type = other DNA
                        organism = synthetic construct
SEQUENCE: 27
gaggaatccg ctctctgaca gacgggcaat tgattac                           37

SEQ ID NO: 28           moltype = DNA  length = 66
FEATURE                 Location/Qualifiers
source                  1..66
                        mol_type = other DNA
                        organism = synthetic construct
SEQUENCE: 28
gaatgttgct gaggagccgc tcttgcatct ttgcaaagat gcaagagcgg ctcctcagca  60
acattc                                                             66

SEQ ID NO: 29           moltype = DNA  length = 35
FEATURE                 Location/Qualifiers
source                  1..35
                        mol_type = other DNA
                        organism = synthetic construct
SEQUENCE: 29
gcaagagcgg ctcctcagca acattcgcca tgttc                             35

SEQ ID NO: 30           moltype = DNA  length = 49
FEATURE                 Location/Qualifiers
source                  1..49
                        mol_type = other DNA
                        organism = synthetic construct
SEQUENCE: 30
actaaaggga acaaaagctg gagctcagct ccactgctca tagtctttg              49

SEQ ID NO: 31           moltype = DNA  length = 48
```

```
FEATURE                Location/Qualifiers
source                 1..48
                       mol_type = other DNA
                       organism = synthetic construct
SEQUENCE: 31
acacaattct ctatctcaga tttgctacta tgaaagaccg cgatgggc             48

SEQ ID NO: 32          moltype = DNA  length = 50
FEATURE                Location/Qualifiers
source                 1..50
                       mol_type = other DNA
                       organism = synthetic construct
SEQUENCE: 32
ttcagtttcg tccgaggact tttggaattc aaatctgaga tagagaattg           50

SEQ ID NO: 33          moltype = DNA  length = 43
FEATURE                Location/Qualifiers
source                 1..43
                       mol_type = other DNA
                       organism = synthetic construct
SEQUENCE: 33
cgaggtcgac ggtatcgata acggatcggc aaagcaatct acg                  43

SEQ ID NO: 34          moltype = DNA  length = 30
FEATURE                Location/Qualifiers
source                 1..30
                       mol_type = other DNA
                       organism = synthetic construct
SEQUENCE: 34
atccaaccca tcagaggtcg gagcccaggc                                 30

SEQ ID NO: 35          moltype = DNA  length = 32
FEATURE                Location/Qualifiers
source                 1..32
                       mol_type = other DNA
                       organism = synthetic construct
SEQUENCE: 35
cgacctctga tgggttggat gacgatgact tc                              32

SEQ ID NO: 36          moltype = DNA  length = 44
FEATURE                Location/Qualifiers
source                 1..44
                       mol_type = other DNA
                       organism = synthetic construct
SEQUENCE: 36
agtggatccc ccgggctgca ctcgagctta caagaagtag cctg                 44

SEQ ID NO: 37          moltype = DNA  length = 42
FEATURE                Location/Qualifiers
source                 1..42
                       mol_type = other DNA
                       organism = synthetic construct
SEQUENCE: 37
gcccggggga tccactagtt gctggagcta gtggaggtca ac                   42

SEQ ID NO: 38          moltype = DNA  length = 31
FEATURE                Location/Qualifiers
source                 1..31
                       mol_type = other DNA
                       organism = synthetic construct
SEQUENCE: 38
ctgtacagag cggtcggcat ctactctatt c                               31

SEQ ID NO: 39          moltype = DNA  length = 31
FEATURE                Location/Qualifiers
source                 1..31
                       mol_type = other DNA
                       organism = synthetic construct
SEQUENCE: 39
atgccgaccg ctctgtacag tgaccggtga c                               31

SEQ ID NO: 40          moltype = DNA  length = 43
FEATURE                Location/Qualifiers
source                 1..43
                       mol_type = other DNA
                       organism = synthetic construct
SEQUENCE: 40
agggaacaaa agctggagct tctagagaat tgtgtgggat gag                  43
```

```
SEQ ID NO: 41          moltype = DNA  length = 40
FEATURE                Location/Qualifiers
source                 1..40
                       mol_type = other DNA
                       organism = synthetic construct
SEQUENCE: 41
ctctcatccc acacaattct gagcatcatc ccatgatagc                        40

SEQ ID NO: 42          moltype = DNA  length = 34
FEATURE                Location/Qualifiers
source                 1..34
                       mol_type = other DNA
                       organism = synthetic construct
SEQUENCE: 42
aaaggggcga actgttgtag aagatatccg ttag                              34

SEQ ID NO: 43          moltype = DNA  length = 30
FEATURE                Location/Qualifiers
source                 1..30
                       mol_type = other DNA
                       organism = synthetic construct
SEQUENCE: 43
ctacaacagt tcgccccttt cctcctcttc                                   30

SEQ ID NO: 44          moltype = DNA  length = 48
FEATURE                Location/Qualifiers
source                 1..48
                       mol_type = other DNA
                       organism = synthetic construct
SEQUENCE: 44
gggaacaaaa gctggagctt ctagacgagc aatacggaag cgaatatc               48

SEQ ID NO: 45          moltype = DNA  length = 56
FEATURE                Location/Qualifiers
source                 1..56
                       mol_type = other DNA
                       organism = synthetic construct
SEQUENCE: 45
ctcgaggtcg acggtatcga tagtttaaac tgaggtgcag tggatgatta ttaatc      56

SEQ ID NO: 46          moltype = DNA  length = 30
FEATURE                Location/Qualifiers
source                 1..30
                       mol_type = other DNA
                       organism = synthetic construct
SEQUENCE: 46
gaggtcaacg ttgatctgct tgatctcgtc                                   30

SEQ ID NO: 47          moltype = DNA  length = 31
FEATURE                Location/Qualifiers
source                 1..31
                       mol_type = other DNA
                       organism = synthetic construct
SEQUENCE: 47
agcagatcaa cgttgacctc acagggattt c                                 31

SEQ ID NO: 48          moltype = DNA  length = 37
FEATURE                Location/Qualifiers
source                 1..37
                       mol_type = other DNA
                       organism = synthetic construct
SEQUENCE: 48
aaaggggcga cttactgttg tagaagatat ccgttag                           37

SEQ ID NO: 49          moltype = DNA  length = 30
FEATURE                Location/Qualifiers
source                 1..30
                       mol_type = other DNA
                       organism = synthetic construct
SEQUENCE: 49
caacagtaag tcgccccttt cctcctcttc                                   30

SEQ ID NO: 50          moltype = DNA  length = 33
FEATURE                Location/Qualifiers
source                 1..33
                       mol_type = other DNA
                       organism = synthetic construct
SEQUENCE: 50
gacagggcag ttatgaagtc tcccgaacta cgc                               33
```

-continued

```
SEQ ID NO: 51          moltype = DNA  length = 35
FEATURE                Location/Qualifiers
source                 1..35
                       mol_type = other DNA
                       organism = synthetic construct
SEQUENCE: 51
gacttcataa ctgccctgtc gagtaagtaa atttg                          35

SEQ ID NO: 52          moltype = DNA  length = 48
FEATURE                Location/Qualifiers
source                 1..48
                       mol_type = other DNA
                       organism = synthetic construct
SEQUENCE: 52
actagtggat cccccgggct gcaagcttac tacagagagg agctgaag            48

SEQ ID NO: 53          moltype = DNA  length = 32
FEATURE                Location/Qualifiers
source                 1..32
                       mol_type = other DNA
                       organism = synthetic construct
SEQUENCE: 53
atggccactg ttgatctgct tgatctcgtc tc                             32

SEQ ID NO: 54          moltype = DNA  length = 35
FEATURE                Location/Qualifiers
source                 1..35
                       mol_type = other DNA
                       organism = synthetic construct
SEQUENCE: 54
caaggcctag ctgccctgtc gagtaagtaa atttg                          35

SEQ ID NO: 55          moltype = DNA  length = 55
FEATURE                Location/Qualifiers
source                 1..55
                       mol_type = other DNA
                       organism = synthetic construct
SEQUENCE: 55
tcttcagctc ctctctgtag tactaggcct tgacgatctt gcagacaaga tcctg    55

SEQ ID NO: 56          moltype = DNA  length = 30
FEATURE                Location/Qualifiers
source                 1..30
                       mol_type = other DNA
                       organism = synthetic construct
SEQUENCE: 56
cttcaaaatg gctgctcccc gccagcccga                                30

SEQ ID NO: 57          moltype = DNA  length = 34
FEATURE                Location/Qualifiers
source                 1..34
                       mol_type = other DNA
                       organism = synthetic construct
SEQUENCE: 57
ggggagcagc cattttgaag atggatgaga agtc                           34

SEQ ID NO: 58          moltype = DNA  length = 50
FEATURE                Location/Qualifiers
source                 1..50
                       mol_type = other DNA
                       organism = synthetic construct
SEQUENCE: 58
ctccaccgcg gtggcggccg ctgtttaaac agtggccatg aaatccaatc          50

SEQ ID NO: 59          moltype = DNA  length = 42
FEATURE                Location/Qualifiers
source                 1..42
                       mol_type = other DNA
                       organism = synthetic construct
SEQUENCE: 59
cgaggtcgac ggtatcgata cagaagatga tattgaagga gc                  42

SEQ ID NO: 60          moltype = DNA  length = 31
FEATURE                Location/Qualifiers
source                 1..31
                       mol_type = other DNA
                       organism = synthetic construct
SEQUENCE: 60
```

```
aagtagtcat ttggatgctt gggtagaata g                              31

SEQ ID NO: 61           moltype = DNA  length = 32
FEATURE                 Location/Qualifiers
source                  1..32
                        mol_type = other DNA
                        organism = synthetic construct
SEQUENCE: 61
aagcatccaa atgactactt tggatgacac tg                             32

SEQ ID NO: 62           moltype = DNA  length = 32
FEATURE                 Location/Qualifiers
source                  1..32
                        mol_type = other DNA
                        organism = synthetic construct
SEQUENCE: 62
aaagctagag ttatggacat ggcatggaca tg                             32

SEQ ID NO: 63           moltype = DNA  length = 39
FEATURE                 Location/Qualifiers
source                  1..39
                        mol_type = other DNA
                        organism = synthetic construct
SEQUENCE: 63
atgtccataa ctctagcttt gtattgtctt taaatttac                      39

SEQ ID NO: 64           moltype = DNA  length = 40
FEATURE                 Location/Qualifiers
source                  1..40
                        mol_type = other DNA
                        organism = synthetic construct
SEQUENCE: 64
agtggatccc ccgggctgca gtaagtagaa agctttgggg                     40

SEQ ID NO: 65           moltype = DNA  length = 43
FEATURE                 Location/Qualifiers
source                  1..43
                        mol_type = other DNA
                        organism = synthetic construct
SEQUENCE: 65
cgaggtcgac ggtatcgata acagaagatg atattgaagg agc                 43

SEQ ID NO: 66           moltype = DNA  length = 31
FEATURE                 Location/Qualifiers
source                  1..31
                        mol_type = other DNA
                        organism = synthetic construct
SEQUENCE: 66
aacgaagagg cagtaagtag aaagctttgg g                              31

SEQ ID NO: 67           moltype = DNA  length = 30
FEATURE                 Location/Qualifiers
source                  1..30
                        mol_type = other DNA
                        organism = synthetic construct
SEQUENCE: 67
ctacttactg cctcttcgtt tctgtgatgc                                30

SEQ ID NO: 68           moltype = DNA  length = 34
FEATURE                 Location/Qualifiers
source                  1..34
                        mol_type = other DNA
                        organism = synthetic construct
SEQUENCE: 68
cggtcgtatg cattttgaag atggatgaga agtc                           34

SEQ ID NO: 69           moltype = DNA  length = 30
FEATURE                 Location/Qualifiers
source                  1..30
                        mol_type = other DNA
                        organism = synthetic construct
SEQUENCE: 69
cttcaaaatg catacgaccg agaagatacc                                30

SEQ ID NO: 70           moltype = DNA  length = 41
FEATURE                 Location/Qualifiers
source                  1..41
                        mol_type = other DNA
                        organism = synthetic construct
```

```
SEQUENCE: 70
agtggatccc ccgggctgca ggttctctcc ttgcagcaaa g                        41

SEQ ID NO: 71           moltype = DNA  length = 45
FEATURE                 Location/Qualifiers
source                  1..45
                        mol_type = other DNA
                        organism = synthetic construct
SEQUENCE: 71
gaggtcgacg gtatcgataa gcttctcagc tgggtgaaga acaac                    45

SEQ ID NO: 72           moltype = DNA  length = 31
FEATURE                 Location/Qualifiers
source                  1..31
                        mol_type = other DNA
                        organism = synthetic construct
SEQUENCE: 72
tagctccagc gtgatagtgt tggtcatgct g                                   31

SEQ ID NO: 73           moltype = DNA  length = 32
FEATURE                 Location/Qualifiers
source                  1..32
                        mol_type = other DNA
                        organism = synthetic construct
SEQUENCE: 73
acactatcac gctggagcta gtggaggtca ac                                  32

SEQ ID NO: 74           moltype = DNA  length = 32
FEATURE                 Location/Qualifiers
source                  1..32
                        mol_type = other DNA
                        organism = synthetic construct
SEQUENCE: 74
cgttagtatg cggtcggcat ctactctatt cc                                  32

SEQ ID NO: 75           moltype = DNA  length = 30
FEATURE                 Location/Qualifiers
source                  1..30
                        mol_type = other DNA
                        organism = synthetic construct
SEQUENCE: 75
atgccgaccg catactaacg gaagggtcag                                     30

SEQ ID NO: 76           moltype = DNA  length = 42
FEATURE                 Location/Qualifiers
source                  1..42
                        mol_type = other DNA
                        organism = synthetic construct
SEQUENCE: 76
agtggatccc ccgggctgca gtaccacgca agcttcgata tg                       42

SEQ ID NO: 77           moltype = DNA  length = 44
FEATURE                 Location/Qualifiers
source                  1..44
                        mol_type = other DNA
                        organism = synthetic construct
SEQUENCE: 77
gaggtcgacg gtatcgatat ctagagtaaa ctggtgcagc tatc                     44

SEQ ID NO: 78           moltype = DNA  length = 33
FEATURE                 Location/Qualifiers
source                  1..33
                        mol_type = other DNA
                        organism = synthetic construct
SEQUENCE: 78
tagctccagc aggtgaggat gaggagagct tag                                 33

SEQ ID NO: 79           moltype = DNA  length = 32
FEATURE                 Location/Qualifiers
source                  1..32
                        mol_type = other DNA
                        organism = synthetic construct
SEQUENCE: 79
atcctcacct gctggagcta gtggaggtca ac                                  32

SEQ ID NO: 80           moltype = DNA  length = 32
FEATURE                 Location/Qualifiers
source                  1..32
                        mol_type = other DNA
```

```
                        organism = synthetic construct
SEQUENCE: 80
gactgtcttg cggtcggcat ctactctatt cc                                  32

SEQ ID NO: 81           moltype = DNA  length = 32
FEATURE                 Location/Qualifiers
source                  1..32
                        mol_type = other DNA
                        organism = synthetic construct
SEQUENCE: 81
atgccgaccg caagacagtc gatttcatcc tc                                  32

SEQ ID NO: 82           moltype = DNA  length = 41
FEATURE                 Location/Qualifiers
source                  1..41
                        mol_type = other DNA
                        organism = synthetic construct
SEQUENCE: 82
agtggatccc ccgggctgca cacttgtcca gaccgaggta c                        41

SEQ ID NO: 83           moltype = DNA  length = 44
FEATURE                 Location/Qualifiers
source                  1..44
                        mol_type = other DNA
                        organism = synthetic construct
SEQUENCE: 83
gaggtcgacg gtatcgatag aggatatgat ctcttcaact atac                     44

SEQ ID NO: 84           moltype = DNA  length = 30
FEATURE                 Location/Qualifiers
source                  1..30
                        mol_type = other DNA
                        organism = synthetic construct
SEQUENCE: 84
tagctccagc tctcaggaga catctgtctc                                     30

SEQ ID NO: 85           moltype = DNA  length = 32
FEATURE                 Location/Qualifiers
source                  1..32
                        mol_type = other DNA
                        organism = synthetic construct
SEQUENCE: 85
tctcctgaga gctggagcta gtggaggtca ac                                  32

SEQ ID NO: 86           moltype = DNA  length = 32
FEATURE                 Location/Qualifiers
source                  1..32
                        mol_type = other DNA
                        organism = synthetic construct
SEQUENCE: 86
ctaccatcga cggtcggcat ctactctatt cc                                  32

SEQ ID NO: 87           moltype = DNA  length = 30
FEATURE                 Location/Qualifiers
source                  1..30
                        mol_type = other DNA
                        organism = synthetic construct
SEQUENCE: 87
atgccgaccg tcgatggtag taggatgtgg                                     30

SEQ ID NO: 88           moltype = DNA  length = 40
FEATURE                 Location/Qualifiers
source                  1..40
                        mol_type = other DNA
                        organism = synthetic construct
SEQUENCE: 88
agtggatccc ccgggctgca cagagaaggt gcagattgtg                          40

SEQ ID NO: 89           moltype = DNA  length = 41
FEATURE                 Location/Qualifiers
source                  1..41
                        mol_type = other DNA
                        organism = synthetic construct
SEQUENCE: 89
cgaggtcgac ggtatcgata gctggcggta gaaggatttt c                        41

SEQ ID NO: 90           moltype = DNA  length = 32
FEATURE                 Location/Qualifiers
source                  1..32
```

```
                         mol_type = other DNA
                         organism = synthetic construct
SEQUENCE: 90
tagctccagc aattggctga cgaagagtat ag                                      32

SEQ ID NO: 91            moltype = DNA  length = 29
FEATURE                  Location/Qualifiers
source                   1..29
                         mol_type = other DNA
                         organism = synthetic construct
SEQUENCE: 91
tcagccaatt gctggagcta gtggaggtc                                          29

SEQ ID NO: 92            moltype = DNA  length = 31
FEATURE                  Location/Qualifiers
source                   1..31
                         mol_type = other DNA
                         organism = synthetic construct
SEQUENCE: 92
actgaagacg cggtcggcat ctactctatt c                                       31

SEQ ID NO: 93            moltype = DNA  length = 32
FEATURE                  Location/Qualifiers
source                   1..32
                         mol_type = other DNA
                         organism = synthetic construct
SEQUENCE: 93
atgccgaccg cgtcttcagt gatgccgata tc                                      32

SEQ ID NO: 94            moltype = DNA  length = 41
FEATURE                  Location/Qualifiers
source                   1..41
                         mol_type = other DNA
                         organism = synthetic construct
SEQUENCE: 94
agtggatccc ccgggctgca cgtttgggct ttgtccttta g                            41

SEQ ID NO: 95            moltype = DNA  length = 41
FEATURE                  Location/Qualifiers
source                   1..41
                         mol_type = other DNA
                         organism = synthetic construct
SEQUENCE: 95
cgaggtcgac ggtatcgata ccaactggcg ctgtatagat c                            41

SEQ ID NO: 96            moltype = DNA  length = 30
FEATURE                  Location/Qualifiers
source                   1..30
                         mol_type = other DNA
                         organism = synthetic construct
SEQUENCE: 96
tagctccagc ggtctgaaag tagtcctgtg                                         30

SEQ ID NO: 97            moltype = DNA  length = 29
FEATURE                  Location/Qualifiers
source                   1..29
                         mol_type = other DNA
                         organism = synthetic construct
SEQUENCE: 97
ctttcagacc gctggagcta gtggaggtc                                          29

SEQ ID NO: 98            moltype = DNA  length = 31
FEATURE                  Location/Qualifiers
source                   1..31
                         mol_type = other DNA
                         organism = synthetic construct
SEQUENCE: 98
acgaggattg cggtcggcat ctactctatt c                                       31

SEQ ID NO: 99            moltype = DNA  length = 34
FEATURE                  Location/Qualifiers
source                   1..34
                         mol_type = other DNA
                         organism = synthetic construct
SEQUENCE: 99
atgccgaccg caatcctcgt cgaccatcaa aaag                                    34

SEQ ID NO: 100           moltype = DNA  length = 39
FEATURE                  Location/Qualifiers
```

```
source                  1..39
                        mol_type = other DNA
                        organism = synthetic construct
SEQUENCE: 100
agtggatccc ccgggctgca agagggtatg aaggaggag                          39

SEQ ID NO: 101          moltype = DNA  length = 43
FEATURE                 Location/Qualifiers
source                  1..43
                        mol_type = other DNA
                        organism = synthetic construct
SEQUENCE: 101
aggtcgacgg tatcgatatc acagaagatg atattgaagg agc                     43

SEQ ID NO: 102          moltype = DNA  length = 41
FEATURE                 Location/Qualifiers
source                  1..41
                        mol_type = other DNA
                        organism = synthetic construct
SEQUENCE: 102
gatagggtgg ttgtctggat cagtaagtag aaagctttgg g                       41

SEQ ID NO: 103          moltype = DNA  length = 41
FEATURE                 Location/Qualifiers
source                  1..41
                        mol_type = other DNA
                        organism = synthetic construct
SEQUENCE: 103
cgaggtcgac ggtatcgata tccagacaac caccctatct c                       41

SEQ ID NO: 104          moltype = DNA  length = 30
FEATURE                 Location/Qualifiers
source                  1..30
                        mol_type = other DNA
                        organism = synthetic construct
SEQUENCE: 104
gtctggacat cttgatgaag gtctgggttg                                    30

SEQ ID NO: 105          moltype = DNA  length = 30
FEATURE                 Location/Qualifiers
source                  1..30
                        mol_type = other DNA
                        organism = synthetic construct
SEQUENCE: 105
cttcatcaag atgtccagac tcgataagtc                                    30

SEQ ID NO: 106          moltype = DNA  length = 33
FEATURE                 Location/Qualifiers
source                  1..33
                        mol_type = other DNA
                        organism = synthetic construct
SEQUENCE: 106
cgtgatacgc tccatgattc atgacgtata ttc                                33

SEQ ID NO: 107          moltype = DNA  length = 30
FEATURE                 Location/Qualifiers
source                  1..30
                        mol_type = other DNA
                        organism = synthetic construct
SEQUENCE: 107
gaatcatgga gcgtatcacg aggccctttc                                    30

SEQ ID NO: 108          moltype = DNA  length = 31
FEATURE                 Location/Qualifiers
source                  1..31
                        mol_type = other DNA
                        organism = synthetic construct
SEQUENCE: 108
gccgaagacc gatcctcaat caccatcctc c                                  31

SEQ ID NO: 109          moltype = DNA  length = 37
FEATURE                 Location/Qualifiers
source                  1..37
                        mol_type = other DNA
                        organism = synthetic construct
SEQUENCE: 109
attgaggatc ggtcttcggc tatagttcat ttttatc                            37

SEQ ID NO: 110          moltype = DNA  length = 42
```

```
FEATURE                 Location/Qualifiers
source                  1..42
                        mol_type = other DNA
                        organism = synthetic construct
SEQUENCE: 110
agtggatccc ccgggctgca gttgcgatca ggtgtgtaat tg                    42

SEQ ID NO: 111          moltype = DNA  length = 33
FEATURE                 Location/Qualifiers
source                  1..33
                        mol_type = other DNA
                        organism = synthetic construct
SEQUENCE: 111
tcatcctcag gaacgactcc agaagtgact aag                               33

SEQ ID NO: 112          moltype = DNA  length = 31
FEATURE                 Location/Qualifiers
source                  1..31
                        mol_type = other DNA
                        organism = synthetic construct
SEQUENCE: 112
gttcaatcat ggtgaaattt gggattgtga c                                 31

SEQ ID NO: 113          moltype = DNA  length = 32
FEATURE                 Location/Qualifiers
source                  1..32
                        mol_type = other DNA
                        organism = synthetic construct
SEQUENCE: 113
aaatttcacc atgattgaac aagatggatt gc                                32

SEQ ID NO: 114          moltype = DNA  length = 41
FEATURE                 Location/Qualifiers
source                  1..41
                        mol_type = other DNA
                        organism = synthetic construct
SEQUENCE: 114
agtggatccc ccgggctgca gactctgcta agctattctt c                      41

SEQ ID NO: 115          moltype = DNA  length = 70
FEATURE                 Location/Qualifiers
source                  1..70
                        mol_type = other DNA
                        organism = synthetic construct
SEQUENCE: 115
ggtcgacggt atcgataata acttcgtata gcatacatta tacgaagtta tgaacgactc  60
cagaagtgac                                                         70

SEQ ID NO: 116          moltype = DNA  length = 70
FEATURE                 Location/Qualifiers
source                  1..70
                        mol_type = other DNA
                        organism = synthetic construct
SEQUENCE: 116
atcccccggg ctgcaataac ttcgtataat gtatgctata cgaagttatg actctgctaa  60
gctattcttc                                                         70

SEQ ID NO: 117          moltype = DNA  length = 52
FEATURE                 Location/Qualifiers
source                  1..52
                        mol_type = other DNA
                        organism = synthetic construct
SEQUENCE: 117
attgggtacc gggccccccc gtttaaactt cggagtagca acgagtattt tc          52

SEQ ID NO: 118          moltype = DNA  length = 30
FEATURE                 Location/Qualifiers
source                  1..30
                        mol_type = other DNA
                        organism = synthetic construct
SEQUENCE: 118
attgtttaga agcgcagtta atggtgtatg                                   30

SEQ ID NO: 119          moltype = DNA  length = 30
FEATURE                 Location/Qualifiers
source                  1..30
                        mol_type = other DNA
                        organism = synthetic construct
SEQUENCE: 119
```

```
taactgcgct tctaaacaat gcccgccacc                                     30

SEQ ID NO: 120          moltype = DNA  length = 22
FEATURE                 Location/Qualifiers
source                  1..22
                        mol_type = other DNA
                        organism = synthetic construct
SEQUENCE: 120
tcccatactg ctcccataga ag                                             22

SEQ ID NO: 121          moltype = DNA  length = 22
FEATURE                 Location/Qualifiers
source                  1..22
                        mol_type = other DNA
                        organism = synthetic construct
SEQUENCE: 121
tctatgggag cagtatggga tc                                             22

SEQ ID NO: 122          moltype = DNA  length = 31
FEATURE                 Location/Qualifiers
source                  1..31
                        mol_type = other DNA
                        organism = synthetic construct
SEQUENCE: 122
cttcatcaag atggaactga tgatcgtcca g                                   31

SEQ ID NO: 123          moltype = DNA  length = 30
FEATURE                 Location/Qualifiers
source                  1..30
                        mol_type = other DNA
                        organism = synthetic construct
SEQUENCE: 123
tcagttccat cttgatgaag gtctgggttg                                     30

SEQ ID NO: 124          moltype = DNA  length = 41
FEATURE                 Location/Qualifiers
source                  1..41
                        mol_type = other DNA
                        organism = synthetic construct
SEQUENCE: 124
tattatcgat accgtcgacc tccagacaac caccctatct c                        41

SEQ ID NO: 125          moltype = DNA  length = 43
FEATURE                 Location/Qualifiers
source                  1..43
                        mol_type = other DNA
                        organism = synthetic construct
SEQUENCE: 125
atacgaagtt attgcagccc gggacatgct ggaagggatt ttc                      43

SEQ ID NO: 126          moltype = DNA  length = 33
FEATURE                 Location/Qualifiers
source                  1..33
                        mol_type = other DNA
                        organism = synthetic construct
SEQUENCE: 126
gcacgatcat tttgaagatg gatgagaagt cgg                                 33

SEQ ID NO: 127          moltype = DNA  length = 30
FEATURE                 Location/Qualifiers
source                  1..30
                        mol_type = other DNA
                        organism = synthetic construct
SEQUENCE: 127
catcttcaaa atgatcgtgc tggtcacggg                                     30

SEQ ID NO: 128          moltype = DNA  length = 51
FEATURE                 Location/Qualifiers
source                  1..51
                        mol_type = other DNA
                        organism = synthetic construct
SEQUENCE: 128
ctagaactag tggatccccc gtttaaacca atgggatccc gtaatcaatt g             51

SEQ ID NO: 129          moltype = DNA  length = 1272
FEATURE                 Location/Qualifiers
source                  1..1272
                        mol_type = genomic DNA
                        organism = Aspergillus niger
```

```
SEQUENCE: 129
atgcatacga ccgagaagat acccagcttc ctatctcgcc ggaaacccag caatgattca  60
gaacacgtac ccccaccacc cgatggagga gtccaagcct ggacccaagt cgtctgcatg  120
cacttcgtat tcttcaacac ctgggggatc accactagct tctccgtctt tgagcaatta  180
tacaccaaaa ccctaccaca gtcagcatcc tctatctcct ggatcggcag cgtccaggta  240
tctctcctgt tcttcctgag cgcccttgcc ggacgcgcaa cagacgccgg cttcttcaga  300
gtcatgtacc cactcggggt cctcctccag ctcgtgggaa tcttcatgct ctctctgtgc  360
aagacctact ggcaaatctt cctcgctcag gcggtatgca tgggtctcgg caatggactt  420
accttcagcc ccggactttc agtcatgtcc gcctacttca tgaaaaaccg agcctttgca  480
gtgggcttgg ctgcgtctgg tgcagcaaca gggggtttga tataccccgt actcatcaac  540
caattgctct ataatcacca gataggcttc gcatggacaa tacgcgcagc aggacttctc  600
atgctaatta cccatatctt tggcctggtt ttcttcagac cccgtcttcc accccggacc  660
accggccctc tcatcgaact cggcgcattt accgagccgc ctttcgtctt cttcacctta  720
tgctacttct tcaccttctg ggcctgtac ttcgcctggt tctatcttgg cacctttgcc  780
cgagaccgtc tcggcatcgc ggatacacag aacctgctcc ttgtgttgaa tggagtcggc  840
atcgtcggac gtatcggcc gagtataatt ggtgatcgat ggacggggcg attaaacatc  900
ttgatcccca tcactctttc atgtgcgatt ctgatgtttt gctggatagc cgtcagtact  960
gttgcagggc tgtatgcgtt tgttgttgtg tatgggctcg tgggtggcgc cgcgcaatcg  1020
gtgatccctg cgacggcgac gaccatgacg ccggatatca atcggacggg tacaaggctg  1080
ggaatgatca tgagtattgt gggatttgct acgctgactg gaccggctat tgaaggggcg  1140
ttgatcgcta ctgacggggg gaggtatgtg gcggctcaga tttttgcggg tgtgagtatt  1200
ctgctgggcg tgtgtgcggt tgcggcggcg cgggtggcta aggctgggtg ggggttggat  1260
gtgaaggtgt ga                                                     1272

SEQ ID NO: 130         moltype = DNA  length = 1623
FEATURE                Location/Qualifiers
source                 1..1623
                       mol_type = other DNA
                       organism = synthetic construct
SEQUENCE: 130
atgcccgcca ccggcgagga ccaggacctg gtgcaggacc tgatcgagga acccgccacc  60
ttctccgacg ccgtcctgtc ctccgacgag gaactgttcc accagaagtg ccccaagccg  120
gctccgatct acagccccgt cagcaagccc gtcagcttcg agtccctgcc gaaccgccgc  180
ctgcacgaag agttcctccg ctcctccgtc gacgtcctgc tgcaagaggc cgtgttcgag  240
ggcaccaacc gcaagaaccg cgtcctgcag tggcgcgagc ccgaagaact gcgccgcctg  300
atggacttcg gcgtccgcag cgcccccgtcc acgcatgagg aactgctcga ggtcctgaag  360
aaggtcgtca cctactccgt caagaccggc catccgtact tcgtcaacca gctgttctcc  420
gccgtcgatc cctacggcct ggtcgcccag tgggccaccg acgcgctgaa cccctccgtc  480
tacacctacg aggtcagccc cgtgttcgtc ctgatggaag aggtcgtcct gcgcgagatg  540
cgcgccatcg tcggcttcga aggcggcaaa ggcgacggca tcttctgccc tggcggctcg  600
atcgccaacg gctacgccat cagctgcgcc cgctaccgct tcatgcccga catcaagaag  660
aagggcctgc actccctgcc gcgcctggtc ctgttcacct ccgaggacgc ccactactcg  720
atcaagaagc tggcctcgtt ccaaggcatc ggcaccgaca acgtctacct gatccgcacc  780
gacgctcgcg gtcgcatgga cgtcagccac ctggtcgaag agatcgagcg ctccctccgc  840
gagggcgctg ccccgttcat ggtcagcgcc accgccggca ccaccgtcat cggcgccttc  900
gatcccatcg agaagatcgc cgacgtctgc cagaagtaca agctctggct gcacgtcgac  960
gccgcctggg gcggaggcgc tctggtgtcc gccaagcacc gccatctgct gaagggcatc  1020
gagcgcgccg actccgtcac ctggaatccc cacaagctgc tgaccgctcc gcagcagtgc  1080
agcaccctgc tgctgcgcca cgagggcgtc ctggccgagg cgcactccac caacgccgcc  1140
tacctgttcc agaaggacaa gttctacgac accaagtacg acaccggcga caagcacatc  1200
cagtgcggcc gtcgcgccga cgtgctgaag ttctggttca tgtggaaggc caagggcacc  1260
tccggcctcg agaagcacgt ggacaaggtg ttcgagaacg cccgcttctt caccgactgc  1320
atcaagaacc gtgagggctt cgagatggtg atcgccgagc ctgagtacac caacatctgt  1380
ttctggtacg tccccaagag cctgcgcgga cgcaaggacg aggccgacta caaggacaag  1440
ctgcacaagg tcgcccctcg catcaaagaa cgcatgatga aggaaggctc catgatggtc  1500
acctaccagg cgcagaaggg ccatccgaat ttcttccgca tcgtctttca gaactccggc  1560
ctggacaagg ccgacatggt ccatctggtc gaggaaatcg aacgcctggg ctccgacctc  1620
tga                                                               1623

SEQ ID NO: 131         moltype = DNA  length = 1356
FEATURE                Location/Qualifiers
source                 1..1356
                       mol_type = other DNA
                       organism = synthetic construct
SEQUENCE: 131
atggaactga tgatcgtcca ggtcaccgag cagacccaga gcctgaagaa aaccgacgag  60
aagtacctgt ggcacgccat gcgcggtgcc gctccgagtc cgaccaacct gatcatcacc  120
aaggccgaag gcgcgtgggt caccgacatc gacggcaacc gctacctgga cggcatgtcc  180
ggcctgtggt gcgtcaacgt cggctacggc cgcaaagagc tggctcgcgc tgccttcgag  240
cagctggaag agatgccgta cttcccgctg acgcagtcgc acgtccccgc catcaagctg  300
gccgagaagc tgaacgagtg gctggacgac gagtacgtca tcttcttctc caactccggc  360
tcggaggcca acgaaaccgc cttcaagatc gcccgccagt accaccagca gaagggtgac  420
cacggccgct acaagttcat ctctcgctac cgcgcctacc acggcaactc catgggtgcc  480
ctggccgcga ccggtcaggc ccagcgcaag tacaagtacg agcccctcgg tcagggcttc  540
ctgcacgtgg cccctccgga cacctatcgc aaccccgagg acgtgcacac cctggcctcc  600
gccgaagaaa tcgaccgcgt catgacctgg gagctgtccc agaccgtcgc cggcgtcatc  660
atggaaccca tcatcaccgg tggtggcatc ctgatgccgc cggacggcta catggaaaag  720
gtcaaagaga tctgcgaaaa gcacggcgcc ctgctgatct gcgacgaggt catctgcggc  780
ttcggtcgca ccggcaagcc cttcggcttc atgaactacg gcgtcaagcc cgacattatc  840
```

```
accatggcca agggtatcac ctcggcctac ctgccgctgt ctgccaccgc ggtccgccgc  900
gaggtctacg aggccttcgt cggctccgac gactacgacc gcttccgcca tgtcaacacc  960
ttcggcggca accctgccgc ctgcgcgctg gccctgaaga acctcgagat catggaaaac  1020
gagaagctca tcgagcggtc caaagaactg ggcgagcgcc tgctgtacga gttggaggac  1080
gtcaaagagc accccaacgt cggggacgtc cgcggcaagg gcctcctgct gggtatcgaa  1140
ctcgtcgagg ataagcagac caaagagccc gcctccatcg aaaagatgaa caaggtcatc  1200
aacgcctgca aagagaaggg tctgatcatc ggcaagaacg gcgacaccgt ggccggctac  1260
aacaacatcc tgcagctcgc ccctccgctg tccatcaccg aagaggactt caccttcatc  1320
gtcaagacta tgaaggaatg tctggcccag ctctga                            1356
```

```
SEQ ID NO: 132          moltype = DNA  length = 747
FEATURE                 Location/Qualifiers
source                  1..747
                        mol_type = other DNA
                        organism = synthetic construct
SEQUENCE: 132
atgatcgtgc tggtcacggg cgcgaccgcc ggtttcggcg agtgcatcac ccgccgcttc  60
atccagcagg gccacaaggt gatcgctacc ggacgccgcc aagagcgcct ccaagagctg  120
aaggatgagc tgggcgacaa cctgtacatt gcccagctgg acgtgcgcaa ccgggctgcc  180
atcgaagaaa tgctcgcctc gctgcccgcc gagtggtgca acatcgacat cctggtcaac  240
aacgccggtc tggccctcgg catggaaccg gcgcacaagg ccagcgtcga ggactgggaa  300
accatgatcg acaccaacaa caagggactc gtctacatga cccgcgctgt gctgcccggc  360
atggtcgagc gcaaccacgg ccacatcatc aacatcggct ccaccgctgg cagctggccc  420
tacgctggcg gcaacgtcta tggcgcgacc aaggcgttcg tccgccagtt ctccctgaac  480
ctgcgcaccg acctgcacgg caccgccgtc cgcgtgaccg acattgagcc cggtctggtc  540
ggcggcaccg agttcagcaa cgtccgcttc aagggcgacg acggcaaggc cgagaaaacc  600
taccagaaca ccgtcgctct gacccctgag gatgtcagcg aggccgtctg gtgggtcagc  660
actctgcccg cgcacgtcaa catcaacacc ctcgagatga tgcccgtcac gcagtcctac  720
gccggcctga acgtccaccg ccaatag                                      747
```

```
SEQ ID NO: 133          moltype = DNA  length = 3579
FEATURE                 Location/Qualifiers
source                  1..3579
                        mol_type = genomic DNA
                        organism = Aspergillus niger
SEQUENCE: 133
atggctgctc cccgccagcc cgaggaggcg gtcgatgaca ccgagttcat cgatgaccac  60
catgaccagc accgggactc tgtccacacc cgtctgcgtg ccaattcggc tatcatgcag  120
ttccaaaaga tccttgttgc caaccgtggt gaaatcccca ttcgtatctt ccggacggct  180
cacgagctgt ccctgcagac cgtcgccgtc tactcccatg aggaccgtct ctccatgcac  240
cgtcagaagg ccgacgaggc ctacatgatt ggcaagcgcg gtcaatatac accggttggg  300
gcctacttgg ccattgacga gatcgtcaag attgctctgg agcatggtgt acacctgatc  360
cacccgggtt acggtttcct gtccgagaac gccgagtttg cccgcaaggt ggagcagtcc  420
ggcatggttt tcgtcggccc tacccccag accatcgaga gcctcggtga caaggtctcc  480
gcccgtcagc tggctatccg ctgcgacgtg cccgtcgtgc ccggtacccc gggccctgtc  540
gagcgctacg aggaggtcaa ggccttcacc gacacctacg gcttccccat catcatcaag  600
gccgcctttg gtggtggtgg tcgtggtatg cgtgtcgttc gcgaccaggc cgaactgcgt  660
gactccttcg agcgtgccac ctccgaggcc cgctctgcct ttggcaacgg caccgtcttc  720
gtcgagcgct tcctcgaccg ccccaagcac atcgaagtcc agctgctggg tgacaaccac  780
ggcaacgtcg tccacctgtt cgagcgtgac tgctccgtcc agcgtcgcca ccagaaggtc  840
gttgaaattg ccccggccaa ggacctgcct gccgatgtcc gtgaccgcat cctggctgat  900
gctgtcaagc tggccaagtc ggtcaactac cgcaacgccg gtactgcaga gttcctggtt  960
gaccagcaga accgttacta cttcattgag atcaaccccc gtatccaggt cgagcacact  1020
atcaccgaag agatcacggg tatcgatatc gttgctgctc agatccagat tgcggccggt  1080
gctaccctgg aacagctggg tctgacccag gaccgcatct ccactcgtgg attcgccatt  1140
cagtgccgta tcaccaccga ggacccctcc aagggcttct cccccgacac cggtaagatc  1200
gaggtctacc gctccgccgg tggtaacggt gtccgtctgg atggtggaaa cggtttcgcc  1260
ggtgccatca tcacccctca ctacgactcc atgttggtca agtgtacctg ccgtggttcc  1320
acctatgaga tcgctcgccg caaggtcgtt cgtgctttgg tcgagttccg tatccgtggt  1380
gtcaagacca acattccttt cctcacctct cttctgagtc accctgtgtt cgtggatggt  1440
acctgctgga ccacgttcat tgatgacact cccgagctgt tcgcccttgt cggcagtcag  1500
aaccgtgccc agaagctgct ggcttacctg ggtgatgtgg ctgtcaacgg cagcagcatc  1560
aagggccaga tcggcgagcc caagctcaag ggcgatatca tcaagcccgt tctgcatgac  1620
gctgccggca agcccctcga cgtctctgtc cccgccacca agggatggaa gcagatcctg  1680
gacagtgagg gtcccgaggc ttttgcccgc gctgtgcgtg ccaacaaggg ctgcttgatc  1740
atggatacta cctggcgtga tgcccaccag tcgctgctgg ccactcgtgt gcgtaccatt  1800
gacctcctga acatcgccca cgagacgagc cacgccctcg ccaacgccta cagtttggaa  1860
tgctggggtg gtgccacctt cgatgtcgcc atgcgcttcc tgtacgagga cccctgggac  1920
cgtcttcgca agctgcgcaa ggccgttccc aacatcccct tccagatgtt gctccgtggt  1980
gccaacggtg ttgcttactc ctccctccct gacaacgcca tctaccactt ctgtaagcag  2040
gccaagaagt gcggtgtcga catcttccgt gtcttcgatg ctctcaacga cgttgaccag  2100
ctcgaggtcg gtatcaaggc tgtccacgct gccgagggtg ttgttgaggc tactatttgc  2160
tacagtggtg atatgctcaa ccccagcaag aagtacaacc tgccttacta cctcgacctt  2220
gttgataagg tggtccaatt caagccccac gtcttgggta tcaaggacat ggctggtgtg  2280
ctgaagcccc aggctgctcg tctgctgatc ggttccatcc gcgagcgcta ccccgacctc  2340
cccatccacg tgcacaccca cgattctgct ggtaccggtg tggcttccat gattgcttgc  2400
gctcaggccg gtgctgatgc cgttgatgct gccacggaca gcctttccgg tatgacctcc  2460
cagcccagca ttggtgctat cctcgcttcc ctcgagggaa ctgagcacga ccccggcctc  2520
aactcggccc aggttcgcgc ccttgacacc tactgggcgc agctgcgtct cctctactcg  2580
```

```
cccttcgagg caggtctgac tggtcccgac cccgaggttt acgagcatga gatccctggt  2640
ggtcaattga ccaacctgat cttccaggcc agccagcttg gtctgggcca gcagtgggcg  2700
gagacgaaga aggcttacga gtctgccaac gatcttttgg gcgatgtcgt caaggtcacc  2760
cccacttcca aggtggtcgg tgatttggct cagttcatgg tctccaacaa gttgactgct  2820
gaagatgtga ttgctcgcgc cggcgagctt gacttccccg gttccgttct ggagttcctc  2880
gagggtctca tgggccagcc ctacggtgga ttccccgagc ctctgcgctc tcgcgctctg  2940
cgtgaccgtc gcaagctcga caagcgccct ggtctgtacc tggagcccct tgacctggcc  3000
aagatcaaga gccagatccg ggagaactat ggcgcagcta ccgagtacga tgtggccagc  3060
tatgccatgt accccaaggt cttcgaggat tacaagaagt ttgtcgccaa gttcggtgat  3120
ttgtccgtcc tgcccacgcg ttacttcttg gccaagcccg agatcggcga ggaattccac  3180
gtcgagctgg agaagggtaa ggtgctgatc ctgaagttgt tggccattgg tcccctctcc  3240
gagcagaccg gccagcgtga ggtcttctac gaagtcaacg gtgaggttcg ccaggttagt  3300
gtggacgaca agaaggcgtc cgtcgagaac accgcccgcc ccaaggccga gctgggtgac  3360
agcagccagg ttggtgctcc tatgagcggt gtggttgtcg agatccgcgt ccacgacggc  3420
ctggaagtca agaagggtga ccccattgcc gtcctgagcg ccatgaagat ggaaatggtt  3480
atctctgctc cccacagtgg caaggtctcc agcttgctgg tcaaggaagg tgactcggtg  3540
gatggccagg atcttgtctg caagatcgtc aaggcctag                          3579

SEQ ID NO: 134         moltype = DNA  length = 827
FEATURE                Location/Qualifiers
source                 1..827
                       mol_type = genomic DNA
                       organism = Aspergillus niger
SEQUENCE: 134
cttcggagta gcaacgagta ttttcaccgg gagtttcaac gggttctatt tcaggaacac  60
ggctgcggtc tggattgggt cgggctgaga taccgactgg tggcgtcagt ggcgggtacg  120
gacggagtcg tcctggccgc tcgtagacac tcccccggac tgatatcagg ccccggcaac  180
tggcttcgtc tcactccagg gcatcaggag tgcctaccac atgggttcag gctttgcccc  240
gtcgtctaag tttgcaggac aaaattttcg tatgcgttac cactctttcc tttcagcaac  300
cattccgtag tgaaaaccca ataataggtg gctgccgtgg gagcctgagt caacccaacc  360
agaacctttc tagtagattc tcccccaagc gcttcagcaa cgaagcgtat tggagaacca  420
aatgacgcag accaagcgga ttccggtgca atagccggat ggcaagggaa tcccccagga  480
ggtgccagaa gcgtcgcccg aaaggtactt cgtctgacag gctaacaccg ctcgggctaa  540
ggtccctgct gctcttttcc ctttattgcg acttaacctc taagccattc ccttgcatca  600
cgttatctca ctgaccgacc tctgactaag gcgcttcgcc tccgccgcct cccctcattc  660
acctcctctc ctgactactt aagccttctc ttccttcctc tcactaccaa ccctccttca  720
tccctcatac ctctcatcct accactcacc tttcgcgcat cgccatctgc gatcctcccc  780
acaacactcc acctagatac atacaccatt aactgcgctt ctacaac                  827

SEQ ID NO: 135         moltype = DNA  length = 826
FEATURE                Location/Qualifiers
source                 1..826
                       mol_type = genomic DNA
                       organism = Aspergillus niger
SEQUENCE: 135
cattatcgat ctatccacat tgcctcttat aactgacggg aggaggcgac ctgtggcctg  60
tgagggtttg aaacattatt tcaccttcc tctgcaatag ccgatttaat aattgacgcc  120
tatcccgcat gctattcaat caataattag caacagcgag ccgagggatg agagggcggc  180
aaatgatgac gatgacgaag ttgacgtcga tgctgagagg ctggattgac cacttcgtct  240
agttggtttt aggcctagtc gtactttctg cctggctttt ccgggccgtg cctatgcctg  300
gcgatgcagg caccaaactg acgtatccaa gaaaccgtta aagtcagcaa atcccgtgac  360
ctcagccgca gaccatcaca tgactgagga cccggagggc tgattatccg agtgtccacc  420
cgcactacgc ctgactcggt aatctggaca ccacgtgacc gcacaaccga ttttaacgaa  480
gcccaccacc accgaggata ttttcctacc acgatcgccg aaggtttagg aagacaagtc  540
ttgtcgaggt gagttgatga ccctatacat ttactatgtg acaaggaaaa ggattcaata  600
ttatttggaa catctcatct tcatttcttt ccacttatcc cagaaaatac ctcctgcgca  660
cactttagcg cgcgagatac caaaattccg gggagtaat atgttgaaca agaaacgaag  720
atgagagctg cgacgcagat aatattgaac tttatccttg ctcacgcacc agtatcaagt  780
aaaacaatga actaacatcc tttttccaac ccagaccttc atcaag                  826

SEQ ID NO: 136         moltype = DNA  length = 1198
FEATURE                Location/Qualifiers
source                 1..1198
                       mol_type = genomic DNA
                       organism = Aspergillus niger
SEQUENCE: 136
ggacatgctg gaagggattt tctggctcaa taccacgtct gtatttgacc ctttccagac  60
agttaatccg ctgcaggagg gcgaactgta gctcctcgtt ctccttgtag cgcttgatcc  120
agtctttttg gatgttgcac ttgcttggcc tatgcttctc atataatctt gccctgtcat  180
agagacgacg tctgagattg tagcgttcgt ctttgatcac ccggagccag ataggcctga  240
gtatatctga cattagatca aagggtctgt ggatagtctc cttcagcatc agcgacgcat  300
gtgactcgca tgtcggagag agcttgtggg tggtcatctt tgatggcgtc ctctgctttc  360
ccttgatttt cgttgattgt ttttcgaaag ttaagtctgg aagtcaagag aatccttctg  420
ccagacatta tatttacgta tactgacgta gtagaaacag cgtcaggatg aggacatggt  480
gtgtgctgga ccacggaatc atagttcatc agtatattgg gttggacaaa taacgctgag  540
catgtatatg tctttacaca ctataaaagc cagcgaacgc caataaaata gggcatattg  600
atgtgaaaat atgacaccag ttaaaagcag tgtattgatt ttatctctct tcacctcgga  660
cctatactac cgtatacaag actcaactta cttccagata tagtaatata caccctatgg  720
acgaaccagc acaataatta cagccaaaca acaccaccca aatggcatat tcctaatcag  780
```

```
cactaagcac aaataccact gtcatcacag cataatcaat aagaatccca gacaaccgac  840
tcactctgac tcaccttaca caaaccccca agcaaagcgc agcccagaac ctcagccaac  900
aatcgggcaa cgtacgggga aagattggcc gatccatgat gtcagcagcc ctaacccaaa  960
gcggactagc gcataccgcc cctctgactc cgccatccca gggctcgaga agcttccgtg  1020
gcgtcgatat aaattcagcg ggccttgaac atccctcctt acgacacacc tcacgcgatc  1080
gattttgaca ctcacacacc gccaccctca catcctccac ccacaccaca ccccttaatc  1140
aacccaccat caccgctaga acgtctatct catcaccgac ttctcatcca tcttcaaa    1198

SEQ ID NO: 137         moltype = AA  length = 423
FEATURE                Location/Qualifiers
source                 1..423
                       mol_type = protein
                       organism = Aspergillus niger
SEQUENCE: 137
MHTTEKIPSF LSRRKPSNDS EHVPPPPDGG VQAWTQVVCM HFVFFNTWGI TTSFSVFEQL  60
YTKTLPQSAS SISWIGSVQV SLLFFLSALA GRATDAGFFR VMYPLGVLLQ LVGIFMLSLC  120
KTYWQIFLAQ AVCMGLGNGL TFSPGLSVMS AYFMKNRAFA VGLAASGAAT GGLIYPVLIN  180
QLLYNHQIGF AWTIRAAGLL MLITHIFGLV FFRPRLPPRT TGPLIELGAF TEPPFVFFTL  240
CYFFTFWGLY FAWFYLGTFA RDRLGIADTQ NLLLVLNGVG IVGRIGPSII GDRWTGRLNI  300
LIPITLSCAI LMFCWIAVST VAGLYAFVVV YGLVGGAAQS VIPATATTMT PDINRTGTRL  360
GMIMSIVGFA TLTGPAIEGA LIATDGGRYV AAQIFAGVSI LLGVCAVAAA RVAKAGWGLD  420
VKV                                                                423

SEQ ID NO: 138         moltype = AA  length = 418
FEATURE                Location/Qualifiers
source                 1..418
                       mol_type = protein
                       organism = Aspergillus niger
SEQUENCE: 138
MGSTTPSVFS TAVVPAAPED ALFGLAQAFR QDSSDKKVDL VIGAYRDDNA KPWILPVVKK  60
ADELVRNDPA LNHEYLPIKG LADYTTAAQK LIIGADSPAI RENRVCTFQT ISGTGAVHLG  120
ALFLSKFHPS NPKPTVYLSN PTWANHNQIF TNVNLSLANY PYFDPQTKGL NFSGMLSALR  180
DAPTGSIILL HVCAHNPTGV DLTQSQWKDV AVVMRERNHF PFFDCAYQGF ASGDLIRDSW  240
AVRYFVEQGF ELCVAQSFAK NFGLYGQRTG AFHFVSAPGA EASQANAHVA SQLAILQRSE  300
ISNPPAYGAR IASRVLNDEG LFKEWEEDLK TMSGRIAEMR QGLRERLEKK GTPGTWNHIT  360
DQIGMFSFTG LTESQVKVLK EKWHVYMTKN GRISMAGLNT HNLDYFAEAV DSVVRETS    418

SEQ ID NO: 139         moltype = DNA  length = 1404
FEATURE                Location/Qualifiers
source                 1..1404
                       mol_type = other DNA
                       organism = synthetic construct
SEQUENCE: 139
atgtcgcccc tttcctcctc ttcttcttct ccatcttctt ctctctccct cacttcttct  60
tcatcctctc catccgcctc ctcctccatc gcttctactt ctacttctac cgctcgttcc  120
cgtctcgctt ctctctcctc ccacatcatg ggctctacca ccccctccgt cttttccacc  180
gccgtcgtgc ccgccgcgcc agaagatgct ctcttcggtc tggctcaggc gtttcgccag  240
gattcctccg acaagaaggt cgatctagtc attggcgctt atcgcgacga caatgccaaa  300
ccctggatcc tgcccgtggt caagaaggct gacgagctcg ttcgcaatga ccccgccctc  360
aatcacgaat acctccccat caaaggtctc gccgactaca ccactgccgc ccagaaattg  420
atcattggcg ctgatagccc tgccattcgc gagaaccgcg tatgcacctt ccaaaccatc  480
tccggcaccg gtgccgtgca cctgggcgct ctcttcctct ccaaattcca cccctccaac  540
cctaaaccca ccgtctacct ctccaaccca acctgggcca accacaacca aatcttcacc  600
aacgtcaacc tctccctcgc caactaccoc tacttcgacc cgcaaaccaa aggcctcaac  660
ttctccggca tgctctccgc cctgcgcgat gctcccaccg gctccatcat cctcctgcac  720
gtctgcgccc acaaccccac cggtgtcgat ctgacccagt cccaatggaa ggacgtcgcc  780
gtcgtcatgc gcgagcgcaa ccatttcccc ttctttgact gcgcctacca gggtttcgcc  840
tctggtgatc tcattcgcga ctcctgggcc gtgcgctact tcgtcgagca gggcttcgag  900
ctgtgcgtgg cccaatcctt cgctaagaac tttggtctgt atggccagcg cacgggcgca  960
ttccatttcg tttccgcacc cggtgcggag gccagccagg ctaatgcgca tgtcgcgtcg  1020
cagctggcta ttctgcagcg cagtgagatc agtaacccgc cggcgtatgg cgcgcgtatc  1080
gctagccggg tgttgaatga tgagggactg ttcaaggagt gggaggagga tctgaagacg  1140
atgagtggtc gcattgcgga gatgcgccag ggcctgaggg agcgcttgga gaagaagggc  1200
acgccgggca cttggaacca cattacggat cagattggca tgttcagttt cacgggtttg  1260
accgagtcgc aagttaaggt gttgaaggag aagtggcatg tttacatgac caagaacggc  1320
cgcatctcca tggcgggtct aaacacacat aacctggact acttcgccga agcagtggac  1380
agcgtagttc gggagacttc ataa                                         1404

SEQ ID NO: 140         moltype = DNA  length = 810
FEATURE                Location/Qualifiers
source                 1..810
                       mol_type = genomic DNA
                       organism = Aspergillus niger
SEQUENCE: 140
ctactatgaa agaccgcgat gggccgatag tagtagttac ttccattaca tcatctcatc  60
cgcccggttc ctcgcctccg cggcagtcta cgggtaggat cgtagcaaaa acccggggga  120
tagacccgtc gtcccgagct ggagttccgt ataacctagg tagaaggtat caattgaacc  180
cgaacaactg gcaaaacatt ctcgagatcg taggagtgag tacccggcgt gatggagggg  240
gagcacgctc attggtccgt acggcagctg ccgaggggga gcaggagatc caaatatcgt  300
```

```
gagtctcctg ctttgcccgg tgtatgaaac cggaaaggac tgctggggaa ctggggagcg  360
gcgcaagccg ggaatcccag ctgacaattg acccatcctc atgccgtggc agagcttgag  420
gtagcttttg ccccgtctgt ctccccggtg tgcgcattcg actgggcgcg gcatctgtgc  480
ctcctccagg agcggaggac ccagtagtaa gtaggcctga cctggtcgtt gcgtcagtcc  540
agaggttccc tcccctaccc tttttctact tcccctcccc cgccgctcaa cttttctttc  600
ccttttactt tctctctctc ttcctcttca tccatcctct cttcatcact tccctcttcc  660
cttcatccaa ttcatcttcc aagtgagtct tcctccccat ctgtccctcc atctttccca  720
tcatcatctc ccttcccagc tcctcccctc ctctcgtctc ctcacgaagc ttgactaacc  780
attaccccgc cacatagaca catctaaaca                                    810

SEQ ID NO: 141          moltype = DNA  length = 704
FEATURE                 Location/Qualifiers
source                  1..704
                        mol_type = genomic DNA
                        organism = Aspergillus niger
SEQUENCE: 141
ctcgagctta caagaagtag cctgtagcaa gtctgtggtc gtgtttatta tttatctact  60
acttccccct cctccctcct cctcttgtgt taagagtact ctcaaaaaaa gcctttctta  120
gatagtacaa ccaccatctt caaggtcctg taagtatgac ttgtcccata tactcatttt  180
atcacccctc ccatctttct ctgtccattt catcctcctc ttcttcctct tagctgctag  240
tcatgacccc gccatcatcc caccatgttg tgcttgaccc ctccatctat ccatccatcc  300
atcctcctgt ctatatgcca tcactccatc ctgtctgtct atcaatgatc tggcatctcc  360
ggatttagca ccaagtccca ttgattagtt gatcatttgg gaaacttggc tgtgccgagc  420
ctggtctatt tgatggatcg gacctctcca cctctaattc cccccccgtc cttcccttct  480
ccgtcactca tccgccatcc gctcattctt tttgggtcct cggtgaacac tcaccacctt  540
ccccccccgct gctgctagtg cacaccgaaa cagcaagtcc ggagcgctta catttttgcc  600
tcctccgttt tttcctatat ctgggccatg ttctcccttt gccatctttg ttttctccca  660
gtttcactga tccataactc atccccctcc agtccatcaa catg                    704

SEQ ID NO: 142          moltype = DNA  length = 10353
FEATURE                 Location/Qualifiers
source                  1..10353
                        mol_type = other DNA
                        organism = synthetic construct
SEQUENCE: 142
gtttaaactt cggagtagca acgagtattt tcaccgggag tttcaacggg ttctatttca  60
ggaacacggc tgcggtctgg attgggtcgg gctgagatac cgactggtgg cgtcagtggc  120
gggtacggac ggagtcgtcc tggccgctcg tagacactcc cccggactga tatcaggccc  180
cggcaactgg cttcgtctca ctccagggca tcaggagtgc ctaccacatg ggttcaggct  240
ttgccccgtc gtctaagttt gcaggacaaa attttcgtat gcgttaccac tctttccttt  300
cagcaaccat tccgtagtga aaacccaata ataggtggct gccgtgggag cctgagtcaa  360
cccaaccaga acctttctag tagattctcc cccaagcgct tcagcaacga agcgtattgg  420
agaaccaaat gacgcagacc aagcggattc cggtgcaata gccggatggc aagggaatcc  480
cccaggaggt gccagaagcg tcgcccgaaa ggtacttcgt ctgacaggct aacaccgctc  540
gggctaaggt ccctgctgct cttttccctt tattgcgact taacctctaa gccattccct  600
tgcatcacgt tatctcactg accgacctct gactaaggcg cttcgcctcc gccgcctccc  660
ctcattcacc tcctctcctg actacttaag ccttctcttc cttcctctca ctaccaaccc  720
tccttcatcc ctcatacctc tcatcctacc actcaccttt cgcgcatcgc catctgcgat  780
cctccccaca acactccacc tagatacata caccattaac tgcgcttcta aacaatgccc  840
gccaccggcg aggaccagga cctggtgcag gacctgatcg aggaacccgc caccttctcc  900
gacgccgtcc tgtcctccga cgaggaactg ttccaccaga agtgccccaa gccggctccg  960
atctacagcc ccgtcagcaa gcccgtcagc ttcgagtccc tgccgaaccg ccgcctgcac  1020
gaagagttcc tccgctcctc cgtcgacgtc ctgctgcaag aggccgtgtt cgagggcacc  1080
aaccgcaaga accgcgtcct gcagtggcgc gagcccgaag aactgcgccg cctgatggac  1140
ttcggcgtcc gcagcgcccc gtccacgcat gaggaactgc tcgaggtcct gaagaaggtc  1200
gtcacctact ccgtcaagac cggccatccg tacttcgtca accagctgtt ctccgccgtc  1260
gatccctacg gcctggtcgc ccagtgggcc accgacgcgc tgaacccctc cgtctacacc  1320
tacgaggtca gccccgtgtt cgtcctgatg gaagaggtcg tcctgcgcga gatgcgcgcc  1380
atcgtcggct tcgaaggcgg caaaggcgac ggcatcttct gccctggcgg ctcgatcgcc  1440
aacggctacg ccatcagctg cgcccgctac cgcttcatgc ccgacatcaa gaagaagggc  1500
ctgcactccc tgccgcgcct ggtcctgttc acctccgagg acgcccacta ctcgatcaag  1560
aagctggcct cgttccaagg catcggcacc gacaacgtct acctgatccg caccgacgct  1620
cgcggtcgca tggacgtcag ccacctggtc gaagagatcg agcgctccct ccgcgagggc  1680
gctgccccgt tcatggtcag cgccaccgcc ggcaccaccg tcatcggcgc cttcgatccc  1740
atcgagaaga tcgccgacgt ctgccagaag tacaagctct ggctgcacgt cgacgccgcc  1800
tggggcggag gcgctctggt gtccgccaag caccgccatc tgctgaaggg catcgagcgc  1860
gccgactccg tcacctggaa tccccacaag ctgctgaccg ctccgcagca gtgcagcacc  1920
ctgctgctgc gccacgaggg cgtcctggcc gaggcgcact ccaccaacgc cgcctacctg  1980
ttccagaagg acaagttcta cgacaccaag tacgacaccg gcgacaagca catccagtgc  2040
ggccgtcgcg ccgacgtgct gaagttctgg ttcatgtgga aggccaaggg cacctccggc  2100
ctcgagaagc acgtggacaa ggtgttcgag aacgcccgct tcttcaccga ctgcatcaag  2160
aaccgtgagg gcttcgagat ggtgatcgcc gagcctgagt acaccaacat ctgtttctgg  2220
tacgtcccca agagcctgcg cggacgcaag gacgaggccg actacaagga caagctgcac  2280
aaggtcgccc ctcgcatcaa agaacgcatg atgaaggaag gctccatgat ggtcacctac  2340
caggcgcaga agggccatcc gaatttcttc cgcatcgtct ttcagaactc cggcctggac  2400
aaggccgaca tggtccatct ggtcgaggaa atcgaacgcc tgggctccga cctctgatgg  2460
gttggatgac gatgacttca tgtgattttg ttatttagaa tattttatat ttccttttct  2520
tcttctcacc accgatcccc ttaacactct tgcttcattt gcttcagatt tctcggtttc  2580
ttctttttc ttctccccag ttatccacta tatctttgct agaccggcct gcgccctggc  2640
```

-continued

```
atgcatcata aaatcatgtc cgttggtcat catctgtttt gtatatccgt catataaagt  2700
attcttttat tccctccccc ctcggtcgtc tttcgctgtc ccgcttccta cctccggttt  2760
atagagcatg gttcatctct tccgtacatt tccgttggta ctagcattta tgtcttcagc  2820
tagtatagaa gctgccgcag ttgttcgctt actacctgcc taagtcctta actttttaaa  2880
gtgtttaacc tatacgtagt gttaaacgag tactgggagg tggtgaggta gaaaatgttc  2940
tgcacgggca gtgggtattt ggtagtgtgt aaggcggtta tttatcaggc tgacgctaaa  3000
gacttctatg ggagcagtat gggatcgcgg ctcatagaag tacacaaaat ctaagagtcg  3060
tttgataatt aattgattcc cggcagggtc ttcttgggat tgagagaact ggttactttg  3120
atttgagata ttgtaaagct taaggctctt aacacgtacg agcgaaacag caggggggaa  3180
atcgggaaaa ggggcgtggg gtgaataaaa aagttgaaat aagacactgt atcttgctgg  3240
gggtgaataa agagagaata aaagagaggt aaattccact cagccccttt tcttcgctct  3300
ccaaacatca aactccgccg gccgacccac aggatcccga acaagtggaa gatatgtgcc  3360
ggtccagacc cttcgcacag ctaaaagcag accttcataa gcgtttccgg gtagtattcg  3420
cacacctgaa ctggcacgtc ggggacacaa ctgtttttga tacacaagaa cacacaccac  3480
ccatctagga ctcagagctg ggccagacat tccttcatag tcttgacgat gaaggtgaag  3540
tcctcttcgg tgatggacag cggaggggcg agctgcagga tgttgttgta gccggccacg  3600
gtgtcgccgt tcttgccgat gatcagaccc ttctctttgc aggcgttgat gaccttgttc  3660
atcttttcga tggaggcggg ctctttggtc tgcttatcct cgacgagttc gatacccagc  3720
aggaggccct tgccgcggac gtccccgacg ttggggtgct ctttgacgtc ctccaactcg  3780
tacagcaggc gctcgcccag ttctttggac cgctcgatga gcttctcgtt ttccatgatc  3840
tcgaggttct tcagggccag cgcgcaggcg gcagggttgc cgccgaaggt gttgacatgg  3900
cggaagcggt cgtagtcgtc ggagccgacg aaggcctcgt agacctcgcg gcggaccgcg  3960
gtggcagaca gcggcaggta ggccgaggtg ataccettgg ccatggtgat aatgtcgggc  4020
ttgacgccgt agttcatgaa gccgaagggc ttgccggtgc gaccgaagcc gcagatgacc  4080
tcgtcgcaga tcagcagggc gccgtgcttt tcgcagatct ctttgacctt ttccatgtag  4140
ccgtccggcg gcatcaggat gccaccaccg gtgatgatgg gttccatgat gacgccggcg  4200
acggtctggg acagctccca ggtcatgacg cggtcgattt cttcggcgga ggccagggtg  4260
tgcacgtcct cggggttgcg ataggtgtcc ggaggggcca cgtgcaggaa gccctgaccg  4320
aggggctcgt acttgtactt gcgctgggcc tgaccggtcg cggccagggc acccatggag  4380
ttgccgtggt aggcgcggta gcgagagatg aacttgtagc ggccgtggtc acccttctgc  4440
tggtggtact ggcgggcgat cttgaaggcg gtttcgttgg cctccgagcc ggagttggag  4500
aagaagatga cgtactcgtc gtccagccac tcgttcagct tctcggccag cttgatggcg  4560
gggacgtgcg actgcgtcag cgggaagtac ggcatctctt ccagctgctc gaaggcagcg  4620
cgagccagct ctttgcggcc gtagccgacg ttgacgcacc acaggccgga catgccgtcc  4680
aggtagcggt tgccgtcgat gtcggtgacc cacgcgcctt cggccttggt gatgatcagg  4740
ttggtcggac tcggagcggc accgcgcatg gcgtgccaca ggtacttctc gtcggttttc  4800
ttcaggctct gggtctgctc ggtgacctgg acgatcatca gttccatctt gatgaaggtc  4860
tgggttggaa aaggatgtt agttcattgt tttacttgat actggtgcgt gagcaaggat  4920
aaagttcaat attatctgcg tcgcagctct catcttcgtt tcttgttcaa catattactc  4980
ccccggaatt ttggtatctc gcgcgctaaa gtgtgcgcag gaggtatttt ctgggataag  5040
tggaaagaaa tgaagatgag atgttccaaa taatattgaa tccttttcct tgtcacatag  5100
taaatgtata gggtcatcaa ctcacctcga caagacttgt cttcctaaac cttcggcgat  5160
cgtggtagga aaatatcctc ggtggtggtg ggcttcgtta aaatcggttg tgcggtcacg  5220
tggtgtccag attaccgagt caggcgtagt gcgggtggac actcggataa tcagccctcc  5280
gggtcctcag tcatgtgatg gtctgcggct gaggtcacgg gatttgctga ctttaacggt  5340
ttcttggata cgtcagtttg gtgcctgcat cgccaggcat aggcacggcc cggaaaagcc  5400
aggcagaaag tacgactagg cctaaaacca actagacgaa gtggtcaatc cagcctctca  5460
gcatcgacgt caacttcgtc atcgtcatca tttgccgccc tctcatccct cggctcgctg  5520
ttgctaatta ttgattgaat agcatgcggg ataggcgtca attattaaat cggctattgc  5580
agaggaaggg tgaaataatg tttcaaaccc tcacaggcca caggtcgcct cctcccgtca  5640
gttataagag gcaatgtgga tagatcgata atggagatag ggtggttgtc tggaggtcga  5700
cggtatcgat aataacttcg tatagcatac attatacgaa gttatgaacg actccagaag  5760
tgactaagca accgtaaacc ggaagcaaca atccggctct catggcaaag atggcatgtc  5820
cggattgcgg aggaaagatt tggcgtgtgc ctgacggttt tgttccacaa ggaccctgta  5880
aacttggtga tggtaatgag gtgctctggc cttgattgag caaaagtcag ctcgcgggga  5940
ctacgtgagt tgatggtgga ggatcatgta ctaaatagag catacctagg ggatggtgaa  6000
cggacgtcca gggttccgta gaattgtaac aactctactc gacttgctgc ccactggggt  6060
atgtaaatac atgccttttc aaagttgccg agtgtactaa atggagtgta tgtttggcca  6120
atgtcatttg ggaggggccg ggaacccttt gggacacccg cggatgggct ggatctcggt  6180
cactggagac atagcctagt ggtctagtag tctagcagca ggacagcttc atggttaacc  6240
ccacatgtga tcctccgtcc ggtttccgta gtatataatg gacctgaagc ttctccctct  6300
ctcgatgcgg ttgaaacata aatttgctca taacgtatgt ccatctaacc ctttcattgt  6360
ttcttgacca ctgtctcctt tctggaaaaa aaaagactct ggtaagtatg ggcctaggat  6420
cgagctactg atcccccaat ccttcctaat ccctctgcca cttgccccga cctgttcacc  6480
gtgaccgtac caccaccacc ccgccccctc ctcaactaaa cccctccctt cccctccccc  6540
ctgatgtttt ctcttttctt taatctgact gtcacctccc tctctacttc ttttccctca  6600
atttcttct cctcttctta ctctctgtca tctgtttcga tacccatact aatctcgcgt  6660
gctttttctt caccttcgtg tatagatttg tcacaatccc aaatttcacc atgattgaac  6720
aagatggatt gcacgcaggt tctccggccg cttgggtgga gaggctattc ggctatgact  6780
gggcacaaca gacaatcggc tgctctgatg ccgccgtgtt ccggctgtca gcgcaggggc  6840
gcccggttct ttttgtcaag accgacctgt ccggtgccct gaatgaactg caggacgagg  6900
cagcgcggct atcgtggctg gccacgacgg gcgttccttg cgcagctgtg ctcgacgttg  6960
tcactgaagc gggaagggac tggctgctat tgggcgaagt gccggggcag gatctcctgt  7020
catctcacct tgctcctgcc gagaaagtat ccatcatggc tgatgcaatg cggcggctgc  7080
atacgcttga tccggctacc tgcccattcg accaccaagc gaaacatcgc atcgagcgag  7140
cacgtactcg gatggaagcc ggtcttgtcg atcaggatga tctggacgaa gagcatcagg  7200
ggctcgcgcc agccgaactg ttcgccaggc tcaaggcgcg catgcccgac ggcgatgatc  7260
tcgtcgtgac ccatggcgat gcctgcttgc cgaatatcat ggtggaaaat ggccgctttt  7320
ctggattcat cgactgtggc cggctgggtg tggcggaccg ctatcaggac atagcgttgg  7380
```

-continued

```
ctacccgtga tattgctgaa gagcttggcg gcgaatgggc tgaccgcttc ctcgtgcttt  7440
acggtatcgc cgctcccgat tcgcagcgca tcgccttcta tcgccttctt gacgagttct  7500
tctgagcggg actctggggt tcgaaatgac cgaccaagcg acgatccact taacgttact  7560
gaaatcatca aacagcttga cgaatctgga tataagatcg ttggtgtcga tgtcagctcc  7620
ggagttgaga caaatggtgt tcaggatctc gataagatac gttcatttgt ccaagcagca  7680
aagagtgcct tctagtgatt taatagctcc atgtcaacaa gaataaaacg cgtttcgggt  7740
ttacctcttc cagatacagc tcatctgcaa tgcattaatg cattggacct cgcaacccta  7800
gtacgccctt caggctccgg cgaagcagaa gaatagctta gcagagtcat aacttcgtat  7860
agcatacatt atacgaagtt attgcagccc gggacatgct ggaagggatt ttctggctca  7920
ataccacgtc tgtatttgac cctttccaga cagttaatcc gctgcaggag ggcgaactgt  7980
agctcctcgt tctccttgta gcgcttgatc cagtcttttt ggatgttgca cttgcttggc  8040
ctatgcttct catataatct tgccctgtca tagagacgac gtctgagatt gtagcgttcg  8100
tctttgatca cccggagcca gataggcctg agtatatctg acattagatc aaagggtctg  8160
tggatagtct ccttcagcat cagcgacgca tgtgactcgc atgtcggaga gagcttgtgg  8220
gtggtcatct ttgatggcgt cctctgcttt cccttgattt tcgttgattg tttttcgaaa  8280
gttaagtctg gaagtcaaga gaatccttct gccagacatt atatttacgt atactgacgt  8340
agtagaaaca gcgtcaggat gaggacatgg tgtgtgctgg accacggaat catagttcat  8400
cagtatattg ggttggacaa ataacgctga gcatgtatat gtctttacac actataaaag  8460
ccagcgaacg ccaataaaat agggcatatt gatgtgaaaa tatgacacca gttaaaagca  8520
gtgtattgat tttatctctc ttcacctcgg acctatacta ccgtatacaa gactcaactt  8580
acttccagat atagtaatat acaccctatg gacgaaccag cacaataatt acagccaaac  8640
aacaccaccc aaatggcata ttcctaatca gcactaagca caaataccac tgtcatcaca  8700
gcataatcaa taagaatccc agacaaccga ctcactctga ctcaccttac acaaaccccc  8760
aagcaaagcg cagcccagaa cctcagccaa caatcgggca acgtacgggg aaagattggc  8820
cgatccatga tgtcagcagc cctaacccaa agcggactag cgcataccgc ccctctgact  8880
ccgccatccc agggctcgag aagcttccgt ggcgtcgata taaattcagc gggccttgaa  8940
catccctcct tacgacacac ctcacgcgat cgattttgac actcacacac cgccaccctc  9000
acatcctcca cccacaccac acccccttaat caacccacca tcaccgctag aacgtctatc  9060
tcatcaccga cttctcatcc atcttcaaaa tgatcgtgct ggtcacgggc gcgaccgccg  9120
gtttcggcga gtgcatcacc cgccgcttca tccagcaggg ccacaaggtg atcgctaccg  9180
gacgccgcca agagcgcctc caagagctga aggatgagct gggcgacaac ctgtacattg  9240
cccagctgga cgtgcgcaac cgggctgcca tcgaagaaat gctcgcctcg ctgcccgccg  9300
agtggtgcaa catcgacatc ctggtcaaca acgccggtct ggccctcggc atggaaccgg  9360
cgcacaaggc cagcgtcgag gactgggaaa ccatgatcga caccaacaac aagggactcg  9420
tctacatgac ccgcgctgtg ctgcccggca tggtcgagcg caaccacggc cacatcatca  9480
acatcggctc caccgctggc agctggccct acgctggcgg caacgtctat ggcgcgacca  9540
aggcgttcgt ccgccagttc tccctgaacc tgcgcaccga cctgcacggc accgccgtcc  9600
gcgtgaccga cattgagccc ggtctggtcg gcggcaccga gttcagcaac gtccgcttca  9660
agggcgacga cggcaaggcc gagaaaacct accagaacac cgtcgctctg accccctgagg  9720
atgtcagcga ggccgtctgg tgggtcagca ctctgcccgc gcacgtcaac atcaacaccc  9780
tcgagatgat gcccgtcacg cagtcctacg ccggcctgaa cgtccaccgc caataggacc  9840
gatggctgtg tagaagtact cgccgatagt ggaaaccgac gccccagcac tcgtccgagg  9900
gcaaaggaat agagtagatg ccgaccggga tccacttaac gttactgaaa tcatcaaaca  9960
gcttgacgaa tctggatata agatcgttgg tgtcgatgtc agctccggag ttgagacaaa  10020
tggtgttcag gatctcgata agatacgttc atttgtccaa gcagcaaaga gtgccttcta  10080
gtgatttaat agctccatgt caacaagaat aaaacgcgtt tcgggtttac ctcttccaga  10140
tacagctcat ctgcaatgca ttaatgcatt ggacctcgca accctagtac gcccttcagg  10200
ctccggcgaa gcagaagaat agcttagcag agtctatttt cattttcggg agacgagatc  10260
aagcagatca acggtcgtca agagacctac gagactgagg aatccgctct ctgacagacg  10320
ggcaattgat tacgggatcc cattggttta aac                              10353

SEQ ID NO: 143          moltype = DNA  length = 47
FEATURE                 Location/Qualifiers
source                  1..47
                        mol_type = other DNA
                        organism = synthetic construct
SEQUENCE: 143
acaggctact tcttgtaagc tcgagtttct gtacagtgac cggtgac                47
```

PROCESS CONTROL FOR 3-HYDROXYPROPIONIC ACID PRODUCTION BY ENGINEERED STRAINS OF ASPERGILLUS NIGER

CROSS REFERENCE TO RELATED APPLICATION

This application claims priority to U.S. Provisional Application No. 63/394,663, filed Aug. 3, 2022, which is incorporated by reference in its entirety.

ACKNOWLEDGMENT OF GOVERNMENT SUPPORT

This disclosure was made with Government support under Contract DE-AC0576RL01830 awarded by the U.S. Department of Energy. The Government has certain rights in the invention.

INCORPORATION OF SEQUENCE LISTING

The Sequence Listing is submitted as an XML file named "Sequence.xml" (173,791 bytes), created on Aug. 3, 2023, which is incorporated by reference herein.

FIELD

This application relates to the biosynthesis of 3-hydroxypropionic acid (3-HP), particularly in *Aspergillus niger.*

BACKGROUND

Fuels and chemicals derived from non-fossil sources are needed to lessen human impacts on the environment while providing a healthy and growing economy. 3-hydroxypropionic acid (3-HP) is an important chemical building block that can be used for many products. While biosynthetic pathways have been designed to produce 3-HP from a variety of feedstocks in different microorganisms, low production is typically observed. Thus, there is a need for improved compositions and methods for 3-HP biosynthesis.

SUMMARY

Provided herein are recombinant *Aspergillus niger* capable of producing 3-hydroxypropionic acid (3-HP). The recombinant *Aspergillus niger* include one or more exogenous nucleic acid molecules encoding aspartate 1-decarboxylase (PAND), β-alanine-pyruvate aminotransferase (BAPAT), and 3-hydroxypropionate dehydrogenase (HPDH). In some examples, the copy number of each of PAND, BAPAT, and HPDH is independently about 1 to about 80, for example, about 10 to about 30, or about 25 to about 30. In some implementations, the recombinant *Aspergillus niger* includes an exogenous nucleic acid molecule encoding pyruvate carboxylase (pyc), aspartate aminotransferase (aat1), and/or monocarboxylate transporter (mct1), resulting in overexpression of pyc, aat1, and/or mct1, respectively, in the recombinant *Aspergillus niger*. In some implementations, an ald6a, ald6b, ald3, and/or oahA gene is not present or does not produce a functional product in the recombinant *Aspergillus niger*. In a non-limiting example, the recombinant *Aspergillus niger* includes one or more exogenous nucleic acid molecules encoding PAND, BAPAT, HPDH, and pyc; and ald6a is not present or does not produce a functional product in the recombinant *Aspergillus niger*. In some examples, the PAND is from Tribolium castaneum. In some examples, the BAPAT is from *Bacillus cereus*. In some examples, the HPDH is from *Escherichia coli*. In some examples, the pyc is from *Aspergillus niger*. The exogenous nucleic acid molecules can be operably linked to a promoter and/or included on a vector.

Also disclosed are methods of producing 3-HP, including inoculating a media with *Aspergillus niger* comprising a 3-HP β-alanine pathway (e.g., a recombinant *Aspergillus niger* disclosed herein) thereby generating a cultured media, and fermenting the cultured media at a temperature of 30° C. to 37° C., under acidic and microaerobic conditions. In a non-limiting example, fermentation is performed at about 34° C., at about pH 2, and with a dissolved oxygen (DO) content of less than 10%. In some implementations, the media is Riscaldati B medium or a modified Riscaldati B medium. The media can further include trace elements, corn steep liquor, peptone, tryptone, soy protein, sodium chloride, yeast extract, sorbitol, and/or phosphorous. The media can further include glucose, maltose, fructose, maltodextrin, and/or a glucose:xylose mixture as a carbon source.

BRIEF DESCRIPTION OF THE DRAWINGS

FIG. 1A: The effects of different trace elements and YPD on 3-HP production in the *A. pseudoterreus* transgenic strain Ap3HP6. The strain was inoculated in mRDM medium with various amounts of components and grown at 30° C. and 200 rpm. Each data point is the average of three biological replicates. FIG. 1B: The effects of additional copies of 3HP pathway (3HP::hph: 3HP4070) or 3HP pathway+aat1 over-expression (3HP::hph/aat1: 3HP4071) on 3-HP production in the *A. pseudoterreus* transgenic strain Ap3HP6 background. The strain was inoculated in mRDM medium and grown at 30° C. and 200 rpm for 7 days. Each data point is the average of three biological replicates.

FIGS. 2A-2D. 3-hydroxypropionic acid production FIG. 2A: in the selected *A. niger* transgenic strains of An3HP5, An3HP9, and An3HP10; FIG. 2B: in the selected *A. niger* transgenic strains with over-expression of pyruvate carboxylase (pyc) or cytosolic aspartate aminotransferase (aat) in An3HP9 strain; FIG. 2C: in the *A. niger* transgenic strains with gene disruption of ald6a, ald6b, ald3, and oahA or over-expression of mct1 gene in the *A. niger* transgenic strain An3HP9/pyc2 strain; FIG. 2D: in the selected *A. niger* transgenic strains with additional copies of (3-alanine 3HP pathway. The strains were grown in mRDM medium at 30° C. and 200 rpm for 7 days. The data is the average of three biological replicates.

FIG. 3A: Shake-flask cultivation of the indicated *Aspergillus* strains engineered to produce 3-HP. FIG. 3B: Extracellular metabolites detected and quantified by GC-MS at day four. FIG. 3C: Protein and intracellular metabolite levels relative to the un-engineered parent strains at day four. FIG. 3D: Targeted peptide quantification of the heterologous pathway proteins at day four. Multiple boxes for a single protein indicate different targeted peptides. The data represents four biological replicates.

FIG. 4A: the effects of manganese on 3-HP production. FIG. 4B: the effects of different nitrogen sources on 3-HP production. The data is the average of three biological replicates.

FIGS. 5A-5C. Optimization of 3-HP production in RDM with sugars from DDR-EH using *A. niger* strain An3HP9/pyc2/ald6aA at 200 rpm for 7 days. FIG. 5A: Ability of *A. niger* to germinate and grow in increasing DDR-EH concentrations from 100 to 250 g/L total sugar. FIG. 5B: 3-HP production in DDR-EH-100 at 30, 34, 37, and 40° C. FIG. 5C: 3-HP production in DDR-EH-100 with limiting (0.2×) and excess (5×) concentrations of phosphate, ammonia, and trace elements. The data is the average of three biological replicates and is corrected for evaporative loss. Asterisks indicate statistically significant differences ($p<0.05$) from the baseline condition (RDM with 100 g/L total sugars from DDR-EH at 30° C.).

FIGS. 8A-8B. Parent and transgenic strains of *A. pseudoterreus* and *A. niger* used herein.

FIG. 9. Copy number estimate of genes in selected strains from whole genome sequencing FIG. 10. Nutritional conditions for 3-HP production from sugar monomers.

FIG. 11A: The diagram of the β-alanine 3HP pathway (3HP4028, Ap3HP). FIG. 11B: The diagram of the β-alanine 3HP pathway with the pattern of restriction endonuclease BamHI, EcoRV, and HindIII. FIG. 11C: The restriction fragment length polymorphism of BamHI or EcoRV in selected transgenic strains. FIG. 11D: The restriction fragment length polymorphism of HindIII in selected transgenic strains.

FIG. 16A: restriction map of the plasmid DNA fragments containing the β-alanine 3HP pathway used for random integration with restriction endonucleases of BamHI (FIG. 16B, southern blot), or HindIII (FIG. 16C, southern blot). Southern blots show the hybridization pattern of the parent strain (no detection) and single spore isolates of transgenic strain An3HP5, An3HP9, An3HP10, and An2×3HP1. The expected sizes of the hybridizing fragments for the restriction endonuclease digestion were >2.34 kb (BamHI) or >7.43 kb (HindIII). P is probe used for Southern blot analysis.

FIG. 17A: The ble, the bacterial bleomycin resistance gene; tef1p, *A. niger* tef1 gene promoter; aat1, *A. niger* aspartate aminotransferase; pgkt, *A. niger* pgk gene transcriptional terminator (3HP4074); FIG. 17B & FIG. 17C: mbf1P, *A. niger* mbf1 gene promoter; pyc, *A. niger* pyc gene without aat1 (3HP4076) & with aat1 (3HP4077); FIG. 17D: the nat1 (*Streptomyces noursei* nourseothricin N-acetyl transferase optimized for the codon usage of *Saccharomyces cerevisiae*) selection marker under the control of *A. nidulans* trpC gene promoter and *A. niger* trpC gene transcriptional terminator FIG. 17E: the nat selection marker gene; the mct1, *A. niger* monocarboxylate transporter; the mct1t, *A. niger* mct1 gene transcriptional terminator.

FIGS. 18A-18C. 3-hydroxypropionic acid production in the selected individual transgenic strains of *A. niger* with overexpression of cytosolic aspartate aminotransferase (aat, FIG. 18A), pyruvate carboxylase (pyc, FIG. 18B), or aspartate aminotransferase+pyruvate carboxylase (aat-pyc, FIG. 18C) in An3HP9 strain grown in modified RDM medium at 30° C. and 200 rpm for 7 days. All data were average of two biological replates.

FIG. 19A: 5'-oahA and 3'-oahA are DNA fragments of upstream and downstream fragments of oahA gene (3HP4102); FIG. 19B: 5'-ald6a and 3'-ald6a are DNA fragments of upstream and downstream of ald6a gene (3HP4103); FIG. 19C: 5'-ald6b and 3'-ald6b are DNA fragments of upstream and downstream of ald6b gene (3HP4104); FIG. 19D: 5'-ald3 and 3'-ald3 are DNA fragments of upstream and downstream of ald3 gene (3HP4108); and FIG. 19E: 5'-uga2 and 3'-uga2 are DNA fragments of upstream and downstream fragments of uga2 gene (3HP4109).

FIG. 20A: the Tet-On/Cre-loxP system (3HP4140) for marker gene recycle conditionally activated by doxycycline, nat1, *S. noursei* nourseothricin acetyltransferase (resistance) gene; ubi1S27p, *A. niger* ubi1S27 promoter; rtTA2A, the reverse tetracycline transactivator; TetO7, tetracycline resistance operon; Pmn, *A. nidulans* gpdA minimal promoter; Cre, Cre recombinase; ActrpCt, *A. carbonarius* trpC transcriptional terminator; FIG. 20B: the bacterial neomycin-resistance (nptII) marker gene under the control of *A. niger* malate dehydrogenase (mdhp) promoter and *A. nidulans* trpC transcriptional terminator (trpCt) (3HP4134); FIG. 20C: the nptII marker gene cassette with 31 bp loxP fragments fused at 5'- and 3'-end of its marker gene cassette (3HP3136); FIG. 20D: the intermediate transgene expression cassette (3HP4144) contains the ubi4p, *A. niger* ubi4 gene promoter; PAND, T, castaneum aspartate 1-decarboxylase; elf3t, *A. niger* elongation factor 3 transcriptional terminator; BAPAT, *B. cereus* β-alanine-pyruvate aminotransferase; and ubiSp, *A. niger* ubi1S promoter. FIG. 20E: the final new β-alanine 3-HP pathway (3HP4145) was assembled with the HPDH, K *coli* 3-hydroxypropionate dehydrogenase under the control of *A. niger* mbfA promoter (mbfAp) and *A. nidulans* trpC transcriptional terminator (trpCt).

FIG. 21A: 3-HP and DCW titer and yield and (FIG. 21B) the percentage of spore germination. The data is the average of three biological replicates. Asterisks indicate statistically significant differences ($p<0.05$) from mRDM, pH 3.4.

FIGS. 23A-23C. 0.5 L fermentation dynamic profiles and byproduct ranges using optimal pH (2.0, NaOH base addition) and aeration rates (0.2 vvm) at various sugar concentrations. The base medium (control) was RisB with glucose as the sole carbon source (150 g/L, 150 G reactors). The G+X reactors had a 2:1 glucose:xylose ratio (100 g/L glucose, 50 g/L xylose). The 150 G+salt stress reactors added NaCl as an osmolyte to examine production during salt stress. All reactors were inoculated with spores to an initial concentration of 1×10ˆ6 spores/mL. Growth occurred at 34° C.

FIG. 30. Sugar uptake rate (Carbon mmol consumed per h) from shaking flask conditions taken at 48 and 96 h (related to FIG. 29). The control medium (RisB+glucose) was modified by substituting glucose with either maltose, fructose, or maltodextrose (aka maltodextrin). Total sugar concentration was at an initial concentration of 100 g/L. Additives of Peptone, Tryptone, Corn Steep Liquor or Soy Protein were added at a weight percent of 0.2% to media conditions. Ammonia Sulfate (AS) was removed from the based medium of certain conditions with the specified additives. Additional phosphorus (2×P) was also added in select conditions. Maltodextrin was not measurable via HPLC. Growth occurred at 30° C.

SEQUENCE LISTING

The nucleic and amino acid sequences listed in the accompanying sequence listing are shown using standard letter abbreviations for nucleotide bases, and single letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is an exemplary aspartate 1-decarboxylase (PAND) amino acid sequence (*Tribolium castaneum*).

MPATGEDQDLVQDLIEEPATFSDAVLSSDEELFHQKCPKP

APIYSPVSKPVSFESLPNRRLHEEFLRSSVDVLLQEAVFE

GTNRKNRVLQWREPEELRRLMDFGVRSAPSTHEELLEVLK

KVVTYSVKTGHPYFVNQLFSAVDPYGLVAQWATDALNPSV

YTYEVSPVFVLMEEVVLREMRAIVGFEGGKGDGIFCPGGS

IANGYAISCARYRFMPDIKKKGLHSLPRLVLFTSEDAHYS

IKKLASFQGIGTDNVYLIRTDARGRMDVSHLVEEIERSLR

EGAAPFMVSATAGTTVIGAFDPIEKIADVCQKYKLWLHVD

AAWGGGALVSAKHRHLLKGIERADSVTWNPHKLLTAPQQC

STLLLRHEGVLAEAHSTNAAYLFQKDKFYDTKYDTGDKHI

QCGRRADVLKFWFMWKAKGTSGLEKHVDKVFENARFFTDC

IKNREGFEMVIAEPEYTNICFWYVPKSLRGRKDEADYKDK

LHKVAPRIKERMMKEGSMMVTYQAQKGHPNFFRIVFQNSG

LDKADMVHLVEEIERLGSDL

SEQ ID NO: 2 is an exemplary β-alanine-pyruvate aminotransferase (BAPAT) amino acid sequence (*Bacillus cereus*).

MELMIVQVTEQTQSLKKTDEKYLWHAMRGAAPSPTNLIIT

KAEGAWVTDIDGNRYLDGMSGLWCVNVGYGRKELARAAFE

QLEEMPYFPLTQSHVPAIKLAEKLNEWLDDEYVIFFSNSG

SEANETAFKIARQYHQQKGDHGRYKFISRYRAYHGNSMGA

LAATGQAQRKYKYEPLGQGFLHVAPPDTYRNPEDVHTLAS

AEEIDRVMTWELSQTVAGVIMEPIITGGGILMPPDGYMEK

VKEICEKHGALLICDEVICGFGRTGKPFGFMNYGVKPDII

TMAKGITSAYLPLSATAVRREVYEAFVGSDDYDRFRHVNT

FGGNPAACALALKNLEIMENEKLIERSKELGERLLYELED

VKEHPNVGDVRGKGLLLGIELVEDKQTKEPASIEKMNKVI

NACKEKGLIIGKNGDTVAGYNNILOLAPPLSITEEDFTFI

VKTMKECLAQL

SEQ ID NO: 3 is an exemplary 3-hydroxypropionate dehydrogenase (HPDH) amino acid sequence (*E. coli*).

MIVLVTGATAGFGECITRRFIQQGHKVIATGRRQERLQEL

KDELGDNLYIAQLDVRNRAAIEEMLASLPAEWCNIDILVN

NAGLALGMEPAHKASVEDWETMIDTNNKGLVYMTRAVLPG

MVERNHGHIINIGSTAGSWPYAGGNVYGATKAFVRQFSLN

LRTDLHGTAVRVTDIEPGLVGGTEFSNVRFKGDDGKAEKT

YQNTVALTPEDVSEAVWWVSTLPAHVNINTLEMMPVTQSY

AGLNVHRQ

-continued

Figure 13:
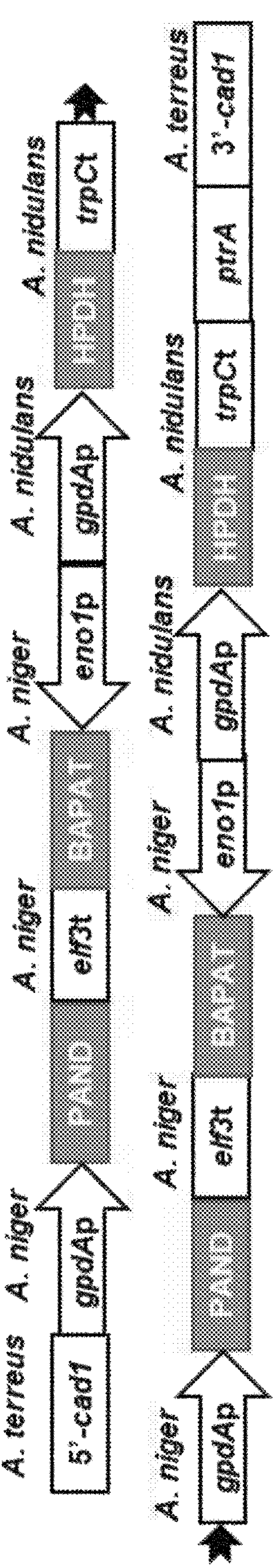
FIG. 13. A diagram of a β-alanine 3HP pathway transgene expression cassette with two identical copies of the β-alanine 3HP pathway (3HP4046, 2×3HP). 5'-Cad1, upstream region of cis-aconitate decarboxylase; gpdAp, glyceraldehyde-3-phosphate dehydrogenase promoter from either *A. niger* or *A. nidulans*; PAND, *T. castaneum* aspartate 1-decarboxylase; elf3t, *A. niger* elongation factor 3 transcriptional terminator; BAPAT, *B. cereus* β-alanine-pyruvate aminotransferase; eno1p, *A. niger* enolase promoter; HPDH, *E. coli* 3-hydroxypropionate dehydrogenase; trpCt, *A. nidulans* trpC transcriptional terminator; ptrA, pyrithiamine resistance gene of *A. oryzae*, and 3'-Cad1, downstream region of cis-aconitate decarboxylase.

SEQ ID NO: 4 is an exemplary nucleic acid sequence encoding a 3-HP β-alanine pathway expression cassette (including aspartate 1-decarboxylase, β-alanine-pyruvate aminotransferase, and 3-hydroxypropionate dehydrogenase; see, FIG. 13).

GGTTGTAGCAGCGTAAACACATGGATAGTTAAATAATCGG

ATGTACACCCACTGTTGGAAATGACGGGGGCCTACAACAC

GAGATTATCTGATCCAATTTCTGTTCGTTGGCATTCTATC

ATTCGCAGCGAAAATTGTCCTATTAAATTGACCATGACCA

AACAATCTGCGGACAGCAACGCAAAGTCAGGAGTTACGTC

CGAAATATGTCATTGGGCATCCAACCTGGCCACTGACGAC

ATCCCTTCGGACGTATTAGAAAGAGCAAAATACCTTATTC

TCGACGGTATTGCATGTGCCTGGGTTGGTGCAAGAGTGCC

TTGGTCAGAGAAGTATGTTCAGGCAACGATGAGCTTTGAG

CCGCCGGGGGCCTGCAGGGTGATTGGATATGGACAGGTAA

ATTTTATTCACTCTAGACGGTCCACAAAGTATACTGACGA

TCCTTCGTATAGAAACTGGGGCCTGTTGCAGCAGCCATGA

CCAATTCCGCTTTCATACAGGCTACGGAGCTTGACGACTA

CCACAGCGAAGCCCCCCTACACTCTGCAAGCATTGTCCTT

CCTGCGGTCTTTGCAGCAAGTGAGGTCTTAGCCGAGCAGG

GCAAAACAATTTCCGGTATAGATGTTATTCTAGCCGCCAT

TGTGGGGTTTGAATCTGGCCCACGGATCGGCAAAGCAATC

TACGGATCGGACCTCTTGAACAACGGCTGGCATTGTGGAG

CTGTGTATGGCGCTCCAGCCGGTGCGCTGGCCACAGGAAA

GCTCCTCGGTCTAACTCCAGACTCCATGGAAGATGCTCTC

GGAATTGCGTGCACGCAAGCCTGTGGTTTAATGTCGGCGC

AATACGGAGGCATGGTAAAGCGTGTGCAACACGGATTCGC

AGCGCGTAATGGTCTTCTTGGGGGACTGTTGGCCCATGGT

GGGTACGAGGCAATGAAAGGTGTCCTGGAGAGATCTTACG

GCGGTTTCCTCAAGATGTTCACCAAGGCTACTATGAAAGA

CCGCGATGGGCCGATAGTAGTAGTTACTTCCATTACATCA

TCTCATCCGCCCGGTTCCTCGCCTCCGCGGCAGTCTACGG

GTAGGATCGTAGCAAAAACCCGGGGGATAGACCCGTCGTC

CCGAGCTGGAGTTCCGTATAACCTAGGTAGAAGGTATCAA

TTGAACCCGAACAACTGGCAAAACATTCTCGAGATCGTAG

GAGTGAGTACCCGGCGTGATGGAGGGGGAGCACGCTCATT

GGTCCGTACGGCAGCTGCCGAGGGGGAGCAGGAGATCCAA

ATATCGTGAGTCTCCTGCTTTGCCCGGTGTATGAAACCGG

AAAGGACTGCTGGGGAACTGGGGAGCGGCGCAAGCCGGGA

ATCCCAGCTGACAATTGACCCATCCTCATGCCGTGGCAGA

GCTTGAGGTAGCTTTTGCCCCGTCTGTCTCCCCGGTGTGC

GCATTCGACTGGGCGCGGCATCTGTGCCTCCTCCAGGAGC

-continued

GGAGGACCCAGTAGTAAGTAGGCCTGACCTGGTCGTTGCG

TCAGTCCAGAGGTTCCCTCCCCTACCCTTTTTCTACTTCC

CCTCCCCCGCCGCTCAACTTTTCTTTCCCTTTTACTTTCT

CTCTCTCTTCCTCTTCATCCATCCTCTCTTCATCACTTCC

CTCTTCCCTTCATCCAATTCATCTTCCAAGTGAGTCTTCC

TCCCCATCTGTCCCTCCATCTTTCCCATCATCATCTCCCT

TCCCAGCTCCTCCCCTCCTCTCGTCTCCTCACGAAGCTTG

ACTAACCATTACCCCGCCACATAGACACATCTAAACAATG

CCCGCCACCGGCGAGGACCAGGACCTGGTGCAGGACCTGA

TCGAGGAACCCGCCACCTTCTCCGACGCCGTCCTGTCCTC

CGACGAGGAACTGTTCCACCAGAAGTGCCCCAAGCCGGCT

CCGATCTACAGCCCCGTCAGCAAGCCCGTCAGCTTCGAGT

CCCTGCCGAACCGCCGCCTGCACGAAGAGTTCCTCCGCTC

CTCCGTCGACGTCCTGCTGCAAGAGGCCGTGTTCGAGGGC

ACCAACCGCAAGAACCGCGTCCTGCAGTGGCGCGAGCCCG

AAGAACTGCGCCGCCTGATGGACTTCGGCGTCCGCAGCGC

CCCGTCCACGCATGAGGAACTGCTCGAGGTCCTGAAGAAG

GTCGTCACCTACTCCGTCAAGACCGGCCATCCGTACTTCG

TCAACCAGCTGTTCTCCGCCGTCGATCCCTACGGCCTGGT

CGCCCAGTGGGCCACCGACGCGCTGAACCCCTCCGTCTAC

ACCTACGAGGTCAGCCCCGTGTTCGTCCTGATGGAAGAGG

TCGTCCTGCGCGAGATGCGCGCCATCGTCGGCTTCGAAGG

CGGCAAAGGCGACGGCATCTTCTGCCCTGGCGGCTCGATC

GCCAACGGCTACGCCATCAGCTGCGCCCGCTACCGCTTCA

TGCCCGACATCAAGAAGAAGGGCCTGCACTCCCTGCCGCG

CCTGGTCCTGTTCACCTCCGAGGACGCCCACTACTCGATC

AAGAAGCTGGCCTCGTTCCAAGGCATCGGCACCGACAACG

TCTACCTGATCCGCACCGACGCTCGCGGTCGCATGGACGT

CAGCCACCTGGTCGAAGAGATCGAGCGCTCCCTCCGCGAG

GGCGCTGCCCCGTTCATGGTCAGCGCCACCGCCGGCACCA

CCGTCATCGGCGCCTTCGATCCCATCGAGAAGATCGCCGA

CGTCTGCCAGAAGTACAAGCTCTGGCTGCACGTCGACGCC

GCCTGGGGCGGAGGCGCTCTGGTGTCCGCCAAGCACCGCC

ATCTGCTGAAGGGCATCGAGCGCGCCGACTCCGTCACCTG

GAATCCCCACAAGCTGCTGACCGCTCCGCAGCAGTGCAGC

ACCCTGCTGCTGCGCCACGAGGGCGTCCTGGCCGAGGCGC

ACTCCACCAACGCCGCCTACCTGTTCCAGAAGGACAAGTT

CTACGACACCAAGTACGACACCGGCGACAAGCACATCCAG

TGCGGCCGTCGCGCCGACGTGCTGAAGTTCTGGTTCATGT

GGAAGGCCAAGGGCACCTCCGGCCTCGAGAAGCACGTGGA

CAAGGTGTTCGAGAACGCCCGCTTCTTCACCGACTGCATC

-continued

AAGAACCGTGAGGGCTTCGAGATGGTGATCGCCGAGCCTG

AGTACACCAACATCTGTTTCTGGTACGTCCCCAAGAGCCT

GCGCGGACGCAAGGACGAGGCCGACTACAAGGACAAGCTG

CACAAGGTCGCCCCTCGCATCAAAGAACGCATGATGAAGG

AAGGCTCCATGATGGTCACCTACCAGGCGCAGAAGGGCCA

TCCGAATTTCTTCCGCATCGTCTTTCAGAACTCCGGCCTG

GACAAGGCCGACATGGTCCATCTGGTCGAGGAAATCGAAC

GCCTGGGCTCCGACCTCTGATGGGTTGGATGACGATGACT

TCATGTGATTTTGTTATTTAGAATATTTTATATTTCCTTT

TCTTCTTCTCACCACCGATCCCCTTAACACTCTTGCTTCA

TTTGCTTCAGATTTCTCGGTTTCTTCTTTTTTCTTCTCCC

CAGTTATCCACTATATCTTTGCTAGACCGGCCTGCGCCCT

GGCATGCATCATAAAATCATGTCCGTTGGTCATCATCTGT

TTTGTATATCCGTCATATAAAGTATTCTTTTATTCCCTCC

CCCCTCGGTCGTCTTTCGCTGTCCCGCTTCCTACCTCCGG

TTTATAGAGCATGGTTCATCTCTTCCGTACATTTCCGTTG

GTACTAGCATTTATGTCTTCAGCTAGTATAGAAGCTGCCG

CAGTTGTTCGCTTACTACCTGCCTAAGTCCTTAACTTTTT

AAAGTGTTTAACCTATACGTAGTGTTAAACGAGTACTGGG

AGGTGGTGAGGTAGAAAATGTTCTGCACGGGCAGTGGGTA

TTTGGTAGTGTGTAAGGCGGTTATTTATCAGGCTGACGCT

AAAGACTTCTATGGGAGCAGTATGGGATCGCGGCTCATAG

AAGTACACAAAATCTAAGAGTCGTTTGATAATTAATTGAT

TCCCGGCAGGGTCTTCTTGGGATTGAGAGAACTGGTTACT

TTGATTTGAGATATTGTAAAGCTTAAGGCTCTTAACACGT

ACGAGCGAAACAGCAGGGGGGAAATCGGGAAAAGGGGCGT

GGGGTGAATAAAAAAGTTGAAATAAGACACTGTATCTTGC

TGGGGGTGAATAAAGAGAGAATAAAAGAGAGGTAAATTCC

ACTCAGCCCCTTTTCTTCGCTCTCCAAACATCAAACTCCG

CCGGCCGACCCACAGGATCCCGAACAAGTGGAAGATATGT

GCCGGTCCAGACCCTTCGCACAGCTAAAAGCAGACCTTCA

TAAGCGTTTCCGGGTAGTATTCGCACACCTGAACTGGCAC

GTCGGGGACACAACTGTTTTTGATACACAAGAACACACAC

CACCCATCTAGGACTCAGAGCTGGGCCAGACATTCCTTCA

TAGTCTTGACGATGAAGGTGAAGTCCTCTTCGGTGATGGA

CAGCGGAGGGGCGAGCTGCAGGATGTTGTTGTAGCCGGCC

ACGGTGTCGCCGTTCTTGCCGATGATCAGACCCTTCTCTT

TGCAGGCGTTGATGACCTTGTTCATCTTTTCGATGGAGGC

GGGCTCTTTGGTCTGCTTATCCTCGACGAGTTCGATACCC

AGCAGGAGGCCCTTGCCGCGGACGTCCCCGACGTTGGGGT

-continued

GCTCTTTGACGTCCTCCAACTCGTACAGCAGGCGCTCGCC

CAGTTCTTTGGACCGCTCGATGAGCTTCTCGTTTTCCATG

ATCTCGAGGTTCTTCAGGGCCAGCGCGCAGGCGGCAGGGT

TGCCGCCGAAGGTGTTGACATGGCGGAAGCGGTCGTAGTC

GTCGGAGCCGACGAAGGCCTCGTAGACCTCGCGGCGGACC

GCGGTGGCAGACAGCGGCAGGTAGGCCGAGGTGATACCCT

TGGCCATGGTGATAATGTCGGGCTTGACGCCGTAGTTCAT

GAAGCCGAAGGGCTTGCCGGTGCGACCGAAGCCGCAGATG

ACCTCGTCGCAGATCAGCAGGGCGCCGTGCTTTTCGCAGA

TCTCTTTGACCTTTTCCATGTAGCCGTCCGGCGGCATCAG

GATGCCACCACCGGTGATGATGGGTTCCATGATGACGCCG

GCGACGGTCTGGGACAGCTCCCAGGTCATGACGCGGTCGA

TTTCTTCGGCGGAGGCCAGGGTGTGCACGTCCTCGGGGTT

GCGATAGGTGTCCGGAGGGGCCACGTGCAGGAAGCCCTGA

CCGAGGGGCTCGTACTTGTACTTGCGCTGGGCCTGACCGG

TCGCGGCCAGGGCACCCATGGAGTTGCCGTGGTAGGCGCG

GTAGCGAGAGATGAACTTGTAGCGGCCGTGGTCACCCTTC

TGCTGGTGGTACTGGCGGGCGATCTTGAAGGCGGTTTCGT

TGGCCTCCGAGCCGGAGTTGGAGAAGAAGATGACGTACTC

GTCGTCCAGCCACTCGTTCAGCTTCTCGGCCAGCTTGATG

GCGGGGACGTGCGACTGCGTCAGCGGGAAGTACGGCATCT

CTTCCAGCTGCTCGAAGGCAGCGCGAGCCAGCTCTTTGCG

GCCGTAGCCGACGTTGACGCACCACAGGCCGGACATGCCG

TCCAGGTAGCGGTTGCCGTCGATGTCGGTGACCCACGCGC

CTTCGGCCTTGGTGATGATCAGGTTGGTCGGACTCGGAGC

GGCACCGCGCATGGCGTGCCACAGGTACTTCTCGTCGGTT

TTCTTCAGGCTCTGGGTCTGCTCGGTGACCTGGACGATCA

TCAGTTCCATGTTGATGGACTGGAGGGGGATGAGTTATGG

ATCAGTGAAACTGGGAGAAAACAAAGATGGCAAAGGGAGA

ACATGGCCCAGATATAGGAAAAAACGGAGGAGGCAAAAAT

GTAAGCGCTCCGGACTTGCTGTTTCGGTGTGCACTAGCAG

CAGCGGGGGGGAAGGTGGTGAGTGTTCACCGAGGACCCAA

AAAGAATGAGCGGATGGCGGATGAGTGACGGAGAAGGGAA

GGACGGGGGGGGAATTAGAGGTGGAGAGGTCCGATCCATC

AAATAGACCAGGCTCGGCACAGCCAAGTTTCCCAAATGAT

CAACTAATCAATGGGACTTGGTGCTAAATCCGGAGATGCC

AGATCATTGATAGACAGACAGGATGGAGTGATGGCATATA

GACAGGAGGATGGATGGATGGATAGATGGAGGGGTCAAGC

ACAACATGGTGGGATGATGGCGGGGTCATGACTAGCAGCT

AAGAGGAAGAAGAGGAGGATGAAATGGACAGAGAAAGATG

GGAGGGGTGATAAAATGAGTATATGGGACAAGTCATACTT

-continued

ACAGGACCTTGAAGATGGTGGTTGTACTATCTAAGAAAGG

CTTTTTTTGAGAGTACTCTTAACACAAGAGGAGGAGGGAG

GAGGGGGAAGTAGTAGATAAATAATAAACACGACCACAGA

CTTGCTACAGGCTACTTCTTGTAAGCTCGAGTTTCTGTAC

AGTGACCGGTGACTCTTTCTGGCATGCGGAGAGACGGACG

GACGCAGAGAGAAGGGCTGAGTAATAAGCCACTGGCCAGA

CAGCTCTGGCGGCTCTGAGGTGCAGTGGATGATTATTAAT

CCGGGACCGGCCGCCCCTCCGCCCCGAAGTGGAAAGGCTG

GTGTGCCCCTCGTTGACCAAGAATCTATTGCATCATCGGA

GAATATGGAGCTTCATCGAATCACCGGCAGTAAGCGAAGG

AGAATGTGAAGCCAGGGGTGTATAGCCGTCGGCGAAATAG

CATGCCATTAACCTAGGTACAGAAGTCCAATTGCTTCCGA

TCTGGTAAAAGATTCACGAGATAGTACCTTCTCCGAAGTA

GGTAGAGCGAGTACCCGGCGCGTAAGCTCCCTAATTGGCC

CATCCGGCATCTGTAGGGCGTCCAAATATCGTGCCTCTCC

TGCTTTGCCCGGTGTATGAAACCGGAAAGGCCGCTCAGGA

GCTGGCCAGCGGCGCAGACCGGGAACACAAGCTGGCAGTC

GACCCATCCGGTGCTCTGCACTCGACCTGCTGAGGTCCCT

CAGTCCCTGGTAGGCAGCTTTGCCCCGTCTGTCCGCCCGG

TGTGTCGGCGGGGTTGACAAGGTCGTTGCGTCAGTCCAAC

ATTTGTTGCCATATTTTCCTGCTCTCCCCACCAGCTGCTC

TTTTCTTTTCTCTTTCTTTTCCCATCTTCAGTATATTCAT

CTTCCCATCCAAGAACCTTTATTTCCCCTAAGTAAGTACT

TTGCTACATCCATACTCCATCCTTCCCATCCCTTATTCCT

TTGAACCTTTCAGTTCGAGCTTTCCCACTTCATCGCAGCT

TGACTAACAGCTACCCCGCTTGAGCAGACATCACCATGAT

CGTGCTGGTCACGGGCGCGACCGCCGGTTTCGGCGAGTGC

ATCACCCGCCGCTTCATCCAGCAGGGCCACAAGGTGATCG

CTACCGGACGCCGCCAAGAGCGCCTCCAAGAGCTGAAGGA

TGAGCTGGGCGACAACCTGTACATTGCCCAGCTGGACGTG

CGCAACCGGGCTGCCATCGAAGAAATGCTCGCCTCGCTGC

CCGCCGAGTGGTGCAACATCGACATCCTGGTCAACAACGC

CGGTCTGGCCCTCGGCATGGAACCGGCGCACAAGGCCAGC

GTCGAGGACTGGGAAACCATGATCGACACCAACAACAAGG

GACTCGTCTACATGACCCGCGCTGTGCTGCCCGGCATGGT

CGAGCGCAACCACGGCCACATCATCAACATCGGCTCCACC

GCTGGCAGCTGGCCCTACGCTGGCGGCAACGTCTATGGCG

CGACCAAGGCGTTCGTCCGCCAGTTCTCCCTGAACCTGCG

CACCGACCTGCACGGCACCGCCGTCCGCGTGACCGACATT

GAGCCCGGTCTGGTCGGCGGCACCGAGTTCAGCAACGTCC

-continued

GCTTCAAGGGCGACGACGGCAAGGCCGAGAAAACCTACCA

GAACACCGTCGCTCTGACCCCTGAGGATGTCAGCGAGGCC

GTCTGGTGGGTCAGCACTCTGCCCGCGCACGTCAACATCA

ACACCCTCGAGATGATGCCCGTCACGCAGTCCTACGCCGG

CCTGAACGTCCACCGCCAATAGGACCGATGGCTGTGTAGA

AGTACTCGCCGATAGTGGAAACCGACGCCCCAGCACTCGT

CCGAGGGCAAAGGAATAGAGTAGATGCCGACCGGGATCCA

CTTAACGTTACTGAAATCATCAAACAGCTTGACGAATCTG

GATATAAGATCGTTGGTGTCGATGTCAGCTCCGGAGTTGA

GACAAATGGTGTTCAGGATCTCGATAAGATACGTTCATTT

GTCCAAGCAGCAAAGAGTGCCTTCTAGTGATTTAATAGCT

CCATGTCAACAAGAATAAAACGCGTTTCGGGTTTACCTCT

TCCAGATACAGCTCATCTGCAATGCATTAATGCATTGGAC

CTCGCAACCCTAGTACGCCCTTCAGGCTCCGGCGAAGCAG

AAGAATAGCTTAGCAGAGTCTATTTTCATTTTCGGGAGAC

GAGATCAAGCAGATCAACGGTCGTCAAGAGACCTACGAGA

CTGAGGAATCCGCTCTCTGACAGACGGGCAATTGATTACG

GGATCCCATTGGTAACGAAATGTAAAAGCTAGGAGATCGT

CCGCCGATGTCAGGATGATTTCACTTGTTTCTTGTCCGGC

TCACCGGTCAAAGCTAAAGAGGAGCAAAAGGAACGGATAG

AATCGGGTGCCGCTGATCTATACGGTATAGTGCCCTTATC

ACGTTGACTCAACCCATGCTATTTAACTCAACCCCTCCTT

CTGAACCCCACCATCTTCTTCCTTTTCCTCTCATCCCACA

CAATTCTCTATCTCAGATTTGAATTCCAAAAGTCCTCGGA

CGAAACTGAACAAGTCTTCCTCCCTTCGATAAACCTTTGG

TGATTGGAATAACTGACCATCTTCTATAGTTCCCAAACCA

ACCGACAATGTAAATACACTCCTCGATTAGCCCTCTAGAG

GGCATACGATGGAAGTCATGGAATACTTTTGGCTGGACTC

TCACAATGATCAAGGTATCTTAGGTAACGTCTTTGGCGTG

GGCCGGTGTTCGTTCCCAGTCATCGATGCATTCACATGCC

CTCCCTAAGCTGGGCCCTAGACTCTAGGATCCTAGTCTAG

AAGGACATGGCATCGATGGACTGGGTTCGTTCTGAGATTA

TACGGCTAAAACTTGATCTGGATAATACCAGCGAAAAGGG

TCATGCCTTCTCTCGTTCTTCCTGTTGATGGAATGGCTAA

CAGATGATAGTCATTGCAACTTGAAACATGTCTCCTCCAG

CTGCCATCTACGAACCCACTGTGGCCGCTACCGGCCTCAA

GGGTAAGGTCGTGGTTTCTGAGACCGTCCCCGTTGAGGGA

GCTTCTCAGACCAAGCTGTTGGACCATTTCGGTGGCAAGT

GGGACGAGTTCAAGTTCGCCCCTATCCGCGAAAGCCAGGT

CTCTCGTGCCATGACCAGACGTTACTTTGAGGACCTGGAC

AAGTACGCTGAAAGTGACGTTGTCATTGTTGGTGCTGGTT

-continued

CCTGCGGTCTGAGCACTGCGTACGTCTTGGCCAAGGCTCG

TCCGGACCTGAAGATTGCTATCGTCGAGGCCAGCGTCTCT

CCTGGTCAGTAGTCCATGATGGATTGCCTTGCACTCAGCT

TTCCGGAACTAACGTGCAATAGGTGGCGGTGCCTGGTTGG

GTGGCCAACTCTTTTCTGCTATGGTCATGCGCCGTCCCGC

GGAAGTCTTCCTGAACGAGCTGGGTGTTCCTTACGAAGAG

GACGCAAACCCCAACTACGTTGTCGTCAAGCACGCCTCCC

TGTTTACCTCGACACTCATGTCGAAGGTTCTCTCCTTCCC

CAATGTCAAGCTCTTCAATGCTACCGCTGTTGAGGACTTG

ATCACCCGTCCGACCGAGAACGGCAACCCCCAGATTGCTG

GTGTTGTCGTCAACTGGACGCTGGTCACCCTTCACCACGA

TGATCACTCCTGCATGGACCCCAACACTATCAACGCTCCT

GTCATCATCAGTACCACTGGTCACGATGGGCCATTCGGCG

CCTTCTGTGCGAAGCGCTTGGTGTCCATGGGCAGCGTCGA

CAAGCTAGGTGGCATGCGTGGTCTCGACATGAGCTCGGCC

GAGGATGCCATCGTCAAGAACACCCGCGAGGTTACTAAGG

GCTTGATAATCGGCGGTATGGAGCTGTCTGAAATTGATGG

CTTTAACCGCATGGGCCCTACCTTCGGTGCCATGGTTCTC

AGTGGTGTCAAGGCTGCCGAGGAGGCATTGAAGGTGTTCG

ACGAGCGTCAGCGCGAGTGTGCTGAGTAAATGACTCACTA

CCCGAATGGGTTCAGTGCATGAACCGGATTTGTCTTACGG

TCTTTGACGATAGGGGAATGATGATTATGTGATAGTTCTG

AGATTTGAATGAACTCGTTAGCTCGTAATCCACATGCATA

TGTAAATGGCTGTGTCCCGTATGTAACGGTGGGGCATTCT

AGAATAATTATGTGTAACAAGAAAGACAGTATAATACAAA

CAAAGATGCAAGAGCGGCTCCTCAGCAACATTCGCCATGT

TCATGTACAGCTTTCAACGGCCTCGAACAGTCACTGTGGA

TGGATACCAGAGGAGAGACCCATCAGTTCAATCGCAGGGC

AGATGAGTGTCGCATACATTCTCGCCGTCCAGCTGGTCGA

CCAGCAATGTCTTTTGTCCCAGTTTTCTGAGTTTGATGAC

AACCTGGAGAGGCCAGAAGTTTGGGATCTGGCCAGGAAGG

TTACTTCATCTCAAAGCGAAGAGTTTGATCAAGACGGCAA

CTGTCTCAGTGCGGGTCGCGTGAGGATTGAGTTCAACGAT

GGTTCTTCTATTACGGAAAGTGTCGAGAAGCCTCTTGGTG

TCAAAGAGCCCATGCCAAACGAACGGATTCTCCACAAATA

CCGAACCCTTGCTGGTAGCGTGACGGACGAATCCCGGGTG

AAAGAGATTGAGGATCTTGTCCTCGGCCTGGACAGGCTCA

CCGACATTAGCCCATTGCTGGAGCTGCTGAATTGCCCCGT

GAAATCGCCACTGGTATAAATGGGAAGCGATATGGAAACA

TTTCATGTCACGGGCACAAATTCTAGGTCATATCGTACCT

-continued

GGATGGTGAAACCACCAGCGGTTTAGCAGATAGAAGATAG

ACTCCTTCTGCTCTGCGTTGCGTCTTGAATTTAGTTCGTT

CACTGGCTTAAGAACTTAGAATGCAATACAGTCTCTCTTA

TTTCTTATTAAAATCACGTATTCCCACATTCGGCGACTGG

AGGATACGAAAGCAGTGTTGGTGGTGCTCCCCGTAATGGA

TATGATTTTGCTGACTGGACTATTCTATGACCATTCCCTC

CAACGGAGATCCTTTCTCGACACTTTAGATGTTGACGCTG

TCTGGAGGAACTACTTTTGCGCTGCAAAGACTATGAGCAG

TGGAGCTG

SEQ ID NO: 5 is an exemplary pyruvate carboxylase (pyc) amino acid sequence from *A. niger*.

MAAPRQPEEAVDDTEFIDDHHDQHRDSVHTRLRANSAIMQ

FQKILVANRGEIPIRIFRTAHELSLQTVAVYSHEDRLSMH

RQKADEAYMIGKRGQYTPVGAYLAIDEIVKIALEHGVHLI

HPGYGFLSENAEFARKVEQSGMVFVGPTPQTIESLGDKVS

ARQLAIRCDVPVVPGTPGPVERYEEVKAFTDTYGFPIIIK

AAFGGGGRGMRVVRDQAELRDSFERATSEARSAFGNGTVF

VERFLDRPKHIEVQLLGDNHGNVVHLFERDCSVQRRHQKV

VEIAPAKDLPADVRDRILADAVKLAKSVNYRNAGTAEFLV

DQQNRYYFIEINPRIQVEHTITEEITGIDIVAAQIQIAAG

ATLEQLGLTQDRISTRGFAIQCRITTEDPSKGFSPDTGKI

EVYRSAGGNGVRLDGGNGFAGAIITPHYDSMLVKCTCRGS

TYEIARRKVVRALVEFRIRGVKTNIPFLTSLLSHPVFVDG

TCWTTFIDDTPELFALVGSQNRAQKLLAYLGDVAVNGSSI

KGQIGEPKLKGDIIKPVLHDAAGKPLDVSVPATKGWKQIL

DSEGPEAFARAVRANKGCLIMDTTWRDAHQSLLATRVRTI

DLLNIAHETSHALANAYSLECWGGATFDVAMRFLYEDPWD

RLRKLRKAVPNIPFQMLLRGANGVAYSSLPDNAIYHFCKQ

AKKCGVDIFRVFDALNDVDQLEVGIKAVHAAEGVVEATIC

YSGDMLNPSKKYNLPYYLDLVDKVVQFKPHVLGIKDMAGV

LKPQAARLLIGSIRERYPDLPIHVHTHDSAGTGVASMIAC

AQAGADAVDAATDSLSGMTSQPSIGAILASLEGTEHDPGL

NSAQVRALDTYWAQLRLLYSPFEAGLTGPDPEVYEHEIPG

GQLTNLIFQASQLGLGQQWAETKKAYESANDLLGDVVKVT

PTSKVVGDLAQFMVSNKLTAEDVIARAGELDFPGSVLEFL

EGLMGQPYGGFPEPLRSRALRDRRKLDKRPGLYLEPLDLA

KIKSQIRENYGAATEYDVASYAMYPKVFEDYKKFVAKFGD

LSVLPTRYFLAKPEIGEEFHVELEKGKVLILKLLAIGPLS

EQTGQREVFYEVNGEVRQVSVDDKKASVENTARPKAELGD

SSQVGAPMSGVVVEIRVHDGLEVKKGDPIAVLSAMKMEMV

ISAPHSGKVSSLLVKEGDSVDGQDLVCKIVKA

-continued

SEQ ID NO: 6 is an exemplary nucleic acid sequence encoding ald6a from *A. niger*.

ATGGCCGCCCGTCGGTCTATTGTCCGTTCCATCCCCGCTC

TCCGCGCCGCCTCTCCCCGCACGGCCGTGGCCACCTCCAG

ATCTGTAGCTGCAGCTTCGGCCTCGAGGCGCCTTTCTACT

GTTATAATGCCCTCTTCTTCTTCGACAACTTCTTCTGCAA

CATCTAAGCTCTCCTCATCCTCACCTGCCACCATGTCAGC

AACACGTCGACTCCACGCTACTGCCCAGCAGTTCACCCCC

GCAACTACCTCCGCGGCTACTACCGCCACCGAGTACCCGA

CGGACCATAGCCCCATCGCCAACCCCATCGACACCGCCAA

TTTCCTGGACAACCAATTTGTGGCTTCTAAGGCTACCACC

TGGATCGATCTGCACGATCCTGCTACCAACAACCTCGTTA

CTCGGGTGCCGCAAAGCACCGATGAGGAACTCCGTGCCGC

CGTCGAGTCGGCCGAGAAGGCCTTCCCAGCCTGGCGCGCA

ACCAGCGTTATTGCCAAGCAGCAGATCATGTTCAAGTTCG

TGAGCTTGATTCGTGCCAACTGGGACCGACTTGCTGCATC

CATCACTCTCGAGCAGGGCAAGACCTTTGCCGATGCCAAG

GGCGATGTTCTCCGCGGTCTTCAAGTTGCCGAAACAGCAT

GTGGTATTACCACCCAGCTAACGGGCGAGGTGCTCGAAGT

GGCCAAGGATATGGAGACTAGGAGCTACAGAGAGCCCTTG

GGTGTGGTTGCTGCCATTTGTCCTTTCAGTAAGTGATTCT

GCATCCGTCCTGCAAGCTAGGTGACATTGTCCGACGCTAA

CCGCACCCCCTCGCCTTCTCGGCAGACTTCCCCGCAATGA

TTCCCCTGTGGTGCATCCCCATCGCTACCGTGACGGGCAA

CTGTCTCATCCTCAAGCCATCTGAGCGGGACCCCGGAGCT

GCAATGATCCTGGCCGAGCTGGCCCGGGAAGCAGGCTTCC

CCCCCGGTGTCATCAACATTGTCCACGGCTCCGCCAAGAC

AGTCGATTTCATCCTCGACGAACCCGCCATCAAGGCCATC

AGCTTCGTCGGCAGCAACCGCGCCGGAGAGTACATCTACA

CCCGCGGCTCTGCCAACGGCAAGCGTGTCCAGGCCAATCT

GGGCGCCAAGAACCATGCCGCCGTAGTCCCAGACTGCAAC

AAGAACCAGACCCTGAACGCCCTCGTCGGAGCGGCCTTCG

GTGCTGCCGGCCAACGCTGCATGGCCCTCAGTACGGTCGT

CATGGTCGGCGAGACTCAGGACTGGCTCCCCGAGATGGCC

GAACGGGCCAAGGCCCTGAACGTCAACGGAGGCTTCGAAG

AAGGCGCTGACCTCGGCCCCGTCATCAGCCCCGAAAGCAA

GAAGCGCATCGAAGACCTGATCGCCAGCGCCGAAGAAGAG

GGTGCGACCATCCTCCTCGACGGCAGAGGCTACAAGCCAG

AGAAGTACCCCAACGGCAACTTTGTAAGCTTCCACCCAAC

CCCCTTCCCCGTCTCCTATCCAGCTACATCTTCTCTCTAA

CCAGCACCAAAACCACAGGTTGGCCCCACCATCATCACCA

ACGTAACCCCCGAAATGAAATGCTACAAGGAAGAAATCTT

-continued

CGGCCCCGTCCTCGTCTGCTTGTCCGTGCCCACACTAGAC

GACGCCATTGAGCTCATCAACAAGAACGAGTACGGAAACG

GAGCTGCCATCTTCACTCGCTCCGGTTCCACGGCCTCTCG

CTTCCAGAAGGACATCGAGGCCGGCCAGGTCGGTGTTAAC

GTGCCCATTCCTGTGCCGTTGCCCATGTTCTCTTTCACCG

GTAACAAGAAGAGTATTGCCGGCGGTGGCGCTAATACTTT

CTATGGTAAGCCCGGGTTGCAATTTTACACGCAGCAGAAG

ACGGTGACTAGTTTGTGGAGGAGTGAGGATGCTGTTAGCA

CTAAGGCTCATACGGTTATGCCGACTCATTCGTGA

SEQ ID NO: 7 is an exemplary nucleic acid sequence encoding ald6b from *A. niger*.

ATGTCAAGATCGCAGAATTGGACGAATGCTTTGGATCCGG

TATTTGGTTTGATCAACCTCAGATTATTGCGATTAGTGCT

AAAGTGAAGGACAGGTTTCACAACGTCTACTTTGCAGGGT

CCCGGGGAGTACGCTTCAGGAAGTAAAGCGGGCTGTTGAT

GCTGCTGAAGATGCCCAGCCTGGATGGGCTGCTCTGGGGT

TCCAGGTGAGGCGTGAACATCTGTTGCGGCTGGTGGATGT

ATTGAGACAGATGTCTCCTGAGATTGTAAGCTGCCGGGAC

AGCTGACAGGCAAAGGAGTGGAACTGACGATCGTAGGTGA

CCTGCCTGTCTCGAGAAGTTGGAAAGACATTAGCCGATGC

AGACGCGGAGGTTTTCCGTGGTCTGGACTGCATACATGCC

GCATGTTCGATCGGGCCTGAAATGGCTGGCATGTTTTTAG

GAGGCGATGCAACATTGCTGCAAACTTTCTACGAGCCAGT

TGTGAGTCTAGATGCCGGTTAACTACAGATATGCTACTAA

CAGACCGTGGCAGGGCGTCTGTGTCTCAATCACTCCATTT

AGCTTTCCCTTCATGATTCCCCTGTGGTCGCTTCCGTACG

CGCTTATCACTGGCAACACCGTCATCCTGAAACCATCCGA

GAAAACACCAACTACGTCTTCGTTATTAGCGCAGGCATTC

ATCAAGACTGGCTTCCCTCCCGGGGTCTTCAATGTGCTCC

ACGGCGGCCCATCCACAGTGCAGATGCTTGTGACCCAGCC

GACGGTTCAAGCGGTGAGTTTCGTTGGGTCCGAGTCAGCA

GCTAGGCAGGTGCATGACCTGGCAAGGGCCGCAGGGAAGC

GAATACAAGCCGAGTGTGGTGGTAAGAATCATGGGGTTGT

CTTGGAGGATGCTAATATGTCCTCGACGCTTTTTGCGATC

GCTGGAAGTGCCTTTGGGGCCGCCGGTCAGCGTTGTATGG

CCTTGAGCGTAGCGGTGTTTGTAGGTGCGACGAGAGACTG

GATACCTAGGCTGGTGGAGCTGGCACAGTCGATGGTAGTA

GGATGTGGTGGTGATCAGGAATCTAAGATTGGGCCGTTGA

TTGACAAAACAGCCAAAGACAAAGTCAGCGAGATGATCCA

GCGAGCAGTTGAGGAGAGAGCAACCGTTCTTTTGGACGGT

CGAGATATTGAGGTCCCCGGCTATCCGGATGGCAACTTCA

-continued

TGGGCCCAACTATTCTCGGGGATGTGCAGACTTACATGGA
ATGCTATCAGGCGGAAATATTTGGGCCTGTGCTCATCTGC
ATGGAGGTGGACACTCTTGAGGAAGCGATCGATCTGATAA
GCCAAAATAAGTGTCAGTCTCCCACAACCCGGGCTTGAAG
GGGATGGATTGCTGACCTGATCGCAGATGGTAACGGATGC
TCTATTTTCACCACCAGCGGCAAGCATGCAAATACGTTCC
AACGCTGTGTCAATGTTGGTCAGATTGGTGTCAACATCCC
GTTGATCGGTATGGCGGTCCCCATTTCCGTAGCGCAACCA
ACCCCTGACAGTACAACAGCGCCGTATGGAACCGCGGTCC
GAACGAGCAACAAAGATTCTTTCCTGGGTGGTGAGTGCCC
AGACATCTCCGGTGGAAGGAAAGCTGACCTCTGCAGATCG
ACATTCCCCTGGGAAGACATATTGGCCATTTTTCACAACA
ACTAAAACGGTCTCATCTCGATGGGATCAGTGA

SEQ ID NO: 8 is an exemplary nucleic acid sequence encoding ald3 from *A. niger*.

ATGCCCTTCTCCTCCTTCCCCGCTCCCTTTCGCTGTCTTT
CCTTCTCCTCTCTGCGGCTGCGTGGTGTGTCATTCTCCCG
TCTGCCAGTTGTTCCTTTCTCCCCTCATCGTCATCACTTC
CATAGCTCGTCCATCACAATGAGCGATCTGTCCGTGCAGC
TGACAGCCCCGAATGGGCGCACATACGCCCAGCCGGTTGG
TTTGTTCATCAACAATGAATTTGTCGCTTCCAAGTCCGGC
GAGAAGTTCGCCACCATCAACCCTTCGTACGTGACCTCCC
AATCCTAGTATCTTTCTTGGATCTGCTGCTGACCAGTGCT
AGAAATGAAGCGGAAATCACCTCGGTCTATGCTGCGGGTG
AAGAAGACGTGGATATTGCTGTGAAGGCTGCCCGGAAAGC
CCTCAACCACCCGTCATGGAAGTTGTTGCCTCCGACTGAA
CGGGGCACCCTGATGTTGAAGCTGGCCGACTTGATCGAGC
AGCACAAGGAGACGCTTGCCACCATTGAAACGTGGGACAA
TGGTAGGGAGCCTCGCATTGTCCTCAAAGGCGATCACCAT
GTACTGATTCTCTCCAGGCAAGCCATACTCAGTTTCGCTG
AACGATGACCTGGGAGAGGTTGTTGGCTGCCTCCGGTACT
ATGCTGGATACGCCGACAAGGTCCATGGTCAGACTATTAG
CACCACCCCGGCCAAGTTTGCCTATACTCTTCGTCAGCCA
ATTGGTGTCGTGGGTCAGATTATCCCCTGGAACTTCCCTC
TCGCGATGGCTGCCTGGAAGTTGGGTCCTGCCTTGGCCTG
CGGAAACACCGTGGTTCTGAAACCGGCTGAGCAGACTCCG
CTCAGTGTTCTCTATCTTGCCAATCTCATCAAGGAAGCCG
GTTTCCCGCCAGGTGTTGTCAACATCCTGAACGGCTTTGG
ACGCGTAGCTGGAAGTGCGCTCGTGACCCACCCCGGGGTG
GACAAGGTTGCCTTCACAGGTTCGACGTTGACTGGCCGCG
AAATTATGAAGTTGGCTGCAGGCACCCTGAAGAACATTAC
GCTCGAGACAGGTGGCAAATCTCCTCTGGTCGTCTTCAGT

-continued

GATGCCGATATCGACCAGGCCGCTAAGTGGGCGCATGCGG
GTATCATGTACAACCAAGGACAGGTTTGCACCGCCACCTC
TCGTATCCTGGTGCACGAGTCCGTCTATGACAAGTTCGTG
GCGCTCTTCAAGGAAGCCGTGGCCAACACCAGCAAGGTGG
GCGATCCCTTTGCCGACGACACCTTCCAGGGTCCCCAGGT
CACCAAGGCCCAATACGACCGCGTGCTCTCCTATATCGAA
GCTGGAAAGTCCGAAGGAGCGACCCTGGTGGCCGGTGGCG
AGCCGTTCAAGAACGTCGGCGACGGCAAGGGTTTCTTTAT
CGCGCCCACCATCTTCACCAACGTCAAGGATAACATGCGG
ATCTACCGGGAGGAGGTTTTCGGACCATTTGTCGTGATTT
CCAGCTTCTCAGAGGAGGATGAGGCTGTGAGACGGGCCAA
CGATACGACCTATGGACTGGGCGCTGCCCTGTTCACCAAG
GACATTGAGCGTGCACACCGGGTTGCGTCGGAGATCGAAG
CGGGCATGGTCTGGATCAACAGCAGCAACGACAGCGATAT
CCGTGTGCCTTTCGGGGGTGTGAAGCAGAGCGGAATTGGG
CGCGAACTTGGCGAGGCCGGTCTGGAGGCCTACTCACAGA
TCAAAGCGGTCCATGTCAACTTGGGAACGAAGCTGTAG

SEQ ID NO: 9 is an exemplary nucleic acid sequence encoding oahA from *A. niger*.

ATGAAAGTTGATACCCCCGATTCTGCTTCcaccatcagca
tgaccaacactatcaccatcaccGTAGAGCAGGACGGTAT
CTATGAGATCAACGGTGCCCGTCAAGAGCCCGTGGTCAAC
CTGAACATGGTCACCGGTGCGAGCAAACTGCGCAAGCAGC
TTCGCGAGACCAATGAGTTGCTCGTGTGTCCTGGTGTGTA
CGACGGTCTGTCCGCCCGTATTGCCATCAACCTGGGCTTC
AAGGGCATGTACATGGTATGTTGGATTCCTCACACTACCT
TTCCCCACAGTCAACACTTCTCCGCTTCCGCGATGGAGAA
AAAAGATCATACTAACGGAAGGGTCAGACCGGCGCCGGTA
CTACCGCGTCTAGACTGGGCATGGCCGATCTGGGTCTAGC
CCACATCTACGACATGAAGACCAACGCGGAGATGATCGCA
AACCTGGACCCCTACGGTCCTCCCCTGATCGCAGACATGG
ACACTGGCTACGGAGGTGAGAATCCCCCATCTCCACTGTC
TGCCAAGACATAATGATCTACCCGCGCCAAAAAGCAAAAC
GGCAATATAGACCCAGTTCCCCACTAACACAAAAAAAAAA
CAAAAATAGGCCCCCTGATGGTCGCCCGTTCCGTTCAACA
ATACATCCAAGCCGGAGTCGCGGGATTCCACATCGAAGAT
CAGATCCAAAACAAGCGATGCGGACACCTGGCAGGCAAGC
GCGTCGTCACCATGGACGAATACTTGACTCGCATCCGCGC
CGCCAAGCTCACCAAGGACCGCCTCCGCAGCGACATCGTG
CTGATTGCCCGCACCGACGCCCTCCAGCAGCACGGCTACG
ACGAGTGCATTCGCCGCCTTAAGGCCGCCCGCGATCTTGG -continued

CGCCGATGTTGGTCTCCTCGAGGGCTTCACCAGTAAGGAG

ATGGCGAGGCGGTGTGTCCAGGACCTTGCGCCTTGGCCGC

TTCTTCTCAACATGGTGGAGAACGGTGCTGGGCCGGTTAT

TTCCGTCGATGAGGCTAGGGAAATGGGCTTCCGCATTATG

ATCTTCTCGTTCGCTTGCATTACTCCTGCCTATATGGGGA

TTACGGCTGCTCTGGAGAGGCTCAAGAAGGATGGTGTGGT

TGGGTTGCCCGAGGGGATGGGGCCGAAGAAGCTGTTTGAG

GTTTGCGGATTGATGGACTCGGTGAGGGTTGATACCGAGG

CTGGTGGAGATGGGTTTGCTAATGGTGTTTAA

SEQ ID NOS: 10-128 and 143 are oligonucleotide primer sequences.

SEQ ID NO: 129 is an exemplary nucleic acid sequence encoding mctl from *A. niger*.

ATGCATACGACCGAGAAGATACCCAGCTTCCTATCTCGCC

GGAAACCCAGCAATGATTCAGAACACGTACCCCCACCACC

CGATGGAGGAGTCCAAGCCTGGACCCAAGTCGTCTGCATG

CACTTCGTATTCTTCAACACCTGGGGGATCACCACTAGCT

TCTCCGTCTTTGAGCAATTATACACCAAAACCCTACCACA

GTCAGCATCCTCTATCTCCTGGATCGGCAGCGTCCAGGTA

TCTCTCCTGTTCTTCCTGAGCGCCCTTGCCGGACGCGCAA

CAGACGCCGGCTTCTTCAGAGTCATGTACCCACTCGGGGT

CCTCCTCCAGCTCGTGGGAATCTTCATGCTCTCTCTGTGC

AAGACCTACTGGCAAATCTTCCTCGCTCAGGCGGTATGCA

TGGGTCTCGGCAATGGACTTACCTTCAGCCCCGGACTTTC

AGTCATGTCCGCCTACTTCATGAAAAACCGAGCCTTTGCA

GTGGGCTTGGCTGCGTCTGGTGCAGCAACAGGGGGTTTGA

TATACCCCGTACTCATCAACCAATTGCTCTATAATCACCA

GATAGGCTTCGCATGGACAATACGCGCAGCAGGACTTCTC

ATGCTAATTACCCATATCTTTGGCCTGGTTTTCTTCAGAC

CCCGTCTTCCACCCCGGACCACCGGCCCTCTCATCGAACT

CGGCGCATTTACCGAGCCGCCTTTCGTCTTCTTCACCTTA

TGCTACTTCTTCACCTTCTGGGGCCTGTACTTCGCCTGGT

TCTATCTTGGCACCTTTGCCCGAGACCGTCTCGGCATCGC

GGATACACAGAACCTGCTCCTTGTGTTGAATGGAGTCGGC

ATCGTCGGACGTATCGGGCCGAGTATAATTGGTGATCGAT

GGACGGGGCGATTAAACATCTTGATCCCCATCACTCTTTC

ATGTGCGATTCTGATGTTTTGCTGGATAGCCGTCAGTACT

GTTGCAGGGCTGTATGCGTTTGTTGTTGTGTATGGGCTCG

TGGGTGGCGCCGCGCAATCGGTGATCCCTGCGACGGCGAC

GACCATGACGCCGGATATCAATCGGACGGGTACAAGGCTG

GGAATGATCATGAGTATTGTGGGATTTGCTACGCTGACTG

GACCGGCTATTGAAGGGGCGTTGATCGCTACTGACGGGGG

-continued

GAGGTATGTGGCGGCTCAGATTTTTGCGGGTGTGAGTATT

CTGCTGGGCGTGTGTGCGGTTGCGGCGGCGCGGGTGGCTA

AGGCTGGGTGGGGGTTGGATGTGAAGGTGTGA

SEQ ID NO: 130 is an exemplary nucleic acid encoding aspartate 1-decarboxylase (PAND) (codon optimized for *Aspergillus*).

ATGCCCGCCACCGGCGAGGACCAGGACCTGGTGCAGGACC

TGATCGAGGAACCCGCCACCTTCTCCGACGCCGTCCTGTC

CTCCGACGAGGAACTGTTCCACCAGAAGTGCCCCAAGCCG

GCTCCGATCTACAGCCCCGTCAGCAAGCCCGTCAGCTTCG

AGTCCCTGCCGAACCGCCGCCTGCACGAAGAGTTCCTCCG

CTCCTCCGTCGACGTCCTGCTGCAAGAGGCCGTGTTCGAG

GGCACCAACCGCAAGAACCGCGTCCTGCAGTGGCGCGAGC

CCGAAGAACTGCGCCGCCTGATGGACTTCGGCGTCCGCAG

CGCCCCGTCCACGCATGAGGAACTGCTCGAGGTCCTGAAG

AAGGTCGTCACCTACTCCGTCAAGACCGGCCATCCGTACT

TCGTCAACCAGCTGTTCTCCGCCGTCGATCCCTACGGCCT

GGTCGCCCAGTGGGCCACCGACGCGCTGAACCCCTCCGTC

TACACCTACGAGGTCAGCCCCGTGTTCGTCCTGATGGAAG

AGGTCGTCCTGCGCGAGATGCGCGCCATCGTCGGCTTCGA

AGGCGGCAAAGGCGACGGCATCTTCTGCCCTGGCGGCTCG

ATCGCCAACGGCTACGCCATCAGCTGCGCCCGCTACCGCT

TCATGCCCGACATCAAGAAGAAGGGCCTGCACTCCCTGCC

GCGCCTGGTCCTGTTCACCTCCGAGGACGCCCACTACTCG

ATCAAGAAGCTGGCCTCGTTCCAAGGCATCGGCACCGACA

ACGTCTACCTGATCCGCACCGACGCTCGCGGTCGCATGGA

CGTCAGCCACCTGGTCGAAGAGATCGAGCGCTCCCTCCGC

GAGGGCGCTGCCCCGTTCATGGTCAGCGCCACCGCCGGCA

CCACCGTCATCGGCGCCTTCGATCCCATCGAGAAGATCGC

CGACGTCTGCCAGAAGTACAAGCTCTGGCTGCACGTCGAC

GCCGCCTGGGGCGGAGGCGCTCTGGTGTCCGCCAAGCACC

GCCATCTGCTGAAGGGCATCGAGCGCGCCGACTCCGTCAC

CTGGAATCCCCACAAGCTGCTGACCGCTCCGCAGCAGTGC

AGCACCCTGCTGCTGCGCCACGAGGGCGTCCTGGCCGAGG

CGCACTCCACCAACGCCGCCTACCTGTTCCAGAAGGACAA

GTTCTACGACACCAAGTACGACACCGGCGACAAGCACATC

CAGTGCGGCCGTCGCGCCGACGTGCTGAAGTTCTGGTTCA

TGTGGAAGGCCAAGGGCACCTCCGGCCTCGAGAAGCACGT

GGACAAGGTGTTCGAGAACGCCCGCTTCTTCACCGACTGC

ATCAAGAACCGTGAGGGCTTCGAGATGGTGATCGCCGAGC

CTGAGTACACCAACATCTGTTTCTGGTACGTCCCCAAGAG

CCTGCGCGGACGCAAGGACGAGGCCGACTACAAGGACAAG

-continued

CTGCACAAGGTCGCCCCTCGCATCAAAGAACGCATGATGA
AGGAAGGCTCCATGATGGTCACCTACCAGGCGCAGAAGGG
CCATCCGAATTTCTTCCGCATCGTCTTTCAGAACTCCGGC
CTGGACAAGGCCGACATGGTCCATCTGGTCGAGGAAATCG
AACGCCTGGGCTCCGACCTCTGA

SEQ ID NO: 131 is an exemplary nucleic acid encoding β-alanine-pyruvate aminotransferase (BAPAT) (codon optimized for *Aspergillus*).

ATGGAACTGATGATCGTCCAGGTCACCGAGCAGACCCAGA
GCCTGAAGAAAACCGACGAGAAGTACCTGTGGCACGCCAT
GCGCGGTGCCGCTCCGAGTCCGACCAACCTGATCATCACC
AAGGCCGAAGGCGCGTGGGTCACCGACATCGACGGCAACC
GCTACCTGGACGGCATGTCCGGCCTGTGGTGCGTCAACGT
CGGCTACGGCCGCAAAGAGCTGGCTCGCGCTGCCTTCGAG
CAGCTGGAAGAGATGCCGTACTTCCCGCTGACGCAGTCGC
ACGTCCCCGCCATCAAGCTGGCCGAGAAGCTGAACGAGTG
GCTGGACGACGAGTACGTCATCTTCTTCTCCAACTCCGGC
TCGGAGGCCAACGAAACCGCCTTCAAGATCGCCCGCCAGT
ACCACCAGCAGAAGGGTGACCACGGCCGCTACAAGTTCAT
CTCTCGCTACCGCGCCTACCACGGCAACTCCATGGGTGCC
CTGGCCGCGACCGGTCAGGCCCAGCGCAAGTACAAGTACG
AGCCCCTCGGTCAGGGCTTCCTGCACGTGGCCCCTCCGGA
CACCTATCGCAACCCCGAGGACGTGCACACCCTGGCCTCC
GCCGAAGAAATCGACCGCGTCATGACCTGGGAGCTGTCCC
AGACCGTCGCCGGCGTCATCATGGAACCCATCATCACCGG
TGGTGGCATCCTGATGCCGCCGGACGGCTACATGGAAAAG
GTCAAAGAGATCTGCGAAAAGCACGGCGCCCTGCTGATCT
GCGACGAGGTCATCTGCGGCTTCGGTCGCACCGGCAAGCC
CTTCGGCTTCATGAACTACGGCGTCAAGCCCGACATTATC
ACCATGGCCAAGGGTATCACCTCGGCCTACCTGCCGCTGT
CTGCCACCGCGGTCCGCCGCGAGGTCTACGAGGCCTTCGT
CGGCTCCGACGACTACGACCGCTTCCGCCATGTCAACACC
TTCGGCGGCAACCCTGCCGCCTGCGCGCTGGCCCTGAAGA
ACCTCGAGATCATGGAAAACGAGAAGCTCATCGAGCGGTC
CAAAGAACTGGGCGAGCGCCTGCTGTACGAGTTGGAGGAC
GTCAAAGAGCACCCCAACGTCGGGGACGTCCGCGGCAAGG
GCCTCCTGCTGGGTATCGAACTCGTCGAGGATAAGCAGAC
CAAAGAGCCCGCCTCCATCGAAAAGATGAACAAGGTCATC
AACGCCTGCAAAGAGAAGGGTCTGATCATCGGCAAGAACG
GCGACACCGTGGCCGGCTACAACAACATCCTGCAGCTCGC
CCCTCCGCTGTCCATCACCGAAGAGGACTTCACCTTCATC
GTCAAGACTATGAAGGAATGTCTGGCCCAGCTCTGA

-continued

SEQ ID NO: 132 is an exemplary nucleic acid sequence encoding 3-hydroxypropionate dehydrogenase (HPDH) (codon optimized for *Aspergillus*).

ATGATCGTGCTGGTCACGGGCGCGACCGCCGGTTTCGGCG
AGTGCATCACCCGCCGCTTCATCCAGCAGGGCCACAAGGT
GATCGCTACCGGACGCCGCCAAGAGCGCCTCCAAGAGCTG
AAGGATGAGCTGGGCGACAACCTGTACATTGCCCAGCTGG
ACGTGCGCAACCGGGCTGCCATCGAAGAAATGCTCGCCTC
GCTGCCCGCCGAGTGGTGCAACATCGACATCCTGGTCAAC
AACGCCGGTCTGGCCCTCGGCATGGAACCGGCGCACAAGG
CCAGCGTCGAGGACTGGGAAACCATGATCGACACCAACAA
CAAGGGACTCGTCTACATGACCCGCGCTGTGCTGCCCGGC
ATGGTCGAGCGCAACCACGGCCACATCATCAACATCGGCT
CCACCGCTGGCAGCTGGCCCTACGCTGGCGGCAACGTCTA
TGGCGCGACCAAGGCGTTCGTCCGCCAGTTCTCCCTGAAC
CTGCGCACCGACCTGCACGGCACCGCCGTCCGCGTGACCG
ACATTGAGCCCGGTCTGGTCGGCGGCACCGAGTTCAGCAA
CGTCCGCTTCAAGGGCGACGACGGCAAGGCCGAGAAAACC
TACCAGAACACCGTCGCTCTGACCCCTGAGGATGTCAGCG
AGGCCGTCTGGTGGGTCAGCACTCTGCCCGCGCACGTCAA
CATCAACACCCTCGAGATGATGCCCGTCACGCAGTCCTAC
GCCGGCCTGAACGTCCACCGCCAATAG

SEQ ID NO: 133 is an exemplary nucleic acid encoding pyruvate carboxylase (pyc) from *A. niger*.

ATGGCTGCTCCCCGCCAGCCCGAGGAGGCGGTCGATGACA
CCGAGTTCATCGATGACCACCATGACCAGCACCGGGACTC
TGTCCACACCCGTCTGCGTGCCAATTCGGCTATCATGCAG
TTCCAAAAGATCCTTGTTGCCAACCGTGGTGAAATCCCCA
TTCGTATCTTCCGGACGGCTCACGAGCTGTCCCTGCAGAC
CGTCGCCGTCTACTCCCATGAGGACCGTCTCTCCATGCAC
CGTCAGAAGGCCGACGAGGCCTACATGATTGGCAAGCGCG
GTCAATATACACCGGTTGGGGCCTACTTGGCCATTGACGA
GATCGTCAAGATTGCTCTGGAGCATGGTGTACACCTGATC
CACCCGGGTTACGGTTTCCTGTCCGAGAACGCCGAGTTTG
CCCGCAAGGTGGAGCAGTCCGGCATGGTTTTCGTCGGCCC
TACCCCCCAGACCATCGAGAGCCTCGGTGACAAGGTCTCC
GCCCGTCAGCTGGCTATCCGCTGCGACGTGCCCGTCGTGC
CCGGTACCCCGGGCCCTGTCGAGCGCTACGAGGAGGTCAA
GGCCTTCACCGACACCTACGGCTTCCCCATCATCATCAAG
GCCGCCTTTGGTGGTGGTGGTCGTGGTATGCGTGTCGTTC
GCGACCAGGCCGAACTGCGTGACTCCTTCGAGCGTGCCAC
CTCCGAGGCCCGCTCTGCCTTTGGCAACGGCACCGTCTTC

-continued

GTCGAGCGCTTCCTCGACCGCCCCAAGCACATCGAAGTCC
AGCTGCTGGGTGACAACCACGGCAACGTCGTCCACCTGTT
CGAGCGTGACTGCTCCGTCCAGCGTCGCCACCAGAAGGTC
GTTGAAATTGCCCCGGCCAAGGACCTGCCTGCCGATGTCC
GTGACCGCATCCTGGCTGATGCTGTCAAGCTGGCCAAGTC
GGTCAACTACCGCAACGCCGGTACTGCAGAGTTCCTGGTT
GACCAGCAGAACCGTTACTACTTCATTGAGATCAACCCCC
GTATCCAGGTCGAGCACACTATCACCGAAGAGATCACGGG
TATCGATATCGTTGCTGCTCAGATCCAGATTGCGGCCGGT
GCTACCCTGGAACAGCTGGGTCTGACCCAGGACCGCATCT
CCACTCGTGGATTCGCCATTCAGTGCCGTATCACCACCGA
GGACCCCTCCAAGGGCTTCTCCCCCGACACCGGTAAGATC
GAGGTCTACCGCTCCGCCGGTGGTAACGGTGTCCGTCTGG
ATGGTGGAAACGGTTTCGCCGGTGCCATCATCACCCCTCA
CTACGACTCCATGTTGGTCAAGTGTACCTGCCGTGGTTCC
ACCTATGAGATCGCTCGCCGCAAGGTCGTTCGTGCTTTGG
TCGAGTTCCGTATCCGTGGTGTCAAGACCAACATTCCTTT
CCTCACCTCTCTTCTGAGTCACCCTGTGTTCGTGGATGGT
ACCTGCTGGACCACGTTCATTGATGACACTCCCGAGCTGT
TCGCCCTTGTCGGCAGTCAGAACCGTGCCCAGAAGCTGCT
GGCTTACCTGGGTGATGTGGCTGTCAACGGCAGCAGCATC
AAGGGCCAGATCGGCGAGCCCAAGCTCAAGGGCGATATCA
TCAAGCCCGTTCTGCATGACGCTGCCGGCAAGCCCCTCGA
CGTCTCTGTCCCCGCCACCAAGGGATGGAAGCAGATCCTG
GACAGTGAGGGTCCCGAGGCTTTTGCCCGCGCTGTGCGTG
CCAACAAGGGCTGCTTGATCATGGATACTACCTGGCGTGA
TGCCCACCAGTCGCTGCTGGCCACTCGTGTGCGTACCATT
GACCTCCTGAACATCGCCCACGAGACGAGCCACGCCCTCG
CCAACGCCTACAGTTTGGAATGCTGGGGTGGTGCCACCTT
CGATGTCGCCATGCGCTTCCTGTACGAGGACCCCTGGGAC
CGTCTTCGCAAGCTGCGCAAGGCCGTTCCCAACATCCCCT
TCCAGATGTTGCTCCGTGGTGCCAACGGTGTTGCTTACTC
CTCCCTCCCTGACAACGCCATCTACCACTTCTGTAAGCAG
GCCAAGAAGTGCGGTGTCGACATCTTCCGTGTCTTCGATG
CTCTCAACGACGTTGACCAGCTCGAGGTCGGTATCAAGGC
TGTCCACGCTGCCGAGGGTGTTGTTGAGGCTACTATTTGC
TACAGTGGTGATATGCTCAACCCCAGCAAGAAGTACAACC
TGCCTTACTACCTCGACCTTGTTGATAAGGTGGTCCAATT
CAAGCCCCACGTCTTGGGTATCAAGGACATGGCTGGTGTG
CTGAAGCCCCAGGCTGCTCGTCTGCTGATCGGTTCCATCC
GCGAGCGCTACCCCGACCTCCCCATCCACGTGCACACCCA
CGATTCTGCTGGTACCGGTGTGGCTTCCATGATTGCTTGC
GCTCAGGCCGGTGCTGATGCCGTTGATGCTGCCACGGACA
GCCTTTCCGGTATGACCTCCCAGCCCAGCATTGGTGCTAT
CCTCGCTTCCCTCGAGGGAACTGAGCACGACCCCGGCCTC
AACTCGGCCCAGGTTCGCGCCCTTGACACCTACTGGGCGC
AGCTGCGTCTCCTCTACTCGCCCTTCGAGGCAGGTCTGAC
TGGTCCCGACCCCGAGGTTTACGAGCATGAGATCCCTGGT
GGTCAATTGACCAACCTGATCTTCCAGGCCAGCCAGCTTG
GTCTGGGCCAGCAGTGGGCGGAGACGAAGAAGGCTTACGA
GTCTGCCAACGATCTTTTGGGCGATGTCGTCAAGGTCACC
CCCACTTCCAAGGTGGTCGGTGATTTGGCTCAGTTCATGG
TCTCCAACAAGTTGACTGCTGAAGATGTGATTGCTCGCGC
CGGCGAGCTTGACTTCCCCGGTTCCGTTCTGGAGTTCCTC
GAGGGTCTCATGGGCCAGCCCTACGGTGGATTCCCCGAGC
CTCTGCGCTCTCGCGCTCTGCGTGACCGTCGCAAGCTCGA
CAAGCGCCCTGGTCTGTACCTGGAGCCCCTTGACCTGGCC
AAGATCAAGAGCCAGATCCGGGAGAACTATGGCGCAGCTA
CCGAGTACGATGTGGCCAGCTATGCCATGTACCCCAAGGT
CTTCGAGGATTACAAGAAGTTTGTCGCCAAGTTCGGTGAT
TTGTCCGTCCTGCCCACGCGTTACTTCTTGGCCAAGCCCG
AGATCGGCGAGGAATTCCACGTCGAGCTGGAGAAGGGTAA
GGTGCTGATCCTGAAGTTGTTGGCCATTGGTCCCCTCTCC
GAGCAGACCGGCCAGCGTGAGGTCTTCTACGAAGTCAACG
GTGAGGTTCGCCAGGTTAGTGTGGACGACAAGAAGGCGTC
CGTCGAGAACACCGCCCGCCCCAAGGCCGAGCTGGGTGAC
AGCAGCCAGGTTGGTGCTCCTATGAGCGGTGTGGTTGTCG
AGATCCGCGTCCACGACGGCCTGGAAGTCAAGAAGGGTGA
CCCCATTGCCGTCCTGAGCGCCATGAAGATGGAAATGGTT
ATCTCTGCTCCCCACAGTGGCAAGGTCTCCAGCTTGCTGG
TCAAGGAAGGTGACTCGGTGGATGGCCAGGATCTTGTCTG
CAAGATCGTCAAGGCCTAG

SEQ ID NO: 134 is an exemplary ubi4p sequence from *A. niger*.

CTTCGGAGTAGCAACGAGTATTTTCACCGGGAGTTTCAAC
GGGTTCTATTTCAGGAACACGGCTGCGGTCTGGATTGGGT
CGGGCTGAGATACCGACTGGTGGCGTCAGTGGCGGGTACG
GACGGAGTCGTCCTGGCCGCTCGTAGACACTCCCCCGGAC
TGATATCAGGCCCCGGCAACTGGCTTCGTCTCACTCCAGG
GCATCAGGAGTGCCTACCACATGGGTTCAGGCTTTGCCCC
GTCGTCTAAGTTTGCAGGACAAAATTTTCGTATGCGTTAC
CACTCTTTCCTTTCAGCAACCATTCCGTAGTGAAAACCCA

-continued

ATAATAGGTGGCTGCCGTGGGAGCCTGAGTCAACCCAACC

AGAACCTTTCTAGTAGATTCTCCCCCAAGCGCTTCAGCAA

CGAAGCGTATTGGAGAACCAAATGACGCAGACCAAGCGGA

TTCCGGTGCAATAGCCGGATGGCAAGGGAATCCCCCAGGA

GGTGCCAGAAGCGTCGCCCGAAAGGTACTTCGTCTGACAG

GCTAACACCGCTCGGGCTAAGGTCCCTGCTGCTCTTTTCC

CTTTATTGCGACTTAACCTCTAAGCCATTCCCTTGCATCA

CGTTATCTCACTGACCGACCTCTGACTAAGGCGCTTCGCC

TCCGCCGCCTCCCCTCATTCACCTCCTCTCCTGACTACTT

AAGCCTTCTCTTCCTTCCTCTCACTACCAACCCTCCTTCA

TCCCTCATACCTCTCATCCTACCACTCACCTTTCGCGCAT

CGCCATCTGCGATCCTCCCCACAACACTCCACCTAGATAC

ATACACCATTAACTGCGCTTCTACAAC

SEQ ID NO: 135 is an exemplary ubi1S27p sequence from *A. niger*.

CATTATCGATCTATCCACATTGCCTCTTATAACTGACGGG

AGGAGGCGACCTGTGGCCTGTGAGGGTTTGAAACATTATT

TCACCCTTCCTCTGCAATAGCCGATTTAATAATTGACGCC

TATCCCGCATGCTATTCAATCAATAATTAGCAACAGCGAG

CCGAGGGATGAGAGGGCGGCAAATGATGACGATGACGAAG

TTGACGTCGATGCTGAGAGGCTGGATTGACCACTTCGTCT

AGTTGGTTTTAGGCCTAGTCGTACTTTCTGCCTGGCTTTT

CCGGGCCGTGCCTATGCCTGGCGATGCAGGCACCAAACTG

ACGTATCCAAGAAACCGTTAAAGTCAGCAAATCCCGTGAC

CTCAGCCGCAGACCATCACATGACTGAGGACCCGGAGGGC

TGATTATCCGAGTGTCCACCCGCACTACGCCTGACTCGGT

AATCTGGACACCACGTGACCGCACAACCGATTTTAACGAA

GCCCACCACCACCGAGGATATTTTCCTACCACGATCGCCG

AAGGTTTAGGAAGACAAGTCTTGTCGAGGTGAGTTGATGA

CCCTATACATTTACTATGTGACAAGGAAAAGGATTCAATA

TTATTTGGAACATCTCATCTTCATTTCTTTCCACTTATCC

CAGAAAATACCTCCTGCGCACACTTTAGCGCGCGAGATAC

CAAAATTCCGGGGGAGTAATATGTTGAACAAGAAACGAAG

ATGAGAGCTGCGACGCAGATAATATTGAACTTTATCCTTG

CTCACGCACCAGTATCAAGTAAAACAATGAACTAACATCC

TTTTTCCAACCCAGACCTTCATCAAG

SEQ ID NO: 136 is an exemplary mbfAp sequence from *A. niger*.

GGACATGCTGGAAGGGATTTTCTGGCTCAATACCACGTCT

GTATTTGACCCTTTCCAGACAGTTAATCCGCTGCAGGAGG

GCGAACTGTAGCTCCTCGTTCTCCTTGTAGCGCTTGATCC

AGTCTTTTTGGATGTTGCACTTGCTTGGCCTATGCTTCTC

ATATAATCTTGCCCTGTCATAGAGACGACGTCTGAGATTG

-continued

TAGCGTTCGTCTTTGATCACCCGGAGCCAGATAGGCCTGA

GTATATCTGACATTAGATCAAAGGGTCTGTGGATAGTCTC

CTTCAGCATCAGCGACGCATGTGACTCGCATGTCGGAGAG

AGCTTGTGGGTGGTCATCTTTGATGGCGTCCTCTGCTTTC

CCTTGATTTTCGTTGATTGTTTTTCGAAAGTTAAGTCTGG

AAGTCAAGAGAATCCTTCTGCCAGACATTATATTTACGTA

TACTGACGTAGTAGAAACAGCGTCAGGATGAGGACATGGT

GTGTGCTGGACCACGGAATCATAGTTCATCAGTATATTGG

GTTGGACAAATAACGCTGAGCATGTATATGTCTTTACACA

CTATAAAAGCCAGCGAACGCCAATAAAATAGGGCATATTG

ATGTGAAAATATGACACCAGTTAAAAGCAGTGTATTGATT

TTATCTCTCTTCACCTCGGACCTATACTACCGTATACAAG

ACTCAACTTACTTCCAGATATAGTAATATACACCCTATGG

ACGAACCAGCACAATAATTACAGCCAAACAACACCACCCA

AATGGCATATTCCTAATCAGCACTAAGCACAAATACCACT

GTCATCACAGCATAATCAATAAGAATCCCAGACAACCGAC

TCACTCTGACTCACCTTACACAAACCCCCAAGCAAAGCGC

AGCCCAGAACCTCAGCCAACAATCGGGCAACGTACGGGGA

AAGATTGGCCGATCCATGATGTCAGCAGCCCTAACCCAAA

GCGGACTAGCGCATACCGCCCCTCTGACTCCGCCATCCCA

GGGCTCGAGAAGCTTCCGTGGCGTCGATATAAATTCAGCG

GGCCTTGAACATCCCTCCTTACGACACACCTCACGCGATC

GATTTTGACACTCACACACCGCCACCCTCACATCCTCCAC

CCACACCACACCCCTTAATCAACCCACCATCACCGCTAGA

ACGTCTATCTCATCACCGACTTCTCATCCATCTTCAAA

SEQ ID NO: 137 is an exemplary mct1 amino acid sequence from *A. niger*.

MHTTEKIPSFLSRRKPSNDSEHVPPPPDGGVQAWTQVVCM

HFVFFNTWGITTSFSVFEQLYTKTLPQSASSISWIGSVQV

SLLFFLSALAGRATDAGFFRVMYPLGVLLQLVGIFMLSLC

KTYWQIFLAQAVCMGLGNGLTFSPGLSVMSAYFMKNRAFA

VGLAASGAATGGLIYPVLINQLLYNHQIGFAWTIRAAGLL

MLITHIFGLVFFRPRLPPRTTGPLIELGAFTEPPFVFFTL

CYFFTFWGLYFAWFYLGTFARDRLGIADTQNLLLVLNGVG

IVGRIGPSIIGDRWTGRLNILIPITLSCAILMFCWIAVST

VAGLYAFVVVYGLVGGAAQSVIPATATTMTPDINRTGTRL

GMIMSIVGFATLTGPAIEGALIATDGGRYVAAQIFAGVSI

LLGVCAVAAARVAKAGWGLDVKV

SEQ ID NO: 138 is an exemplary aat1 amino acid sequence from *A. niger*.

MGSTTPSVFSTAVVPAAPEDALFGLAQAFRQDSSDKKVDL

VIGAYRDDNAKPWILPVVKKADELVRNDPALNHEYLPIKG

-continued

LADYTTAAQKLIIGADSPAIRENRVCTFQTISGTGAVHLG

ALFLSKFHPSNPKPTVYLSNPTWANHNQIFTNVNLSLANY

PYFDPQTKGLNFSGMLSALRDAPTGSIILLHVCAHNPTGV

DLTQSQWKDVAVVMRERNHFPFFDCAYQGFASGDLIRDSW

AVRYFVEQGFELCVAQSFAKNFGLYGQRTGAFHFVSAPGA

EASQANAHVASQLAILQRSEISNPPAYGARIASRVLNDEG

LFKEWEEDLKTMSGRIAEMRQGLRERLEKKGTPGTWNHIT

DQIGMFSFTGLTESQVKVLKEKWHVYMTKNGRISMAGLNT

HNLDYFAEAVDSVVRETS

SEQ ID NO: 139 is an exemplary cDNA encoding aat1 from *A. niger*.

ATGTCGCCCCTTTCCTCCTCTTCTTCTTCTCCATCTTCTT

CTCTCTCCCTCACTTCTTCTTCATCCTCTCCATCCGCCTC

CTCCTCCATCGCTTCTACTTCTACTTCTACCGCTCGTTCC

CGTCTCGCTTCTCTCTCCTCCCACATCATGGGCTCTACCA

CCCCCTCCGTCTTTTCCACCGCCGTCGTGCCCGCCGCGCC

AGAAGATGCTCTCTTCGGTCTGGCTCAGGCGTTTCGCCAG

GATTCCTCCGACAAGAAGGTCGATCTAGTCATTGGCGCTT

ATCGCGACGACAATGCCAAACCCTGGATCCTGCCCGTGGT

CAAGAAGGCTGACGAGCTCGTTCGCAATGACCCCGCCCTC

AATCACGAATACCTCCCCATCAAAGGTCTCGCCGACTACA

CCACTGCCGCCCAGAAATTGATCATTGGCGCTGATAGCCC

TGCCATTCGCGAGAACCGCGTATGCACCTTCCAAACCATC

TCCGGCACCGGTGCCGTGCACCTGGGCGCTCTCTTCCTCT

CCAAATTCCACCCCTCCAACCCTAAACCCACCGTCTACCT

CTCCAACCCAACCTGGGCCAACCACAACCAAATCTTCACC

AACGTCAACCTCTCCCTCGCCAACTACCCCTACTTCGACC

CGCAAACCAAAGGCCTCAACTTCTCCGGCATGCTCTCCGC

CCTGCGCGATGCTCCCACCGGCTCCATCATCCTCCTGCAC

GTCTGCGCCCACAACCCCACCGGTGTCGATCTGACCCAGT

CCCAATGGAAGGACGTCGCCGTCGTCATGCGCGAGCGCAA

CCATTTCCCCTTCTTTGACTGCGCCTACCAGGGTTTCGCC

TCTGGTGATCTCATTCGCGACTCCTGGGCCGTGCGCTACT

TCGTCGAGCAGGGCTTCGAGCTGTGCGTGGCCCAATCCTT

CGCTAAGAACTTTGGTCTGTATGGCCAGCGCACGGGCGCA

TTCCATTTCGTTTCCGCACCCGGTGCGGAGGCCAGCCAGG

CTAATGCGCATGTCGCGTCGCAGCTGGCTATTCTGCAGCG

CAGTGAGATCAGTAACCCGCCGGCGTATGGCGCGCGTATC

GCTAGCCGGGTGTTGAATGATGAGGGACTGTTCAAGGAGT

GGGAGGAGGATCTGAAGACGATGAGTGGTCGCATTGCGGA

GATGCGCCAGGGCCTGAGGGAGCGCTTGGAGAAGAAGGGC

ACGCCGGGCACTTGGAACCACATTACGGATCAGATTGGCA

-continued

TGTTCAGTTTCACGGGTTTGACCGAGTCGCAAGTTAAGGT

GTTGAAGGAGAAGTGGCATGTTTACATGACCAAGAACGGC

CGCATCTCCATGGCGGGTCTAAACACACATAACCTGGACT

ACTTCGCCGAAGCAGTGGACAGCGTAGTTCGGGAGACTTC

ATAA

SEQ ID NO: 140 is an exemplary gpdA promoter (gpdAp) sequence from *A. niger*.

CTACTATGAAAGACCGCGATGGGCCGATAGTAGTAGTTAC

TTCCATTACATCATCTCATCCGCCCGGTTCCTCGCCTCCG

CGGCAGTCTACGGGTAGGA

TCGTAGCAAAAACCCGGGGGATAGACCCGTCGTCCCGAGC

TGGAGTTCCGTATAACCTAGGTAGAAGGTATCAATTGAAC

CCGAACAACTGGCAAAACATTCTCGAGATCGTAGGAGTGA

GTACCCGGCGTGATGGAGGGGGAGCACGCTCATTGGTCCG

TACGGCAGCTGCCGAGGGGGAGCAGGAGATCCAAATATCG

TGAGTCTCCTGCTTTGCCCGGTGTATGAAACCGGAAAGGA

CTGCTGGGGAACTGGGGAGCGGCGCAAGCCGGGAATCCCA

GCTGACAATTGACCCATCCTCATGCCGTGGCAGAGCTTGA

GGTAGCTTTTGCCCCGTCTGTCTCCCCGGTGTGCGCATTC

GACTGGGCGCGGCATCTGTGCCTCCTCCAGGAGCGGAGGA

CCCAGTAGTAAGTAGGCCTGACCTGGTCGTTGCGTCAGTC

CAGAGGTTCCCTCCCCTACCCTTTTTCTACTTCCCCTCCC

CCGCCGCTCAACTTTTCTTTCCCTTTTACTTTCTCTCTCT

CTTCCTCTTCATCCATCCTCTCTTCATCACTTCCCTCTTC

CCTTCATCCAATTCATCTTCCAAGTGAGTCTTCCTCCCCA

TCTGTCCCTCCATCTTTCCCATCATCATCTCCCTTCCCAG

CTCCTCCCCTCCTCTCGTCTCCTCACGAAGCTTGACTAAC

CATTACCCCGCCACATAGACACATCTAAACA

SEQ ID NO: 141 is an exemplary eno1 promoter (eno1p) sequence from *A. niger*.

CTCGAGCTTACAAGAAGTAGCCTGTAGCAAGTCTGTGGTC

GTGTTTATTATTTATCTACTACTTCCCCCTCCTCCCTCCT

CCTCTTGTGTTAAGAGTACTCTCAAAAAAAGCCTTTCTTA

GATAGTACAACCACCATCTTCAAGGTCCTGTAAGTATGAC

TTGTCCCATATACTCATTTTATCACCCCTCCCATCTTTCT

CTGTCCATTTCATCCTCCTCTTCTTCCTCTTAGCTGCTAG

TCATGACCCCGCCATCATCCCACCATGTTGTGCTTGACCC

CtccatctatccatccatccatccTCCTGTCTATATGCCA

TCACTCCATCCTGTCTGTCTATCAATGATCTGGCATCTCC

GGATTTAGCACCAAGTCCCATTGATTAGTTGATCATTTGG

GAAACTTGGCTGTGCCGAGCCTGGTCTATTTGATGGATCG

GACCTCTCCACCTCTAATTCCCCCCCCGTCCTTCCCTTCT

-continued

CCGTCACTCATCCGCCATCCGCTCATTCTTTTTGGGTCCT

CGGTGAACACTCACCACCTTCCCCCCCGCTGCTGCTAGTG

CACACCGAAACAGCAAGTCCGGAGCGCTTACATTTTTGCC

TCCTCCGTTTTTTCCTATATCTGGGCCATGTTCTCCCTTT

GCCATCTTTGTTTTCTCCCAGTTTCACTGATCCATAACTC

ATCCCCCTCCAGTCCATCAACATG

Figures 20A, 20B, 20C, 20D, 20E:
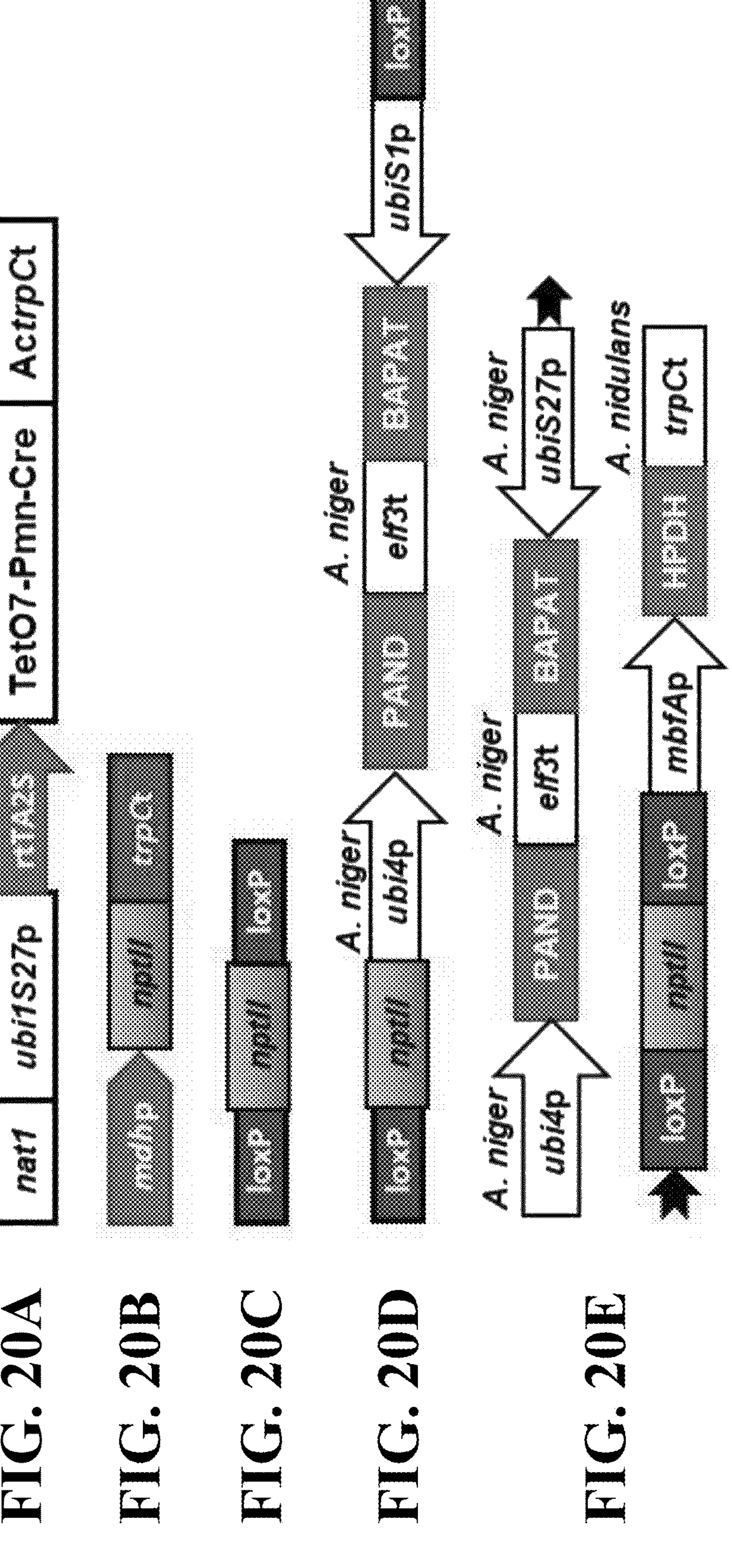
FIGS. 20A-20E. A diagram of the Tet-On/Cre-loxP (3HP4140) system and the new β-alanine 3-HP pathway transgene expression cassette (3HP4145) with loxP-nptII marker gene recycle for *A. niger*.
Figure 21A:
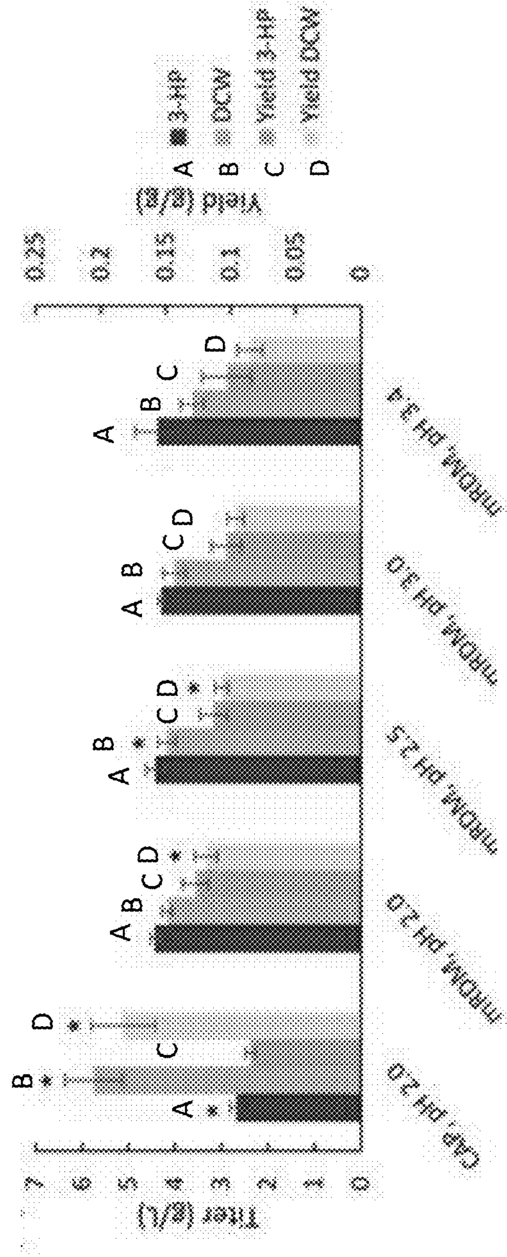
FIGS. 21A-21B. The effects of culture medium and pH on 3-HP production and spore germination in *A. niger* strain An3HP9 grown at 30° C. and 200 rpm for 7 days.
Figure 21B:
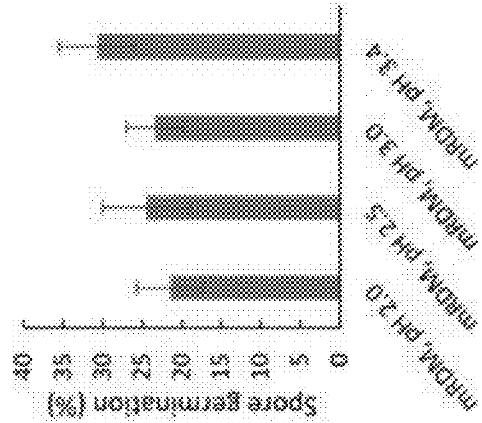

SEQ ID NO: 142 is an exemplary nucleic acid sequence encoding the construct of FIG. 20E.

GTTTAAACTTCGGAGTAGCAACGAGTATTTTCACCGGGAG

TTTCAACGGGTTCTATTTCAGGAACACGGCTGCGGTCTGG

ATTGGGTCGGGCTGAGATACCGACTGGTGGCGTCAGTGGC

GGGTACGGACGGAGTCGTCCTGGCCGCTCGTAGACACTCC

CCCGGACTGATATCAGGCCCCGGCAACTGGCTTCGTCTCA

CTCCAGGGCATCAGGAGTGCCTACCACATGGGTTCAGGCT

TTGCCCCGTCGTCTAAGTTTGCAGGACAAAATTTTCGTAT

GCGTTACCACTCTTTCCTTTCAGCAACCATTCCGTAGTGA

AAACCCAATAATAGGTGGCTGCCGTGGGAGCCTGAGTCAA

CCCAACCAGAACCTTTCTAGTAGATTCTCCCCCAAGCGCT

TCAGCAACGAAGCGTATTGGAGAACCAAATGACGCAGACC

AAGCGGATTCCGGTGCAATAGCCGGATGGCAAGGGAATCC

CCCAGGAGGTGCCAGAAGCGTCGCCCGAAAGGTACTTCGT

CTGACAGGCTAACACCGCTCGGGCTAAGGTCCCTGCTGCT

CTTTTCCCTTTATTGCGACTTAACCTCTAAGCCATTCCCT

TGCATCACGTTATCTCACTGACCGACCTCTGACTAAGGCG

CTTCGCCTCCGCCGCCTCCCCTCATTCACCTCCTCTCCTG

ACTACTTAAGCCTTCTCTTCCTTCCTCTCACTACCAACCC

TCCTTCATCCCTCATACCTCTCATCCTACCACTCACCTTT

CGCGCATCGCCATCTGCGATCCTCCCCACAACACTCCACC

TAGATACATACACCATTAACTGCGCTTCTAAACAATGCCC

GCCACCGGCGAGGACCAGGACCTGGTGCAGGACCTGATCG

AGGAACCCGCCACCTTCTCCGACGCCGTCCTGTCCTCCGA

CGAGGAACTGTTCCACCAGAAGTGCCCCAAGCCGGCTCCG

ATCTACAGCCCCGTCAGCAAGCCCGTCAGCTTCGAGTCCC

TGCCGAACCGCCGCCTGCACGAAGAGTTCCTCCGCTCCTC

CGTCGACGTCCTGCTGCAAGAGGCCGTGTTCGAGGGCACC

AACCGCAAGAACCGCGTCCTGCAGTGGCGCGAGCCCGAAG

AACTGCGCCGCCTGATGGACTTCGGCGTCCGCAGCGCCCC

GTCCACGCATGAGGAACTGCTCGAGGTCCTGAAGAAGGTC

GTCACCTACTCCGTCAAGACCGGCCATCCGTACTTCGTCA

ACCAGCTGTTCTCCGCCGTCGATCCCTACGGCCTGGTCGC

CCAGTGGGCCACCGACGCGCTGAACCCCTCCGTCTACACC

TACGAGGTCAGCCCCGTGTTCGTCCTGATGGAAGAGGTCG

-continued

TCCTGCGCGAGATGCGCGCCATCGTCGGCTTCGAAGGCGG

CAAAGGCGACGGCATCTTCTGCCCTGGCGGCTCGATCGCC

AACGGCTACGCCATCAGCTGCGCCCGCTACCGCTTCATGC

CCGACATCAAGAAGAAGGGCCTGCACTCCCTGCCGCGCCT

GGTCCTGTTCACCTCCGAGGACGCCCACTACTCGATCAAG

AAGCTGGCCTCGTTCCAAGGCATCGGCACCGACAACGTCT

ACCTGATCCGCACCGACGCTCGCGGTCGCATGGACGTCAG

CCACCTGGTCGAAGAGATCGAGCGCTCCCTCCGCGAGGGC

GCTGCCCCGTTCATGGTCAGCGCCACCGCCGGCACCACCG

TCATCGGCGCCTTCGATCCCATCGAGAAGATCGCCGACGT

CTGCCAGAAGTACAAGCTCTGGCTGCACGTCGACGCCGCC

TGGGGCGGAGGCGCTCTGGTGTCCGCCAAGCACCGCCATC

TGCTGAAGGGCATCGAGCGCGCCGACTCCGTCACCTGGAA

TCCCCACAAGCTGCTGACCGCTCCGCAGCAGTGCAGCACC

CTGCTGCTGCGCCACGAGGGCGTCCTGGCCGAGGCGCACT

CCACCAACGCCGCCTACCTGTTCCAGAAGGACAAGTTCTA

CGACACCAAGTACGACACCGGCGACAAGCACATCCAGTGC

GGCCGTCGCGCCGACGTGCTGAAGTTCTGGTTCATGTGGA

AGGCCAAGGGCACCTCCGGCCTCGAGAAGCACGTGGACAA

GGTGTTCGAGAACGCCCGCTTCTTCACCGACTGCATCAAG

AACCGTGAGGGCTTCGAGATGGTGATCGCCGAGCCTGAGT

ACACCAACATCTGTTTCTGGTACGTCCCCAAGAGCCTGCG

CGGACGCAAGGACGAGGCCGACTACAAGGACAAGCTGCAC

AAGGTCGCCCCTCGCATCAAAGAACGCATGATGAAGGAAG

GCTCCATGATGGTCACCTACCAGGCGCAGAAGGGCCATCC

GAATTTCTTCCGCATCGTCTTTCAGAACTCCGGCCTGGAC

AAGGCCGACATGGTCCATCTGGTCGAGGAAATCGAACGCC

TGGGCTCCGACCTCTGATGGGTTGGATGACGATGACTTCA

TGTGATTTTGTTATTTAGAATATTTTATATTTCCTTTTCT

TCTTCTCACCACCGATCCCCTTAACACTCTTGCTTCATTT

GCTTCAGATTTCTCGGTTTCTTCTTTTTTCTTCTCCCCAG

TTATCCACTATATCTTTGCTAGACCGGCCTGCGCCCTGGC

ATGCATCATAAAATCATGTCCGTTGGTCATCATCTGTTTT

GTATATCCGTCATATAAAGTATTCTTTTATTCCCTCCCCC

CTCGGTCGTCTTTCGCTGTCCCGCTTCCTACCTCCGGTTT

ATAGAGCATGGTTCATCTCTTCCGTACATTTCCGTTGGTA

CTAGCATTTATGTCTTCAGCTAGTATAGAAGCTGCCGCAG

TTGTTCGCTTACTACCTGCCTAAGTCCTTAACTTTTTAAA

GTGTTTAACCTATACGTAGTGTTAAACGAGTACTGGGAGG

TGGTGAGGTAGAAAATGTTCTGCACGGGCAGTGGGTATTT

-continued

GGTAGTGTGTAAGGCGGTTATTTATCAGGCTGACGCTAAA
GACTTCTATGGGAGCAGTATGGGATCGCGGCTCATAGAAG
TACACAAAATCTAAGAGTCGTTTGATAATTAATTGATTCC
CGGCAGGGTCTTCTTGGGATTGAGAGAACTGGTTACTTTG
ATTTGAGATATTGTAAAGCTTAAGGCTCTTAACACGTACG
AGCGAAACAGCAGGGGGGAAATCGGGAAAAGGGGCGTGGG
GTGAATAAAAAAGTTGAAATAAGACACTGTATCTTGCTGG
GGGTGAATAAAGAGAGAATAAAAGAGAGGTAAATTCCACT
CAGCCCCTTTTCTTCGCTCTCCAAACATCAAACTCCGCCG
GCCGACCCACAGGATCCCGAACAAGTGGAAGATATGTGCC
GGTCCAGACCCTTCGCACAGCTAAAAGCAGACCTTCATAA
GCGTTTCCGGGTAGTATTCGCACACCTGAACTGGCACGTC
GGGGACACAACTGTTTTTGATACACAAGAACACACACCAC
CCATCTAGGACTCAGAGCTGGGCCAGACATTCCTTCATAG
TCTTGACGATGAAGGTGAAGTCCTCTTCGGTGATGGACAG
CGGAGGGGCGAGCTGCAGGATGTTGTTGTAGCCGGCCACG
GTGTCGCCGTTCTTGCCGATGATCAGACCCTTCTCTTTGC
AGGCGTTGATGACCTTGTTCATCTTTTCGATGGAGGCGGG
CTCTTTGGTCTGCTTATCCTCGACGAGTTCGATACCCAGC
AGGAGGCCCTTGCCGCGGACGTCCCCGACGTTGGGGTGCT
CTTTGACGTCCTCCAACTCGTACAGCAGGCGCTCGCCCAG
TTCTTTGGACCGCTCGATGAGCTTCTCGTTTTCCATGATC
TCGAGGTTCTTCAGGGCCAGCGCGCAGGCGGCAGGGTTGC
CGCCGAAGGTGTTGACATGGCGGAAGCGGTCGTAGTCGTC
GGAGCCGACGAAGGCCTCGTAGACCTCGCGGCGGACCGCG
GTGGCAGACAGCGGCAGGTAGGCCGAGGTGATACCCTTGG
CCATGGTGATAATGTCGGGCTTGACGCCGTAGTTCATGAA
GCCGAAGGGCTTGCCGGTGCGACCGAAGCCGCAGATGACC
TCGTCGCAGATCAGCAGGGCGCCGTGCTTTTCGCAGATCT
CTTTGACCTTTTCCATGTAGCCGTCCGGCGGCATCAGGAT
GCCACCACCGGTGATGATGGGTTCCATGATGACGCCGGCG
ACGGTCTGGGACAGCTCCCAGGTCATGACGCGGTCGATTT
CTTCGGCGGAGGCCAGGGTGTGCACGTCCTCGGGGTTGCG
ATAGGTGTCCGGAGGGGCCACGTGCAGGAAGCCCTGACCG
AGGGGCTCGTACTTGTACTTGCGCTGGGCCTGACCGGTCG
CGGCCAGGGCACCCATGGAGTTGCCGTGGTAGGCGCGGTA
GCGAGAGATGAACTTGTAGCGGCCGTGGTCACCCTTCTGC
TGGTGGTACTGGCGGGCGATCTTGAAGGCGGTTTCGTTGG
CCTCCGAGCCGGAGTTGGAGAAGAAGATGACGTACTCGTC
GTCCAGCCACTCGTTCAGCTTCTCGGCCAGCTTGATGGCG
GGGACGTGCGACTGCGTCAGCGGGAAGTACGGCATCTCTT

-continued

CCAGCTGCTCGAAGGCAGCGCGAGCCAGCTCTTTGCGGCC
GTAGCCGACGTTGACGCACCACAGGCCGGACATGCCGTCC
AGGTAGCGGTTGCCGTCGATGTCGGTGACCCACGCGCCTT
CGGCCTTGGTGATGATCAGGTTGGTCGGACTCGGAGCGGC
ACCGCGCATGGCGTGCCACAGGTACTTCTCGTCGGTTTTC
TTCAGGCTCTGGGTCTGCTCGGTGACCTGGACGATCATCA
GTTCCATCTTGATGAAGGTCTGGGTTGGAAAAAGGATGTT
AGTTCATTGTTTTACTTGATACTGGTGCGTGAGCAAGGAT
AAAGTTCAATATTATCTGCGTCGCAGCTCTCATCTTCGTT
TCTTGTTCAACATATTACTCCCCCGGAATTTTGGTATCTC
GCGCGCTAAAGTGTGCGCAGGAGGTATTTTCTGGGATAAG
TGGAAAGAAATGAAGATGAGATGTTCCAAATAATATTGAA
TCCTTTTCCTTGTCACATAGTAAATGTATAGGGTCATCAA
CTCACCTCGACAAGACTTGTCTTCCTAAACCTTCGGCGAT
CGTGGTAGGAAAATATCCTCGGTGGTGGTGGGCTTCGTTA
AAATCGGTTGTGCGGTCACGTGGTGTCCAGATTACCGAGT
CAGGCGTAGTGCGGGTGGACACTCGGATAATCAGCCCTCC
GGGTCCTCAGTCATGTGATGGTCTGCGGCTGAGGTCACGG
GATTTGCTGACTTTAACGGTTTCTTGGATACGTCAGTTTG
GTGCCTGCATCGCCAGGCATAGGCACGGCCCGGAAAAGCC
AGGCAGAAAGTACGACTAGGCCTAAAACCAACTAGACGAA
GTGGTCAATCCAGCCTCTCAGCATCGACGTCAACTTCGTC
ATCGTCATCATTTGCCGCCCTCTCATCCCTCGGCTCGCTG
TTGCTAATTATTGATTGAATAGCATGCGGGATAGGCGTCA
ATTATTAAATCGGCTATTGCAGAGGAAGGGTGAAATAATG
TTTCAAACCCTCACAGGCCACAGGTCGCCTCCTCCCGTCA
GTTATAAGAGGCAATGTGGATAGATCGATAATGGAGATAG
GGTGGTTGTCTGGAGGTCGACGGTATCGATAATAACTTCG
TATAGCATACATTATACGAAGTTATGAACGACTCCAGAAG
TGACTAAGCAACCGTAAACCGGAAGCAACAATCCGGCTCT
CATGGCAAAGATGGCATGTCCGGATTGCGGAGGAAAGATT
TGGCGTGTGCCTGACGGTTTTGTTCCACAAGGACCCTGTA
AACTTGGTGATGGTAATGAGGTGCTCTGGCCTTGATTGAG
CAAAAGTCAGCTCGCGGGGACTACGTGAGTTGATGGTGGA
GGATCATGTACTAAATAGAGCATACCTAGGGGATGGTGAA
CGGACGTCCAGGGTTCCGTAGAATTGTAACAACTCTACTC
GACTTGCTGCCCACTGGGGTATGTAAATACATGCCTTTTC
AAAGTTGCCGAGTGTACTAAATGGAGTGTATGTTTGGCCA
ATGTCATTTGGGAGGGGCCGGGAACCCTTTGGGACACCCG
CGGATGGGCTGGATCTCGGTCACTGGAGACATAGCCTAGT

-continued

GGTCTAGTAGTCTAGCAGCAGGACAGCTTCATGGTTAACC
CCACATGTGATCCTCCGTCCGGTTTCCGTAGTATATAATG
GACCTGAAGCTTCTCCCTCTCTCGATGCGGTTGAAACATA
AATTTGCTCATAACGTATGTCCATCTAACCCTTTCATTGT
TTCTTGACCACTGTCTCCTTTCTGGAAAAAAAAAGACTCT
GGTAAGTATGGGCCTAGGATCGAGCTACTGATCCCCCAAT
CCTTCCTAATCCCTCTGCCACTTGCCCCGACCTGTTCACC
GTGACCGTACCACCACCACCCCGCCCCCTCCTCAACTAAA
CCCCTCCCTTCCCCTCCCCCCTGATGTTTTCTCTTTTCTT
TAATCTGACTGTCACCTCCCTCTCTACTTCTTTTCCCTCA
ATTTTCTTCTCCTCTTCTTACTCTCTGTCATCTGTTTCGA
TACCCATACTAATCTCGCGTGCTTTTTCTTCACCTTCGTG
TATAGATTTGTCACAATCCCAAATTTCACCATGATTGAAC
AAGATGGATTGCACGCAGGTTCTCCGGCCGCTTGGGTGGA
GAGGCTATTCGGCTATGACTGGGCACAACAGACAATCGGC
TGCTCTGATGCCGCCGTGTTCCGGCTGTCAGCGCAGGGGC
GCCCGGTTCTTTTTGTCAAGACCGACCTGTCCGGTGCCCT
GAATGAACTGCAGGACGAGGCAGCGCGGCTATCGTGGCTG
GCCACGACGGGCGTTCCTTGCGCAGCTGTGCTCGACGTTG
TCACTGAAGCGGGAAGGGACTGGCTGCTATTGGGCGAAGT
GCCGGGGCAGGATCTCCTGTCATCTCACCTTGCTCCTGCC
GAGAAAGTATCCATCATGGCTGATGCAATGCGGCGGCTGC
ATACGCTTGATCCGGCTACCTGCCCATTCGACCACCAAGC
GAAACATCGCATCGAGCGAGCACGTACTCGGATGGAAGCC
GGTCTTGTCGATCAGGATGATCTGGACGAAGAGCATCAGG
GGCTCGCGCCAGCCGAACTGTTCGCCAGGCTCAAGGCGCG
CATGCCCGACGGCGATGATCTCGTCGTGACCCATGGCGAT
GCCTGCTTGCCGAATATCATGGTGGAAAATGGCCGCTTTT
CTGGATTCATCGACTGTGGCCGGCTGGGTGTGGCGGACCG
CTATCAGGACATAGCGTTGGCTACCCGTGATATTGCTGAA
GAGCTTGGCGGCGAATGGGCTGACCGCTTCCTCGTGCTTT
ACGGTATCGCCGCTCCCGATTCGCAGCGCATCGCCTTCTA
TCGCCTTCTTGACGAGTTCTTCTGAGCGGGACTCTGGGGT
TCGAAATGACCGACCAAGCGACGATCCACTTAACGTTACT
GAAATCATCAAACAGCTTGACGAATCTGGATATAAGATCG
TTGGTGTCGATGTCAGCTCCGGAGTTGAGACAAATGGTGT
TCAGGATCTCGATAAGATACGTTCATTTGTCCAAGCAGCA
AAGAGTGCCTTCTAGTGATTTAATAGCTCCATGTCAACAA
GAATAAAACGCGTTTCGGGTTTACCTCTTCCAGATACAGC
TCATCTGCAATGCATTAATGCATTGGACCTCGCAACCCTA
GTACGCCCTTCAGGCTCCGGCGAAGCAGAAGAATAGCTTA

-continued

GCAGAGTCATAACTTCGTATAGCATACATTATACGAAGTT
ATTGCAGCCCGGGACATGCTGGAAGGGATTTTCTGGCTCA
ATACCACGTCTGTATTTGACCCTTTCCAGACAGTTAATCC
GCTGCAGGAGGGCGAACTGTAGCTCCTCGTTCTCCTTGTA
GCGCTTGATCCAGTCTTTTTGGATGTTGCACTTGCTTGGC
CTATGCTTCTCATATAATCTTGCCCTGTCATAGAGACGAC
GTCTGAGATTGTAGCGTTCGTCTTTGATCACCCGGAGCCA
GATAGGCCTGAGTATATCTGACATTAGATCAAAGGGTCTG
TGGATAGTCTCCTTCAGCATCAGCGACGCATGTGACTCGC
ATGTCGGAGAGAGCTTGTGGGTGGTCATCTTTGATGGCGT
CCTCTGCTTTCCCTTGATTTTCGTTGATTGTTTTTCGAAA
GTTAAGTCTGGAAGTCAAGAGAATCCTTCTGCCAGACATT
ATATTTACGTATACTGACGTAGTAGAAACAGCGTCAGGAT
GAGGACATGGTGTGTGCTGGACCACGGAATCATAGTTCAT
CAGTATATTGGGTTGGACAAATAACGCTGAGCATGTATAT
GTCTTTACACACTATAAAAGCCAGCGAACGCCAATAAAAT
AGGGCATATTGATGTGAAAATATGACACCAGTTAAAAGCA
GTGTATTGATTTTATCTCTCTTCACCTCGGACCTATACTA
CCGTATACAAGACTCAACTTACTTCCAGATATAGTAATAT
ACACCCTATGGACGAACCAGCACAATAATTACAGCCAAAC
AACACCACCCAAATGGCATATTCCTAATCAGCACTAAGCA
CAAATACCACTGTCATCACAGCATAATCAATAAGAATCCC
AGACAACCGACTCACTCTGACTCACCTTACACAAACCCCC
AAGCAAAGCGCAGCCCAGAACCTCAGCCAACAATCGGGCA
ACGTACGGGGAAAGATTGGCCGATCCATGATGTCAGCAGC
CCTAACCCAAAGCGGACTAGCGCATACCGCCCCTCTGACT
CCGCCATCCCAGGGCTCGAGAAGCTTCCGTGGCGTCGATA
TAAATTCAGCGGGCCTTGAACATCCCTCCTTACGACACAC
CTCACGCGATCGATTTTGACACTCACACACCGCCACCCTC
ACATCCTCCACCCACACCACACCCCTTAATCAACCCACCA
TCACCGCTAGAACGTCTATCTCATCACCGACTTCTCATCC
ATCTTCAAAATGATCGTGCTGGTCACGGGCGCGACCGCCG
GTTTCGGCGAGTGCATCACCCGCCGCTTCATCCAGCAGGG
CCACAAGGTGATCGCTACCGGACGCCGCCAAGAGCGCCTC
CAAGAGCTGAAGGATGAGCTGGGCGACAACCTGTACATTG
CCCAGCTGGACGTGCGCAACCGGGCTGCCATCGAAGAAAT
GCTCGCCTCGCTGCCCGCCGAGTGGTGCAACATCGACATC
CTGGTCAACAACGCCGGTCTGGCCCTCGGCATGGAACCGG
CGCACAAGGCCAGCGTCGAGGACTGGGAAACCATGATCGA
CACCAACAACAAGGGACTCGTCTACATGACCCGCGCTGTG

-continued

```
CTGCCCGGCATGGTCGAGCGCAACCACGGCCACATCATCA

ACATCGGCTCCACCGCTGGCAGCTGGCCCTACGCTGGCGG

CAACGTCTATGGCGCGACCAAGGCGTTCGTCCGCCAGTTC

TCCCTGAACCTGCGCACCGACCTGCACGGCACCGCCGTCC

GCGTGACCGACATTGAGCCCGGTCTGGTCGGCGGCACCGA

GTTCAGCAACGTCCGCTTCAAGGGCGACGACGGCAAGGCC

GAGAAAACCTACCAGAACACCGTCGCTCTGACCCCTGAGG

ATGTCAGCGAGGCCGTCTGGTGGGTCAGCACTCTGCCCGC

GCACGTCAACATCAACACCCTCGAGATGATGCCCGTCACG

CAGTCCTACGCCGGCCTGAACGTCCACCGCCAATAGGACC

GATGGCTGTGTAGAAGTACTCGCCGATAGTGGAAACCGAC

GCCCCAGCACTCGTCCGAGGGCAAAGGAATAGAGTAGATG

CCGACCGGGATCCACTTAACGTTACTGAAATCATCAAACA

GCTTGACGAATCTGGATATAAGATCGTTGGTGTCGATGTC

AGCTCCGGAGTTGAGACAAATGGTGTTCAGGATCTCGATA

AGATACGTTCATTTGTCCAAGCAGCAAAGAGTGCCTTCTA

GTGATTTAATAGCTCCATGTCAACAAGAATAAAACGCGTT

TCGGGTTTACCTCTTCCAGATACAGCTCATCTGCAATGCA

TTAATGCATTGGACCTCGCAACCCTAGTACGCCCTTCAGG

CTCCGGCGAAGCAGAAGAATAGCTTAGCAGAGTCTATTTT

CATTTTCGGGAGACGAGATCAAGCAGATCAACGGTCGTCA

AGAGACCTACGAGACTGAGGAATCCGCTCTCTGACAGACG

GGCAATTGATTACGGGATCCCATTGGTTTAAAC
```

DETAILED DESCRIPTION

I. Abbreviations

3-HP: 3-hydroxypropionic acid
aat1: aspartate aminotransferase
ald3: malonate semialdehyde dehydrogenase 3
ald6: malonate semialdehyde dehydrogenase 6
BAPAT: β-alanine-pyruvate aminotransferase
cad1: cis-aconitate decarboxylase
CAP: citric acid production medium
DDR-EH: disk refining and enzymatic hydrolysis
CM: complete medium
DBTL: design-build-test-learn
elf3: elongation factor 3
eno1: alpha-enolase
gpdA: glyceraldehyde-3-phosphate dehydrogenase
HPDH (3-HPDH): 3-hydroxypropionate dehydrogenase
hph: hygromycin B phosphotransferase marker gene
KOH: potassium hydroxide
mct1: monocarboxylate transporter
MM: minimal medium
mRDM: modified production medium B
nat1: nourseothricin N-acetyl transferase
NaOH: sodium hydroxide
$NH_3$: ammonia
nptII: bacterial neomycin-resistance (nptII) marker gene
oahA: oxaloacetate hydrolase
PAND: aspartate 1-decarboxylase
PDA: potato dextrose agar
pyc: pyruvate carboxylase
RDM: production medium B
TE: trace elements
trpC: tryptophan C gene
uga2: succinate semialdehyde dehydrogenase

II. Summary of Terms

Unless otherwise noted, technical terms are used according to conventional usage. Definitions of many common terms in molecular biology may be found in Krebs et al. (eds.), *Lewin's genes XII*, published by Jones & Bartlett Learning, 2017. As used herein, the singular forms "a," "an," and "the," refer to both the singular as well as plural, unless the context clearly indicates otherwise. For example, the term "a gene" includes singular or plural genes and can be considered equivalent to the phrase "at least one gene." As used herein, the term "comprises" means "includes." Unless context clearly indicates otherwise, "about" refers to plus or minus 5% of a reference value. For example, "about" 100 refers to 95 to 105. It is further to be understood that any and all base sizes or amino acid sizes, and all molecular weight or molecular mass values, given for nucleic acids or polypeptides are approximate, and are provided for descriptive purposes, unless otherwise indicated. The sequences associated with the GenBank Accession numbers provided herein are incorporated herein by reference in their entireties (specifically the sequences available on Aug. 3, 2023).

Although many methods and materials similar or equivalent to those described herein can be used, particular suitable methods and materials are described herein. The materials, methods, and examples are illustrative only and not intended to be limiting. In case of conflict, the present specification, including explanations of terms, will control. To facilitate review of the disclosure, the following explanations of terms are provided:

3-HP β-alanine pathway: An artificial pathway for the production of 3-HP in fungi that includes aspartate decarboxylase (PAND), β-alanine pyruvate transaminase (BAPAT), and 3-HP dehydrogenase (HPDH) (see, e.g., Borodina et al. "Establishing a synthetic pathway for high-level production of 3-hydroxypropionic acid in *Saccharomyces cerevisiae* via β-alanine," *Metab Eng.* 27:57-64, 2015). In some examples, the PAND gene is from Tribolium castaneum. In some examples, the BAPAT gene is from *Bacillus cereus*. In some examples, the HPDH is from *Escherichia coli*. In some examples, one or more genes of the 3-HP β-alanine pathway are codon optimized for expression in a fungus, for example, in an *Aspergillus* species (e.g., *Aspergillus* pseudoterreus).

3-hydroxypropionic acid (3-HP or 3HP): A 3-hydroxy monocarboxylic acid that is propionic acid in which one of the hydrogens attached to the terminal carbon is replaced by a hydroxy group (see, PubChem CID 68152). It can be used in the production of chemicals, such as acrylic acid, malonic acid, acrylamide, 1,3-propanediol, and biodegradable polymers.

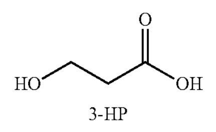

3-HP 3-hydroxypropionate dehydrogenase (HPDH): An enzyme that catalyzes the reduction of 3-oxopropanoate to 3-hydroxypropanoate:

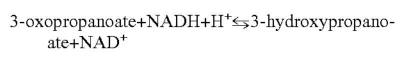

Expression of HPDH in a recombinant *Aspergillus niger* also expressing BAPAT and PAND (and in some examples also having a genetically inactivated ald6a gene and/or over-expressed pyc gene) results in a recombinant *A. niger* capable of producing 3-HP at higher titers.

An exemplary HPDH amino acid sequence is provided in SEQ ID NO: 3, however, additional HPDH sequences are also publicly available. For example, GenBank® Accession No: WP_000636571 discloses a HPDH protein sequence; GenBank® Accession Nos. FR729477.2 (nt 1005136 . . . 1005885) and CBY27203.1 disclose exemplary *Yersinia enterocolitica* subsp. *palearctica* Y11 HPDH nucleic acid and protein sequences, respectively; and GenBank® Accession Nos: CP004083.1 (complement(1399227 . . . 1399973)) and AJQ99264.1 disclose exemplary Enterobacteriaceae bacterium bta3-1 HPDH nucleic acid and protein sequences, respectively. In some examples, a nucleic acid sequence encoding HPDH is codon optimized for expression in *Aspergillus* (see, e.g., SEQ ID NO: 132). A practitioner will appreciate that HPDH sequences include variant sequences (such as allelic variants or homologs) that retain HPDH activity when expressed in *Aspergillus niger.*

Aspartate 1-decarboxylase (PAND): An enzyme that catalyzes the formation of β-alanine from aspartic acid in the following chemical reaction:

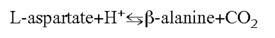

Expression of PAND in a recombinant *Aspergillus niger* also expressing BAPAT and HPDH (and in some examples also having a genetically inactivated ald6a gene and/or over-expressed pyc gene) results in a recombinant *A. niger* capable of producing 3-HP in high titers.

An exemplary PAND amino acid sequence is provided in SEQ ID NO: 1, however, additional PAND sequences are also publicly available. For example, GenBank® Accession Nos: NM_001102585.1 and NP_001096055.1 disclose Tribolium castaneum PAND nucleic acid and protein sequences, respectively; GenBank® Accession Nos. CP002745.1 (complement(4249351 . . . 4249824)) and AEK63458.1 disclose exemplary *Collimonas fungivorans* Ter331 PAND nucleic acid and protein sequences, respectively; and GenBank® Accession Nos: CP029034.1 (nt 1201611 . . . 1201994) and AWE15802.1 disclose exemplary *Bacillus* velezensis PAND nucleic acid and protein sequences, respectively. In some examples, a nucleic acid sequence encoding PAND is codon optimized for expression in *Aspergillus* (see, e.g., SEQ ID NO: 130). A practitioner will appreciate that PAND sequences include variant sequences (such as allelic variants or homologs) that retain PAND activity when expressed in *Aspergillus niger.*

β-alanine-pyruvate aminotransferase (BAPAT): An enzyme that catalyzes the following chemical reaction:

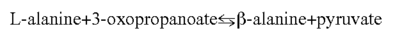

Expression of BAPAT in a recombinant *Aspergillus niger* also expressing PAND and HPDH (and in some examples also having a genetically inactivated ald6a gene and/or over-expressed pyc gene) results in a recombinant *A. niger* capable of producing 3-HP in high titers.

An exemplary BAPAT amino acid sequence is provided in SEQ ID NO: 2, however additional BAPAT sequences are also publicly available. For example, GenBank® Accession Nos: ACMS01000158.1 (complement(10606 . . . 11961)) and EEL86940.1 disclose *Bacillus cereus* AH1272 BAPAT nucleic acid and protein sequences, respectively; GenBank® Accession Nos. DF820429.1 (complement (241627 . . . 242967)) and GAK28710.1 disclose exemplary *Serratia liquefaciens* FK01 BAPAT nucleic acid and protein sequences, respectively; and GenBank Accession Nos: LGUJ01000001.1 complement (92812 . . . 94140) and KOY12524.1 disclose exemplary *Bradyrhizobium diazoefficiens* BAPAT nucleic acid and protein sequences, respectively. In some examples, a nucleic acid sequence encoding BAPAT is codon optimized for expression in *Aspergillus* (see, e.g., SEQ ID NO: 131). A practitioner will appreciate that BAPAT sequences include variant sequences (such as allelic variants or homologs) that retain BAPAT activity when expressed in *Aspergillus niger.*

Control: A reference standard. A control can be a positive or negative control. In some examples, the control is a historical control or standard reference value or range of values (such as a previously tested control sample or a group of samples that represent baseline or normal values). In some examples, the control is wild-type (unmodified) *A. niger*. In some examples, the control is *A. niger* expressing the 3-HP β-alanine pathway (absent further modifications, such as an exogenous nucleic acid encoding pyc and/or mct1).

A difference between a test sample and a control can be an increase or conversely a decrease. In some examples, the difference is statistically significant. In some examples, a difference is an increase relative to a control, for example, an increase of at least 5%, at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, or at least 500%. In other examples, a difference is a decrease relative to a control, for example, a decrease of at least 5%, at least 10%, at least 20%, at least 30%, at least 40%, at least 50%, at least 60%, at least 70%, at least 80%, at least 90%, at least 95%, at least 98%, or at least 99%.

Copy number: The number of copies of a particular gene in a particular genotype, for example, the number of copies of a gene (e.g., PAND, BAPAT, HPDH, pyc, and/or mct1) in a recombinant *A. niger* strain.

Detectable: Capable of having an existence or presence ascertained.

Exogenous: Originating from a different source. For example, a nucleic acid molecule that is exogenous to an organism (e.g., *Aspergillus niger*) is a nucleic acid that originated from a source other than the organism itself (e.g., a synthetic nucleic acid introduced into the *Aspergillus niger*). A cell including an exogenous nucleic acid is not, or excludes, any naturally occurring cell or organism. In some examples, the PAND, BAPAT, and/or HPDH nucleic acid or protein does not naturally occur in *Aspergillus niger*, and therefore are exogenous to *Aspergillus niger*. For example, PAND, BAPAT, and HPDH nucleic acid molecules introduced into an *Aspergillus niger* can be from another organism, such as a bacterial PAND, BAPAT, and HPDH sequence.

Expression cassette: A nucleic acid fragment designed for expression of a particular gene (or genes) in a host cell (e.g., *A. niger*). Expression cassettes can be included in a vector. An expression cassette can include regulatory elements, such as promoters and/or terminators.

Genetic inactivation or down-regulation: When used in reference to the expression of a nucleic acid molecule, such as a gene, gene inactivation refers to any process which results in a decrease in production of a gene product. A gene product can be RNA (such as mRNA, rRNA, tRNA, and structural RNA) or protein. Therefore, gene down-regulation or deactivation includes processes that decrease transcription of a gene or translation of mRNA. A mutation, such as a substitution, partial or complete deletion, insertion, or other variation, can be introduced into a gene sequence to significantly reduce (and in some cases eliminate) production of a gene product or renders the gene product substantially or completely non-functional.

For example, a genetic inactivation of an endogenous ald6a, ald6b, ald3, and/or oahA gene in *Aspergillus niger* results in the *Aspergillus* having non-functional or non-detectable ald6a, ald6b, ald3, and/or oahA protein, respectively. In some examples, genetic inactivation of an endogenous gene in *Aspergillus niger* (including a recombinant *Aspergillus niger* disclosed herein) increases production of 3-HP by the *Aspergillus niger*. Genetic inactivation is also referred to herein as a "functional deletion."

Increase or decrease: A positive (increase) or negative (decrease) difference relative to a reference value, such as a control. The difference can be a qualitative or quantitative. In some examples, the difference is statistically significant (e.g., P-Value less than 0.05 or 0.01). In some examples, the difference is an increase relative to a control of at least 5%, such as at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 500%, or greater than 500%. In some examples, the difference is a decrease relative to a control of at least 5%, such as at least 10%, at least 20%, at least 30%, at least 40%, at least 50%, at least 60%, at least 70%, at least 80%, at least 90%, at least 95%, at least 98%, or 100%.

Isolated or purified: An "isolated" or "purified" biological component (such as a nucleic acid, protein, or cell) is one that has been substantially separated from other biological components in the environment in which the component occurs, e.g., separated from other chromosomal and extra-chromosomal DNA and RNA, proteins and/or cells. Nucleic acids and proteins that have been "isolated" include nucleic acids and proteins purified by standard purification methods. The term also embraces nucleic acids and proteins prepared by recombinant expression in a host cell as well as chemically synthesized nucleic acids. An "isolated" microorganism (such as a recombinant *Aspergillus niger*) has been substantially separated or purified away from microorganisms of different types, strains, or species. Microorganisms can be isolated by a variety of techniques, such as serial culturing and/or using selection markers conferring resistance to certain chemicals, such as antibiotics.

Absolute purity or isolation is not required, it is intended as a relative term. Thus, for example, a purified/isolated protein, nucleic acid, or cell preparation is one in which the protein, nucleic acid, or cell is more enriched than the protein, nucleic acid, or cell is in its initial environment. In one example, a preparation is purified/isolated such that the protein, nucleic acid, or cell represents at least 50% of the total content of the preparation, such as at least 60%, at least 70%, at least 80%, at least 90%, at least 95%, at least 98%, or at least 99% pure. In some examples, an isolated, recombinant *Aspergillus niger* strain is at least 90% (for example, at least 95%, as at least 98%, at least 99%, or at least 99.99%) pure.

Malonate semialdehyde dehydrogenase (ald): An enzyme identified as potentially involved in metabolism of the 3-HP pathway (see, e.g., Pomraning et al., Front Bioeng Biotechnol 9:603832, 2021). Multiple malonate semialdehyde dehydrogenase homologs were identified in *A. niger*, including ald6a (Anald6a), ald6b (Anald6b), and ald3 (Anald3). The results disclosed herein show that while Anald6a is likely the major malonate semialdehyde dehydrogenase, all three (Anald6a, Anald6b, and Anald3) contribute to directing flux (precursor) away from 3-HP in *Aspergillus niger* (see, e.g., FIG. 2C). An exemplary genomic nucleic acid sequence of *A. niger* ald6a is provided as SEQ ID NO: 6. An exemplary genomic nucleic acid sequence of *A. niger* ald6b is provided as SEQ ID NO: 7. An exemplary genomic nucleic acid sequence of *A. niger* ald3 is provided as SEQ ID NO: 8.

Monocarboxylate transporter 1 (mct1): A monocarboxylate transporter and putative 3-HP transporter. An exemplary nucleic acid sequence encoding mct1 from *A. niger* is provided as SEQ ID NO: 129. An exemplary amino acid sequence of mct1 from *A. niger* is provided as SEQ ID NO: 137. A practitioner will appreciate that functional mct1 sequences include variant sequences (such as allelic variants or homologs) that retain mct1 activity when expressed in *Aspergillus niger.*

Microaerobic or oxygen limited condition: When oxygen demand of an organism is greater than the oxygen transfer rate from the gaseous to aqueous phase. In some examples, a dissolved oxygen content near zero (0-10% DO) in a reactor (e.g., an aerated reactor) is a microaerobic (oxygen limited) condition.

Mutation: A change in a nucleic acid sequence (such as a gene sequence) or amino acid sequence, for example as compared to a reference sequence (e.g., a wild-type or native sequence). In particular examples, a mutation is introduced into an endogenous ald6a, ald6b, ald3, and/or oahA gene in a recombinant *Aspergillus niger*, thereby rendering the gene(s) non-functional. Mutations can be introduced, for example using standard molecular biology methods. In particular examples, a mutation includes one or more nucleotide substitutions, deletions, insertions, or combinations thereof.

Oxaloacetate hydrolase (oahA): An enzyme involved in the production of oxalate in fungi. An exemplary nucleic acid sequence encoding oahA from *A. niger* is provided as SEQ ID NO: 9.

Operably linked: A nucleic acid sequence is "operably linked" when it is placed in a functional relationship with a second nucleic acid sequence. For instance, a promoter is operably linked to a coding sequence if the promoter affects the transcription or expression of the coding sequence. Generally, operably linked DNA sequences are contiguous and, where necessary to join two protein-coding regions, are in the same reading frame.

Overexpressed: An organism can be modified to overexpress a gene or gene product. An overexpressed gene or gene product is one that has increased expression/accumulation relative to the expression/accumulation of the gene or gene product in the organism prior to overexpression of the gene. For example, overexpression of pyc in *Aspergillus niger* results in increased expression/accumulation of pyc in the *Aspergillus niger* relative to the expression/accumulation of pyc prior to overexpression.

Promoter: A nucleic acid control sequence that directs transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. Constitutive promoters are often used to overexpress a nucleic acid in a host. In contrast, the activity of an "inducible promoter" is regulated by an external signal or molecule (for example, a transcription factor). Native and non-native promoters (i.e., endogenous and exogenous) can be used to drive expression of a gene, such as PAND, BAPAT, HPDH, pyc, and/or MCTL.

Exemplary promoters that can be used include but are not limited to: SV40 promoter, the CMV enhancer-promoter, the CMV enhancer/β-actin promoter, trpC promoter (trpCp), translation elongation factor 1 gene promoter (tef1p), mbfA promoter (mbfAp), ubi4 gene promoter (ubi4p), ubi1S27 promoter (ubi1S27p or ubiS27p), glyceraldehyde-3-phosphate dehydrogenase promoter (gpdAp), and enolase promoter (eno1p). In some examples, the promoter is an *Aspergillus niger* promoter (e.g., *Aspergillus niger* gpdAp, eno1p, teflp, ubi4p, ubi1S27p or mbfAp). Both constitutive and inducible promoters can be used in the fungi and methods provided herein (see e.g., Bitter et al., Methods in Enzymology 153:516-544, 1987). Also included are promoter elements which are sufficient to render promoter-dependent gene expression controllable for cell-type specific, tissue-specific, or inducible by external signals or agents; such elements may be located in the 5' or 3' regions of the gene. Promoters produced by recombinant DNA or synthetic techniques can also be used to provide for transcription of the nucleic acid sequences.

Pyruvate carboxylase (pyc): An enzyme that catalyzes the conversion of pyruvate to oxaloacetate. Typically, yeast have two pyruvate carboxylase genes, pyc1 and pyc2, however, *Aspergillus niger* only has one pyruvate carboxylase gene, which is referred to as "pyc." Reference to "pyc2" as used herein a strain name (e.g., An3HP9/pyc2/ald6aD/3HP-6) refers to a particular transgenic strain expressing *A. niger* pyc (pyc strain 2). An exemplary amino acid sequence of *Aspergillus niger* pyc is provided as SEQ ID NO: 5. An exemplary nucleic acid sequence encoding *Aspergillus niger* pyc is provided as SEQ ID NO: 133. A practitioner will appreciate that functional pyc sequences include variant sequences (such as allelic variants or homologs) that retain pyc activity when expressed in *Aspergillus niger.*

Recombinant: A nucleic acid or protein that has a sequence made by an artificial combination of two otherwise separated segments of sequence (e.g., a "chimeric" sequence). This artificial combination can be accomplished by chemical synthesis or by manipulation of isolated segments of nucleic acids, for example, by standard molecular biology techniques (e.g., cloning; see, Sambrook et al. (ed.), Molecular Cloning: A Laboratory Manual, 3d ed., vol. 1-3, Cold Spring Harbor Laboratory Press, Cold Spring Harbor, NY, 2001). A recombinant or transformed organism or cell, such as a recombinant *Aspergillus niger*, is one that includes at least one exogenous nucleic acid molecule, such as an exogenous nucleic acid molecule encoding one or more of PAND, BAPAT, HPDH, pyc, and/or MCT1.

Regulatory element: A term that includes promoters, enhancers, internal ribosomal entry sites (IRES), and other expression control elements (e.g., transcription termination signals, such as polyadenylation signals and poly-U sequences). Regulatory elements include those that direct constitutive expression of a nucleotide sequence in many types of host cells and those that direct expression of the nucleotide sequence only in certain host cells (e.g., tissue-specific regulatory sequences). Regulatory elements may also direct expression in a temporal-dependent manner, such as in a cell-cycle dependent or developmental stage-dependent manner, which may or may not also be tissue or cell-type specific.

Sequence identity/similarity: The degree of similarity between amino acid or nucleic acid sequences. Sequence identity is frequently measured in terms of percentage identity (or percent identity); the higher the percentage, the more similar the two sequences are. Homologs of a polypeptide (or nucleotide sequence) will possess a relatively high degree of sequence identity when aligned using standard methods.

Methods of alignment of sequences for comparison have been described. The NCBI Basic Local Alignment Search Tool (BLAST) tool is often used and is available from several sources, including the National Center for Biotechnology Information (blast.ncbi.nlm.nih.gov/Blast.cgi). Various types of BLAST are available, for example, blastp, blastn, blastx, tblastn and tblastx. BLASTN is used to compare nucleic acid sequences, while BLASTP is used to compare amino acid sequences. To compare two nucleic acid sequences, the options can be set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\B12seq -i c:\seq1.txt -j c:\seq2.txt -p blastn -o c:\output.txt -q -1 -r 2. In some examples, percent sequence identity is determined by using BLAST with default parameters. Further description of how to determine sequence identity using various blast programs is available on the NCBI website and other resources.

Other various programs and alignment algorithms are also described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, 80%, 85%, 90%, 95%, or 99% sequence identity.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, 70%, 80%, 90%, 95%, 98%, or 99% sequence identity determined by this method.

Sequence identity ranges are provided for guidance only; it is possible that strongly significant homologs could be obtained that fall outside the ranges provided. Thus, a variant PAND, BAPAT, HPDH, or other protein or nucleic acid molecule disclosed herein can have at least 80%, at least 85%, at least 90%, at least 91%, at least 92%, at least 93%, at least 94%, at least 95%, at least 96%, at least 97%, at least 98% or at least 99% sequence identity to the SEQ ID NOs: and/or GenBank® Accession Nos. provided herein.

Transformed: A cell, such as a fungal cell, into which a nucleic acid molecule has been introduced, for example by molecular biology methods. As used herein, the term transformation encompasses all techniques by which a nucleic acid molecule might be introduced into such a cell, including, but not limited to chemical methods (e.g., calcium-polyethylene glycol transfection), physical methods (e.g., electroporation, microinjection, particle bombardment), fusion (e.g., liposomes), receptor-mediated endocytosis (e.g., DNA-protein complexes, viral envelope/capsid-DNA complexes), by biological infection by recombinant *Agrobacterium tumefaciens* or viruses, such as recombinant viruses, etc. In one example, a protoplast transformation provided herein is used, such as in Example 1.

Variant: A nucleic acid or protein that varies in sequence, but retains a desired function. A degenerate variant refers to a nucleic acid sequence variant due to degeneracy (redundancy) of the genetic code. Thus, while the nucleic acid sequence of degenerate variants differ, they encode the same amino acid sequence.

Vector: A nucleic acid molecule that can be introduced into a host cell (for example, by transformation), thereby producing a transformed host cell. Recombinant DNA vectors are vectors having recombinant DNA. A vector may include nucleic acid sequences that permit it to replicate in the host cell, such as an origin of replication. A vector can include a promoter, and/or selectable marker genes, and other genetic elements. A vector can include one or more genes (e.g., PAND, BAPAT, HPDH, pyc, and/or MCT1) and/or a sequence used to genetically inactivate a gene (e.g., ald6a, ald6b, ald3, and/or oahA). A vector can transduce, transform or infect a cell, thereby causing the cell to express nucleic acids and/or proteins. A vector optionally includes materials to aid in achieving entry of the nucleic acid into the cell, such as a viral particle, liposome, protein coating or the like. In one example, a vector is a plasmid, such as a plasmid exogenous to the cell or organism into which it is introduced.

II. Overview

The biosynthesis of 3-HP as a secreted monomer or an intracellular polymer has been examined in a variety of microorganisms and from various feedstocks. Production of monomeric 3-HP as a precursor for commodity chemical production has been proposed and developed primarily using sugars or glycerol as feedstocks, both of which have the potential to offer economic and green-house gas emission benefits compared to petroleum derived feedstocks (Bhagwat et al., ACS Sustain Chem Eng 9(49):16659-69, 2021). Production of 3-HP from glycerol as a feedstock using bacterial hosts has made substantial gains toward economic viability (Chen et al., PloS one 12(9):e0185734, 2017; Wu et al., PloS one 14(9):e0222143, 2019), however, high-yield production from sugar feedstocks has been more challenging (Ji et al., Front Microbiol 9:2185, 2018) with only modest yields achieved in hosts that require expensive nutrient supplements and are limited to production of 3-hydroxypropionate near neutral pH production conditions rather than 3-hydroxypropionic acid. Therefore, engineering the β-alanine pathway in the filamentous fungal hosts *A. pseudoterreus* and *A. niger* is an attractive option. The production can be scaled for industrial production of organic acids at acidic pH (<2.0) and has the capability of converting mixed sugar feedstocks with minimal nutrients and without pH neutralization requirement. After several DBTL (design-build-test-learn) cycles and culture optimizations, the 3-HP production in the best *A. niger* transgenic strain reached 36.0 g/l with the DDR-EH derived sugars from corn stover.

In the first design-build-test-learn (DBTL) cycle, the β-alanine pathway was functionally expressed in the filamentous fungus *A. pseudoterreus* and genes related to 3-HP degradation enzymes (Apald6, Apald3, Apuga2) and monocarboxylate transport across the plasma membrane (Apmct1) were identified via transcriptomic and proteomic analyses (Pomraning et al., Front Bioeng Biotechnol 9:603832, 2021). Next, the process was improved by the transfer of the β-alanine pathway into the *A. niger*, citric acid production strain (Perlman et al., Arch Biochem Biophys 11:123-9, 1946). The same transgene expression cassette used in *A. pseudoterreus* was randomly chromosomally integrated into *A. niger* and conferred a higher initial titer of 3-HP. Analysis of both species revealed that increased 3-HP yield correlates to copy number and expression level of the β-alanine pathway, which may explain the higher initial titers in the *A. niger* strains. Production of other organic acids, such as citric acid was below the detection limit in *A. niger* allowing more carbon to be routed toward 3-HP production.

The effects of increasing the intracellular pool of precursor metabolites such as oxaloacetate and aspartic acid on 3-HP production was first evaluated by increasing the expression of aat1, or pyc in the An3HP9 transgenic strain with about 30 to 90% improvements in 3-HP titer in the selected transgenic strains. Elimination of carbon fluxes competing with β-alanine pathway metabolic intermediates oxaloacetate, malonic semialdehyde, and glutamate/α-ketoglutarate was also examined in transgenic strain An3HP9/pyc2. All exhibited positive effects on 3-HP production and 83% improvement in titer of 3-HP production was observed with the disruption of ald6a gene. Previously significant improvements in flux toward 3-HP in *A. pseudoterreus* were observed after disruption of Apald6 (Pomraning et al., Front Bioeng Biotechnol 9:603832, 2021) that are consistent with results from the homolog in *Candida albicans* (Otzen et al., J Biol Chem 289(12):8151-69, 2014). This highlights that while ald6a may be the major contributor to the pathway competition, *A. niger* encodes at least three enzymes capable of metabolizing the 3-HP precursor malonic semialdehyde that may need to be simultaneously disrupted to maximize yield of 3-HP.

To test for the possibility of reactions limiting the final steps in conversion of pyruvate to 3-HP, the expression level of the heterologous enzymes was increased in the β-alanine pathway in the An3HP9/pyc2/ald6aA strain by increasing the chromosomally integrated copy-number of the pathway from 12 to 27. MCT1, a putative 3-HP transporter (Pomraning et al., Front Bioeng Biotechnol 9:603832, 2021), was overexpressed to test whether export may be limiting. In both cases, increased expression improved the yield of 3-HP suggesting that expression level of enzymes for 3-HP production is still limiting in the engineered strains and highlighting the need for novel metabolic engineering tools in *Aspergillus* species capable of increasing expression level of enzymes orders of magnitude beyond what is currently possible.

In addition to modifications of pathway enzymes in the transgenic strains, culture conditions play a role in directing metabolic flux toward 3-HP. The initial pH in *A. niger* cultures for citric acid production is 2.0 and manganese is limited to 10 ppb (Dai et al., Appl Environ Microbiol 70(4):2474-85, 2004). Here, an initial pH ranges from 3.4 to 2 did not significantly affect 3-HP yield in the An3HP9 strain though the spore germination frequency is higher at pH 3.4. 3-HP is produced in CAP medium which supports overflow metabolism, but to a lesser extent than in the mRDM medium. Therefore, the effects of the mRDM medium on 3-HP production was further optimized by alternation of individual components. Maintenance of manganese at a very low concentration (~10 ppb) is required to support high-yield production of citric acid in *A. niger* (Dai et al., Appl Environ Microbiol 70(4):2474-85, 2004; Karaffa et al., Microorganisms 9(6):1267, 2021) as well as itaconic acid in *A. pseudoterreus* (Karaffa et al., Appl Microbiol Biotechnol 99(19):7937-44, 2015). In this study, however, 100-fold higher concentrations of manganese in the culture medium support 3-HP production highlighting the difference in metabolism between production of 3-HP and the organic acids typically produced by these organisms. Tolerance, or even a requirement for higher concentrations of trace elements for 3-HP production avoids some of typical challenges with organic acid production by Aspergilli whereby micro-nutrients leaching from metal fermentation vessels or present as contaminants in feedstock sugars negatively impact yield (Karaffa et al., Microorganisms 9(6):1267, 2021).

A component of economically viable 3-HP production is utilization of inexpensive feedstocks (Werpy et al., National Renewable Energy Lab., Golden, CO (US), 2004). The 3-HP production on a DDR-EH derived sugars from corn stover was evaluated and optimized with the higher 3-HP production transgenic strains. Raw DDR-EH requires supplementation macro-nutrients (nitrogen and phosphate) to support growth and 3-HP production by *A. niger*, but that the trace elements added to RDM can be eliminated as an additive to reduce cost. The optimal temperature for 3-HP production was around 34° C., which is consistent with optimal temperatures for enzyme activities of PAND (50° C.) of *T. castaneum* (Wang et al., J Ind Microbiol Biotechnol 47(6-7):465-74, 2020), BAPAT (35° C.) of *B. cereus* (Nakano et al., J Biochem 81(5):1375-81, 1977), and HPDH (37° C.) of *E. coli* K12-TG1 (Guyot et al., MicrobiologyOpen 3(1):52-63, 2014). Increasing the concentration of $(NH_4)_2SO_4$ to the optimal level in RDM supported more growth but reduced the yield of 3-HP in DDR-EH indicating a lower concentration of nitrogen can be used to further reduce production costs.

Engineering efforts to produce 3-HP in fungi have demonstrated modest yields from pure glucose and xylose but typically supplement with vitamins (Kildegaard et al., Microb Cell Fact 15(1):1-13, 2016; Borodina et al., Metab Eng 27:57-64, 2015; Takayama et al., Microb Cell Factories 17(1):1-11, 2018; Kildegaard et al., Metab Eng Commun 2:132-6, 2015). Efforts have been made to produce 3-HP in the yeast *S. cerevisiae* in acidic conditions below the pKa of 3-HP, however yield was nearly half that achieved at pH 5 (Borodina et al., Metab Eng 27:57-64, 2015). Engineering efforts to produce 3-HP from mixed sugars in bacteria (*E. coli* and *C. glutamicum*) have also been successful but typically require growth at neutral pH and supplementation with vitamins and a complex nutrient source such as yeast extract or corn-steep liquor (Chen et al., Metab Eng 39:151-8, 2017; Heo et al., Bioresource Technol 285:121320, 2019; Lee et al., Bioresour Technol 299:122600, 2020; Jung et al., Bioresour Technol 198:709-16, 2015). Production of 3-HP using *A. niger* alleviates many of the economic issues presented by model yeast and bacterial hosts by eliminating the need to supplement with costly vitamins and complex nutrients and allowing for production as a free acid amenable to low-cost purification strategies.

Results from a DBTL cycle comparing multiple species and strains in conjunction with optimization of cultivation conditions dramatically increased the yield of 3-HP to 48% of the no-growth theoretical yield from a corn-stover feedstock. This work establishes *Aspergillus* species as a platform for commercial production of renewable 3-HP as a precursor for a variety of fossil-derived chemicals including 1,3-propanediol, acrylic acid, methyl acrylate, acrylamide, and acrylonitrile. In addition, fermentation conditions were investigated, and it was determined that fermentation at 34° C. under acidic pH (pH 2) and microaerobic conditions provided optimal 3-HP production. It was unexpected that low oxygen availability would be ideal as this is not the case for established organic acid fermentations with *Aspergillus* species. In addition, high production at very acidic pH is also unexpected as this condition is typically toxic for most organisms.

III. Recombinant *Aspergillus niger*

Disclosed herein are recombinant *Aspergillus niger* including a 3-HP β-alanine pathway, which are capable of producing 3-hydroxypropionic acid (3-HP). The recombinant *Aspergillus niger* includes one or more exogenous nucleic acid molecules encoding aspartate 1-decarboxylase (PAND), β-alanine-pyruvate aminotransferase (BAPAT), and 3-hydroxypropionate dehydrogenase (HPDH). In some examples, one exogenous nucleic acid molecule encodes all of PAND, BAPT, and HPDH. In some examples, PAND, BAPT, and HPDH are encoded on separate exogenous nucleic acid molecules.

The copy number of each of PAND, BAPT, and HPDH in the recombinant *Aspergillus niger* is independently about 1 to about 80. Thus, in a non-limiting example, the copy number of PAND can be about 26, the copy number of BAPT can be about 29, and the copy number of HPDH can be about 25. In some examples, the copy number of PAND, BAPT, and HPDH are the same, or about the same, for example, all of PAND, BAPT, and HPDH each have a copy number of about 30. In some examples, the copy number of each of PAND, BAPT, and/or HPDH independently is about 5 to about 80, for example, about 5 to about 80, about 10 to about 80, about 15 to about 80, about 20 to about 80, about 25 to about 80, about 30 to about 80, about 35 to about 80, about 40 to about 80, about 45 to about 80, about 50 to about 80, about 60 to about 80, about 70 to about 80, about 5 to about 60, about 10 to about 60, about 15 to about 60, about 20 to about 60, about 25 to about 60, about 30 to about 60, about 35 to about 60, about 40 to about 60, about 45 to about 60, about 50 to about 60, about 5 to about 50, about 10 to about 50, about 15 to about 50, about 20 to about 50, about 25 to about 50, 30 to about 50, about 35 to about 50, about 40 to about 50, about 45 to about 50, about 5 to about 45, about 10 to about 45, about 15 to about 45, about 20 to about 45, about 25 to about 45, about 30 to about 45, about 35 to about 45, about 40 to about 45, about 5 to about 40, about 10 to about 40, about 15 to about 40, about 20 to about 40, about 25 to about 40, about 30 to about 40, about 35 to about 40, about 5 to about 35, about 10 to about 35, about 15 to about 35, about 20 to about 35, about 25 to about 35, about 30 to about 35, about 5 to about 30, about 10 to about 30, about 15 to about 30, about 20 to about 30, about 25 to about 30, about 5 to about 25, about 10 to about 25, about 15 to about 25, about 20 to about 25, about 5 to about 20, about 10 to about 20, about 15 to about 20, or about 12 to about 27. In some examples, the copy number is about 12 to about 27. In some examples, the copy number is about 25 to about 29.

In some examples, the copy number of each of PAND, BAPT, and/or HPDH independently is at least 5, for example, at least 7, at least 10, at least 12, at least 15, at least 20, at least 25, at least 27, at least 30, at least 35, at least 40, at least 45, at least 50, or more. In a non-limiting example, the copy number of each of PAND, BAPT, and HPDH is at least 12. In some examples, the copy number is about 5, about 10, about 12, about 15, about 20, about 25, about 26, about 27, about 29, about 30, about 35, about 40, about 45, or about 50. In a non-limiting example, the copy number for each of PAND, BAPT, and HPDH is about 27.

The PAND, BAPT, and/or HPDH encoded by the one or more exogenous nucleic acid molecules can be prokaryotic or eukaryotic in origin. In some examples, the PAND, BAPT, and/or HPDH nucleic acid molecules are from an animal (e.g., insect) or bacteria. In a non-limiting example, the PAND coding sequence is from Tribolium castaneum, the BAPAT coding sequence is from *Bacillus cereus*, and/or the HPDH coding sequence is from *Escherichia coli*. In a further non-limiting example, the PAND is from Tribolium castaneum, the BAPAT is from *Bacillus cereus*, and the HPDH is from *Escherichia coli*. In some examples, the one or more exogenous nucleic acids encoding PAND, BAPT, and/or HPDH are codon optimized for expression in a fungi, for example, in *Aspergillus*. In some examples, the PAND, BAPT, and HPDH coding sequences are optimized for expression in an *Aspergillus* species.

In some examples, the PAND amino acid sequence comprises at least 80% sequence identity to SEQ ID NO: 1, for example, at least 85%, at least 90%, at least 95%, at least 98%, at least 99%, or 100% sequence identity to SEQ ID NO: 1. In a non-limiting example, the PAND amino acid sequence comprises at least 95% sequence identity to SEQ ID NO: 1. In a further non-limiting example, the PAND amino acid sequence comprises at least 98% sequence identity to SEQ ID NO: 1. In some examples, the PAND amino acid sequence comprises or consists of SEQ ID NO: 1.

In some examples, the exogenous nucleic acid molecule encoding PAND comprises at least 80% sequence identity to SEQ ID NO: 130, for example, at least 85%, at least 90%, at least 95%, at least 98%, at least 99%, or 100% sequence identity to SEQ ID NO: 130. In a non-limiting example, the exogenous nucleic acid molecule encoding PAND comprises at least 95% sequence identity to SEQ ID NO: 130. In a further non-limiting example, the exogenous nucleic acid molecule encoding PAND comprises at least 98% sequence identity to SEQ ID NO: 130. In some examples, the exogenous nucleic acid molecule encoding PAND comprises or consists of SEQ ID NO: 130, or a degenerate variant thereof.

In some examples, the BAPAT amino acid sequence comprises at least 80% sequence identity to SEQ ID NO: 2, for example, at least 85%, at least 90%, at least 95%, at least 98%, at least 99%, or 100% sequence identity to SEQ ID NO: 2. In a non-limiting example, the BAPAT amino acid sequence comprises at least 95% sequence identity to SEQ ID NO: 2. In a further non-limiting example, the BAPAT amino acid sequence comprises at least 98% sequence identity to SEQ ID NO: 2. In some examples, the BAPAT amino acid sequence comprises or consists of SEQ ID NO: 2.

In some examples, the exogenous nucleic acid molecule encoding BAPAT comprises at least 80% sequence identity to SEQ ID NO: 131, for example, at least 85%, at least 90%, at least 95%, at least 98%, at least 99%, or 100% sequence identity to SEQ ID NO: 131. In a non-limiting example, the exogenous nucleic acid molecule encoding BAPAT comprises at least 95% sequence identity to SEQ ID NO: 131. In a further non-limiting example, the exogenous nucleic acid molecule encoding BAPAT comprises at least 98% sequence identity to SEQ ID NO: 131. In some examples, the exogenous nucleic acid molecule encoding BAPAT comprises or consists of SEQ ID NO: 131, or a degenerate variant thereof.

In some examples, the HPDH amino acid sequence comprises at least 80% sequence identity to SEQ ID NO: 3, for example, at least 85%, at least 90%, at least 95%, at least 98%, at least 99%, or 100% sequence identity to SEQ ID NO: 3. In a non-limiting example, the HPDH amino acid sequence comprises at least 95% sequence identity to SEQ ID NO: 3. In a further non-limiting example, the HPDH amino acid sequence comprises at least 98% sequence identity to SEQ ID NO: 3. In some examples, the HPDH amino acid sequence comprises or consists of SEQ ID NO: 3.

In some examples, the exogenous nucleic acid molecule encoding HPDH comprises at least 80% sequence identity to SEQ ID NO: 132, for example, at least 85%, at least 90%, at least 95%, at least 98%, at least 99%, or 100% sequence identity to SEQ ID NO: 132. In a non-limiting example, the exogenous nucleic acid molecule encoding HPDH comprises at least 95% sequence identity to SEQ ID NO: 132. In a further non-limiting example, the exogenous nucleic acid molecule encoding HPDH comprises at least 98% sequence identity to SEQ ID NO: 132. In some examples, the exogenous nucleic acid molecule encoding HPDH comprises or consists of SEQ ID NO: 132, or a degenerate variant thereof.

The PAND, BAPAT, and HPDH can all be encoded on a single exogenous nucleic acid molecule. In some examples, a single exogenous nucleic acid molecule encoding PAND, BAPAT, and HPDH comprises at least 80% sequence identity to SEQ ID NO: 4, for example, at least 85%, at least 90%, at least 95%, at least 98%, at least 99%, or 100% sequence identity to SEQ ID NO: 4. In a non-limiting example, the single exogenous nucleic acid molecule comprises at least 95% sequence identity to SEQ ID NO: 4. In a further non-limiting example, the exogenous nucleic acid molecule comprises at least 98% sequence identity to SEQ ID NO: 4. In some examples, the single exogenous nucleic acid molecule comprises or consists of SEQ ID NO: 4, or a degenerate variant thereof. In some examples, a single exogenous nucleic acid molecule encoding PAND, BAPAT, and HPDH comprises at least 80% sequence identity to SEQ ID NO: 142, for example, at least 85%, at least 90%, at least 95%, at least 98%, at least 99%, or 100% sequence identity to SEQ ID NO: 142. In a non-limiting example, the single exogenous nucleic acid molecule comprises at least 95% sequence identity to SEQ ID NO: 142. In a further non-limiting example, the exogenous nucleic acid molecule comprises at least 98% sequence identity to SEQ ID NO: 142. In some examples, the single exogenous nucleic acid molecule comprises or consists of SEQ ID NO: 142, or a degenerate variant thereof.

In some examples, the recombinant *Aspergillus niger* includes a nucleic acid molecule having at least 90% sequence identity to SEQ ID NO: 4, and a nucleic acid molecule having at least 90% sequence identity to SEQ ID NO: 142. In some examples, the recombinant *Aspergillus niger* includes a nucleic acid molecule having at least 95% sequence identity to SEQ ID NO: 4, and a nucleic acid molecule having at least 95% sequence identity to SEQ ID NO: 142. In some examples, the recombinant *Aspergillus niger* includes a nucleic acid molecule comprising SEQ ID NO: 4, and a nucleic acid molecule comprising SEQ ID NO: 142. In some examples, the recombinant *Aspergillus niger* includes at least 10 copies (e.g., at least 11, at least 12, at least 13, at least 14, at least 15, at least 16, etc.) of a nucleic acid molecule comprising SEQ ID NO: 4, and at least 10 copies (e.g., at least 11, at least 12, at least 13, at least 14, at least 15, at least 16, etc.) of a nucleic acid molecule comprising SEQ ID NO: 142. In some examples, the recombinant *Aspergillus niger* includes about 10 to about 15 copies of a nucleic acid molecule comprising SEQ ID NO: 4, and about 10 to about 15 copies of a nucleic acid molecule comprising SEQ ID NO: 142. In a non-limiting example, the recombinant *Aspergillus niger* includes about 12 copies of a nucleic acid molecule comprising SEQ ID NO: 4, and about 14 copies of a nucleic acid molecule comprising SEQ ID NO: 142.

In some examples, the PAND, BAPAT, and HPDH are encoded by two or more separate exogenous nucleic acid molecules, such as 2 or 3 separate exogenous nucleic acid molecules.

The recombinant *Aspergillus niger* can include additional genetic modifications, such as an inactivated endogenous gene (a gene native to *Aspergillus niger*), or include additional exogenous nucleic acid molecules (e.g., encoding additional genes). An inactivated gene includes gene deletions or other genetic modifications that prevent or decrease the production of a functional gene product (e.g., a genetic modification that results in an early stop codon, or a modification that disrupts a binding or active site of an enzyme). A 100% decrease is not required. In some examples, an inactivated gene reduces expression of its corresponding protein by at least 50%, at least 75%, at least 90%, at least 95%, at least 99%, at least 99.9% or even 99.99%. Genes can be inactivated by known methods, such as the cre/lox system, or a genome editing system (e.g., clustered regularly interspaced short palindromic repeats)/Cas (CRISPR/Cas) systems, transcription activator like effector nuclease (TALEN) systems, or zinc finger nuclease (ZFN) systems). In some examples, an endogenous ald6a, ald6b, ald3, and/or oahA gene is inactivated in the recombinant *Aspergillus niger*. Exemplary genomic sequences of *Aspergillus niger* ald6a, ald6b, ald3, and oahA are provided herein. An inactivated gene can result in a gene that is not present or does not produce a functional product (e.g., a protein encoded by the gene). In some examples, an endogenous ald6a, ald6b, ald3, and/or oahA gene is not present or does not produce a functional product in the recombinant *Aspergillus niger*. An *Aspergillus niger* having an inactivated gene can be identified using known methods, for example, PCR or a nucleic acid hybridization technique (e.g., Northern and Southern analysis) can be used to confirm that a recombinant *A. niger* includes a genetically inactivated gene. In one example, real-time reverse transcription PCR (qRT-PCR) is used to detect and quantify messenger RNA (mRNA), such as mRNA of ald6a, ald6b, ald3, and/or oahA, to determine whether ald6a, ald6b, ald3, and/or oahA is inactivated. Known biochemical techniques can be used to detect a decrease in functional protein products (e.g., detect whether a protein product (e.g., enzyme) is functional or non-functional).

In some examples, inactivating an endogenous ald6a, ald6b, ald3, and/or oahA gene in the recombinant *Aspergillus niger* increases 3-HP production, for example, by at least 10%, at least 20%, at least 30%, at least 40%, at least 50%, at least 60%, at least 70%, at least 80%, at least 90%, at least 100%, at least 150%, at least 200%, at least 250%, at least 300%, at least 400%, at least 500%, or more relative to a control. In some examples, inactivating an endogenous ald6a, ald6b, ald3, and/or oahA gene in the recombinant *Aspergillus niger* increases 3-HP production by 10% to 500%, for example, by 10% to 400%, 10% to 300%, 10% to 200%, 10% to 100%, 10% to 90%, 10% to 80%, 10% to 70%, 10% to 60%, 10% to 50%, 10% to 40%, 10% to 30%, 10% to 25%, 20% to 400%, 20% to 300%, 20% to 200%, 20% to 100%, 20% to 90%, 20% to 80%, 20% to 70%, 20% to 60%, 20% to 50%, 20% to 40%, 20% to 30%, 20% to 25%, 30% to 400%, 30% to 300%, 30% to 200%, 30% to 100%, 30% to 90%, 30% to 80%, 30% to 70%, 30% to 60%, 30% to 50%, 30% to 40%, 40% to 400%, 40% to 300%, 40% to 200%, 40% to 100%, 40% to 90%, 40% to 80%, 40% to 70%, 40% to 60%, or 40% to 50% relative to a control. In a non-limiting example, inactivating an endogenous ald6a gene in the recombinant *Aspergillus niger* increases 3-HP production by about 40 to 50% relative to the recombinant *Aspergillus niger* with an unmodified (WT) ald6a gene.

In some examples, the recombinant *Aspergillus niger* further includes one or more exogenous nucleic acid molecules encoding a pyruvate carboxylase (e.g., pyc), aspartate aminotransferase (e.g., awl), and/or monocarboxylate transporter (e.g., mct1). In some examples, an exogenous nucleic acid encoding pyc, aat1, and/or mct1 is a recombinant nucleic acid molecule. In some examples, an exogenous nucleic acid encoding pyc, aat1, and/or mct1 results in increased expression (overexpression) of pyc, aat1, and/or mct1, respectively, in the recombinant *Aspergillus niger*. Genes can be overexpressed, for example, by operably linking a nucleic acid encoding the gene to a constitutive promoter. In particular examples, ald6a is not present or does not produce a functional product and pyc and/or aat1 is overexpressed in the recombinant *Aspergillus niger.*

In some examples, further including one or more exogenous nucleic acid molecules encoding a pyruvate carboxylase (e.g., pyc), aspartate aminotransferase (e.g., aat1), or monocarboxylate transporter (e.g., mct1) in the recombinant

*Aspergillus niger* increases 3-HP production, for example, by at least 10%, at least 20%, at least 30%, at least 40%, at least 50%, at least 60%, at least 70%, at least 80%, at least 90%, at least 100%, at least 150%, at least 200%, at least 250%, at least 300%, at least 400%, at least 500%, or more relative to a control. In some examples, further including one or more exogenous nucleic acid molecules encoding a pyruvate carboxylase (e.g., pyc), aspartate aminotransferase (e.g., aat1), or monocarboxylate transporter (e.g., mct1) in the recombinant *Aspergillus niger* increases 3-HP production by 10% to 500%, for example, by 10% to 400%, 10% to 300%, 10% to 200%, 10% to 100%, 10% to 90%, 10% to 80%, 10% to 70%, 10% to 60%, 10% to 50%, 10% to 40%, 10% to 30%, 10% to 25%, 20% to 400%, 20% to 300%, 20% to 200%, 20% to 100%, 20% to 90%, 20% to 80%, 20% to 70%, 20% to 60%, 20% to 50%, 20% to 40%, 20% to 30%, 20% to 25%, 30% to 400%, 30% to 300%, 30% to 200%, 30% to 100%, 30% to 90%, 30% to 80%, 30% to 70%, 30% to 60%, 30% to 50%, 30% to 40%, 40% to 400%, 40% to 300%, 40% to 200%, 40% to 100%, 40% to 90%, 40% to 80%, 40% to 70%, 40% to 60%, 40% to 50%, 50% to 400%, 50% to 300%, 50% to 200%, 50% to 100%, 50% to 90%, 50% to 80%, 50% to 70%, 50% to 60%, 75% to 400%, 75% to 300%, 75% to 200%, 75% to 100%, 75% to 90%, 75% to 80%, 80% to 200%, or 80% to 100% relative to a control. In a non-limiting example, further including an exogenous nucleic acid molecule encoding pyc increases 3-HP production by 80% to 90% relative to the recombinant *Aspergillus niger* without the exogenous pyc. In a non-limiting example, further including an exogenous nucleic acid molecule encoding mct1 increases 3-HP production by 30% to 40% relative to the recombinant *Aspergillus niger* without the exogenous mct1. In some examples, pyc, aat1, and/or mct1 are *Aspergillus niger* pyc, aat1, or mct1, respectively.

In some examples, the pyc amino acid sequence has at least 80% sequence identity to SEQ ID NO: 5, for example, at least 85%, at least 90%, at least 95%, at least 98%, at least 99%, or 100% sequence identity to SEQ ID NO: 5. In a non-limiting example, the pyc amino acid sequence has at least 95% sequence identity to SEQ ID NO: 5. In a further non-limiting example, the pyc amino acid sequence has at least 98% sequence identity to SEQ ID NO: 5. In some examples, the pyc amino acid sequence includes or consists of SEQ ID NO: 5.

In some examples, the exogenous nucleic acid molecule encoding pyc has at least 80% sequence identity to SEQ ID NO: 133, for example, at least 85%, at least 90%, at least 95%, at least 98%, at least 99%, or 100% sequence identity to SEQ ID NO: 133. In a non-limiting example, the exogenous nucleic acid molecule encoding pyc has at least 95% sequence identity to SEQ ID NO: 133. In a further non-limiting example, the exogenous nucleic acid molecule encoding pyc has at least 98% sequence identity to SEQ ID NO: 133. In some examples, the exogenous nucleic acid molecule encoding pyc includes or consists of SEQ ID NO: 133, or a degenerate variant thereof.

In some examples, the mct1 amino acid sequence has at least 80% sequence identity to SEQ ID NO: 137, for example, at least 85%, at least 90%, at least 95%, at least 98%, at least 99%, or 100% sequence identity to SEQ ID NO: 137. In a non-limiting example, the mct1 amino acid sequence has at least 95% sequence identity to SEQ ID NO: 137. In a further non-limiting example, the mct1 amino acid sequence has at least 98% sequence identity to SEQ ID NO: 137. In some examples, the mct1 amino acid sequence includes or consists of SEQ ID NO: 137.

In some examples, the exogenous nucleic acid molecule encoding mct1 has at least 80% sequence identity to SEQ ID NO: 129, for example, at least 85%, at least 90%, at least 95%, at least 98%, at least 99%, or 100% sequence identity to SEQ ID NO: 129. In a non-limiting example, the exogenous nucleic acid molecule encoding mct1 has at least 95% sequence identity to SEQ ID NO: 129. In a further non-limiting example, the exogenous nucleic acid molecule encoding mct1 has at least 98% sequence identity to SEQ ID NO: 129. In some examples, the exogenous nucleic acid molecule encoding mct1 includes or consists of SEQ ID NO: 129, or a degenerate variant thereof.

In some examples, the aat1 amino acid sequence has at least 80% sequence identity to SEQ ID NO: 138, for example, at least 85%, at least 90%, at least 95%, at least 98%, at least 99%, or 100% sequence identity to SEQ ID NO: 138. In a non-limiting example, the aat1 amino acid sequence has at least 95% sequence identity to SEQ ID NO: 138. In a further non-limiting example, the aat1 amino acid sequence has at least 98% sequence identity to SEQ ID NO: 138. In some examples, the aat1 amino acid sequence includes or consists of SEQ ID NO: 138.

In some examples, the exogenous nucleic acid molecule encoding aat1 has at least 80% sequence identity to SEQ ID NO: 139, for example, at least 85%, at least 90%, at least 95%, at least 98%, at least 99%, or 100% sequence identity to SEQ ID NO: 139. In a non-limiting example, the exogenous nucleic acid molecule encoding aat1 has at least 95% sequence identity to SEQ ID NO: 139. In a further non-limiting example, the exogenous nucleic acid molecule encoding aat1 has at least 98% sequence identity to SEQ ID NO: 139. In some examples, the exogenous nucleic acid molecule encoding aat1 includes or consists of SEQ ID NO: 139, or a degenerate variant thereof.

In some examples, an exogenous nucleic acid molecule encoding pyc, aat1, and/or mct1 is operably linked to a promoter that is not naturally operably-linked to pyc, aat1, or mct1, respectively, in *A. niger.*

The copy number of an exogenous nucleic acid molecule encoding pyruvate carboxylase (e.g., pyc), aspartate aminotransferase (e.g., aat1), and/or monocarboxylate transporter (e.g., mct1) in the recombinant *Aspergillus niger* can be about 1 to about 80, for example, about 5 to about 80, about 10 to about 80, about 15 to about 80, about 20 to about 80, about 25 to about 80, about 30 to about 80, about 35 to about 80, about 40 to about 80, about 45 to about 80, about 50 to about 80, about 60 to about 80, about 70 to about 80, about 5 to about 60, about 10 to about 60, about 15 to about 60, about 20 to about 60, about 25 to about 60, about 30 to about 60, about 35 to about 60, about 40 to about 60, about 45 to about 60, about 50 to about 60, about 5 to about 50, about 10 to about 50, about 15 to about 50, about 20 to about 50, about 25 to about 50, 30 to about 50, about 35 to about 50, about 40 to about 50, about 45 to about 50, about 5 to about 45, about 10 to about 45, about 15 to about 45, about 20 to about 45, about 25 to about 45, about 30 to about 45, about 35 to about 45, about 40 to about 45, about 5 to about 40, about 10 to about 40, about 15 to about 40, about 20 to about 40, about 25 to about 40, about 30 to about 40, about 35 to about 40, about 5 to about 35, about 10 to about 35, about 15 to about 35, about 20 to about 35, about 25 to about 35, about 30 to about 35, about 5 to about 30, about 10 to about 30, about 15 to about 30, about 20 to about 30, about 25 to about 30, about 5 to about 25, about 10 to about 25, about 15 to about 25, about 20 to about 25, about 5 to about 20, about 10 to about 20, about 15 to about 20, about 12 to about 27, about 1 to about 3, about 1 to about 5, or about 1 to about 10. In a non-limiting example, the copy number of the exogenous pyc is about 5 to about 10 in the recombinant *Aspergillus niger*. In another non-limiting example, the copy number of the exogenous aat1 is about 1 to about 5 in the recombinant *Aspergillus niger.*

In some examples, the copy number of an exogenous nucleic acid molecule encoding pyc, aat1, and/or mct1 is at least 1, for example, at least 2, at least 3, at least 4, at least 5, at least 6, at least 7, at least 8, at least 9, at least 10, at least 12, at least 15, at least 20, at least 25, at least 27, at least 30, at least 35, at least 40, at least 45, at least 50, or more in the recombinant *A. niger*. In a non-limiting example, the copy number of an exogenous nucleic acid molecule encoding pyc or mct1 is at least 8 in the recombinant *A. niger*. In a non-limiting example, the copy number of an exogenous nucleic acid molecule encoding aat1 is at least 1 in the recombinant *A. niger*. In some examples, the copy number is about 1, about 2, about 3, about 5, about 8, about 10, about 12, about 15, about 20, about 25, about 26, about 27, about 29, about 30, about 35, about 40, about 45, or about 50 in the recombinant *A. niger*. In a non-limiting example, the copy number of pyc is about 8 in the recombinant *A. niger*. In a non-limiting example, the copy number of aat1 is about 1 in the recombinant *A. niger.*

Any of the exogenous nucleic acids disclosed herein (e.g., exogenous nucleic acids encoding PAND, BAPT, HPDH, pyc, aat1, and/or MCT1) can be operably linked to a promoter. Constitutive, inducible, cell/tissue specific, or development specific promoters can be used. Promoters produced by recombinant DNA or synthetic techniques can also be used to provide for transcription of the nucleic acid sequences. Exemplary promoters that can be used include, but are not limited to the SV40 promoter, the CMV enhancer-promoter, CMV enhancer/β-actin promoter, trpC promoter (trpCp), translation elongation factor 1 gene promoter (tef1p), mbfA promoter (mbfAp), ubi4 gene promoter (ubi4p), ubi1S27 promoter (ubi1S27p, ubiS27p, or ubiS1p), glyceraldehyde-3-phosphate dehydrogenase promoter (gpdAp), enolase promoter (eno1p), and malate dehydrogenase 9 (mdhp). In some examples, an exogenous nucleic acid disclosed herein is operably linked to a promoter exogenous to *Aspergillus niger*. In some examples, an exogenous nucleic acid disclosed herein is operably linked to a promoter endogenous to *Aspergillus niger* (e.g., *Aspergillus niger* gpdAp, eno1p, mdhp, tefip, ubi4p, ubi1S27p, or mbf1p). In a non-limiting example, a nucleic acid molecule encoding PAND is operably linked to a ubi4p or gpdAp promoter, a nucleic acid molecule encoding BAPAT is operably linked to an ubi1S27p or eno1p promoter, and/or a nucleic acid molecule encoding HPDH is operably linked to a mbfAp or gpdAp promoter. In some examples, the eno1p, ubi4p, ubi1S27p, and/or mbfAp promoters are from *Aspergillus niger*. In some examples, the gpdAp promoter is from *A. niger* or *A. nidulans.*

Any of the exogenous nucleic acids disclosed herein can be part of a vector, such as a plasmid or viral vector. In some examples, expression of the exogenous nucleic acid molecules is driven by one or more promoters, such as a constitutive or inducible promoter, or a bi-directional promoter. In some examples, the promoter used to drive expression of PAND, BAPAT, and HPDH is a native promoter (e.g., native to the PAND, BAPAT, and HPDH gene being expressed). In other examples, the promoter used to drive expression of PAND, BAPAT, and HPDH is a non-native promoter (e.g., exogenous to the PAND, BAPAT, and HPDH gene being expressed).

Methods of making the recombinant *Aspergillus niger* disclosed herein are also included in the disclosure. The method includes introducing one or more exogenous nucleic acid molecules encoding PAND, BAPAT, and HPDH, or a vector including the exogenous nucleic acid molecules, into the *Aspergillus niger*, thereby producing the recombinant *Aspergillus niger*. In a non-limiting example, *Aspergillus niger* is transformed with a vector including a PAND, BAPAT, and HPDH gene. Multiple copies of PAND, BAPAT, and/or HPDH can be introduced into the *Aspergillus niger*, such as 5, 10, 12, 15, 20, 25, 26, 27, 28, 29, 30, 40, 50 or more PAND, BAPAT, and/or HPDH sequences. In some examples, about 12 to about 30 copies of each of PAND, BAPAT, and HPDH are introduced into the *Aspergillus niger*. The transformed *Aspergillus niger* cells (the recombinant *Aspergillus niger*) produce 3-HP. In one example, the cre-lox system is used for site specific recombination of DNA (for example see Steiger et al., Appl. Environ. Microbiol. 77(1):114, 2011). Using recombination techniques, a targeted gene of interest (e.g., ald6a, ald6b, ald3, and/or oahA) can be deleted in the *Aspergillus niger* genome and replaced with another nucleic acid sequence (e.g., one or more copies of an exogenous nucleic acid encoding PAND, BAPAT, and/or HPDH) flanked by lox sites. Transient expression (by electroporation of a suicide plasmid containing the cre gene under control of a synthetic promoter that functions in *Aspergillus*) of the cre recombinase results in efficient elimination of the lox flanked marker. This process produces *Aspergillus niger* containing the desired insertion mutation and one copy of the lox sequence.

The recombinant *Aspergillus niger* is useful for producing 3-HP. For example, 3-HP can be produced by culturing the recombinant *Aspergillus niger* under conditions that permit the production of 3-HP. Suitable conditions are described herein in the following section.

IV. Methods of Producing 3-HP

Also disclosed are methods of producing 3-HP, which include culturing an *Aspergillus niger* including a 3-HP β-alanine pathway (e.g., the recombinant *Aspergillus niger* disclosed herein). The method can include a first step of inoculating a media (e.g., liquid media) with *Aspergillus niger* comprising a 3-HP β-alanine pathway (e.g., the recombinant *Aspergillus niger* disclosed herein), thereby generating a cultured media. In some examples, $1\times10^3$ to $1\times10^{10}$ spores/mL of the *Aspergillus niger* are used to inoculate the media, for example, $1\times10^3$ to $1\times10^9$, $1\times10^3$ to $1\times10^8$, $1\times10^3$ to $1\times10^7$, $1\times10^3$ to $1\times10^6$, $1\times10^3$ to $1\times10^5$, $1\times10^3$ to $1\times10^4$, $1\times10^4$ to $1\times10^9$, $1\times10^4$ to $1\times10^8$, $1\times10^4$ to $1\times10^7$, $1\times10^4$ to $1\times10^6$, $1\times10^4$ to $1\times10^5$, $1\times10^5$ to $1\times10^9$, $1\times10^5$ to $1\times10^8$, $1\times10^5$ to $1\times10^7$, $1\times10^5$ to $1\times10^6$, $1\times10^6$ to $1\times10^9$, $1\times10^6$ to $1\times10^8$, or $1\times10^6$ to $1\times10^7$ spores/mL. In a specific, non-limiting example, about $1\times10^5$ to about $1\times10^7$ spores/mL of the *Aspergillus niger* are used to inoculate the media. In some examples, about $1\times10^3$, about $1\times10^4$, about $1\times10^5$, about $1\times10^6$, about $1\times10^7$, or about $1\times10^8$ spores/mL of the *Aspergillus niger* are used to inoculate the media. In a non-limiting example, about $1\times10^6$ spores/mL of the *Aspergillus niger* are used to inoculate the media.

In some examples, a seed culture is used to inoculate the media. A seed culture is a culture grown for the purpose of inoculating a media for fermentation. A seed culture can be prepared using known methods about 6 to 48 hours (e.g., 15 to 18 hours) prior to the inoculation step. The media can be inoculated with about 1% to about 50% volume per volume (v/v) of the seed culture of the *Aspergillus niger* (e.g., a recombinant *Aspergillus niger* disclosed herein), for example, 1% to 40%, 1% to 30%, 1% to 25%, 1% to 20%, 1% to 15%, 1% to 10%, 1% to 5%, 5% to 50%, 5% to 40%, 5% to 30%, 5% to 25%, 5% to 20%, 5% to 15%, 5% to 10%, 8% to 50%, 8% to 40%, 8% to 30%, 8% to 25%, 8% to 20%, 8% to 15%, 8% to 12%, 8% to 10%, 10% to 50%, 10% to 40%, 10% to 30%, 10% to 25%, 10% to 20%, 10% to 15%, 15% to 50%, 15% to 40%, 15% to 30%, 15% to 25%, 15% to 20%, 20% to 50%, 20% to 40%, 20% to 30%, 20% to 25%, 25% to 50%, 25% to 40%, or 25% to 30% (v/v) of the seed culture of the *Aspergillus niger*. In a non-limiting example, the media is inoculated with about 5% to about 20% (vol/vol) of the seed culture of *Aspergillus niger*. In some examples, the media is inoculated with about 1%, about 5%, about 8%, about 10%, about 12%, about 15%, about 20%, about 25%, about 30%, about 35%, about 40%, about 45%, or about 50% (v/v) of the seed culture of the *Aspergillus niger*. In a non-limiting example, the media is inoculated with about 10% (vol/vol) of the seed culture of the *Aspergillus niger*.

The method includes fermenting the cultured media at a temperature of about 20° C. to about 40° C., for example, 20° C. to 37° C., 20° C. to 35° C., 20° C. to 30° C., 20° C. to 27° C., 20° C. to 25° C., 25° C. to 40° C., 25° C. to 37° C., 25° C. to 35° C., 25° C. to 30° C., 25° C. to 27° C., 27° C. to 40° C., 27° C. to 37° C., 27° C. to 35° C., 27° C. to 30° C., 30° C. to 40° C., 30° C. to 37° C., 30° C. to 35° C., 32° C. to 40° C., 32° C. to 37° C., 32° C. to 35° C., 33° C. to 40° C., 33° C. to 37° C., 33° C. to 35° C., 35° C. to 40° C., or 35° C. to 37° C. In a non-limiting example, the cultured media is fermented at a temperature of about 33° C. to about 35° C. In some examples, the cultured media is fermented at a temperature of about 25° C., about 27° C., about 30° C., about 32° C., about 34° C., about 36° C., about 37° C., or about 40° C. In a non-limiting example, the cultured media is fermented at a temperature of about 34° C.

The culture is fermented under acidic conditions. Acidic conditions include a pH of about 1 to about 6, for example, 1 to 6, 1 to 5, 1 to 4, 1 to 3, 1 to 2, 2 to 6, 2 to 5, 2 to 4, 2 to 3, 3 to 6, 3 to 5, 3 to 4, 4 to 6, or 4 to 5, during fermentation. In some examples, the pH is about 1 to about 4 during fermentation. In some examples, the pH is 6 or lower during fermentation, for example, a pH of 5, a pH of 4, a pH of 3, a pH of 2, or a pH of 1. In some examples, the pH is lower than 3 during fermentation. In a non-limiting example, the pH is about 2 during fermentation.

The culture is fermented under microaerobic conditions. A microaerobic condition occurs when oxygen demand of an organism is greater than the oxygen transfer rate from the gaseous to aqueous phase. In some examples, the microaerobic condition is a dissolved oxygen content of about 0 to about 15% (DO) during fermentation, for example, about 1% to about 15%, about 1% to about 10%, about 1% to about 8%, about 1% to about 7%, about 1% to about 6%, about 1% to about 5%, about 1% to about 4%, about 1% to about 3%, about 1% to about 2%, about 2% to about 15%, about 2% to about 10%, about 2% to about 9%, about 2% to about 8%, about 2% to about 7%, about 2% to about 6%, about 2% to about 5%, about 2% to about 4%, about 2% to about 3%, about 4% to about 15%, about 4% to about 10%, about 4% to about 9%, about 4% to about 8%, about 4% to about 7%, about 4% to about 6%, about 4% to about 5%, about 5% to about 15%, about 5% to about 10%, about 5% to about 9%, about 5% to about 8%, about 5% to about 7%, about 5% to about 6%, about 6% to about 15%, about 6% to about 10%, about 6% to about 9%, about 6% to about 8%, about 6% to about 7%, about 8% to about 15%, about 8% to about 10%, or about 8% to about 9% (DO) during fermentation. In some examples, the dissolved oxygen content is less than about 15%, for example, less than 10%, less than 8%, less than 6%, less than 5%, less than 4%, less than 3%, less than 2%, or less than 1% (DO) during fermentation. In some examples, the dissolved oxygen content is about 1%, about 2%, about 3%, about 4%, about 5%, about 6%, about 7%, about 8%, about 9%, about 10%, about 12%, or about 15% (DO) during fermentation. In a specific, non-limiting example, the dissolved oxygen content is about 0% to 10% (DO) during fermentation.

The media can be any suitable liquid media, such as Riscaldati B medium (RisB) (100 g Glucose, 0.11 g $KH_2PO_4$, 2.36 g $(NH_4)_2SO_4$, 2.08 g MgSO4*7$H_2O$, 0.074 g NaCl, 0.13 g $CaCl_2$)*2$H_2O$, 1 ml of 1000× trace elements in 1000 ml DI water, adjust pH to 3.4 with $H_2SO_4$, 1000× trace elements contains 1.3 g/L $ZnSO_4$*7$H_2O$, 5.5 g/L $FeSO_4$*7$H_2O$, 0.2 g/L $CuSO_4$*5$H_2O$, 0.7 g/L $MnCl_2$*4$H_2O$)) or modified Riscaldati B medium (RisB) with 20× trace elements. In some examples, the media is an acidic media, such as a media having an initial pH (pH of the media prior to inoculation) of less than 4, such as less than 3.5, for example about pH 2 to 4, 3 to 4, 3.5 to 4, 3.3 to 3.5, for example pH 2, 2.5, 2.8, 2.9, 3, 3.1, 3.2, 3.3, 3.4, 3.5, 3.6, 3.7, 3.8, 3.9 or 4. In some examples, the initial pH of the acidic media is about 3 to about 4.

The media can further include trace elements (TE), corn steep liquor, peptone, tryptone, soy protein, sodium chloride, yeast extract, sorbitol, and/or phosphorous. In biology, trace elements function primarily as catalysts in enzyme systems, for example, some metallic ions, such as iron and copper, participate in oxidation-reduction reactions in energy metabolism. Exemplary trace elements include iron, zinc, nickel, copper, molybdenum, cobalt, chromium, cadmium, selenium, and manganese. In some examples, the trace elements include copper, manganese, iron, and zinc (e.g., 4 mg/l $CuSO_4{\cdot}5H_2O$; 110 mg/l $FeSO_4{\cdot}7H_2O$; 14 mg/l $MnCl_2{\cdot}4H_2O$; and 26 mg/l $ZnSO_4{\cdot}7H_2O$). The media can include glucose, maltose, fructose, maltodextrin, and/or a glucose:xylose mixture as a carbon source. In some examples, the media is supplemented with nitrogen, manganese, and/or phosphate.

In some examples, the methods include aerating the culture, for example, by rotation (e.g., 100 to 300 rpm, such as about 150 rpm or about 200 rpm) or other aeration mechanism. In some examples, the *Aspergillus niger* (e.g., a recombinant *Aspergillus niger* disclosed herein) are grown in culture containers (such as baffled flasks) or in a bioreactor. The cultured media can be aerated before and/or during fermentation. In some examples, fermentation is performed at atmospheric pressure.

In some examples, the methods include purifying or isolating the 3-HP after fermentation. In some examples, the 3-HP is isolated at least 2 days, at least 3 days, at least 5 days, at least 7 days, at least 8 days or at least 10 days after the inoculation step, such as 2, 3, 4, 5, 6, 7, 8, 9, 10, 11, 12, 13, 14, 15, 16, 17, 18, 19 or 20 days after the inoculation step. In some examples, the 3-HP is purified or isolated after 4 days of fermentation. In some examples, the 3-HP is purified or isolated after 7 days of fermentation.

In some examples, the *Aspergillus niger* (e.g., a recombinant *Aspergillus niger* disclosed herein) produces about 0.1 g/l 3-HP to about 50 g/l 3-HP, for example, 0.1 g/l to 40 g/l, 0.1 g/l to 30 g/l, 0.1 g/l to 25 g/l, 0.1 g/l to 20 g/l, 0.1 g/l to 15 g/l, 0.1 g/l to 10 g/l, 0.1 g/l to 5 g/l, 0.1 g/l to 5 g/l, 0.1 g/l to 4.5 g/l, 0.1 g/l to 4 g/l, 0.1 g/l to 3.5 g/l, 0.1 g/l to 3 g/1, 0.1 g/l to 2.5 g/1, 0.1 g/l to 2 g/l, 0.1 g/l to 1.5 g/l, 0.1 g/l to 1 g/l, 0.1 g/l to 0.5 g/l, 0.5 g/l to 40 g/1, 0.5 g/l to 30 g/1, 0.5 g/l to 25 g/1, 0.5 g/l to 20 g/1, 0.5 g/l to 15 g/1, 0.5 g/l to 10 g/l, 0.5 g/l to 5 g/l, 0.5 g/l to 4.5 g/l, 0.5 g/l to 4 g/l, 0.5 g/l to 3.5 g/l, 0.5 g/l to 3 g/l, 0.5 g/l to 2.5 g/l, 0.5 g/l to 2 g/1, 0.5 g/l to 1.5 g/1, 0.5 g/l to 1 g/l, 1 g/l to 40 g/l, 1 g/l to 30 g/1, 1 g/l to 25 g/1, 1 g/l to 20 g/1, 1 g/l to 15 g/1, 1 g/l to 10 g/l, 1 g/l to 5 g/l, 1 g/l to 5 g/l, 1 g/l to 4.5 g/l, 1 g/l to 4 g/l, 1 g/l to 3.5 g/l, 1 g/l to 3 g/1, 1 g/l to 2.5 g/l, 1 g/l to 2 g/l, 1 g/l to 1.5 g/l, 1.5 g/l to 40 g/1, 1.5 g/l to 30 g/1, 1.5 g/l to 25 g/1, 1.5 g/l to 20 g/1, 1.5 g/l to 15 g/1, 1.5 g/l to 10 g/l, 1.5 g/l to 5 g/l, 1.5 g/l to 4.5 g/l, 1.5 g/l to 4 g/l, 1.5 g/l to 3.5 g/l, 1.5 g/l to 3 g/l, 1.5 g/l to 2.5 g/l, 1.5 g/l to 2 g/1, 5 g/l to 50 g/1, 5 g/l to 40 g/1, 5 g/l to 30 g/1, 5 g/l to 25 g/1, 5 g/l to 20 g/1, 5 g/l to 15 g/1, 5 g/l to 10 g/1, 10 g/l to 50 g/1, 10 g/l to 40 g/1, 10 g/l to 30 g/1, 10 g/l to 25 g/1, 10 g/l to 20 g/1, 10 g/l to 15 g/1, 15 g/l to 50 g/1, 15 g/l to 40 g/1, 15 g/l to 30 g/1, 15 g/l to 25 g/1, 15 g/l to 20 g/1, 20 g/l to 50 g/1, 20 g/l to 40 g/1, 20 g/l to 30 g/1, 20 g/l to 25 g/1, 25 g/l to 50 g/1, 25 g/l to 40 g/1, 25 g/l to 30 g/1, 30 g/l to 50 g/1, 30 g/l to 40 g/l, or 30 g/l to 35 g/l 3-HP after about 3, 4, 5, 6, 7, 8, 9, or 10 days of fermentation. In a non-limiting example, 20 g/l to 40 g/l 3-HP is produced after 7 days of fermentation. In a further non-limiting example, 30 g/l to 40 g/l 3-HP is produced after 7 days of fermentation.

In specific examples, the *Aspergillus niger* (e.g., a recombinant *Aspergillus niger* disclosed herein) produces at least 0.1 g/l of 3-HP after at least 2 days of fermentation, for example at least 0.2 g/l, at least 0.25 g/l, at least 0.3 g/l, at least 0.4 g/l, at least 0.5 g/l, at least 0.6 g/l, at least 0.7 g/l, at least 0.8 g/l, at least 0.9 g/l, at least 1.1 g/l, at least 1.2 g/l, at least 1.5 g/l, at least 1.6 g/l, at least 1.8 g/l, at least 2.0 g/l, at least 2.5 g/l, at least 3.0 g/l, at least 3.5 g/l, at least 4.0 g/l, at least 5.0 g/l, at least 10 g/l, at least 15 g/l, at least 20 g/l, at least 30 g/l, at least 40 g/l, at least 50 g/l, or more, after at least 3 days, at least 4 days, at least 5 days, at least 6 days, at least 7 days, at least 8 days, or at least 10 days of fermentation.

In some examples, the method further includes purifying or isolating the 3-HP made by the *Aspergillus niger* (e.g., a recombinant *Aspergillus niger* disclosed herein). Any suitable known method can be used to isolate the 3-HP. For example, separation techniques (such as filtration) can be used to remove the fungal biomass from the culture medium, and isolation procedures (e.g., filtration, distillation, precipitation, electrodialysis, and ion-exchange procedures) can be used to obtain the 3-HP from the broth (such as a fungi-free broth). The 3-HP can be isolated from the culture medium after the 3-HP production phase has been terminated.

In some examples, the generated 3-HP is used to make other chemicals, such as acrylic acid, malonic acid, methyl acrylate, ethyl 3-hydroxypropionic acid, propiolactone, acrylonitrile 1,3-propanediol, and acrylamide. For example, acrylic acid can be made by dehydration, malonic acid by oxidation, esters by esterification reactions with alcohols, and reduction to 1,3 propanediol. In one example, such chemicals are made ex vivo. In some examples, the recombinant *A. niger* disclosed herein can be further modified to express the enzymes needed to generate these other chemicals. Thus, further provided are recombinant *A. niger* that can make 3-HP downstream products (such as acrylic acid, malonic acid, methyl acrylate, ethyl 3-hydroxypropionic acid, propiolactone, acrylonitrile 1,3-propanediol, and acrylamide), as well as methods of making such products.

V. Kits

Also provided are kits for performing a method disclosed herein. The kits can include a recombinant *Aspergillus niger* disclosed herein, a media, carbon source, nutrient additive, antifoam, antibiotic, filter, exclusion column, or combinations thereof. In some examples, the *Aspergillus niger* is freeze dried or lyophilized.

The media can be a media for culturing (including fermenting), storing, or growing the fungus. Exemplary mediums include solid medium (such as those containing agar, for example complete medium (CM) or minimal medium (MM)) and liquid media (such as a fermentation broth, such as CM, MM, Riscaldati B medium (RisB), or CAP medium).

Carbon sources include any chemical or ingredient the *Aspergillus niger* can metabolize and use as a source of carbon. Exemplary carbon sources include, but are not limited to, glucose, maltose, fructose, maltodextrin, and/or a glucose:xylose mixture. Nutrient additives facilitate *Aspergillus niger* growth and/or 3-HP production. Exemplary nutrient additives include, but are not limited to, trace elements, corn steep liquor, peptone, tryptone, soy protein, sodium chloride, yeast extract, sorbitol, and/or phosphorous. An antifoam is a chemical that reduces or prevents the formation of foam during culturing, such as during fermentation. Many antifoams are known and available, and a suitable antifoam (e.g., CLEROL FBA975) can be selected by a practitioner. Antibiotics are compounds that prevent the growth of unwanted organisms. Exemplary antibiotics include, but are not limited to, neomycin, bleomycin, and tetracycline.

VI. Examples

Fuel and chemical products obtained from petroleum refineries have been essential in daily life for more than a century. However, petroleum products are non-renewable and their production and use has contributed to widespread anthropogenic impacts on the earth's atmosphere, lands, and oceans. This has prompted the investigation of alternative routes to produce fuels and chemicals at low carbon intensity from renewable feedstocks.

3-hydroxypropionic acid (3-HP) is a potential bioderived platform chemical that can be converted into various commercial use chemicals, such as acrylic acid, malonic acid, 1,3-propanediol, and acrylamide, as well as direct use for production of biodegradable polymers. Chemical synthesis routes have been explored for 3-HP production, but high costs and adverse environmental impacts have limited chemical synthesis of 3-HP as a bulk chemical (Jiang et al., Appl Microbiol Biotechnol 82(6):995-1003, 2009). However, biological fermentation is a potential route for 3-HP production from renewable feedstocks and has been actively investigated for more than a decade (Kumar et al., 31(6): 945-61, 2013; Matsakas et al., Ferment 4(1):13, 2018). Naturally, there exist several 3-HP production processes, such as C02 assimilation in Chloroflexus *aurantiacus* (Holo, *Arch Microbiol.* 151(3):252-6, 1989) or cyanobacterium *Synechocystis* sp. (Lan et al., *Metab Eng* 31:163-70, 2015; Wang et al., *Metab Eng* 34:60-70, 2016), glycerol oxidation in *Lactobacillus* sp. (Talarico et al., Appl Environ Microbiol 56(4):943-8, 1990), acrylic acid degradation in *Byssochlamys* sp. (Takamizawa et al., Appl Microbiol Biotechnol 40(2):196-200, 1993) or *Rhodococcus erythropolis* (Lee et al., J Microbiol Biotechnol 19(5):474-81, 2009) and uracil catabolism in *Saccharomyces kluyveri* (Andersen et al., J mol biol 380(4):656-66, 2008) or *E. coli* K-12 (Loh et al., Proc Natl Acad Sci USA. 103(13):5114-9, 2006). However, the efficiency of 3-HP production in native microorganisms is very low. Therefore, genetic engineering of non-native hosts with novel synthetic 3-HP production pathways is needed.

Glycerol oxidation through a coenzyme A-independent pathway was initially detailed by Bieble et al. for 1,3-propanediol production in Clostridia and Enterobacteriaceae and the $NAD^+$-dependent aldehyde dehydrogenase that can convert 1,3-propanediol to 3-HP in *Klebsiella pneumoniae* by Raj et al. (Biebl et al., Appl Microbiol Biotechnol 52(3):289-97, 1999; Raj et al., Biotechnol Bioprocess Eng 15(1):131-8, 2010). *E. coli* or *K. pneumoniae* was genetically engineered and optimized for 3-HP production by combination of glycerol reduction and 3-HP production, which led to 70 to 80 g/l 3-HP production titer in fed-batch fermentations with glycerol as a carbon source (Li et al., Sci Rep 6(1):26932, 2016; Chu et al., Biotechnol Bioeng 112 (2):356-64, 2015).

Biosynthetic routes to 3-HP via malonyl-CoA and β-alanine have been demonstrated in *E. coli* (Jessen et al., WO/2008/027742, 2008; Rathnasingh et al., J Biotechnol 157(4):633-40, 2012), and further explored or optimized in various microorganisms such as *E. coli*, cyanobacteria, and *Saccharomyces cerevisiae*. For example, the malonyl-CoA pathway was introduced into *E. coli* for conversion of glucose to 3-HP, which resulted in 10 g/l 3-HP production in 36 hrs (Cheng et al., Bioresour Technol 200:897-904, 2016). Similar results were observed for the same pathway after integration into the chromosomes of *S. cerevisiae* or Schizosaccharoyrnces poinbe (Kildegaard et al., Microb Cell Fact 15(1):1-13, 2016; Suyama et al., J Biosci Bioeng 124(4):392-9, 2017).

The β-alanine 3-HP pathway consisting of Ti?olm castaneum aspartate 1-decarboxylase (PAND), *Bacillus cereus* β-alanine-pyruvate aminotransferase (BAPAT) and *Escherichia coli* 3-hydroxypropionate dehydrogenase (HPDH) was constructed and examined in *S. cerevisiae*, and resulted in a production titer of 13.4 g/l 3-HP in controlled fed-batch fermentation (Borodina et al., Metab Eng 27:57-64, 2015). Recently, it was demonstrated that the β-alanine 3-HP pathway was functional in the acidophilic filamentous fungus *Aspergillus* pseudoterreus (Pomraning et al., Front Bioeng Biotechnol 9:603832, 2021).

Filamentous fungi such as *Aspergillus* species are used industrially for organic acid production because of their ability to grow at very low pH (<2.0) and produce secreted metabolites in nutrient-limited growth conditions, which eliminates the requirement of medium pH neutralization. *A. pseudoterreus* can secrete more than 80 g/l of itaconic acid in culture medium and *Aspergillus niger* can grow in more than 20% glucose or sucrose and convert more than 90% of the feedstock to citric acid (Dai et al., Appl Environ Microbiol 70(4):2474-85, 2004; Karaffa et al., Appl Microbiol Biotechnol 61(3):189-96, 2003). However, it was previously unknown whether *A. niger* is a suitable host for 3-HP production. Here, *A. niger* is confirmed as a host for 3-HP production using the β-alanine 3-HP pathway.

Example 1: Materials and Methods

Strains and Media

The *Escherichia coli* strain Top10 was used for routine plasmid DNA preparation. *A. pseudoterreus* (ATCC 32359) and *A. niger* (ATCC 11414) from the American Type Culture Collection (Rockville, MD, USA), were grown on complete medium (CM) or potato dextrose agar (PDA) plates at 30° C. for culture maintenance and spore preparation. About $1\times10^4$ to $1\times10^5$ spores were inoculated on CM agar (petri dish) plates and incubated for four days at 30° C. Spores were harvested by washing with 5 to 10 ml sterile 0.4% TWEEN 80 (polyoxyethylenesorbitan monooleate) and pelleted by centrifugation at 2500 g for 5 min. The spores were re-suspended in sterile 0.4% TWEEN 80 and enumerated with a hemocytometer. Aliquots of the resulting spore suspension (about $10^8$~$10^9$ spores/ml) were used to inoculate different agar-plates or liquid cultures. The preparation of PDA, CM and minimal medium (MM) followed the description of Bennett and Lasure (Bennett and Lasure. More Gene Manipulations in Fungi. San Diego: Academic Press p. 441-58, 1991). All strains used in this study are shown in FIGS. 8A-8B.

Preparation of Transgene Expression Constructs for Gene Over-Expression or Gene Disruption in *A. pseudoterreus* and *A. niger.*

The β-alanine pathway transgene expression cassette with pyrithiamine resistance gene (ptrA) of *Aspergillus oryzae* as a selection marker was described previously (Pomraning et al., Front Bioeng Biotechnol 9:603832, 2021). In this study, all transgene expression cassettes were prepared with Gibson assembly master mix (NEB, Ipswich, MA, USA) and the DNA fragments isolated by PCR with PHUSION high-fidelity DNA polymerase (Thermo Fisher Scientific, Walrham, MA).

Culture Methods

Pyrex 125 ml or 250 ml glass Erlenmeyer flasks were prepared by filling with 5% CONTRAD 70 (Decon Labs, Inc. King of Prussia, PA, USA) and soaking overnight to remove any potential residues on the inside surface of flasks prior to general dishwashing. Silicon sponge closures were used for all flask cultures. The biomass of transgenic clones and parent strain for genomic DNA isolation were prepared from 2 mL stationary CM cultures with proper antibiotics and grown in 13×100 mm glass culture-tubes for 24 to 36 hrs at 30° C. The biomass formed on the surface of the liquid culture medium was collected, frozen immediately in liquid nitrogen and dried in the VirTis benchtop manifold freeze dryer (SP Scientific, Gardiner, NY, USA). For 3-HP production, 35 ml of citric acid production medium was prepared by following previous descriptions (Dai et al., Appl Environ Microbiol 70(4):2474-85, 2004). Production medium B (RDM) (Riscaldati et al., J Biotechnol 83(3):219-30, 2000) or modified production medium B (mRDM) (Pomraning Front Bioeng Biotechnol 9:603832, 2021; Dai et al., Appl Environ Microbiol 70(4):2474-85, 2004) that contains 20×TE (trace elements: 4 mg/l $CuSO_4 \cdot 5H_2O$; 110 mg/l $FeSO_4 \cdot 7H_2O$; 14 mg/l $MnCl_2 \cdot 4H_2O$; and 26 mg/l $ZnSO_4 \cdot 7H_2O$) was also used. The ferment sugars liberated from corn stover by deacetylated and disk refined process (DDR), in which the biomass was deacetylated with dilute alkaline at low temperature first, then mechanically refined in an industrial size disk refiner, and finally enzymatically hydrolyzed (DDR-EH; Batch 1-19-05, 20190829, (Chen et al., Biotechnol Biofuels 8:173, 2015)), which was obtained from the Pilot Plant at National Renewable Energy Laboratory (Golden, CO, USA).

Chemical-Mediated Protoplast Transformation of *A. niger*

The protoplast preparation and chemical-mediated transformation followed the method described by Dai et al. (Fungal Genet Biol 61:120-32, 2013) for *A. niger*. Briefly, the 14.4 kb plasmid DNA of the β-alanine pathway transgene expression construct was linearized by restriction enzyme EcoRV and concentrated down to about 1 mg/ml with Microcon-30 kDa centrifugal filter unit (MilliporeSigma, Burlington, MA). Ten microliters of the linearized plasmid DNA were used for protoplast transformation in *A. niger*. For transgene overexpression of *A. niger* aat1, pyc, the aat1-pyc, or mct1 gene in *A. niger*, about 3 to 5 mg of linearized plasmid DNAs by proper restriction enzymes were used for protoplast transformation. For the gene deletion construct of ald6a, ald6b, oah1, or uga2 gene homolog, about 1 mg of linearized plasmid DNAs by restriction enzyme PmeI was used for protoplast transformation in *A. niger*. Usually, about 5 to 12 transformed clones were picked randomly for evaluation of 3-HP production and the effects of selected genes on 3-HP production. The chemical-mediated protoplast transformation of *A. pseudoterreus* followed the previous description (Deng et al., Appl Microbiol Biotechnol 104(9):3981-92, 2020).

Total Genomic DNA Isolation for PCR, Southern Blotting Analysis, and Short-Read Whole Genomic DNA Sequencing.

Total genomic DNA was isolated from *A. niger* or *A. pseudoterreus* cells using a cetyltrimethylammonium bromide (CTAB) extraction method with some modifications. Briefly, 50 to 100 mg of lyophilized biomass and two 3.5 mm diameter glass beads were transferred into a 2 mL polypropylene micro-vial, where biomass was pulverized into fine power with a Mini-Beadbeater-8 (Bio Spec Products Inc., Bartlesville, OK) for 50 seconds. The disrupted cells in microcentrifuge tubes were re-suspended with 800 to 900 μl of CTAB solution and incubated at 60° C. for 30-45 min and inverted occasionally. The genomic DNA in the supernatant of the cell extracts was extracted with 300 ml of phenol/chloroform solution and precipitated with 1 volume of 2-propanol. The genomic DNA was resuspended with 200 ml of 50TE (50 mM Tris-HCl, pH8.0 and 10 mM EDTA, pH8.0) and 25 μg of RNase and incubated for 30-45 min at 50° C. After RNase treatment, the genomic DNA was extracted twice with 125 ml of phenol/chloroform solution and once with chloroform. The genomic DNA in the supernatants was precipitated with 1 M NaCl and 2 volume of 95% ethanol for 15 min at room temperature and centrifugation at 10,000×g for 8 min. Finally, the genomic DNA pellet was washed with 70% ethanol and was resuspended in 10 mM Tris-HCl (pH 8.0) buffer at 50° C. for 15 to 20 min and the concentration was determined with a QUBIT fluorometer (Thermo Fisher Scientific, Waltham, MA, USA). Fifty to seventy ng of total genomic DNA were used for PCR analyses.

For Southern blotting analyses of heterologous expression of β-alanine pathway in either *A. niger* or *A. pseudoterreus,* 1 mg of total genomics DNA was digested with the restriction endonuclease BamHI, EcoRV, or HindIII. The genomic DNA fragments were separated in 1% agarose gel electrophoretically and transferred onto the Hybond™-N+ nylon membrane (GE Healthcare Bio-Sciences, Pittsburgh, PA, USA) with alkaline capillary transfer method. The 1.0 kb 3'-end of genomic DNA fragments of *A. pseudoterreus* cad1 gene was used for preparation of the biotin-labeled probe. The genomic DNA in the Hybond™-N+ nylon membrane was hybridized with the biotin-labeled probe overnight at 60° C. in the Problot™ Hybridization Oven (Labnet International, Edison, NJ, USA). The genomic DNA on the hybridized membrane was visualized with North2South™ chemiluminescent detection kit (Pierce Protein Research Products, Rockford, IL, USA) in Analytik jena UVP ChemStudio (Analytik Jena US, Upland, CA, USA).

The short-read whole genomic DNA sequencing was carried out by Azenta Life Sciences (South Plainfield, NJ, USA). The integration copy number was estimated by fold-increase of reads mapped to the expression construct versus background single copy regions of the genome. The sequenced short-reads were mapped to the reference genome sequence of *A. niger* ATCC 1015 (mycocosm.jgi.doe.gov/Aspni7/Aspni7.home.html) augmented with the overexpressed gene sequence using BWA-MEM (Li H et al., arXiv preprint 13033997, 2013). The mapped reads were sorted using SAMtools (Li et al., Bioinformatics 25(16):2078-9, 2009) and duplicate reads were marked using Picard Toolkit (github.com/broadinstitute/picard #citing) to produce BAM files for copy number estimation. The copy numbers of β-alanine pathway genes and engineered native genes were estimated using CNVnator (Abyzov et al., Genome Res 21(6):974-84, 2011). The mapped reads were counted using bin sizes of 100, 200, and 1,000 bp, and the read depth signal was partitioned into segments for each bin size. The average and standard deviation of read depth signal were evaluated for bin sizes of 100 and 200 bp, and copy number genotype was estimated based on the normalized read depth using the bin size of 100 bp.

Metabolites Analysis by HPLC

The extracellular metabolites were quantified by HPLC. Twenty-five microliters of the samples filtered with 0.2 mm syringe filters were analyzed for 45 min using an AMINEX HPX-87H ion exclusion column with a 1 mM $H_2SO_4$ flow of 0.6 ml/ml. The temperature of the column was 60° C. The refractive index at 45° C. and the UV absorption at 210 nm were measured.

Sample Preparation for Metabolomics and Proteomics Analyses

Briefly, the culture supernatants or biomass (cell pellet) for *A. niger* or *A. pseudoterreus* were harvested at day 4. For quantification of extracellular metabolites diluted spent medium samples (by a 1/8 factor) were dried, prepared, and analyzed as described previously (Pomraning et al., Front Bioeng Biotechnol 9:603832, 2021). The cell pellets were extracted using the MPLex protocol (Nakayasu et al., MSystems 1(3):e00043-16, 2016) and extracts were analyzed using GC-MS as explained previously in detail (Kim et al., Front Microbiol 6:209, 2015). The protein interlayer pellet was digested and prepared for global proteomics analysis and targeted proteomics analysis, the latter using heavy labeled peptides. Instrument acquisition and data analysis was done as described in a previous publication (Pomraning et al., Front Bioeng Biotechnol 9:603832, 2021). Global proteomics data were generated using a Q Exactive Plus™ mass spectrometer (Thermo Fisher Scientific, Waltham, MA, USA) in data-dependent acquisition mode.

Bioreactor Operations and Shaking Flasks

Transgenic strains were routinely cultured in Riscaldati 13 medium (RisB) that contained 20×TE (trace elements: 4 mg/L CuSO4·5H2O; 110 mg/L FeSO4·7H2O; 14 mg/L MnCl2·4H2O; and 26 mg/L ZnSO4·7H2O). Glucose, maltose, fructose, maltodextrin, or glucose:xylose mixtures (2:1 g/g ratio) were used as the main carbon sources. The medium was modified with various additives (i.e., Corn steep liquor, peptone, tryptone, soy protein, sodium chloride, yeast extract, sorbitol) at the specified concentrations. The base medium was also modified in specific tests to contain additional phosphorus ranging from 1-10× the normal RisB phosphorus concentration, as specified within the figures. Shaking flasks were inoculated with either spores at a concentration of approximately 1×10^6 spores/mL or with 10% vol/vol of a seed culture. The seed culture media contained 100 mL/1 L of corn steep liquor, 3 mL/1 L of CLEROL FBA975 antifoam, 1 g/L NaH2PO4·$H_2O$, 2.04 g/L MgSO4.7$H_2O$, 100 g/L maltose, 10 g/L glucose, 50 g/L fructose and was inoculated using spores a concentration of approximately 1×10^6 spores/mL and grown overnight (15-

18 h) at 34 C. Before inoculation, the seed culture was washed with deionized water and resuspended in a RisB salt solution containing 1×phosphate. Shaking flasks production cultures occurred at 30 and 35 C. Bioreactor cultivations were performed in an Infors AG Sixfors Fermenter system with 675 mL vessels in RisB salt mediums containing the specified sugars and additives. A working volume of 450 mL was used through fermentations. The bioreactors were inoculated using the spore procedure specified above and allowed to germinate for approximately six hours before aeration was initiated.

The extracellular metabolites were quantified by HPLC. Twenty-five microliters of the samples filtered with 0.2 μm syringe filters were analyzed for 45 min using an AMINEX HPX-87H ion exclusion column with a 1 mM H2SO4 flow of 0.6 mL/mL. The temperature of the column was 60° C. The refractive index at 45° C. and the UV absorption at 210 nm were measured. For dry cell weight determination, 5-10 mLs of culture was pelleted in a pre-weighed conical tube (5 min at 4,000 g), the cells were washed once with water, and frozen at −20 C. The frozen pellet was then lyophilized for 24-36 h.

Detailed Description of Transgene Vector Construction for Gene Overexpression or Disruption in *Aspergillus pseudoterreus* or *Aspergillus niger.*

All transgene over-expression or gene disruption constructs were prepared by Gibson assembly method (Ipswich, MA) with DNA fragments isolated by PCR from either related plasmid or genomic DNAs of *Aspergillus carbonarius, A. niger, Aspergillus oryzae*, or *A. pseudoterreus* with proper oligo pairs and PHUSION high-fidelity DNA polymerase (Thermo Fisher Scientific, Waltham, MA, USA 02451). The first β-alanine pathway transgene expression cassette with pyrithiamine resistance gene (ptrA; Genbank: AF217503) of *A. oryzae* as a selection marker shown in FIG. 11A was prepared as follows: the first 987 bp DNA fragment of cad1 (Genbank: UDM55691.1, 5'-cad1) gene upstream region containing 535 bp coding sequence of N-terminus was isolated by PCR with oligo pair 1969cad1/1670cad1 (Table 1); the second 813 bp DNA fragment of *A. niger* gpdA (Genbank: XP_025477631, gpdAp) promoter with oligo pair 1971gpdA1/1972gpdA2; the third 1623 bp DNA fragment of aspartate 1-decarboxylase (Tribolium castaneum panD, PAND) with 1973pan1/1974pan2 and the synthetic plasmid DNA of codon usage optimization for *A. pseudoterreus* as a template; the forth 1040 bp DNA fragment of bi-direction transcriptional terminator of *A. niger* elf3-multifunctional chaperone (elf3, Genbank: CAK43351.1, elf3t) with oligo pair 1975ter1/1976ter2; the fifth 1350 bp reverse complement DNA fragment of b-alanine-pyruvate aminotransferase (*Bacillus cereus* bapat, BAPAT) with oligo pair 1977bap1/1978bap2 and the synthetic plasmid DNA of codon usage optimization for *A. pseudoterreus* as a template; and final 704 bp complement DNA fragment of *A. niger* enolase (Genbank: AM270411.1, eno1p) promoter with oligo pair 1979eno1/1980eno2-HpaI. All 6 DNA fragments were assembled together into the pBSK(−) vector linearized with restriction endonuclease HindIII and PstI to form new intermediate vector 3HP4025. The 885 bp DNA fragment of *Aspergillus nidulans* gpdA promoter was prepared by PCR with oligo pair 1981gpdA1/1982gpdA2 and pAN7-1 plasmid DNA (Genbank: Z32698.1, gpdAp) as a template; the 744 bp DNA fragment of 3-hydroxypropionate dehydrogenase (*Escherichia coli* hpdh, HPDH) with oligo pair 1983hpd1/1984hpd2 and the synthetic plasmid DNA of codon usage optimization for *A. pseudoterreus* as a template; the 473 bp DNA fragment of *A. nidulans* trpC (trpCt) transcriptional terminator with oligo pair 1985trp1/1986trp2 and pAN7-1 plasmid DNA as a template; the 2005 bp DNA fragment of *A. oryzae* ptrA gene with oligo pair 1987ptrA1/1988ptrA2 (ptrA); and 908 bp DNA fragment of *A. pseudoterreus* cad1 gene downstream region containing 519 bp coding sequence of its C-terminus and transcriptional terminator with oligo pair 1989cad3/1990cad4 (3'-cad1). Above 5 DNA fragments were assembled into the intermediate vector 3HP4025 linearized with the restriction endonuclease HpaI, which was introduced into the 3HP4025 with oligo 1980eno2-HpaI, to form the entire b-alanine pathway transgene expression cassette 3HP4028. The entire transgene expression construct was verified by Sanger DNA sequencing. The second 3-alanine pathway transgene expression cassette was to construct two identical copies of the β-alanine pathway, where the plasmid 3HP4028 was linearized by restriction endonuclease EcoRI and assembled with the entire fragment of the β-alanine pathway, which was isolated by PCR with oligo pair 2085HP2F/2086HP2R and 3HP4028 as a DNA template to form the plasmid 3HP4046 (FIG. 13).

Figure 14:
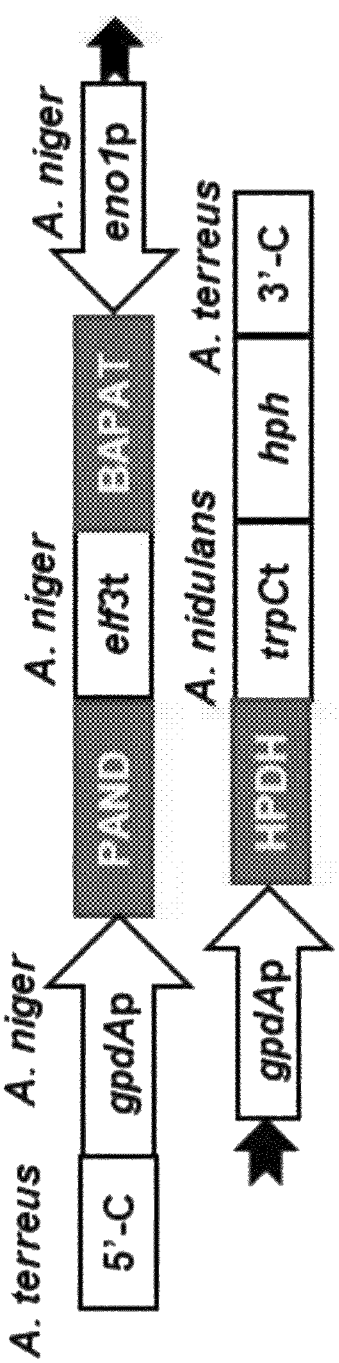
FIG. 14. A diagram of a β-alanine 3HP pathway transgene expression cassette with *E. coli* hygromycin B phosphotransferase (hph) marker gene (3HP4070). 5'-C, 326 bp upstream region of cis-aconitate decarboxylase of *A. pseudoterreus*; gpdAp, glyceraldehyde-3-phosphate dehydrogenase promoter from either *A. niger* or *A. nidulans*; PAND, *T. castaneum* aspartate 1-decarboxylase; elf3t, *A. niger* elongation factor 3 transcriptional terminator; BAPAT, *Bacillus cereus* β-alanine-pyruvate aminotransferase; eno1p, *A. niger* enolase promoter; HPDH, *E. coli* 3-hydroxypropionate dehydrogenase; trpCt, *A. nidulans* trpC transcriptional terminator; hph, *E. coli* hygromycin B phosphotransferase gene marker, and 3'-C, 283 bp upstream region of ptrA gene.

The third β-alanine pathway transgene expression cassette 3HP4070 with *E. coli* hygromycin B phosphotransferase (hph) marker gene (FIG. 14) was prepared with the plasmid 3HP4028 and pCB1003 (fgsc.net/fgn41/carroll.html) as the DNA templates for PCR as follows: the first 2759 bp DNA fragment containing 326 bp of 5'-end cad1 coding sequence of *A. pseudoterreus,* 810 bp of *A. niger* gpdA promoter, and 1623 bp DNA fragment of PAND with oligo pair 2201/2202; the second 3091 bp DNA fragment containing the 1040 bp DNA fragment of bi-direction transcriptional terminator of *A. niger* elf3, the 1350 bp reverse complement DNA fragment of bapat, and 701 bp reverse complement DNA fragment of *A. niger* eno1 promoter with oligo pair 2203/2204. These two fragments were assembled into the pBSK(−) vector linearized with restriction endonuclease HindIII and PstI to form new intermediate vector 3HP4069. The 1360 bp DNA fragment of hph marker gene was prepared by PCR with oligo pair 2213hphF/2214hphR and plasmid DNA pCB1003 as a template. The 2385 bp DNA fragment containing 885 bp DNA fragment of *A. nidulans* gpdA promoter, 744 bp DNA fragment of hpdh, 473 bp DNA fragment of *A. nidulans* trpC transcriptional terminator, and 283 bp upstream region of *A. oryzae* ptrA gene was isolated with oligo pair 2215hpdF/2216hpdR. These two fragments were further assembled into the 3HP4069 linearized with restriction endonuclease XbaI to form the 3HP4070 transgene expression vector. The entire transgene expression construct was verified by Sanger DNA sequencing.

Figure 15:
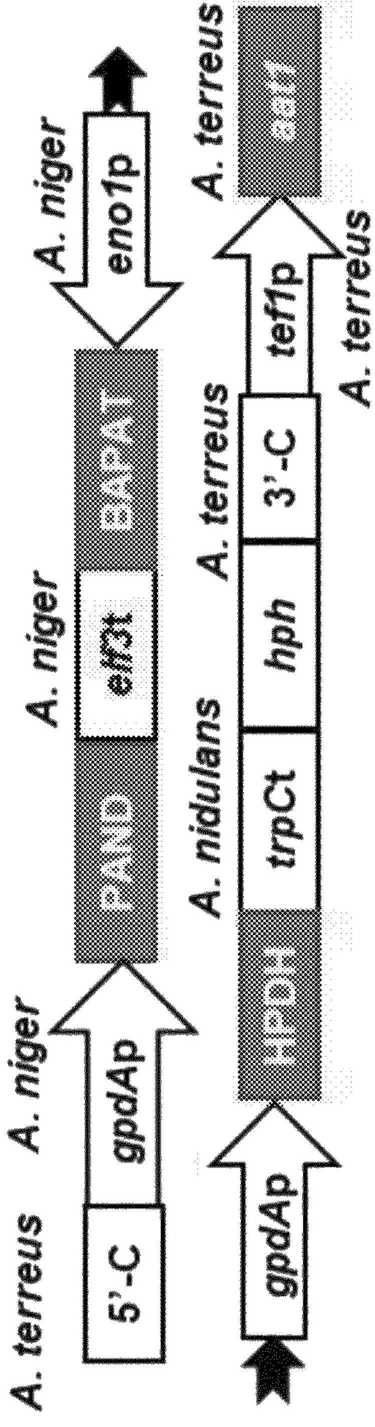
FIG. 15. A diagram of a β-alanine 3HP pathway along with an *A. pseudoterreus* aat1 transgene overexpression under the control of *A. pseudoterreus* tef1 gene promoter (3HP4071). 5'-C, 326 bp upstream region of cis-aconitate decarboxylase of *A. pseudoterreus*; gpdAp, glyceraldehyde-3-phosphate dehydrogenase promoter from either *A. niger* or *A. nidulans*; PAND, *T. castaneum* aspartate 1-decarboxylase; elf3t, *A. niger* elongation factor 3 transcriptional terminator; BAPAT, *B. cereus* β-alanine-pyruvate aminotransferase; eno1p, *A. niger* enolase promoter; HPDH, *E. coli* 3-hydroxypropionate dehydrogenase; trpCt, *A. nidulans* trpC transcriptional terminator; hph, *E. coli* hygromycin B phosphotransferase gene marker, and 3'-C, 283 bp upstream region of ptrA gene; tefip, translation elongation factor 1 (tef1) gene promoter of *A. pseudoterreus*, and aat1, *A. pseudoterreus* aspartate aminotransferase gene.

The fourth β-alanine pathway transgene expression cassette with an additional *A. pseudoterreus* aspartate 1-aminotransferase gene (Apaat1, jgi|Aspte1|7965|ATET_04402; FIG. 15) was prepared by PCR with oligo pairs of PAptefF/PAptefR for 956 bp *A. pseudoterreus* tef1 gene (Aptef1, jgi|Aspte1|9546|ATET_05983) promoter and the ApaatF/Apaat for 1898 bp A. *pseudoterreus* aspartate aminotransferase entire coding region and 269 bp its transcriptional terminator. The fragments were assembled into 3HP4070 linearized with restriction endonuclease XbaI to form transgene expression cassette 3HP4071. The entire transgene expression construct was verified by Sanger DNA sequencing.

Figures 17A, 17B, 17C, 17D, 17E:
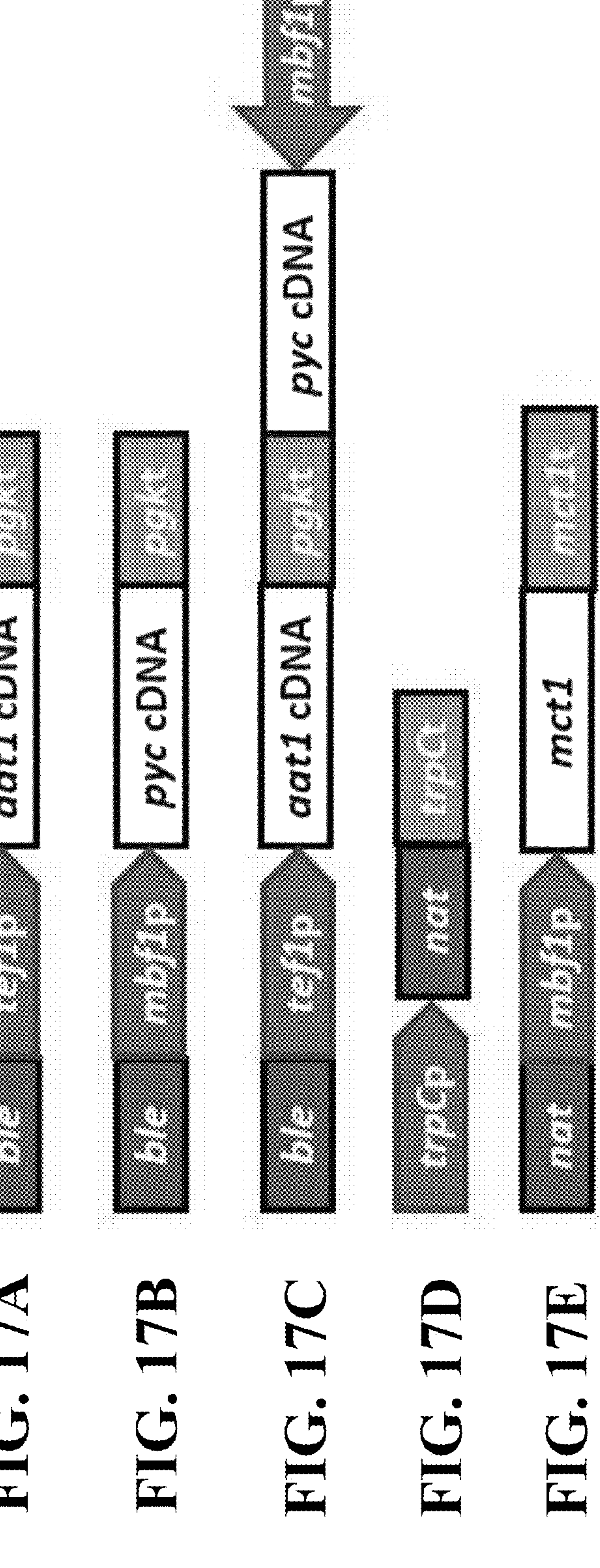
FIGS. 17A-17E. Diagram of transgene overexpression cassettes of *A. niger* aspartate aminotransferase (aat1), pyruvate carboxylase (pyc) or their combination, and monocarboxylate transporter (mct1).

The PCR fragments for *A. niger* aspartate aminotransferase gene (aat1, GenBank: EHA22111) over-expression construct 3HP4074 (FIG. 17A, ble, tef1P:aat:pgk1T) were prepared with the oligo pair bleF1/bleR1 and plasmid DNA pAN8-1 (GenBank: Z32751.1) for 1550 bp DNA fragment of the bacterial bleomycin resistance (ble) marker gene, the oligo pair PAntef1F/PAntef1R for 870 bp DNA fragment of translation elongation factor 1 (tef1, Genbank: CBJ23536.1) promoter of *A. niger*, the oligo pair AnaatF/AnaatR for the 1401 bp aat1 cDNA of *A. niger*, and the oligo pair TAnpgkF1/TAnpgkR1 for 772 bp DNA fragment of the transcriptional terminator of phosphoglerate kinase (pgk, jgi|aspin7|1147902) gene of *A. niger*. All PCR fragments were assembled together into the pBSK(−) linearized by HindIII and PstI restriction enzymes with Gibson assembly master mix (NEB, Ipswich, MA, USA). Similarly, the over-expression transgene construct for pyruvate carboxylase were prepared with the oligo pairs of bleF1/bleR2 (ble) for 1550 bp DNA fragment of the ble gene, TAnpgkF2/TAnpgkR1 (Tpgk) for 772 bp DNA fragment of the transcriptional terminator of pgk, AnpycF/AnpycR for 3579 bp cDNA fragment of *A. niger* pyruvate carboxylase cDNA (pyc; jgi|Aspni7|1031996), and PAnmbf1F/PAnmflR for 1499 bp DNA fragment of *A. niger* mbf1 gene (jgi|Aspni7|1145066) promoter (FIG. 17B, 3HP4076) or their combination, where pyc overexpression cassette was incorporated into the downstream of aat1 overexpression cassette right after the TpgkF2/TpgkR1 (pgkt) DNA fragment (FIG. 17C, 3HP4077). The entire transgene expression construct was verified by Sanger DNA sequencing.

Prior to building the transgene overexpression construct for *A. niger* monocarboxylate transporter (mct1, jgi|Aspni7|1163060), the new selection marker nat1 (*Streptomyces noursei* nourseothricin N-acetyl transferase optimized for the codon usage of *Saccharomyces cerevisiae*) gene under the control of *A. nidulans* trpC promoter and *A. niger* trpC transcriptional terminator cassette was prepared. The DNA fragment for *A. nidulans* trpC promoter and *A. niger* trpC transcriptional terminator were isolated with the oligo pair 2555trpF1/2556trpR1 and 2559trpF2/2560trpR2 with the pCSN44 plasmid (GenBank: LT726870.1) as a template for trpC promoter and with *A. niger* genomic DNA as a template for *A. niger* trpC transcriptional terminator, respectively. The nat1 coding region was obtained by PCR with oligo pair 2557nat1F/2558nat1R and the plasmid DNA CHCp9 (Calvey et al., Curr Genet 60(3):223-30, 2014) as a template. All three DNA fragments were assembled to form vector (FIG. 17D, 3HP4114). The mct1 overexpression construct was prepared with the oligo pairs of nat1F/nat1R for 1250 bp DNA fragment of nat1 marker gene with 3HP4114 as a template, PAnmbf1/PAnmbf1R for 1351 bp DNA fragment of *A. niger* mbf1 gene promoter and AnmctF/AnmctR for 1544 bp DNA fragment of *A. niger* mct gene coding sequence and its transcriptional terminator, which were assembled into pBSK(−) linearized with HindIII/PstI restriction endonucleases to form 3HP4126 (FIG. 17E). The entire transgene expression construct was verified by Sanger DNA sequencing.

Figures 19A, 19B, 19C, 19D, 19E:
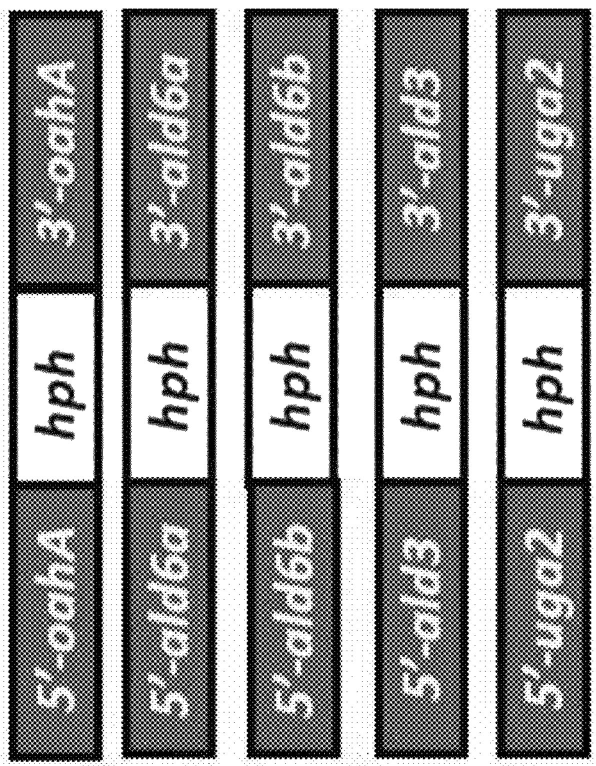
FIGS. 19A-19E. A diagram of gene disruption constructs for *A. niger* oahA, ald6a, ald6b, ald3, and uga2 genes. The hph, *E. coli* hygromycin B phosphotransferase (hph) gene for selection marker.

Gene disruption constructs for oahA (jgi/Aspni7/1145269), ald6a (jgi/Aspni7/1182225), ald6b (jgi/Aspni7/201822), ald3 (jgi/Aspni7/1126238), and uga2 (jgi/Aspni7/57046) from *A. niger* were prepared by Gibson assembly of related DNA fragments isolated via PCR with the following oligo pairs: 5AnoahAF/5AnoahAR, hphF1/hphR1, and 3AnoahAF/3AnoahAR for oahA gene (FIG. 19A, 3HP4102); 5Anald6aF/5Anald6haR, hphF2/hphR2, and 3Anald6aF/3Anald6aR for ald6a gene (FIG. 19B, 3HP4103); 5Anald6bF/5Anald6bR, hphF3/hphR3, and 3Anald6bF/3Anald6bR for ald6b gene (FIG. 19C, 3HP4104); 5Anald3F/5Anald3R, hphF4/hphR4, and 3Anald3F/3Anald3R for ald3 gene (supplementary FIG. 19D, 3HP4108); 5Anuga2F/5Anuga2R, hphF5/hphR5, and 3uga2F/3uga2R for uga2 gene (FIG. 19E; 3HP4109).

For further genetic modification in the transgenic strain, the marker recycling strategy was applied to overcome the limitation of selection marker genes in *A. niger*. The Tet-On/Cre-loxP system (Jiang et al., Front Microbiol 7:485, 2016; Meyer et al., Appl Environ Microbiol. 77(9):2975-83, 2011) was incorporated into the new transgene expression or gene disruption. The Tet-On/Cre-loxP transgene expression construct was prepared with the oligo pairs of nat1F/nat1R for 1250 bp DNA fragment of entire nat1 marker gene with 3HP4114 as a template, ubilF/ubilR, rtTAF/rtTAR, tetO7F/tetO7R, and trpCF/trpCR for 848 bp DNA fragment of *A. niger* ubi1S27 gene (jgi|Aspni7|1135631) promoter, 1036 bp DNA fragment of reverse tetracycline transactivator (rtTA2S), 1550 bp DNA fragment of tetracycline resistance operon/gpdA mini promoter of *A. nidulans*/Cre recombinase (tetO7-Pmn-Cre), in which the rtTA2S and tetO7-Pmn-Cre were synthesized with codon usage optimization for *A. niger*, and 554 bp DNA fragment of *A. carbonarius* trpC transcriptional terminator, respectively. All DNA fragments were assembled into the pBSK(−) linearized with HindIII/PstI restriction endonucleases to form transgene expression vector 3HP4140 (FIG. 20A). The entire transgene expression construct was verified by Sanger DNA sequencing.

The nptII [the neomycin phosphotransferase II gene, (Beck et al., Gene 19(3):327-36, 1982)] marker gene for *A. niger* was constructed with the DNA fragments isolated by PCR with oligo pair 2662mdhFp/2663mdhRp for 965 bp DNA fragment of *A. niger* mdh (jgi|Aspni7|1143375) gene promoter and oligo pair 2664npt2F/2665npt2R for 1138 bp DNA fragment of nptII gene coding region (GenBank: AF485783.1, 795 bp) and *A. nidulans* trpC transcriptional terminator (GenBank: U24705.1, 343 bp). The DNA fragments were assembled into the pBSK(−) linearized with HindIII/PstI restriction endonucleases to form plasmid vector 3HP4134 (FIG. 20B). To introduce the 31 bp loxP fragments into the nptII marker gene, the oligo pair loxPnpt2F/loxPnpt2R was used to isolate the nptII marker gene from 3HP4134 plasmid DNA and assembled into the pBSK(−) linearized with HindIII/PstI restriction endonucleases to form plasmid vector 3HP4136 (FIG. 20C).

To construct the fifth b-alanine 3HP pathway transgene expression cassette with loxP-nptW as a selection marker and a new set of *A. niger* promoters, the 3HP4028 plasmid DNA was used for a DNA template for isolation of panD, bapat, hpdh, elf3t and trpCt with the following oligo pairs: 2728pu4F/2729pu4R for 819 bp DNA fragment of *A. niger* ubi4 (jgi|Aspni7|1146681) gene promoter, 2730panF/2731panR for 2198 bp DNA fragment of panD gene and a part of elf3t, 2732bapatF/2733bapatR for 1823 bp DNA fragment of bapat gene and a part of elf3t, and 847 bp DNA fragment of 2734pus1F/2735pus1R forA. *niger* ubiS27 gene promoter in reverse complementation. The first 4 DNA fragments were assembled into the 3HP4136 vector linearized with restriction endonuclease XhoI to form plasmid 3HP4144 (FIG. 20D). The oligo pair 2736pmbF/273pmbR for 1199 bp DNA fragment of *A. niger* mbfA promoter, and 2738hpdhF/2739hpdhR for 1257 bp DNA fragment of hpdh gene and *A. nidulans* trpC transcriptional terminator. These two fragments were assembled into the plasmid 3HP4144 linearized with restriction endonuclease XbaI to the final transgene expression construct 3HP4145 shown in FIG. 20E. The entire transgene expression construct was verified by Sanger DNA sequencing.

TABLE 1

Oligos used for transgene vector constructions of selected gene over-expressions or disruptions.

| | SEQ ID NO. | |
|---|---|---|
| | | β-alanine pathway transgene expression cassette with ptrA marker gene (plasmid vector 3HP4028) |
| 1969cad1 | SEQ ID NO: 10 | ccctcgaggtcgacggtatcgataGATATCGGTTGTAGCAGCGT AAACAC |
| 1970cad2 | SEQ ID NO: 11 | tctttcatagtagCCTTGGTGAACATCTTGAGG |
| 1971gpdA1 | SEQ ID NO: 12 | atgttcaccaaggCTACTATGAAAGACCGCGATG |
| 1972gpdA2 | SEQ ID NO: 13 | cgccggtggcgggCATTGTTTAGATGTGTCTATGTG |
| 1973pan1 | SEQ ID NO: 14 | catctaaacaatgCCCGCCACCGGCGAGGACCA |
| 1974pan2 | SEQ ID NO: 15 | atccaacccatcaGAGGTCGGAGCCCAGGCGTTCG |
| 1975ter1 | SEQ ID NO: 16 | gggctccgacctcTGATGGGTTGGATGACGATG |
| 1976ter2 | SEQ ID NO: 17 | tctggcccagctcTGAGTCCTAGATGGGTGGTG |
| 1977bap1 | SEQ ID NO: 18 | catctaggactcaGAGCTGGGCCAGACATTCCTTC |
| 1978bap2 | SEQ ID NO: 19 | gtccatcaacatgGAACTGATGATCGTCCAGGTCAC |
| 1979eno1 | SEQ ID NO: 20 | cgatcatcagttcCATGTTGATGGACTGGAGGG |
| 1980eno2-HpaI | SEQ ID NO: 21 | gaactagtggatcccccgggctgc**GttaaC**TCGAGCTTACAAGAA GTAGCC<br>GGCTACTTCTTGTAAGCTCGA**GttaaC**gcagcccgggggatc cactagttc |
| 1981tdhA1 | SEQ ID NO: 143 | acaggctacttcttgtaagctcgagttTCTGTACAGTGACCGGTGA C |
| 1982tdhA2 | SEQ ID NO: 22 | tgaccagcacgatCATGGTGATGTCTGCTCAAG<br>CTTGAGCAGACATCACCATGatcgtgctggtca |
| 1983hpd1 | SEQ ID NO: 23 | agacatcaccatgATCGTGCTGGTCACGGGCGC |
| 1984hpd2 | SEQ ID NO: 24 | gccatcggtcctaTTGGCGGTGGACGTTCAGGC<br>GCCTGAACGTCCACCGCCAAtaggaccgatggc |
| 1985trp1 | SEQ ID NO: 25 | cgtccaccgccaaTAGGACCGATGGCTGTGTAG |
| 1986trp2 | SEQ ID NO: 26 | cccgtctgtcagaGAGCGGATTCCTCAGTCTCG<br>CGAGACTGAGGAATCCGCTCtctgacagacggg |
| 1987ptrA1 | SEQ ID NO: 27 | gaggaatccgctcTCTGACAGACGGGCAATTGATTAC |
| 1988ptrA2 | SEQ ID NO: 28 | gaatgttgctgagGAGCCGCTCTTGCATCTTTG<br>CAAAGATGCAAGAGCGGCTCctcagcaacattc |
| 1989cad3 | SEQ ID NO: 29 | gcaagagcggctcCTCAGCAACATTCGCCATGTTC |
| 1990cad4 | SEQ ID NO: 30 | actaaagggaacaaaagctggagctCAGCTCCACTGCTCATAGT CTTTG |
| | | Two copies of β-alanine pathway transgene expression cassette with ptrA marker gene (plasmid vector 3HP4046, 2x3HP) |
| 2085HP2F | SEQ ID NO: 31 | acacaattctctatctcagatttgCTACTATGAAAGACCGCGATG GGC |
| 2086HP2R | SEQ ID NO: 32 | ttcagtttcgtccgaggacttttggAATTCAAATCTGAGATAGAGA ATTG |
| | | β-alanine pathway transgene expression cassette with hph marker gene (plasmid vector 3HP4070) |
| 2201 | SEQ ID NO: 33 | cgaggtcgacggtatcgataACGGATCGGCAAAGCAATCTAC G |
| 2202 | SEQ ID NO: 34 | atccaacccaTCAGAGGTCGGAGCCCAGGC |

TABLE 1-continued

| Oligos used for transgene vector constructions of selected gene over-expressions or disruptions. | | |
|---|---|---|
| | SEQ ID NO. | |
| 2203 | SEQ ID NO: 35 | cgacctctgaTGGGTTGGATGACGATGACTTC |
| 2212 | SEQ ID NO: 36 | agtggatcccccgggctgcaCTCGAGCTTACAAGAAGTAGCC TG |
| 2213hphF | SEQ ID NO: 37 | gcccgggggatccactagttGCTGGAGCTAGTGGAGGTCAAC |
| 2214hphR | SEQ ID NO: 38 | ctgtacagagCGGTCGGCATCTACTCTATTC |
| 2215hpdF | SEQ ID NO: 39 | atgccgaccgCTCTGTACAGTGACCGGTGAC |
| 2216hpdR-XbaI | SEQ ID NO: 40 | agggaacaaaagctggagcttctAGAGAATTGTGTGGGATGAG |
| | | β-alanine pathway transgene expression cassette with hph marker gene and aat1 (plasmid vector 3HP4071) |
| PAptefF | SEQ ID NO: 41 | ctctcatcccacacaattctGAGCATCATCCCATGATAGC |
| PAptefR | SEQ ID NO: 42 | aaaggggcgaACTGTTGTAGAAGATATCCGTTAG |
| ApaatF | SEQ ID NO: 43 | ctacaacagtTCGCCCCTTTCCTCCTCTTC |
| ApaatR | SEQ ID NO: 44 | gggaacaaaagctggagcttctagaCGAGCAATACGGAAGCGAA TATC |
| | | Over-expression of *A. niger* aat (plasmid vector 3HP4074) |
| bleF1 | SEQ ID NO: 45 | ctcgaggtcgacggtatcgataGtttaaaCTGAGGTGCAGTGGATG ATTATTAATC |
| bleR1 | SEQ ID NO: 46 | gaggtcaacgTTGATCTGCTTGATCTCGTC |
| PAntef1F | SEQ ID NO: 47 | agcagatcaaCGTTGACCTCACAGGGATTTC |
| PAntef1R | SEQ ID NO: 48 | aaaggggcgaCTTACTGTTGTAGAAGATATCCGTTAG |
| Anaat1F | SEQ ID NO: 49 | caacagtaagTCGCCCCTTTCCTCCTCTTC |
| Anaat 1R | SEQ ID NO: 50 | gacagggcagTTATGAAGTCTCCCGAACTACGC |
| TAnpgk1F | SEQ ID NO: 51 | gacttcataaCTGCCCTGTCGAGTAAGTAAATTTG |
| TAnpgk1R | SEQ ID NO: 52 | actagtggatcccccgggctgcaagcttACTACAGAGAGGAGCTG AAG |
| | | Over-expression of *A. niger* pyc (plasmid vector 3HP4076) |
| bleR2 | SEQ ID NO: 53 | atggccactgTTGATCTGCTTGATCTCGTCTC |
| 2271TAnpgkF2 | SEQ ID NO: 54 | caaggcctagCTGCCCTGTCGAGTAAGTAAATTTG |
| AnpycF | SEQ ID NO: 55 | TCttcagctcctctctgtagtaCTAGGCCTTGACGATCTTGCAG ACAAGATCCTG |
| AnpycR | SEQ ID NO: 56 | cttcaaaatgGCTGCTCCCCGCCAGCCCGA |
| PAnmbf1F | SEQ ID NO: 57 | ggggagcagcCATTTTGAAGATGGATGAGAAGTC |
| PAnmbf1R | SEQ ID NO: 58 | CTccaccgcggtggcggccgctGTTTAAACAGTGGCCATGAA ATCCAATC |
| | | Nat1 selection marker gene construct (plasmid vector 3HP4114) |
| 2555trpF1 | SEQ ID NO: 59 | cgaggtcgacggtatcgataCAGAAGATGATATTGAAGGAGC |
| 2556trpR1 | SEQ ID NO: 60 | aagtagtcatTTGGATGCTTGGGTAGAATAG |
| 2557nat1F | SEQ ID NO: 61 | aagcatccaaATGACTACTTTGGATGACACTG |

TABLE 1-continued

| Oligos used for transgene vector constructions of selected gene over-expressions or disruptions. | | |
|---|---|---|
| | SEQ ID NO. | |
| 2558nat1R | SEQ ID NO: 62 | aaagctagagTTATGGACATGGCATGGACATG |
| 2559trpF2 | SEQ ID NO: 63 | atgtccataaCTCTAGCTTTGTATTGTCTTTAAATTTAC |
| 2560trpR2 | SEQ ID NO: 64 | agtggatcccccgggctgcaGTAAGTAGAAAGCTTTGGGG |
| | | mct1 gene overexpression (plasmid vector 3HP4126) |
| nat1F | SEQ ID NO: 65 | cgaggtcgacggtatcgataACAGAAGATGATATTGAAGGAG C |
| nat1R | SEQ ID NO: 66 | aacgaagaggCAGTAAGTAGAAAGCTTTGGG |
| PAnmbf1F | SEQ ID NO: 67 | ctacttactgCCTCTTCGTTTCTGTGATGC |
| PAnmbf1R | SEQ ID NO: 68 | cggtcgtatgCATTTTGAAGATGGATGAGAAGTC |
| AnmctF | SEQ ID NO: 69 | cttcaaaatgCATACGACCGAGAAGATACC |
| AnmctR | SEQ ID NO: 70 | agtggatcccccgggctgcaGGTTCTCTCCTTGCAGCAAAG |
| | | oahA gene deletion (plasmid vector 3HP4102) |
| 5AnoahAF | SEQ ID NO: 71 | gaggtcgacggtatcgataagcttCTCAGCTGGGTGAAGAACAA C |
| 5AnoahAR | SEQ ID NO: 72 | tagctccagcGTGATAGTGTTGGTCATGCTG |
| hphF1 | SEQ ID NO: 73 | acactatcacGCTGGAGCTAGTGGAGGTCAAC |
| hphR1 | SEQ ID NO: 74 | cgttagtatgCGGTCGGCATCTACTCTATTCC |
| 3AnoahAF | SEQ ID NO: 75 | atgccgaccgCATACTAACGGAAGGGTCAG |
| 3AnoahAR | SEQ ID NO: 76 | agtggatcccccgggctgcaGTACCACGCAAGCTTCGATATG |
| | | aldoa gene deletion (plasmid vector 3HP4103) |
| 5Anald6aF | SEQ ID NO: 77 | gaggtcgacggtatcgatatctaGAGTAAACTGGTGCAGCTATC |
| 5Anald6aR | SEQ ID NO: 78 | tagctccagcAGGTGAGGATGAGGAGAGCTTAG |
| hphF2 | SEQ ID NO: 79 | atcctcacctGCTGGAGCTAGTGGAGGTCAAC |
| hphR2 | SEQ ID NO: 80 | gactgtcttgCGGTCGGCATCTACTCTATTCC |
| 3Anald6aF | SEQ ID NO: 81 | atgccgaccgCAAGACAGTCGATTTCATCCTC |
| 3Anald6aR | SEQ ID NO: 82 | agtggatcccccgggctgcaCACTTGTCCAGACCGAGGTAC |
| | | ald6b gene deletion (plasmid vector 3HP4104) |
| 5Anald6bF | SEQ ID NO: 83 | gaggtcgacggtatcgataGAGGATATGATCTCTTCAACTAT AC |
| 5Anald6bR | SEQ ID NO: 84 | tagctccagcTCTCAGGAGACATCTGTCTC |
| hphF3 | SEQ ID NO: 85 | tctcctgagaGCTGGAGCTAGTGGAGGTCAAC |
| hphR3 | SEQ ID NO: 86 | ctaccatcgaCGGTCGGCATCTACTCTATTCC |
| 3Anald6bF | SEQ ID NO: 87 | atgccgaccgTCGATGGTAGTAGGATGTGG |
| 3Anald6bR | SEQ ID NO: 88 | agtggatcccccgggctgcaCAGAGAAGGTGCAGATTGTG |
| | | aldh3 gene deletion (plasmid vector 3HP4108) |
| 5Anald3F | SEQ ID NO: 89 | cgaggtcgacggtatcgataGCTGGCGGTAGAAGGATTTTC |
| 5Anald3R | SEQ ID NO: 90 | tagctccagcAATTGGCTGACGAAGAGTATAG |
| hphF4 | SEQ ID NO: 91 | tcagccaattGCTGGAGCTAGTGGAGGTC |

TABLE 1-continued

Oligos used for transgene vector constructions of selected gene over-expressions or disruptions.

| | SEQ ID NO. | |
|---|---|---|
| hphR4 | SEQ ID NO: 92 | actgaagacgCGGTCGGCATCTACTCTATTC |
| 3Anald3F | SEQ ID NO: 93 | atgccgaccgCGTCTTCAGTGATGCCGATATC |
| 3Anald3R | SEQ ID NO: 94 | agtggatcccccgggctgcaCGTTTGGGCTTTGTCCTTTAG |
| | | uga2 gene deletion (plasmid vector 3HP4109) |
| 5Anuga2F | SEQ ID NO: 95 | cgaggtcgacggtatcgataCCAACTGGCGCTGTATAGATC |
| 5Anuga2R | SEQ ID NO: 96 | tagctccagcGGTCTGAAAGTAGTCCTGTG |
| hphF5 | SEQ ID NO: 97 | ctttcagaccGCTGGAGCTAGTGGAGGTC |
| hphR5 | SEQ ID NO: 98 | acgaggattgCGGTCGGCATCTACTCTATTC |
| 5Anuga2F | SEQ ID NO: 99 | atgccgaccgCAATCCTCGTCGACCATCAAAAAG |
| 5Anuga2R | SEQ ID NO: 100 | agtggatcccccgggctgcaAGAGGGTATGAAGGAGGAG |
| | | rtTA2S-Tet07-Cre system (plasmid vector 3HP4140) |
| nat1F | SEQ ID NO: 101 | aggtcgacggtatcgatatcACAGAAGATGATATTGAAGGAG C |
| nat1R | SEQ ID NO: 102 | gatagggtggttgtctggatCAGTAAGTAGAAAGCTTTGGG |
| ubi1F | SEQ ID NO: 103 | cgaggtcgacggtatcgataTCCAGACAACCACCCTATCTC |
| ubi1R | SEQ ID NO: 104 | gtctggacatCTTGATGAAGGTCTGGGTTG |
| rtTAF | SEQ ID NO: 105 | cttcatcaagATGTCCAGACTCGATAAGTC |
| rtTAR | SEQ ID NO: 106 | cgtgatacgcTCCATGATTCATGACGTATATTC |
| tet07F | SEQ ID NO: 107 | gaatcatggaGCGTATCACGAGGCCCTTTC |
| tet07R | SEQ ID NO: 108 | gccgaagaccGATCCTCAATCACCATCCTCC |
| trpCF | SEQ ID NO: 109 | attgaggatcGGTCTTCGGCTATAGTTCATTTTTATC |
| trpCR | SEQ ID NO: 110 | agtggatcccccgggctgcaGTTGCGATCAGGTGTGTAATTG |
| | | mdhP-neo marker gene (plasmid vector 3HP4134) |
| 2662mdhFp | SEQ ID NO: 111 | tcatcctcagGAACGACTCCAGAAGTGACTAAG |
| 2663mdhRp | SEQ ID NO: 112 | gttcaatcatGGTGAAATTTGGGATTGTGAC |
| 2664npt2F | SEQ ID NO: 113 | aaatttcaccATGATTGAACAAGATGGATTGC |
| 2665npt2R | SEQ ID NO: 114 | agtggatcccccgggctgcaGACTCTGCTAAGCTATTCTTC |
| | | LoxP-nptII vector (plasmid vector 3HP4136) |
| loxPnpt2F | SEQ ID NO: 115 | ggtcgacggtatcgataATAACTTCGTATAGCATACATTATA CGAAGTTATGAACGACTCCAGAAGTGAC |
| loxPnpt2R | SEQ ID NO: 116 | atcccccgggctgcaataacttcgtataatgtatgctatacgaagtt atGACTCTGCTAAGCTATTCTTC |
| | | New b-alanine 3-HP pathway Intermediate vector (plasmid vector 3HP4144) |
| 2728pu4F | SEQ ID NO: 117 | attgggtaccgggccccccgtttaaaCTTCGGAGTAGCAACGAG TATTTTC |
| 2729pu4R | SEQ ID NO: 118 | attgtttagaAGCGCAGTTAATGGTGTATG |
| 2730panF | SEQ ID NO: 119 | taactgcgctTCTAAACAATGCCCGCCACC |
| 2731panR | SEQ ID NO: 120 | TCCCATACTGCTCCCATAGAAG |
| 2732bapatF | SEQ ID NO: 121 | TCTATGGGAGCAGTATGGGATC |

TABLE 1-continued

| Oligos used for transgene vector constructions of selected gene over-expressions or disruptions. | | |
|---|---|---|
| | SEQ ID NO. | |
| 2733bapatR | SEQ ID NO: 122 | cttcatcaagATGGAACTGATGATCGTCCAG |
| 2734pus1F | SEQ ID NO: 123 | tcagttccatCTTGATGAAGGTCTGGGTTG |
| 2735pus1R | SEQ ID NO: 124 | tattatcgataccgtcgaccTCCAGACAACCACCCTATCTC |
| | | Entire new b-alanine 3-HP pathway vector (plasmid vector 3HP4145) |
| 2736pmbF | SEQ ID NO: 125 | atacgaagttattgcagcccGGGACATGCTGGAAGGGATTTTC |
| 2737pmbR | SEQ ID NO: 126 | gcacgatcatTTTGAAGATGGATGAGAAGTCGG |
| 2738hpdhF | SEQ ID NO: 127 | catcttcaaaATGATCGTGCTGGTCACGGG |
| 2739hpdhR | SEQ ID NO: 128 | ctagaactagtggatcccccgtttaaaCCAATGGGATCCCGTAATC AATTG |

Example 2: Evaluation of 3-HP Production in *Aspergillus pseudoterreus*

Figure 1A:
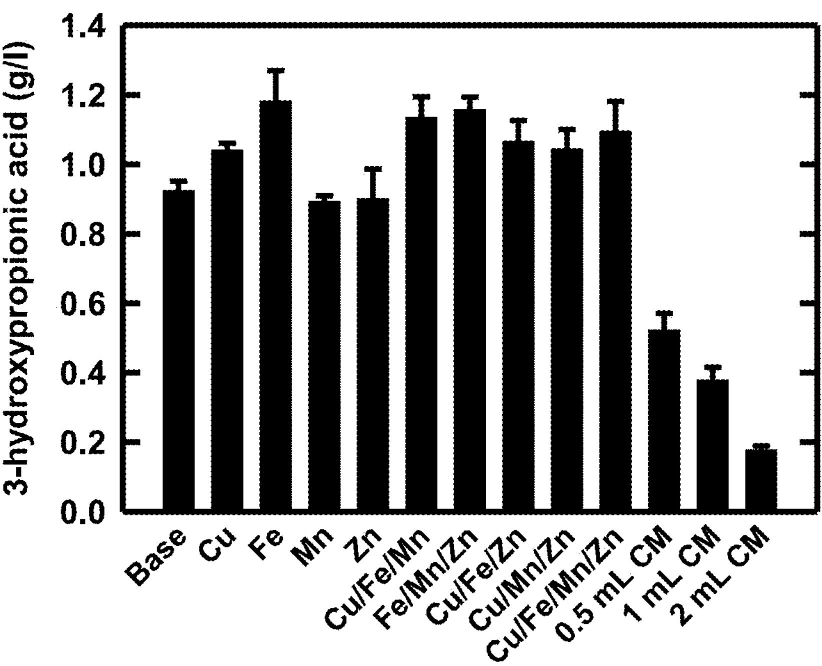
FIGS. 1A-1B.
Figure 11A:
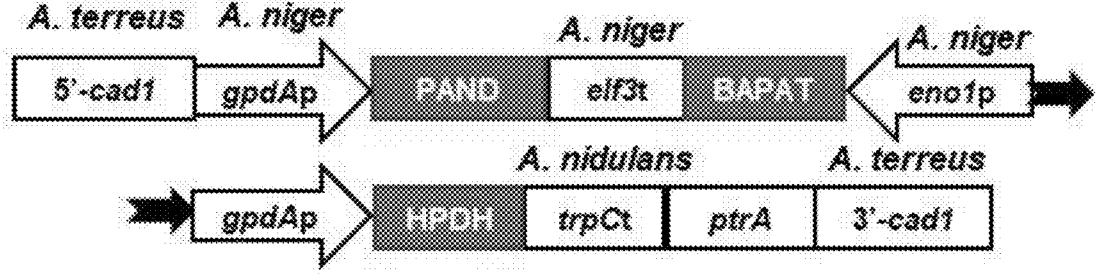
FIGS. 11A-11D. The diagram of the β-alanine 3HP pathway transgene expression cassette with *A. pseudoterreus* cad1 gene locus targeting and Southern blotting analyses of transgenic *A. pseudoterreus*.
Figure 11B:
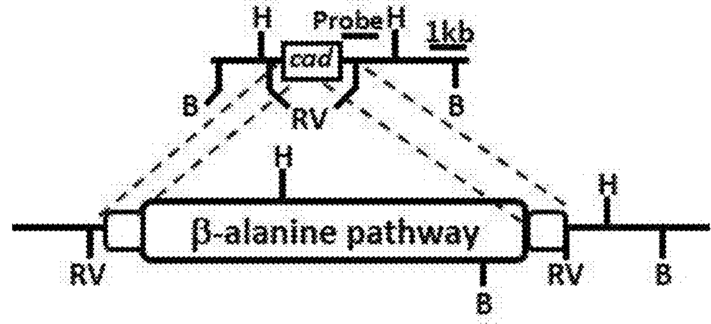
Figures 11C, 11D:
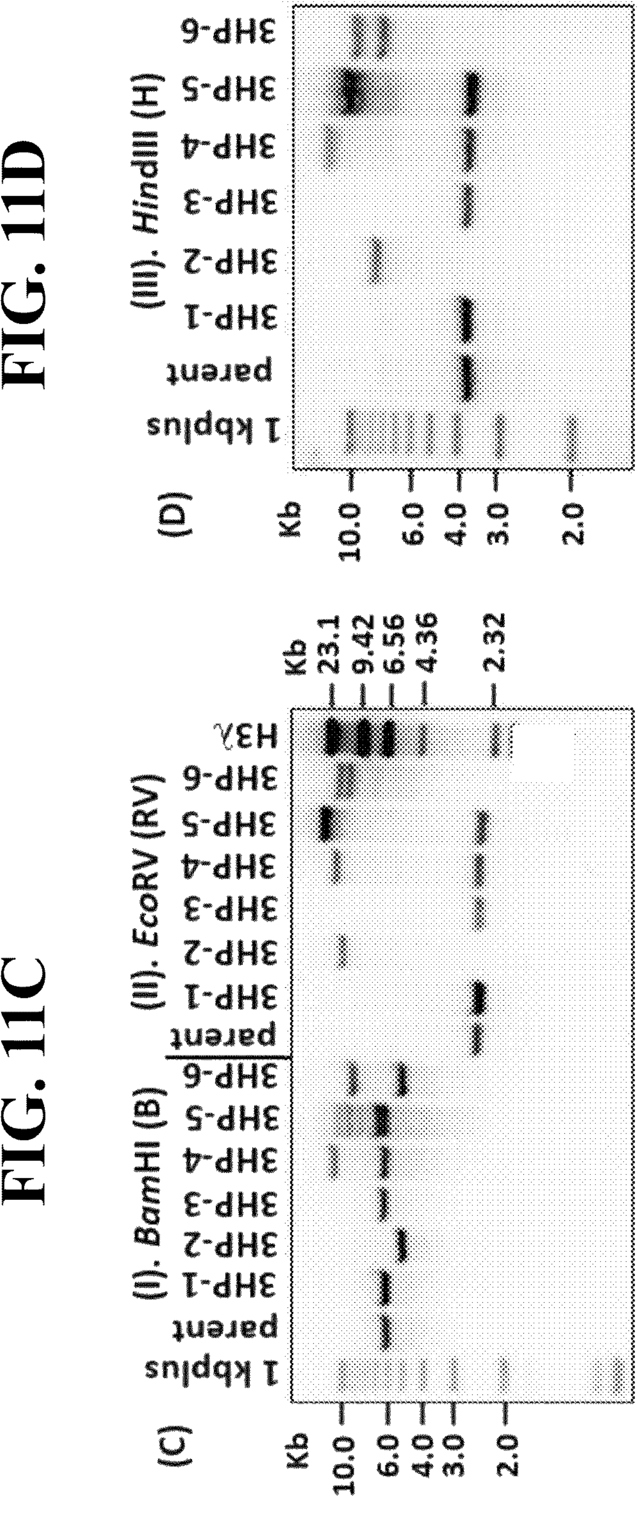
Figure 12A:
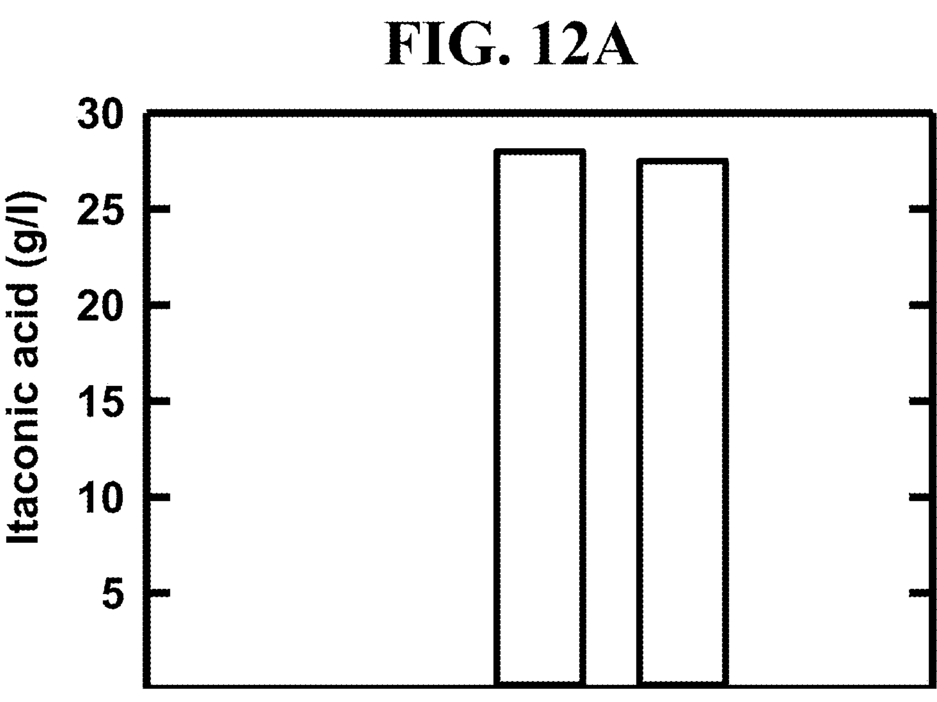
FIGS. 12A-12B. Itaconic acid (FIG. 12A) and 3-hydroxypropionic acid (FIG. 12B) production in the selected individual transgenic strains of *A. pseudoterreus* with overexpression of the β-alanine 3HP pathway transgene expression cassette in the modified RDM medium at 30° C. and 200 rpm for 7 days. The strain 2 and 6 were with the homologous recombination of transgene expression cassette Ap3HP at the cad1 locus (cad1Δ), while strain 4 & 5 with the random integration of the transgene cassette into the chromosomes. All data were average of two biological replates.
Figure 12B:
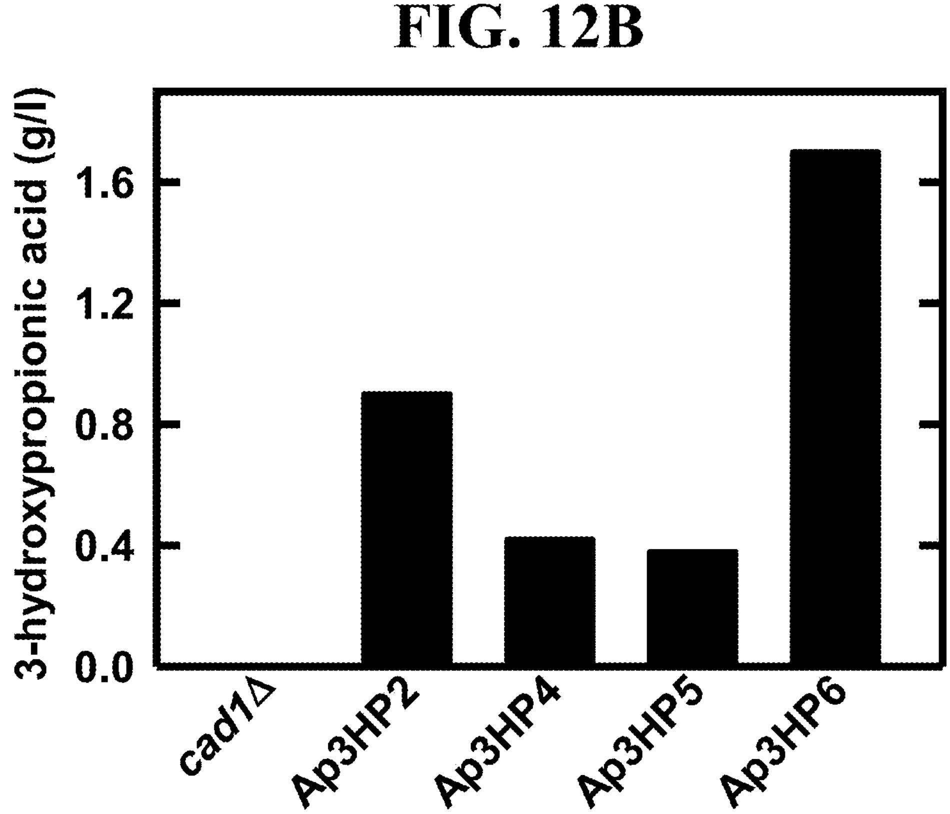

A synthetic β-alanine pathway for 3-HP production using *Tribolium castaneum* aspartate 1-decarboxylase (PAND), *Bacillus cereus* β-alanine-pyruvate aminotransferase (BAPAT) and *Escherichia coli* 3-hydroxypropionate dehydrogenase (HPDH) has been established and demonstrated in *Saccharomyces cerevisiae* (Borodina et al., Metab Eng 27:57-64, 2015) and *Aspergillus pseudoterreus* (Pomraning et al., Front Bioeng Biotechnol 9:603832, 2021). The effect of supplementation with trace elements (TE) and complex nutrients on 3-HP production in transgenic strain *A. pseudoterreus* Ap3HP6 that contains two copies of the β-alanine pathway (FIGS. 11A-11D; FIGS. 12A-12B) was studied, since the production medium B (RDM) was originally optimized for itaconic acid production (Riscaldati et al., J Biotechnol 83(3):219-30, 2000). Individual or combinations of TE were added to the base culture medium at up to 20-fold the original concentration. FIG. 1A shows that both Cu and Fe enhance 3-HP production in modified production medium B (mRDM). However, no synergetic effects were observed when combinations of Cu, Fe, Mn, and Zn were added. In addition, supplementation with small amounts of nutrient rich medium (0.5, 1, or 2 ml YPD) substantially reduced 3-HP production.

Figure 1B:
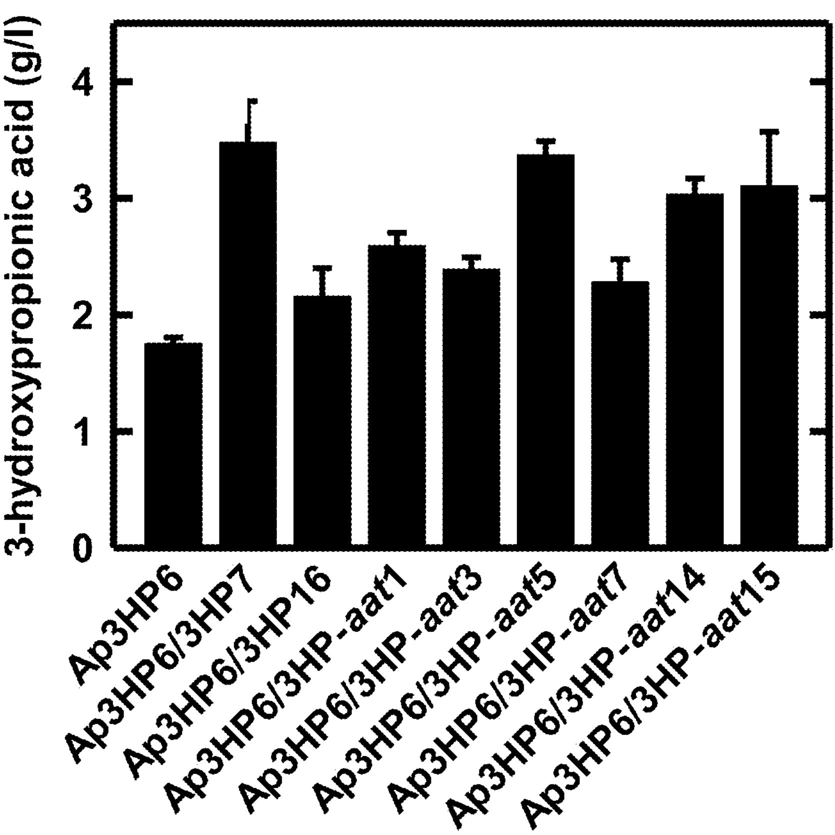

The expression of the β-alanine pathway for 3-HP production was limited by overexpressing additional copies of the pathway was then tested. A transgene expression cassette containing one (3HP) or one with the aat over-expression (3HP-aat) of the β-alanine pathway (FIG. 14; FIG. 15) was randomly integrated into the chromosome of transgenic strain Ap3HP6. 3-HP titer in selected transgenic strains was increased up to 3.4 g/l, about twice the concentration of the parent strain (FIG. 1B). In addition to 3-HP, significant amounts of other organic acids such as aconitic acid and citric acid were produced by *A. pseudoterreus* (Pomraning et al., Front Bioeng Biotechnol 9:603832, 2021) suggesting it may not be an ideal acidophilic filamentous fungus for 3-HP production. Therefore, *A. niger*, an industrial species used for citric acid production, was examined as a host for 3-HP production.

Example 3: Evaluation of 3-HP Production in *A. niger*

Figure 16A:
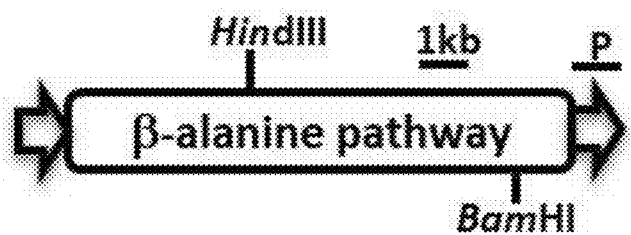
FIGS. 16A-16C. Southern blot analysis confirmed the β-alanine 3HP pathway random integrations into the chromosomes of *A. niger* in the selected single spore isolates of transgenic strain An3HP5, An3HP9, An3HP10, and An2×3HP1 with multiple copies of chromosomal insertion.
Figure 16B:
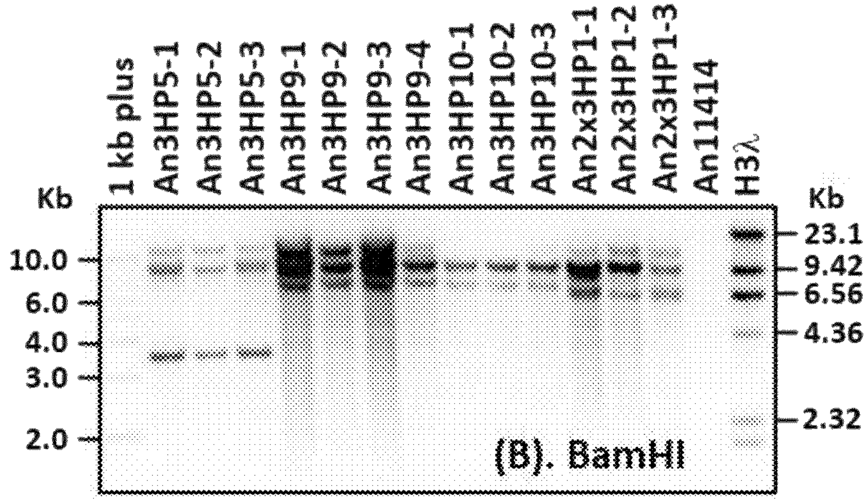
Figure 16C:
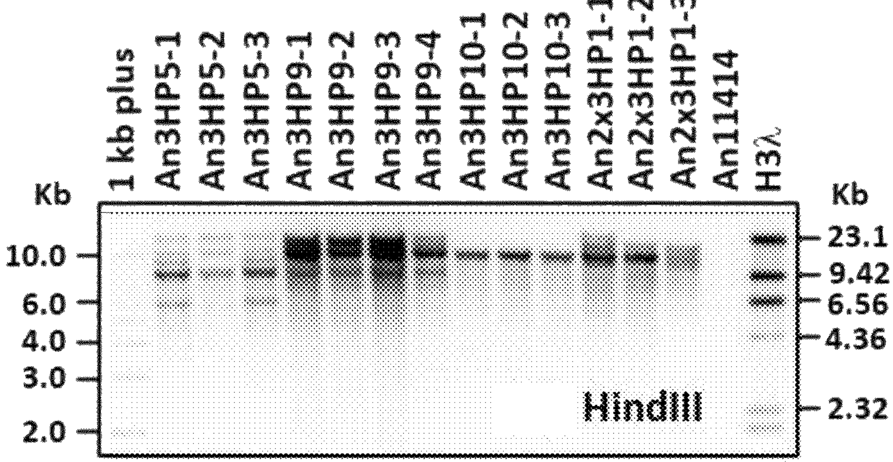

The same linearized transgene expression cassette (FIG. 11A) used in *A. pseudoterreus* was randomly integrated into the chromosomes of *A. niger*. Three transgenic *A. niger* strains, An3HP5, An3HP9, and An3HP10 were selected for evaluation of 3-HP production in mRDM medium. The results in FIG. 2A show that transgenic strain An3HP9 produced the highest 3-HP titer, reaching 6.8 g/l in mRDM, a 200% increase over the highest titers produced by *A. pseudoterreus*. Prior to further genetic engineering in the An3HP9 strain, the copy number was estimated by Southern blotting analysis. The results in FIGS. 16A-16C show that strain An3HP9 contains more than one copy of the β-alanine pathway for 3-HP production. The actual copies of insertion in An3HP9 were estimated as twelve by short-read whole genomic DNA sequencing (FIG. 9).

Example 4: Multi-Omics Analysis of 3-HP Production in *Aspergillus* Species

Figure 3A:
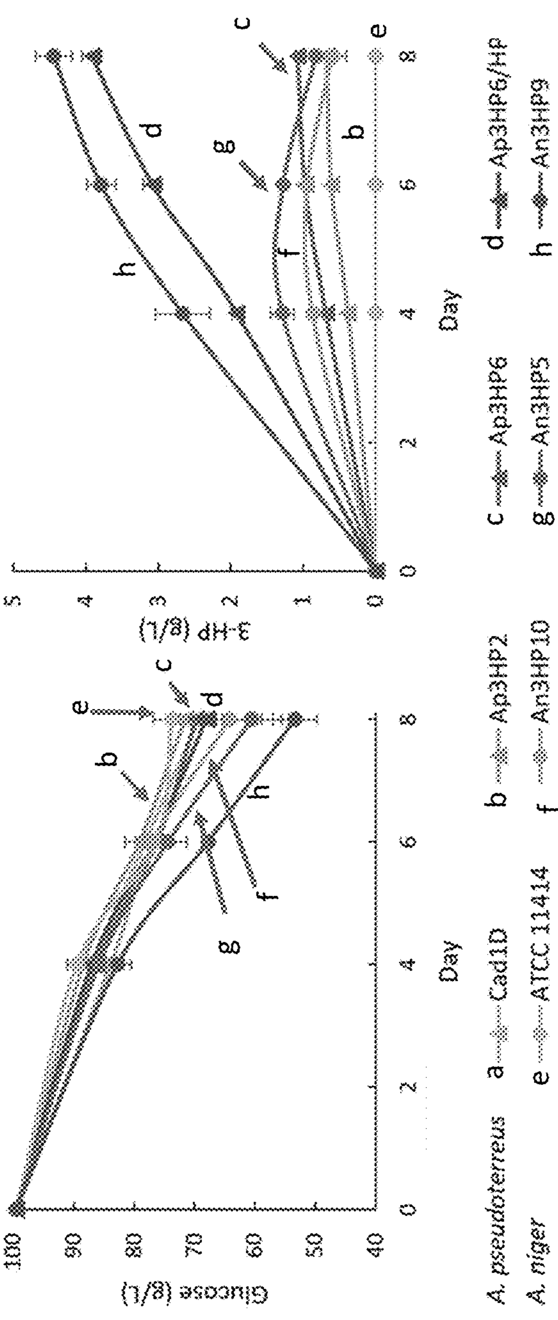
FIGS. 3A-3D. Multi-omic analyses of 3-HP production in *Aspergillus* species.
Figure 3B:
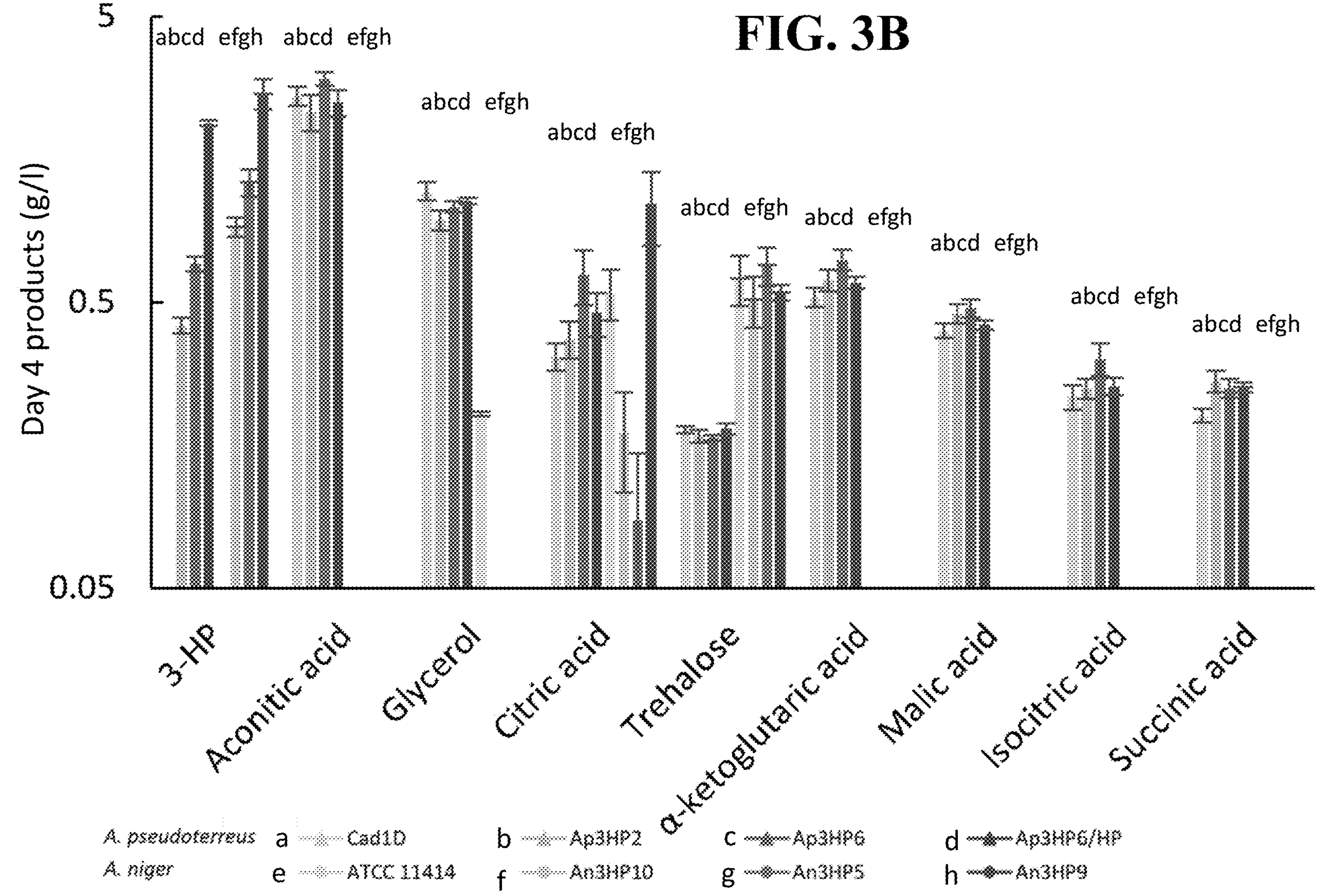
Figure 3C:
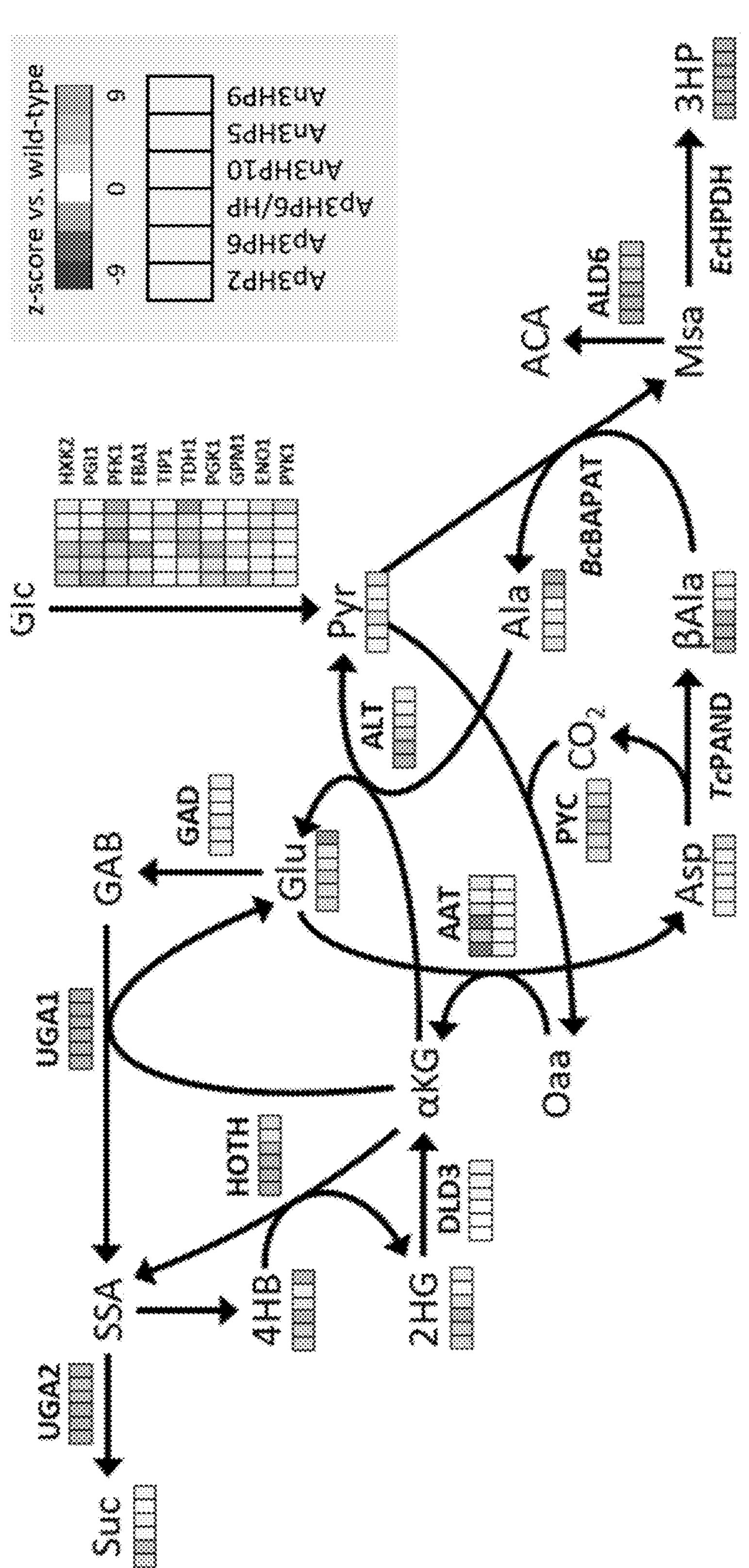

In both *A. pseudoterreus* and *A. niger*, transformants of the same β-alanine pathway for 3-HP production were isolated that produce a broad range of 3-HP titers. The transformants of both species were compared during time-course cultivation in shake-flasks in mRDM (FIG. 3A). In some cases, 3-HP titer declined later in the cultivation consistent with previous observations of 3-HP degradation catalyzed by the methylmalonate semialdehyde dehydrogenase ald6 (Pomraning et al., Front Bioeng Biotechnol 9:603832, 2021). Therefore, the biomass and supernatant samples were collected at day four, prior to decrease in titer, to assess the impacts of 3-HP production on metabolism by global and targeted proteomics, and intra- and extracellular metabolomics. While the range of 3-HP yields is comparable for the transformants obtained from the two *Aspergillus* species, the spectrum of co-products is dissimilar. Aside from 3-HP, from the panel of metabolites quantified, only trehalose and citric acid were detected in the *A. niger* fermentation broth. In contrast, *A. pseudoterreus* produced a wide variety of contaminating co-products that include glycerol and most of the tricarboxylic acid (TCA)-cycle derived organic acids (FIG. 3B). Targeted peptides designed for the heterologous enzymes in the β-alanine pathway were used to compare expression level between the species (FIG. 3C) and confirmed that the pathway is expressed at a higher level in strains that produce more 3-HP.

Figure 3D:
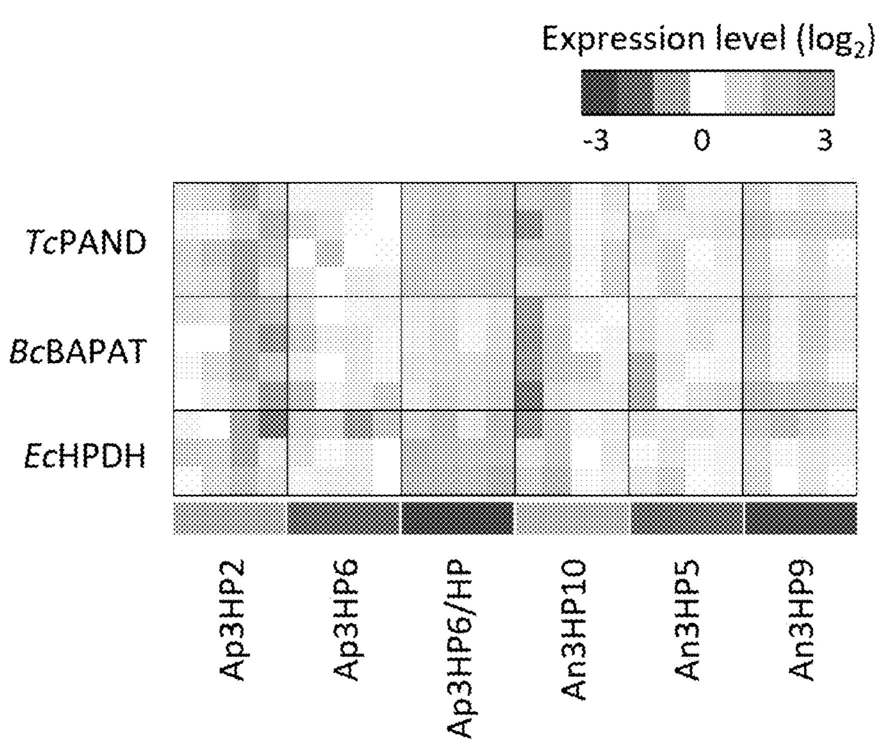

Global proteomics and metabolomics were used to assess the impact of increasing 3-HP production on metabolism. Metabolomics revealed that in both species intracellular β-alanine, 3-HP, and 4-hydroxybutyrate were significantly increased in all transformed strains. Proteomic analysis identified ALD6 as significantly up-regulated in all engineered strains indicating degradation via the pathway intermediate malonate semialdehyde is a conserved aspect of 3-HP metabolism in *Aspergillus* species. Proteins involved in the GABA shunt (UGA1 and UGA2) and a hydroxyacid-oxoacid transhydrogenase involved in conversion of α-ketoglutarate to succinate semialdehyde and mobilization of 4-hydroxybutyrate (Kardon et al., FEBS lett 580(9):2347-50, 2006) are also responsive to 3-HP production and up-regulated in all engineered strains (FIG. 3D).

Most enzymes along the ideal path from glucose to 3-HP do not exhibit a consistent response to the presence of the heterologous 3-HP production pathway. However, in the highest producing *A. niger* strains alanine, glutamate and aspartate are depleted suggesting nitrogen pools may be stressed in this host, while in *A. pseudoterreus* glutamate and alanine are accumulated and both alanine transaminase and aspartate aminotransferase are downregulated.

Example 5: Augmenting Metabolic Flux to Precursor Molecules Required for 3-HP Production in *A. niger*

When directly compared, *A. niger* produced 3-HP with fewer co-products contaminants than *A. pseudoterreus*. Therefore, improvement of 3-HP yield from glucose in *A. niger* was focused on. Carbon efficient flux toward 3-HP relies on the precursor metabolites oxaloacetate and aspartate. Omics analysis indicated that nitrogen pools that support flux through these metabolites may be strained and that expression of pyruvate carboxylase, a key step for carbon efficiency, may be limited in some strains. Flux toward oxaloacetate and aspartate was examined for their contribution to 3-HP production in *A. niger* by overexpression of pyruvate carboxylase (pyc) and aspartate aminotransferase (aat1). cDNA of aat1 or pyc under the control of tef1 promoter (teflp-aat, supplementary FIG. 17A), mbfA (mbfAp-pyc, FIG. 17B) promoter or the combination of aat and pyc (tef1p-aat-pgkt-pyc-mbfAp, FIG. 17C) was integrated into transgenic strain An3HP9. Transformants were evaluated for 3-HP production (FIGS. 18A-18C) and strains with improved titer were purified (FIG. 2B). Overexpression of aat increased titer of 3-HP up to 43%, while pyc overexpression increased titer by as much 93% compared to the original transgenic An3HP9 strain. This indicates that flux toward beach-head metabolites for 3-HP is limiting in An3HP9, however, no synergistic effects were observed in transgenic strains overexpressing both aat and pyc together (FIG. 18C). The copy number of aat or pyc in transgenic strains An3HP9/aat5 and An3HP9/pyc2 (FIG. 9) were estimated as five and eight by short-read whole genomic DNA sequencing, respectively.

Example 6: Effects of Genes Involved in Metabolism of b-Alanine Pathway Intermediates and 3-HP Transport in *A. niger*

Recently, genes potentially involved in metabolism of 3-HP pathway intermediates via multi-omics studies in *A. pseudoterreus* were identified (Pomraning et al., Front Bioeng Biotechnol 9:603832, 2021). Many of these genes are also present in *A. niger*. In this study, the *A. niger* homologs of malonate semialdehyde dehydrogenase (jgi|Asppseute1|414254 [Apald6] and jgi|Asppseute1|497789 [Apald3]), succinate semialdehyde dehydrogenase (jgi|Asppseute1|447301 [Apuga2]), a putative 3-HP transporter identified from *A. pseudoterreus* (jgi|Asppseute1|474223 [Apmct1]), and *A. niger* oxaloacetate hydrolase (AnoahA) were examined for their effect on 3-HP production in the transgenic An3HP9/pyc2 strain (FIG. 17E; FIGS. 19A-19E). Single gene homologs were identified for all the targets except Apald6, where two homologs were identified in *A. niger* (Anald6a and Anald6b). The results in FIG. 2C show that disruption of Anald6a in strain 3HP/pyc2 increased 3-HP titer by 83% to 16.5 g/l, while disruption of Anald6b and Anald3 increased titer by 45% and 26% respectively suggesting that, while Anald6a is likely the major malonate semialdehyde dehydrogenase, all three contribute to directing flux away from 3-HP. In contrast, when Anuga2 was deleted, 3-HP production decreased by 37%. In this strain growth and sugar conversion rate was decreased and the specific yield of 3-HP increased. This suggests that yield of 3-HP from sugars may be improved by limiting flux through the GABA shunt, but that deletion of the pathway entirely is overly detrimental to growth. Disruption of oxaloacetate hydrolase (AnoahA) increased the titer of 3-HP by 45% without impacting growth suggesting that flux toward oxalic acid, a product secreted by *A. niger* (Kobayashi et al., J Ind Microbiol Biotechnol 41(5):749-56, 2014), represents a substantial loss in yield of 3-HP. A monocarboxylate transporter (Anmct1, FIG. 17E), where the homolog in *A. pseudoterreus* responds to the presence of intracellular 3-HP (Pomraning et al., Front Bioeng Biotechnol 9:603832, 2021) was overexpressed, resulting in a 35% improvement in 3-HP suggesting that transport across the plasma membrane may limit 3-HP production.

Example 7: Effects of Additional Copies of β-Alanine Pathway on 3-HP Production in *A. niger*

The initial set of *A. niger* and *A. pseudoterreus* strains expressing various levels of the 3-HP production pathway demonstrated that higher expression level of the β-alanine pathway genes increased the yield of 3-HP (FIG. 3). To determine whether flux through the β-alanine pathway was still a limiting factor for the yield, expression was increased by randomly integrating a new transgene expression cassette (FIG. 20E) into the highest producing An3HP9/pyc2/ald6aD strain. Transformants with higher 3-HP titer than the parents were identified and the best performing single-spore isolate produced 20.5 g/l 3-HP, a 53% improvement over the parent strain (FIG. 2D).

Short-read whole genome sequencing was performed on selected strains at critical points in the construction lineage to estimate copy number of the randomly integrated plasmids (FIG. 9). Approximately 12 copies of the β-alanine pathway were randomly integrated into the *A. niger* chromosomes during construction of strain An3HP9 and that seven additional copies of pyc were integrated into the genome in strain An3HP9/pyc2. In the highest producing strain (An3HP9/pyc2/ald6aA/3HP-6) deletion of ald6a was confirmed and an additional 15 copies of the β-alanine pathway were inserted into the genome bringing the total copy-number of the β-alanine pathway to approximately 27 copies.

Example 8: Optimization of Culture Conditions for 3-HP Production

Culture conditions for citric acid by *A. niger* have been optimized and are dependent on pH, as well as carbon, nitrogen, and manganese concentration (Dai et al., Appl Environ Microbiol 70(4):2474-85, 2004). In this study, the effects of pH, manganese, and nitrogen on 3-HP production was examined with initially genetically engineered strain An3HP9 or 3HP9/pyc2. The effects of citric acid production (CAP) versus mRDM medium were examined in the first *A. niger* transgenic strain An3HP9 by growing them in either CAP medium or mRDM with the pH ranging from 2.0 to 3.4 since pH 2.0 is optimal pH for CAP. 3-HP titer in CAP medium was 2.7 g/L, significantly lower than in mRDM across the pH spectrum. (FIG. 11A). In mRDM, the spore germination rate increased with increasing pH up to 30.7% at pH 3.4 (FIG. 11B) and coincided with increased consumption of glucose resulting in an insignificantly lower yield of 3-HP.

Figures 4A, 4B:
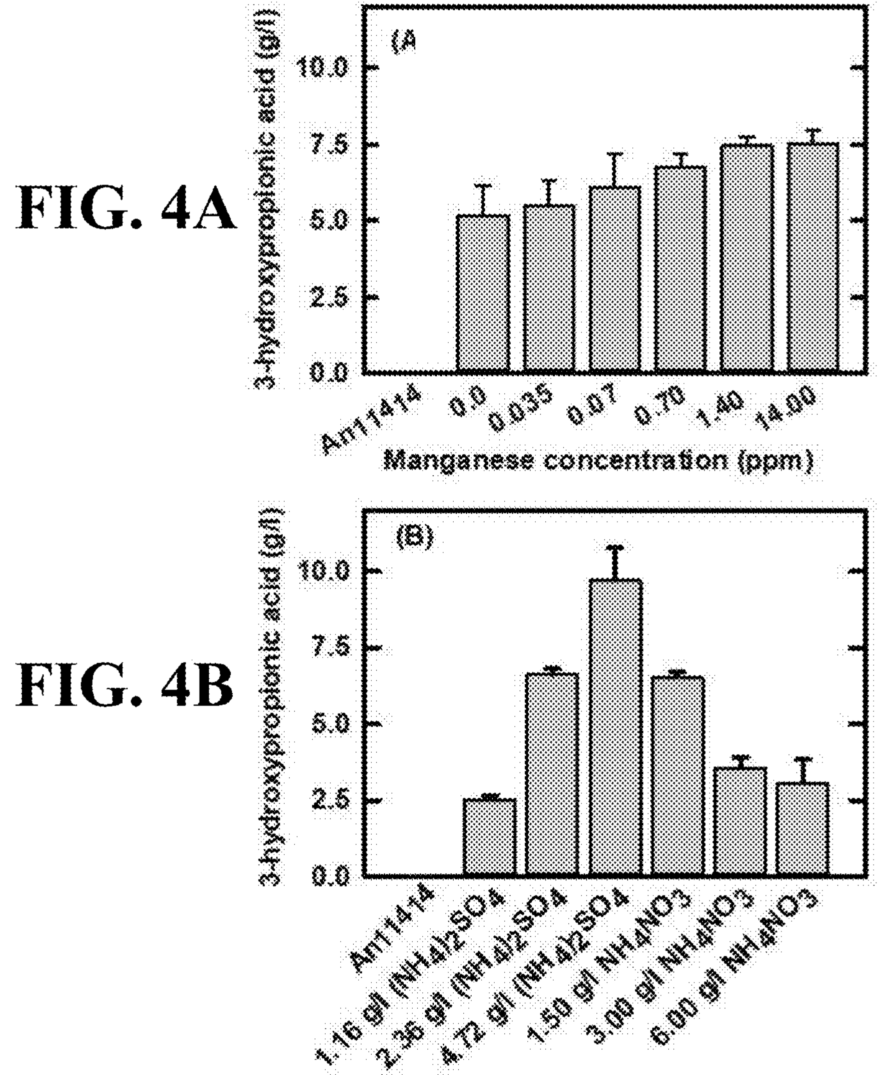
FIGS. 4A-4B. The effects of manganese and nitrogen sources on 3-hydroxypropionic acid production in *A. niger* transgenic strain An3HP/pyc2 grown at 30° C. and 200 rpm for 7 days.

To further increase 3-HP production, effects of manganese on 3-HP production were evaluated in the transgenic strain An3HP9/pyc2 strain, which contains 8 copies of pyc transgene overexpression in An3HP9 with 90% improvement in 3-HP production. When the strain was grown with 0-0.035 ppm manganese, 3-HP titer reached 5.5 g/l but when manganese was increased to 0.07, 0.7, 1.4, 14.0 ppm manganese, the 3-HP titer increased to 6.1, 6.7, 7.4, and 7.5 g/l, respectively suggesting that the required manganese level to support 3-HP metabolism is around 1.4 ppm, about 140-fold higher than that required for citric acid production in *A. niger* (FIG. 4A). At all manganese concentrations the yield of 3-HP was not significantly different while the yield of biomass trended downward with increasing manganese suggesting the increased titer is due to differences in the rate of 3-HP production. The effect of nitrogen concentration and source, in the form of $(NH_4)_2SO_4$ or $NH_4NO_3$, on 3-HP production in the An3HP9/pyc2 strain was also examined (FIG. 4B). 3-HP production increased from 2.5 to 9.7 g/l when the strain was grown in mRDM with 1.16, 2.36, or 4.72 g/l $(NH_4)_2SO_4$, respectively. Increasing nitrogen increased the sugar conversion rate, but overall yield was still significantly higher at the greatest $(NH_4)_2SO_4$ concentration ($p<0.01$). The β-alanine pathway to produce 3-HP is dependent on balanced flux through three transaminases [AAT, alanine transaminase (ALT), and BAPAT] and excess nitrogen may be required to support efficient flux through these reactions. When the strain was grown in mRDM with increasing concentrations of $NH_4NO_3$, 3-HP production decreased suggesting the impact of $NO_3$ as a nitrogen source may be detrimental to 3-HP production. The optimal nitrogen source for batch 3-HP production in shake-flasks was 4.72 g/l of $(NH_4)_2SO_4$, which corresponds to a C/N ratio of 40.

Example 9: Production of 3-HP from Lignocellulosic Feedstock Derived Sugars

Figure 5B:
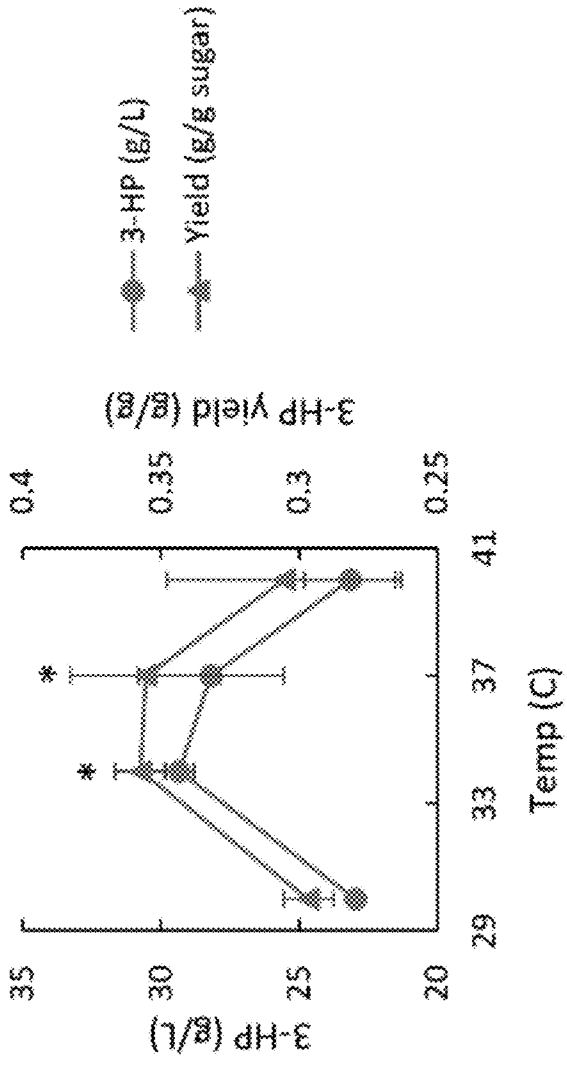

In addition to purified glucose as a carbon source for 3-HP production, sugars derived from lignocellulosic biomass as a feedstock were considered. Corn stover was subjected to dilute alkali deacetylation prior to disk refining and enzymatic hydrolysis (DDR-EH) to release glucose and xylose monomers (Chen et al., Biotechnol Biofuels 7(1):1-12, 2014; Chen et al., Energy Environ Sci 9(4):1237-45, 2016). The conversion of sugars produced by the DDR-EH process using both An3HP9/pyc2/ald6aD and An3HP9/pyc2/ald6aD/3HP-6 strains with the highest 3-HP production titers was investigated. Initially the 3-HP production of An3HP9/pyc-2/ald6aD strain in RDM to provide essential micro and macro-nutrients was tested with increasing concentrations of sugars from the DDR-EH process to identify limits on conversion due to toxicity. *A. niger* was able to germinate and grow in up to 200 g/L total sugars from the DDR-EH process (FIG. 5A) with a significantly lower yield of 3-HP at the highest sugar concentration where growth was maximized. Next, the impact of temperature on conversion in DDR-EH was studied and it was found that 34° C. to 37° C. significantly improved both 3-HP yield and titer with a maximum of 29.4 g/L 3-HP and 0.35 C-mol 3-HP C-$mol^{-1}$ sugars (FIG. 5B). Sugars produced using the DDR-EH process contain a wide variety of characterized and unknown metabolites. To determine whether phosphate, nitrogen, and trace elements (TE) required for growth and production are present at necessary levels in DDR-EH, their concentration were modified up and down by 5-fold to represent limiting and excess concentrations (FIG. 5C). Reducing phosphate or nitrogen concentration reduced biomass production and 3-HP titer suggesting DDR-EH needs to be supplemented with both macronutrients to maximize 3-HP production. However, reduction of TE significantly improved 3-HP titer ($p<0.05$) while excess TE had no impact on growth or productivity suggesting TE in DDR-EH may be present at necessary concentrations without supplementation. When excess nitrogen was supplied, 3-HP titer and yield were both significantly improved without increasing biomass suggesting that supply of precursors for the multiple transaminases of the β-alanine pathway may not be optimized and flux is aided by the presence of excess nitrogen.

Figure 6:
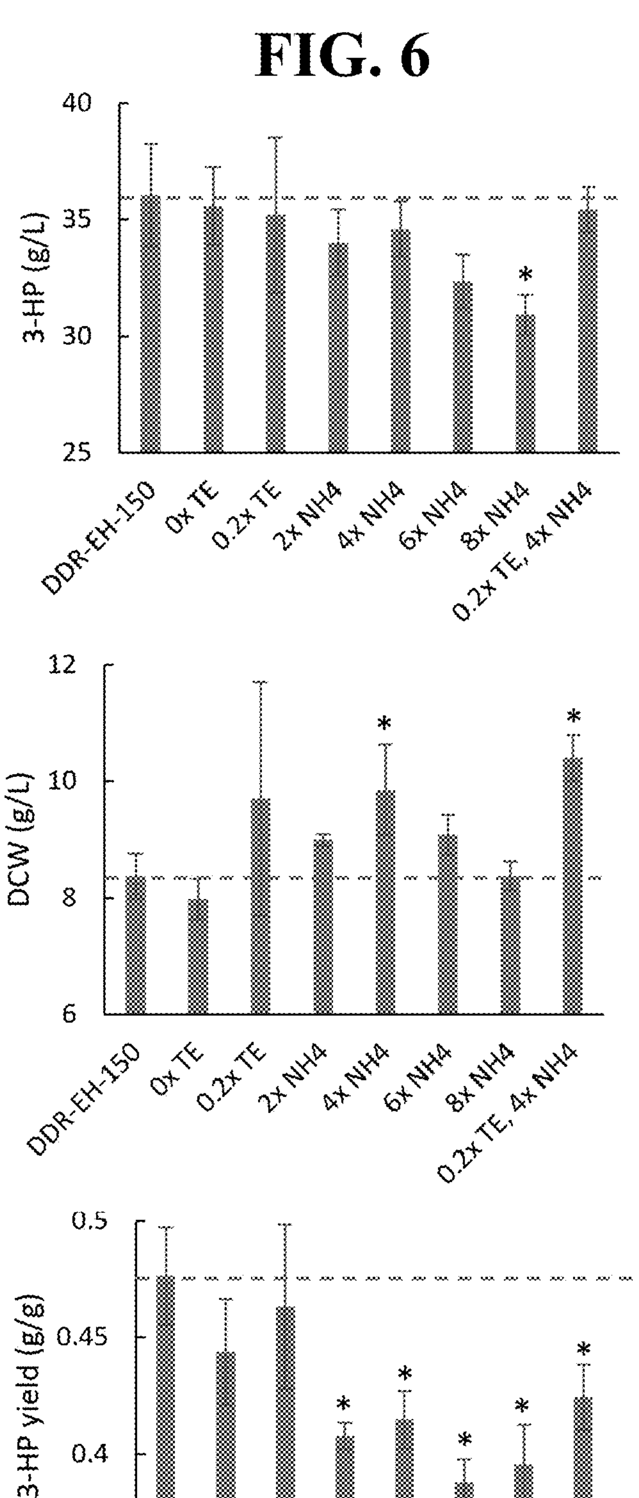
FIG. 6. The impact of nitrogen and trace elements on 3-HP production in RDM with 150 g/L sugars from DDR-EH using *A. niger* strain An3HP9/pyc2/ald6aA/3HP-6 at 200 rpm and 34° C. for 7 days. The data is the average of three biological replicates and is corrected for evaporative loss. Asterisks indicate statistically significant differences ($p<0.05$) from the baseline condition (RDM with 150 g/L total sugars from DDR-EH at 34° C.).
Figure 7:
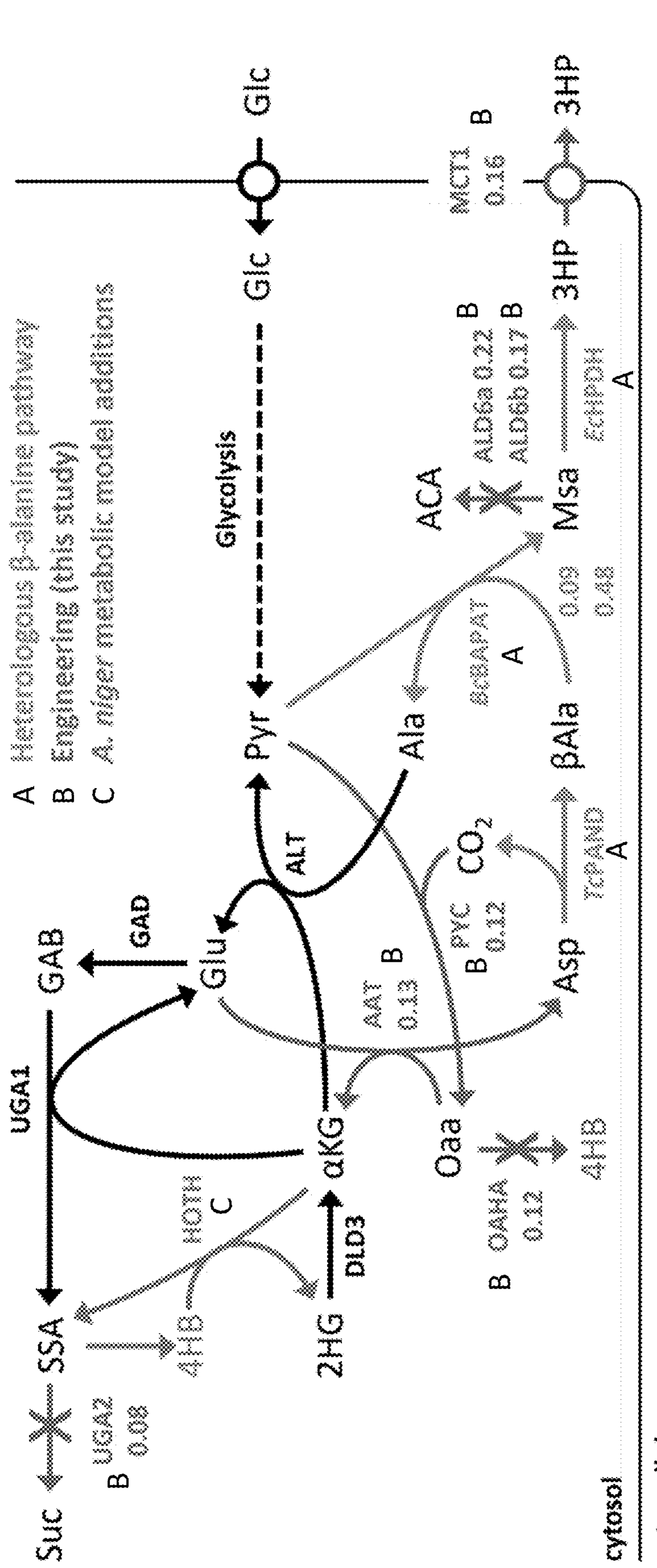
FIG. 7. Summary of strain improvements for 3-HP production in *A. niger*. Yields achieved by over-expression or deletion (indicated by an 'x') of genes involved in 3-HP production. All yields achieved are in the 3HP-PYC background except for the β-alanine base and final pathway yields and the PYC yield.

Some of the potential improvements in cultivation conditions to increase yield, rate, or cost for production of 3-HP from DDR-EH derived sugars were combined and tested with the highest yield An3HP9/pyc2/ald6aA/3HP-6 strain. The standard concentration of sugars was increased to 150 g/L (97.5 g/L glucose and 52.5 g/L xylose) and the temperature increased to 34° C. prior to retesting the impacts of nitrogen and trace elements (FIG. 6). With the combined improvements in the standard RDM with 1× TE and 1× N [2.36 g/l $(NH_4)_2SO_4$], 36.0 g/l 3-HP was produced, and the yield was improved to 0.48 C-mol 3-HP C-$mol^{-1}$ sugars. Reducing or eliminating the addition of TE from the standard RDM did not have a significant impact on growth or 3-HP production. Increasing the concentration of nitrogen tended to increase the amount of biomass produced and, in all cases, significantly decreased the yield of 3-HP.

Example 10: Bioreactor Operations

Figure 22:
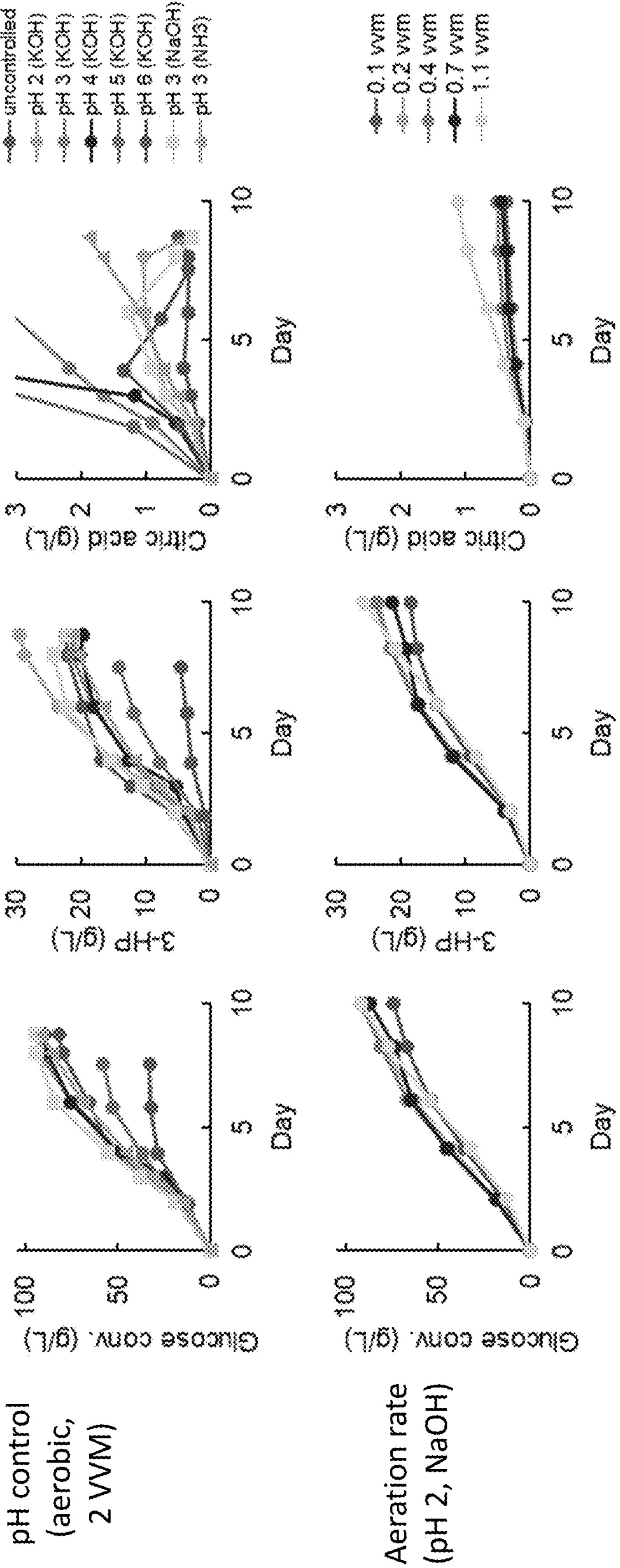
FIG. 22. Establishing scale-up parameters in 0.5 L benchtop bioreactors. 3-HP production across a wide range of pH using different bases for pH control (potassium hydroxide (KOH), sodium hydroxide (NaOH) or ammonia (NH3)) at a high aeration rate (2 vvm). 3-HP was produced as a free acid down to ~pH 2, where the pH drifts to naturally without control. Second, 3-HP production across aeration rates at the best performing pH and base feeding solution (pH 2, NaOH). Highly aerobic conditions were detrimental to production and resulted in by-product secretion, such as citric acid. At low aeration rates, the fungus produces very small amounts of citric acid while maintaining yield. All reactors were inoculated with spores to an initial concentration of 1×10≠spores/mL. Growth occurred at 34° C.
Figure 23B:
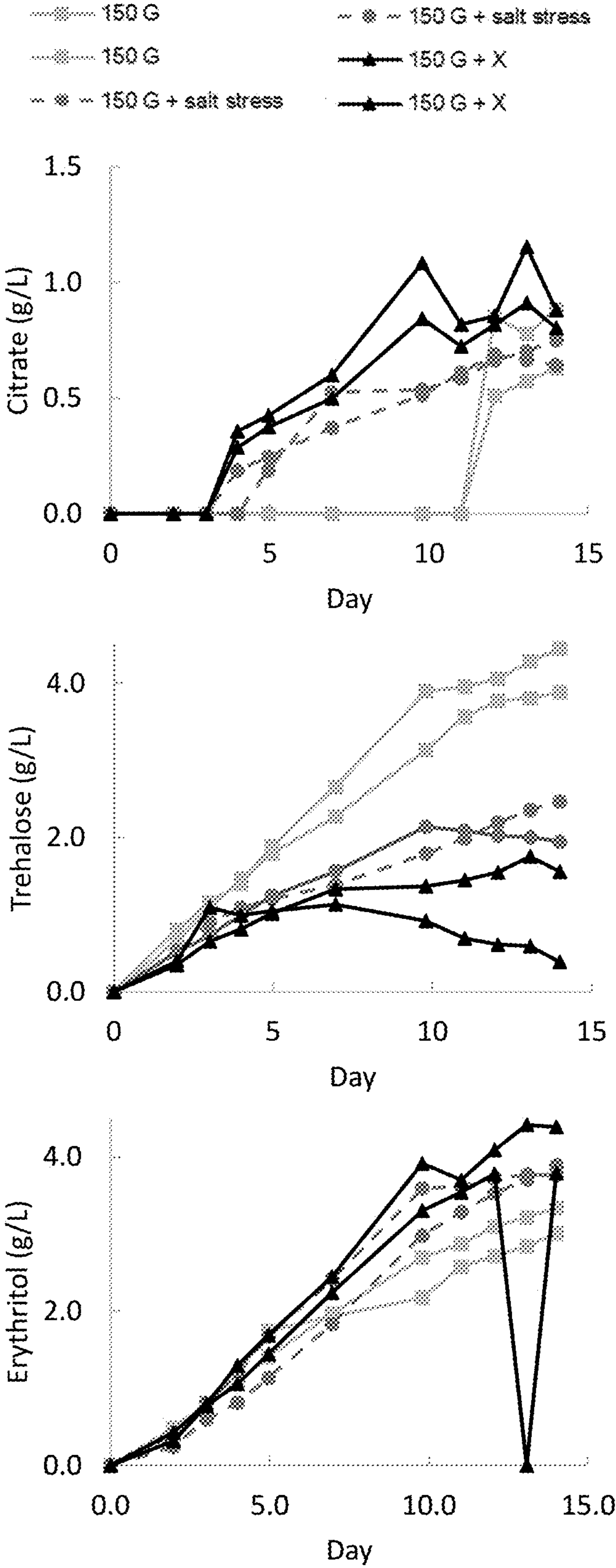
Figure 24:
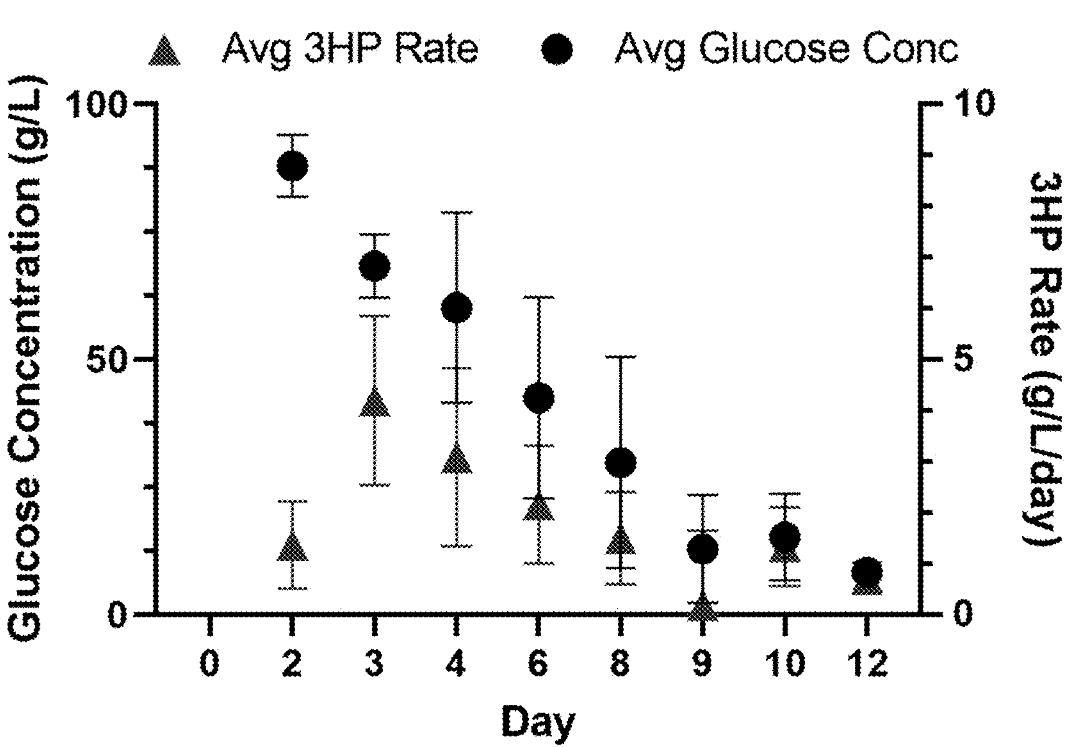
FIG. 24. Composite of 3-HP production rates from multiple bioreactor (0.5 L) runs compared to the average remaining glucose concentration. Across the campaigns, there was a correlation of 3-HP production rates and sugar concentrations, with a notable decrease of production observed at ~50 g/L. All reactors were inoculated with spores to an initial concentration of 1×10ˆ6 spores/mL. Growth occurred at 34° C.

A 3-HP producing *A. niger* strain capable of secreting high levels of 3-HP (~35 g/L achieved) in shaking flasks cultivations was established herein. This strain (An3HP9/pyc2/ald6aA/3HP-6) was used to establish the bioreactor production parameter space in 0.5 L benchtop fermenters. A range of maintained pH's was examined and it was determined that 3-HP could be produced as a free acid down to around pH 2 (FIG. 22) The utilization of sodium hydroxide for pH control led to better 3HP production. NaOH addition lead to more osmotic stressed conditions compared to addition of KOH, an unexpected result. Varied aeration rates in the bioreactors using the optimal pH conditions revealed that highly aerobic conditions were detrimental to production and resulted in increased by-product secretion (FIG. 22). Another round of 0.5 L benchtop reactors were then performed to compare 3-HP production in medium with pure glucose, glucose:xylose at a 2:1 mixture, and glucose with additional NaCl as a salt stress (FIGS. 23A-23C). This data indicated that salt stress has the potential to lower bioproduct formation while maintaining similar 3-HP titers. Interestingly, there was a correlation of glucose concentration to 3-HP production rates over the course of 20 different 0.5 L fermentation runs. At ~50 g/L of sugar, the 3-HP production tended to decrease compared to initial rates (FIG. 24). Once parameter space for bioreactor cultivations had been established, various conditions were screened to increase production and sugar consumption.

Example 11: Shaking Flasks Optimization

Figure 25:
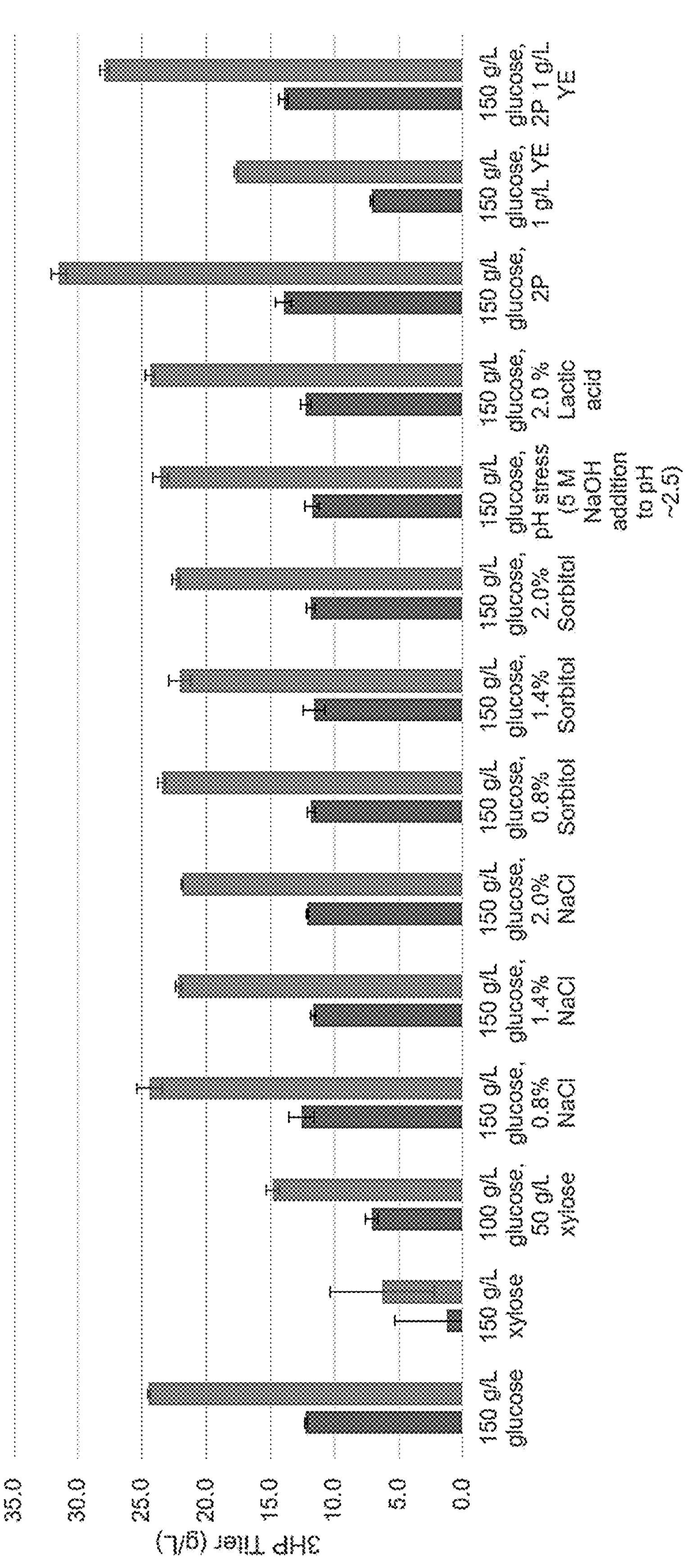
FIG. 25. 3-HP titers under various conditions in shaking flasks (related to FIGS. 26-28C). The control media was RisB medium with glucose at an initial concentration of 150 g/L. In selected conditions, glucose was replaced with a glucose:xylose mixture (2:1 g to g ratio). In other conditions, additives were included in the media at the specified concentrations (2 g/L of Potassium Phosphate (2 g/L P), yeast extract (YE), sodium chloride at various weight percents, lactic acid). In one condition, 5 M NaOH was added at 48 and 96 h to raise the pH to ~2.5. Cultures were inoculated from spores at a concentration of 1×10ˆ6 spores/mL. Growth occurred at 30° C.
Figure 26:
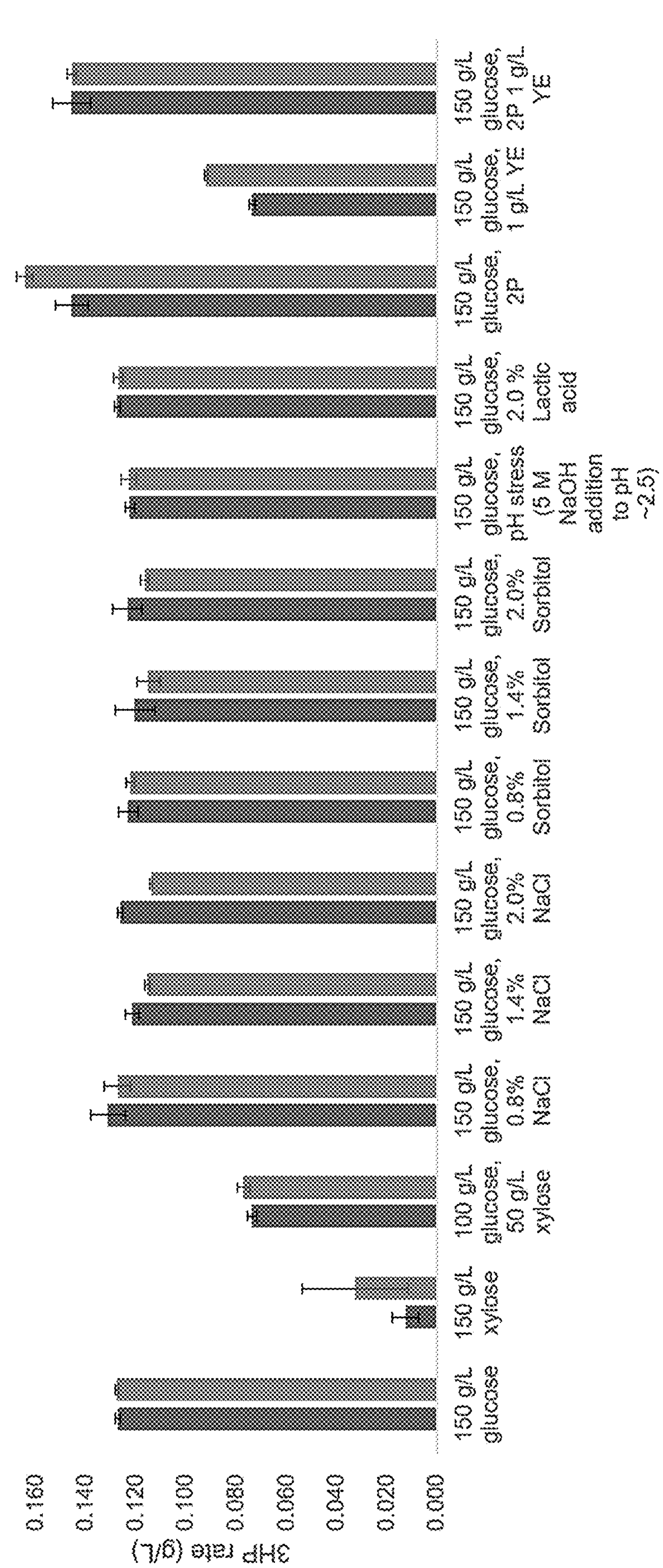
FIG. 26. 3-HP rate of production under various conditions in shaking flasks (related to FIG. 25 and FIGS. 27-28C). The control media was RisB medium with glucose at an initial concentration of 150 g/L. In selected conditions, glucose was replaced with a glucose:xylose mixture (2:1 g to g ratio). In other conditions, additives were included in the media at the specified concentrations (2 g/L of Potassium Phosphate (2 g/L P), yeast extract (YE), sodium chloride at various weight percents, lactic acid). In one condition, 5 M NaOH was added at 48 and 96 h to raise the pH to ~2.5. Cultures were inoculated from spores at a concentration of 1×10ˆ6 spores/mL. Growth occurred at 30° C.
Figure 27:
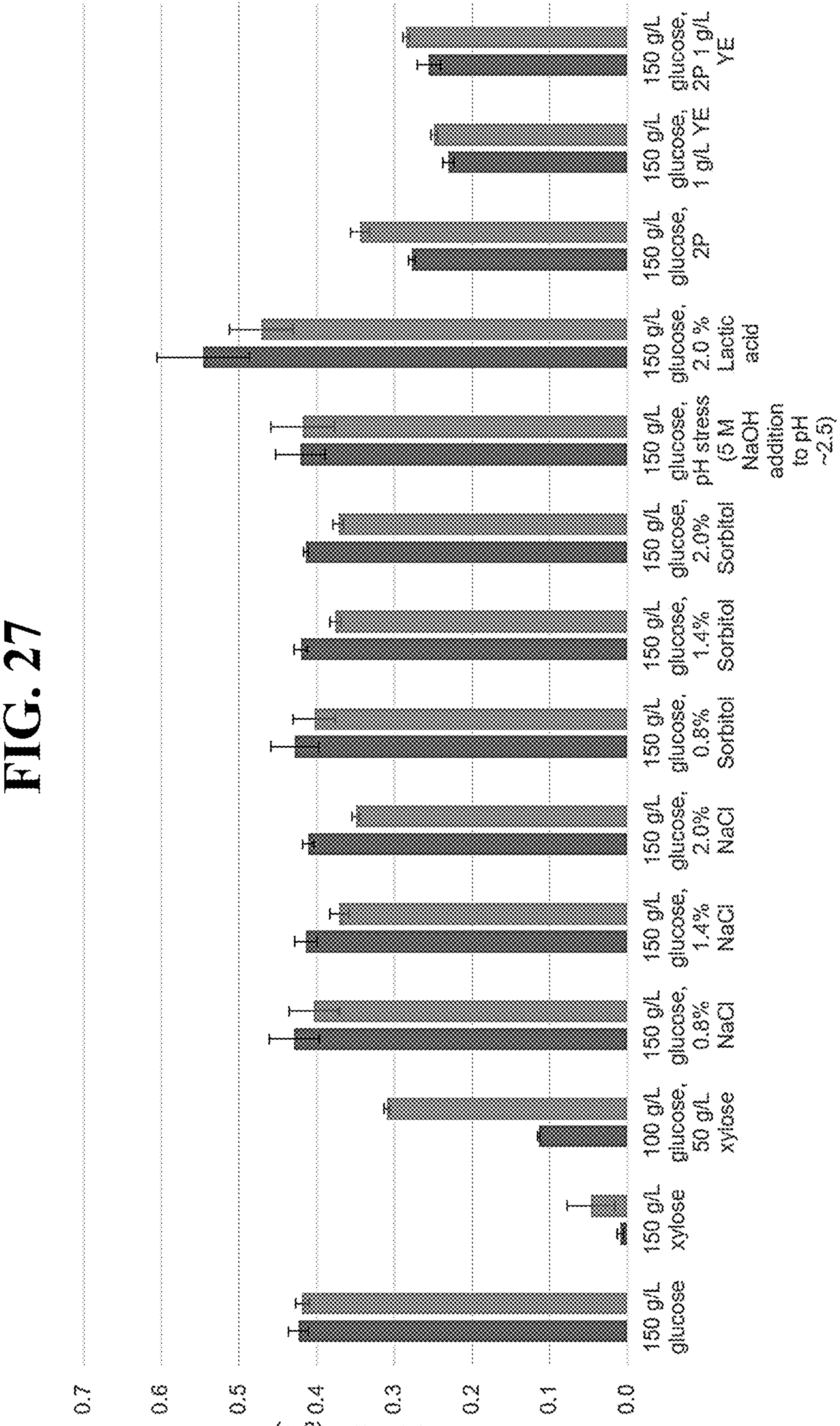
FIG. 27. 3-HP yields under various conditions in shaking flasks (related to FIGS. 25, 26, and 28A-28C). The control media was RisB medium with glucose at an initial concentration of 150 g/L. In selected conditions, glucose was replaced with a glucose:xylose mixture (2:1 g to g ratio). In other conditions, additives were included in the media at the specified concentrations (2 g/L of potassium phosphate (2 g/L P), yeast extract (YE), sodium chloride at various weight percents, lactic acid). In one condition, 5 M NaOH was added at 48 and 96 h to raise the pH to ~2.5. Cultures were inoculated from spores at a concentration of 1×10ˆ6 spores/mL. Growth occurred at 30° C.
Figures 28A, 28B, 28C:
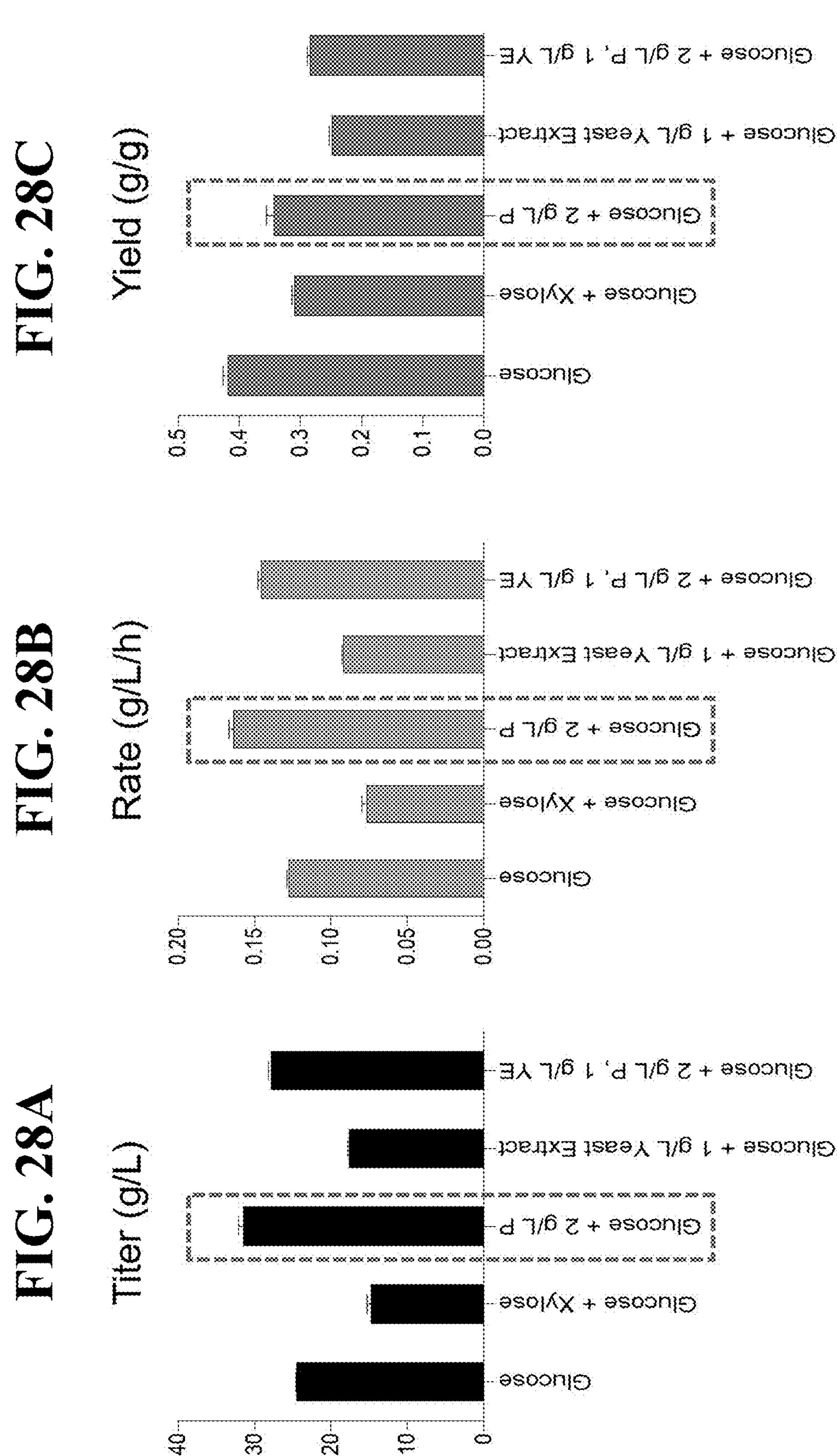
FIGS. 28A-28C. 3HP titers (FIG. 28A), rates (FIG. 28B), and yields (FIG. 28C) of selected shaking flask cultivations (related to FIGS. 25-27). The control media was RisB medium with glucose at an initial concentration of 150 g/L. In selected conditions, glucose was replaced with a glucose:xylose mixture (2:1 g to g ratio). In other conditions, additives were included in the media at the specified concentrations (2 g/L of potassium phosphate (2 g/L P), yeast extract (YE)). Cultures were inoculated from spores at a concentration of 1×10ˆ6 spores/mL. Growth occurred at 30° C.
Figure 29:
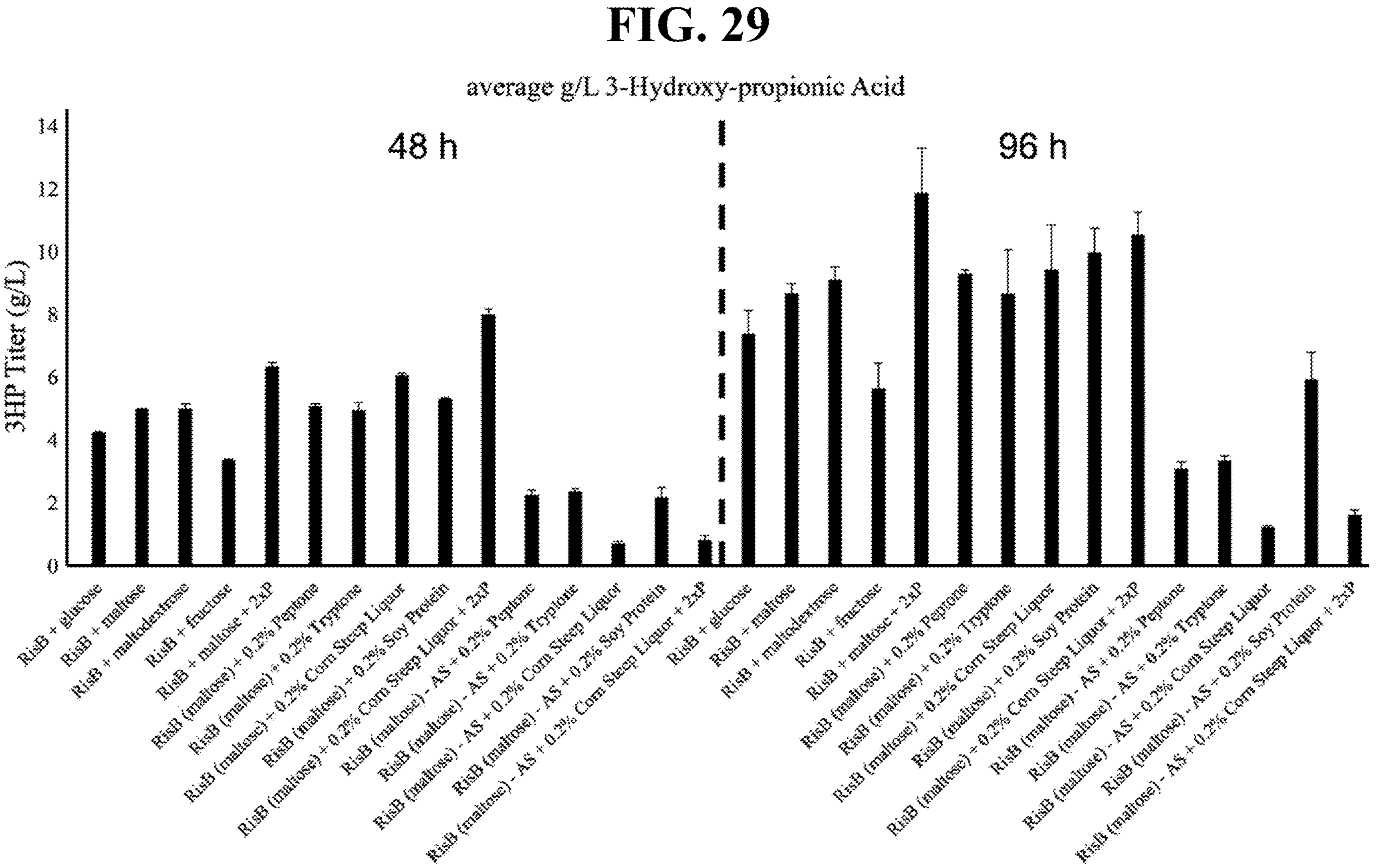
FIG. 29. 3-HP titers from shaking flask conditions taken at 48 and 96 h (related to FIG. 30). The control medium (RisB+glucose at 100 g/L) was modified by substituting glucose with either maltose, fructose, or maltodextrose (aka maltodextrin). Total sugar concentration was initially at a concentration of 100 g/L. Additives of Peptone, Tryptone, Corn Steep Liquor or Soy Protein were added at a weight percent of 0.2% to media conditions. Ammonia Sulfate (AS) was removed from the based medium of certain conditions with the specified additives. Additional phosphorus (2×P) was also added in select conditions. Growth occurred at 30° C.
Figure 31A:
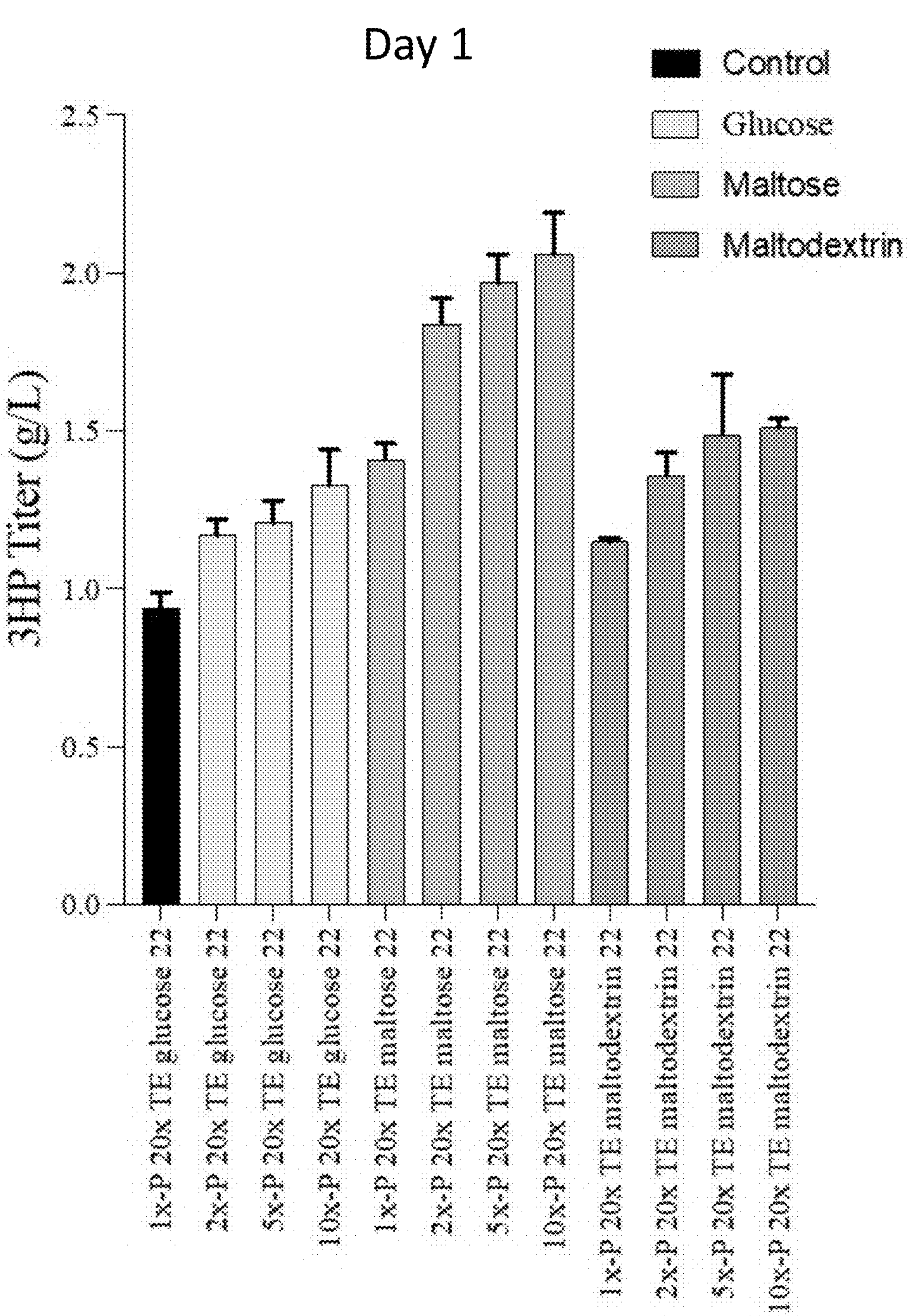
FIGS. 31A-31C. 3-HP production in shaking flask (related to FIGS. 32-24) at day 1 and day 2. The control media is RisB with glucose, 20×Trace elements (20×TE), and 1× Potassium Phosphate (1×-P). The phosphate level was varied and from 1× to 10×. Samples were taken across the shaking flask cultivations. Cultivations occurred at 35° C. and were inoculated at 10% vol/vol from a 10% seed culture. Samples were measure at Day 1 (FIG. 31A), Day 2 (FIG. 31B), and converted sugars on Day 2 (FIG. 31° C.).
Figure 31B:
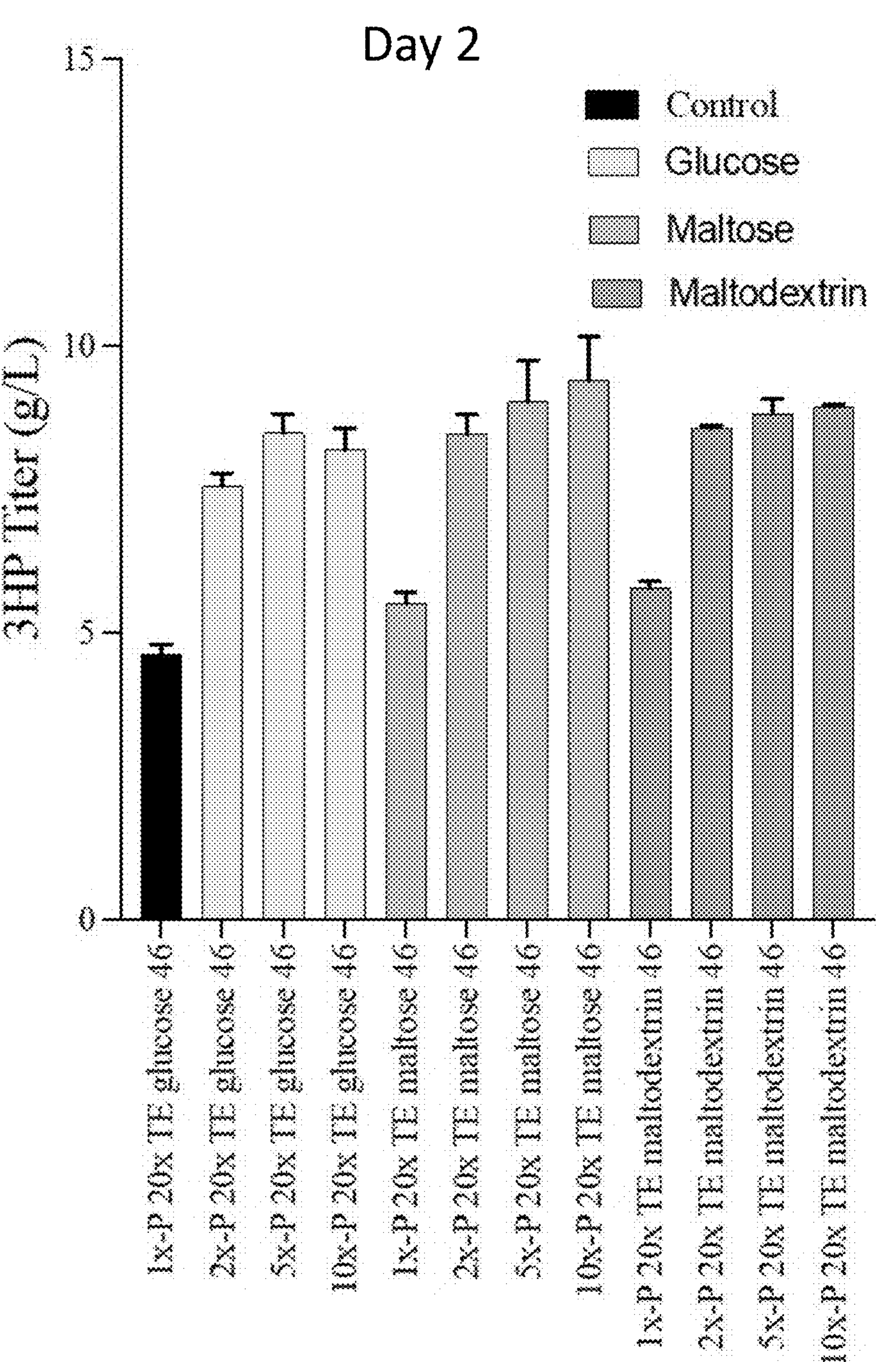
Figure 31C:
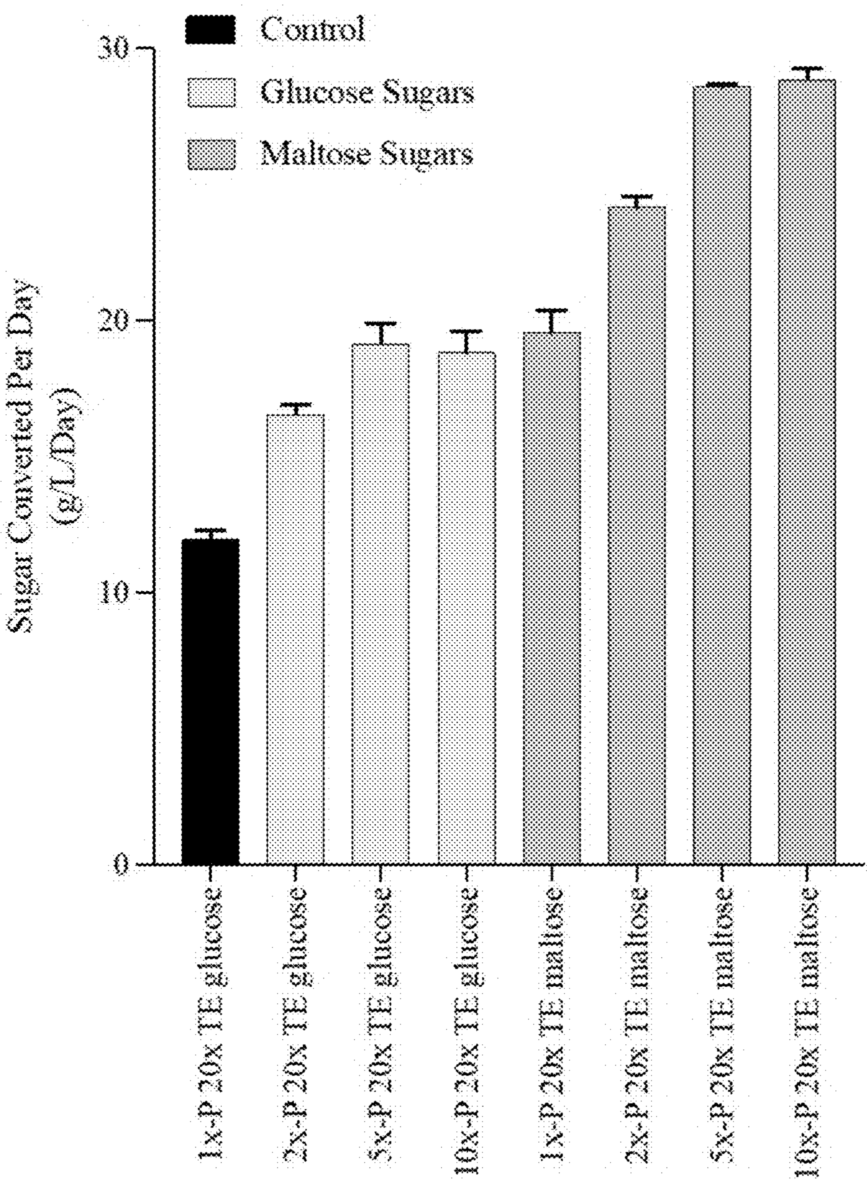
Figure 32A:
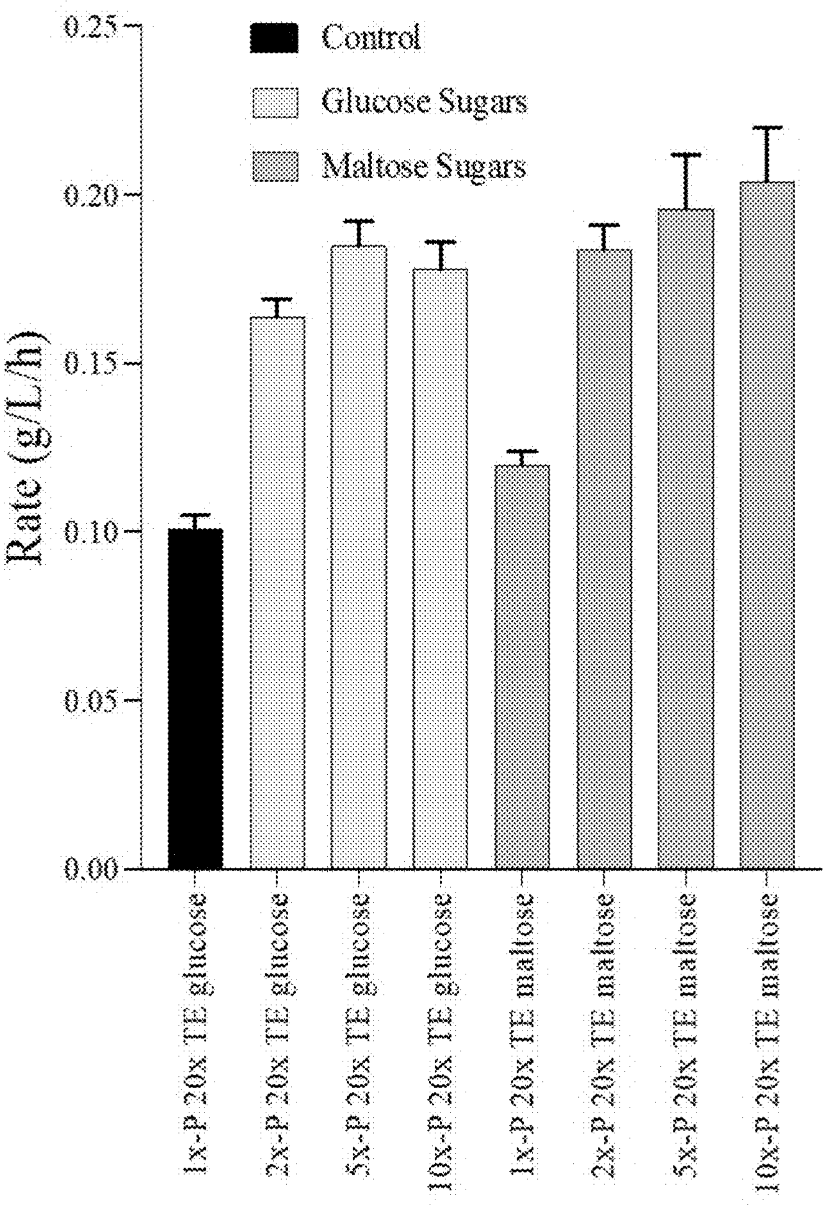
FIGS. 32A-32B. 3-HP rates and yields in shaking flask (related to FIGS. 31A-31C and 33A-34). The control media is RisB with Glucose and 20×Trace elements (20×TE) and 1× Potassium Phosphate (1×-P). The phosphate level was varied and from 1× to 10×. Samples were taken across the shaking flask cultivations at Day 2 (FIG. 32A) and Day 3 (FIG. 32B). Cultivations occurred at 35° C. and were inoculated at 10% vol/vol from a 10% seed culture.
Figure 32B:
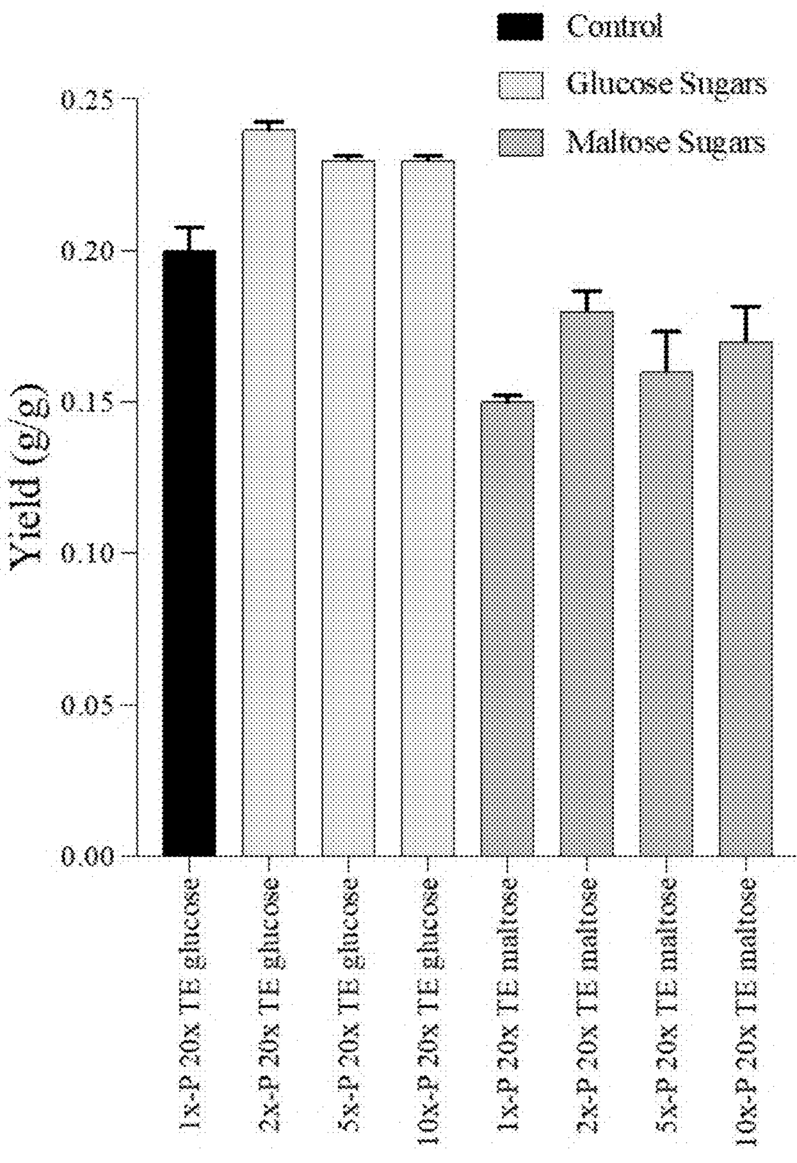
Figure 33A:
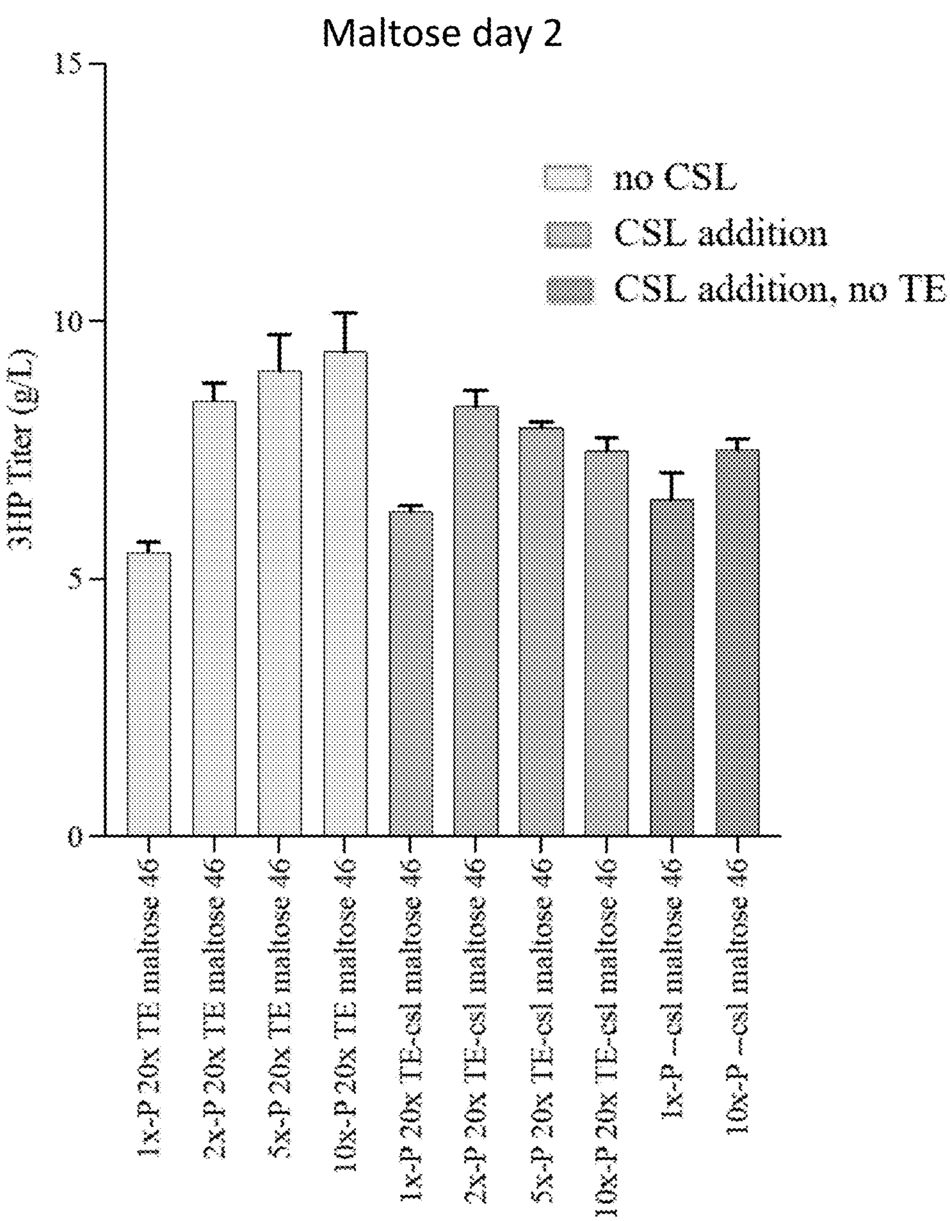
FIGS. 33A-33B. 3-HP titers on maltose and maltodextrin (day 2) in shaking flask (related to FIGS. 31A-32B and 34). The control media is RisB with Glucose and 20×Trace elements (20×TE) and 1× Potassium Phosphate (1×-P). The phosphate level was varied and from 1× to 10×. Samples were taken across the shaking flask cultivations for maltose at Day 2 (FIG. 33A) and maltodextrin at Day 2 (FIG. 33B). Cultivations occurred at 35° C. and were inoculated at 10% vol/vol from a 10% seed culture.
Figure 33B:
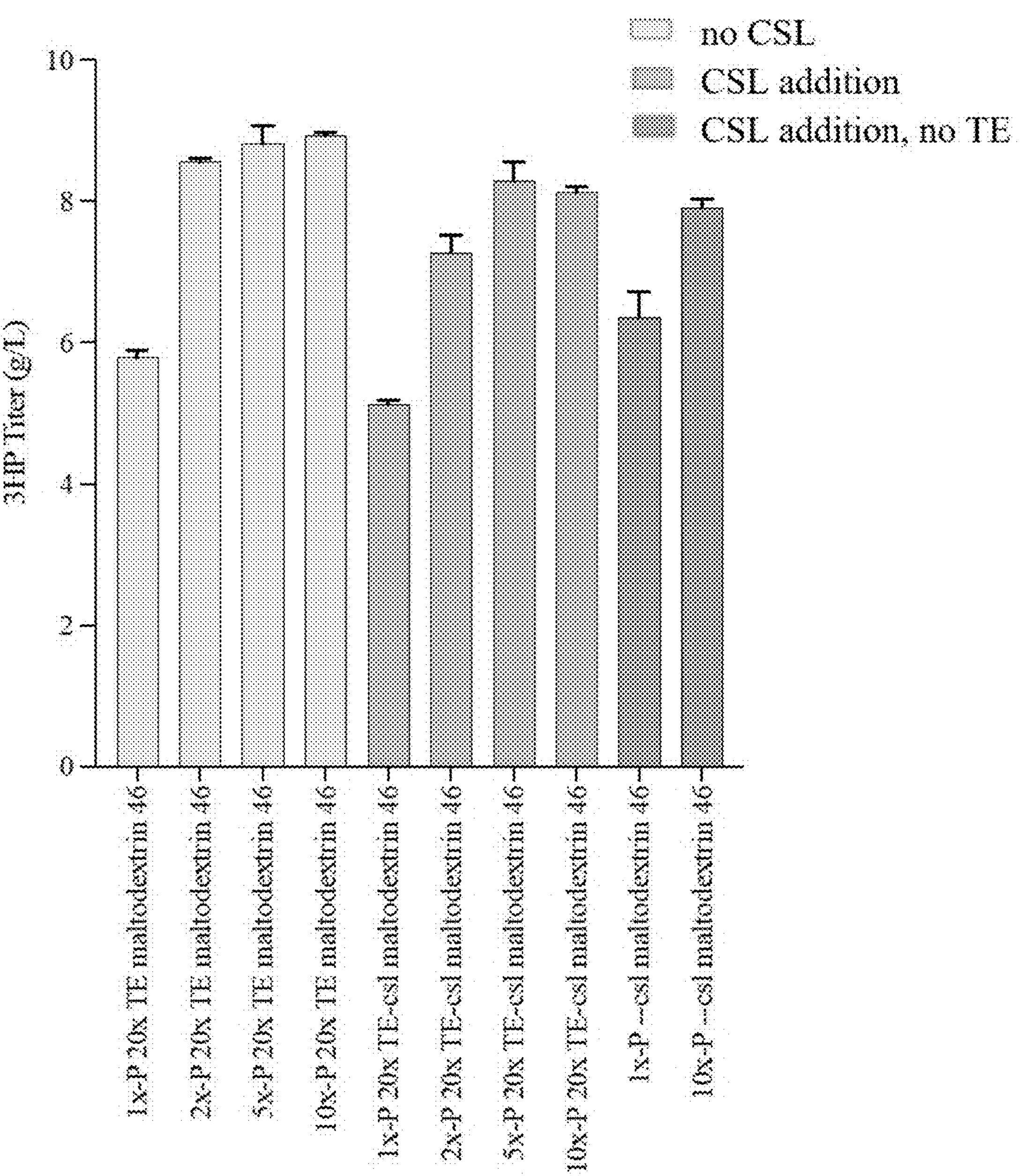
Figure 34:
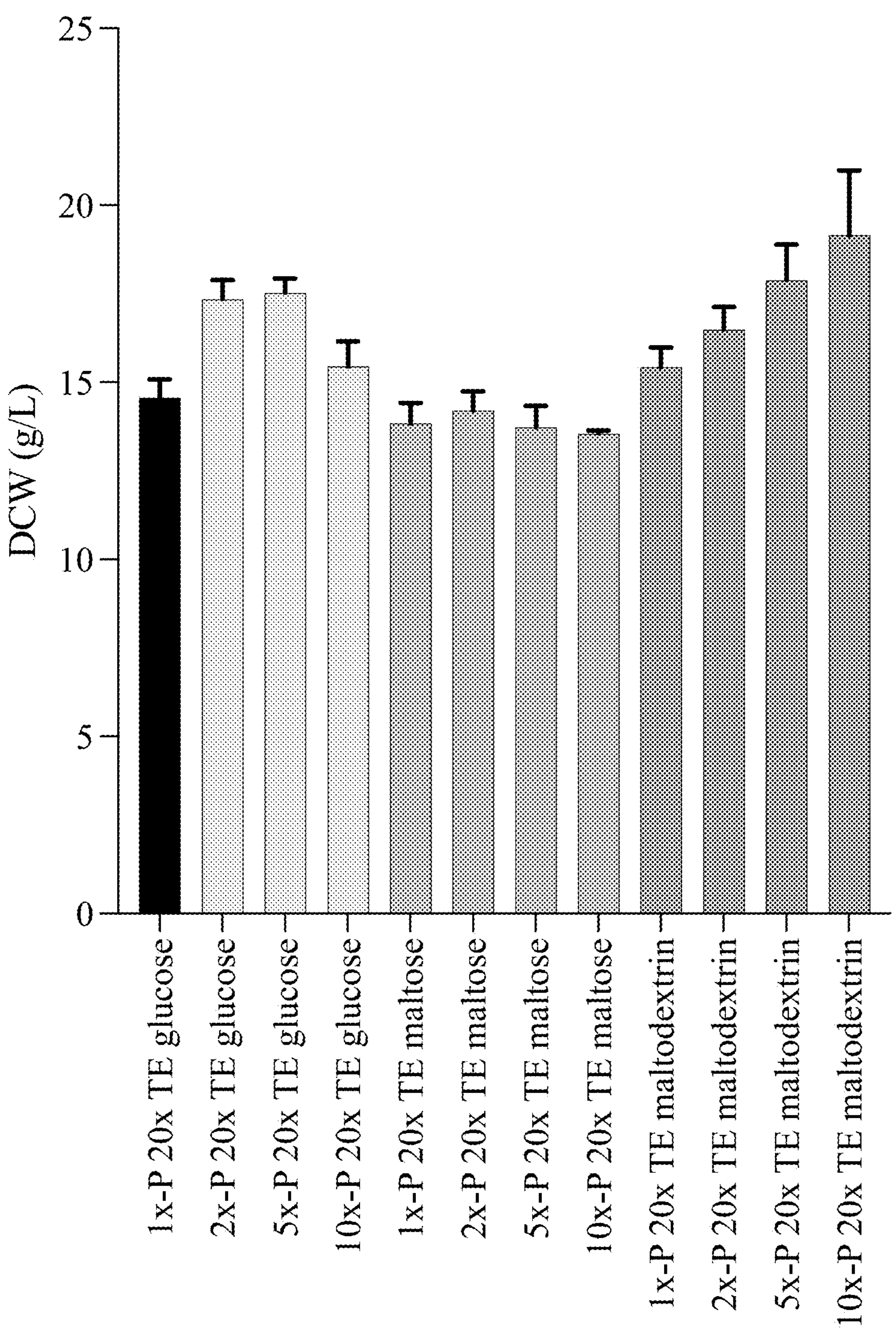
FIG. 34. Dry cell weigh measurements from 3-HP production in shaking flask (related to FIGS. 31A-33B). The control media is RisB with Glucose and 20×Trace elements (20×TE) and 1× Potassium Phosphate (1×-P). The phosphate level was varied and from 1× to 10×. Samples were taken across the shaking flask cultivations. Cultivations occurred at 35° C. and were inoculated at 10% vol/vol from a 10% seed culture.

The initial shaking flask experiment investigated further osmotic stressor effects on production (using NaCl or Sorbitol) or addition of further phosphate and/or yeast extract (rich component). Titers, rates, and yields are shown in FIG. 25, FIG. 26, and FIG. 27, respectively. Compared to the control condition (pure glucose), supplying additional phosphate led to enhanced rates of 3-HP production (FIGS. 28A-28C). Unexpectedly, this did not appear to be due to increased cell mass, as the yeast extract (with rich components for growth) had detrimental effects on 3-HP production. Next, other rich components, such as peptone, tryptone, corn steep liquor and soy protein, were examined. Again, the results indicated that the addition of phosphate, in combination with corn steep liquor, led to the initial highest production of 3-HP (FIG. 29). Interesting, maltose uptake was also at a significantly faster rate (3-5×) than the control condition (FIG. 30). Maltose is a disaccharide and contains two glucose units. Lastly, a screen of culture conditions using maltose, maltodextrin, and glucose as the carbon source across a wide variety of phosphate conditions was performed, as well as the addition of corn steep liquor to the different cultures. The results indicated that maltose led to the fastest initial rates of 3HP production and sugar consumption (note: maltodextrin was not detectable via HPLC and thus, no data is available for sugar consumption in those conditions). Under these experimental conditions, the sugar conversion rate increased from 13.4±0.4 to 30.1±0.1 g/L/day (FIGS. 31A-31C). There was only minimal impact on the yield compared to the control condition (FIGS. 32A-32B). Phosphorus levels was found to have a similar effect on 3-HP production, with limited improvement in production past 5× phosphorus concentrations. Corn steep liquor was found to not significantly enhance production with maltose or maltodextrin as the sole carbon source under the tested conditions (FIGS. 33A-33B). Thus, there is some unexpected phenomena that is unrelated to the biomass production that leads to enhanced 3HP production. Perhaps the most surprising result was that the increased phosphorus concentration did not seem to lead to increased biomass under maltose conditions (FIG. 34).

Based on these findings, maltose was the best carbon source with an additional phosphorus concentration of 5×. It was unexpected to find that conditions with increased nutrients did not lead to enhanced rates of production. Specifically, the lack of increased biomass when further phosphorus was added into the maltose conditions, but the significant increase of production was unexpected. Additionally, maltose is simply two glucose monomers. However, there seems to be a different response to using pure glucose versus maltose for production.

It will be apparent that the precise details of the methods or compositions described may be varied or modified without departing from the spirit of this disclosure. We claim all such modifications and variations that fall within the scope and spirit of the claims below.

We claim:

1. A recombinant *Aspergillus niger*, comprising an exogenous nucleic acid molecule encoding aspartate 1-decarboxylase (PAND), an exogenous nucleic acid molecule encoding β-alanine-pyruvate aminotransferase (BAPAT), and an exogenous nucleic acid molecule encoding 3-hydroxypropionate dehydrogenase (HPDH), wherein:

i) the exogenous nucleic acid molecule encoding PAND encodes an amino acid sequence comprising at least 95% sequence identity to SEQ ID NO: 1;

ii) the exogenous nucleic acid molecule encoding BAPAT encodes an amino acid sequence comprising at least 95% sequence identity to SEQ ID NO: 2; and iii) the exogenous nucleic acid molecule encoding HPDH encodes an amino acid sequence comprising at least 95% sequence identity to SEQ ID NO: 3.

2. The recombinant *Aspergillus niger* of claim 1, wherein the copy number of each of PAND, BAPAT, and HPDH is independently about 1 to about 80 in the recombinant *Aspergillus niger*.

3. The recombinant *Aspergillus niger* of claim 1, wherein the copy number of each of PAND, BAPAT, and HPDH is independently about 10 to about 30 in the recombinant *Aspergillus niger*.

4. The recombinant *Aspergillus niger* of claim 1, wherein:

i) an ald6a, ald6b, ald3, and/or oahA gene is not present or does not produce a functional product in the recombinant *Aspergillus niger*; and/or ii) a pyc, aat1, and/or mct1 gene is overexpressed in the recombinant *Aspergillus niger*.

5. The recombinant *Aspergillus niger* of claim 1, wherein an ald6a gene is not present or does not produce a functional product in the recombinant *Aspergillus niger*, and wherein a pyc gene is overexpressed in the recombinant *Aspergillus niger*.

6. The recombinant *Aspergillus niger* of claim 1, wherein:

i) the exogenous nucleic acid molecule encoding PAND comprises or consists of a sequence encoding SEQ ID NO: 1; and/or ii) the exogenous nucleic acid molecule encoding BAPAT comprises or consists of a sequence encoding SEQ ID NO: 2; and/or iii) the exogenous nucleic acid molecule encoding HPDH comprises or consists of a sequence encoding SEQ ID NO: 3.

7. The recombinant *Aspergillus niger* of claim 1, wherein the exogenous nucleic acid molecules encoding PAND, BAPAT, and HPDH are operably linked to a promoter.

8. The recombinant *Aspergillus niger* of claim 1, wherein the exogenous nucleic acid molecules encoding PAND, BAPAT, and HPDH are encoded by a nucleic acid molecule comprising at least 95% sequence identity to SEQ ID NO: 4 and/or SEQ ID NO: 142.

9. The recombinant *Aspergillus niger* of claim 1, comprising a nucleic acid molecule comprising SEQ ID NO: 4 and/or SEQ ID NO: 142.

10. The recombinant *Aspergillus niger* of claim 1, wherein the exogenous nucleic acid molecules encoding PAND, BAPAT, and HPDH are comprised on a vector.

11. A method of producing 3-hydroxypropionic acid (3-HP), comprising:

culturing the recombinant *Aspergillus niger* of claim 1 under conditions that permit the production of 3-HP, thereby making 3-HP.

12. The method of claim 11, wherein the conditions that permit the production of 3-HP comprise fermenting the *Aspergillus niger* at a temperature of 30° C. to 37° C., under acidic and microaerobic conditions.

13. The method of claim 12, wherein:

(i) the temperature is 33° C. to 35° C., (ii) the acidic conditions comprise a pH of 1 to 4, and/or (iii) the microaerobic conditions comprise a dissolved oxygen content of less than 15%.

14. The method of claim 12, wherein:

(i) the temperature is about 34° C., (ii) the acidic conditions comprise a pH of about 2, and/or (iii) the microaerobic conditions comprise a dissolved oxygen content of 0% to 10%.

15. The method of claim 11, wherein culturing comprises culturing the recombinant *Aspergillus niger* in Riscaldati B medium (RisB).

16. The method of claim 12, wherein the fermenting is performed in a bioreactor.

17. A kit, comprising:

the recombinant *Aspergillus niger* of claim 1, and a media, carbon source, nutrient additive, antifoam, antibiotic, filter, or combinations thereof.

18. The recombinant *Aspergillus niger* of claim 1, wherein the recombinant *Aspergillus niger* produces 3-hydroxypropionic acid (3-HP).

19. The recombinant *Aspergillus niger* of claim 10, wherein the vector is a plasmid.

* * * * *